United States Patent
Baeuerle et al.

(10) Patent No.: US 12,404,328 B2
(45) Date of Patent: Sep. 2, 2025

(54) MULTI-SPECIFIC BINDING PROTEINS AND METHODS OF USE THEREOF

(71) Applicant: Cullinan Management, Inc., Cambridge, MA (US)

(72) Inventors: Patrick A. Baeuerle, Cambridge, MA (US); Jennifer Michaelson, Brighton, MA (US); Bochong Li, Boston, MA (US); Naveen Mehta, Cambridge, MA (US)

(73) Assignee: Cullinan Management, Inc., Cambridge, MA (US)

( * ) Notice: Subject to any disclaimer, the term of this patent is extended or adjusted under 35 U.S.C. 154(b) by 252 days.

(21) Appl. No.: 16/972,460

(22) PCT Filed: Jun. 7, 2019

(86) PCT No.: PCT/US2019/036177
§ 371 (c)(1),
(2) Date: Aug. 11, 2023

(87) PCT Pub. No.: WO2019/237081
PCT Pub. Date: Dec. 12, 2019

(65) Prior Publication Data
US 2021/0238286 A1    Aug. 5, 2021

Related U.S. Application Data

(60) Provisional application No. 62/681,784, filed on Jun. 7, 2018.

(51) Int. Cl.
*C07K 16/28* (2006.01)
*A61K 39/00* (2006.01)
*A61P 35/00* (2006.01)
*C07K 16/18* (2006.01)

(52) U.S. Cl.
CPC .......... *C07K 16/2809* (2013.01); *A61P 35/00* (2018.01); *C07K 16/18* (2013.01); *C07K 16/2803* (2013.01); *A61K 2039/505* (2013.01); *C07K 2317/31* (2013.01); *C07K 2317/565* (2013.01); *C07K 2317/569* (2013.01); *C07K 2317/622* (2013.01); *C07K 2317/73* (2013.01); *C07K 2317/76* (2013.01); *C07K 2317/92* (2013.01)

(58) Field of Classification Search
CPC ............ C07K 16/2809; C07K 2317/31; C07K 2317/565; C07K 2317/569; C07K 2317/622
See application file for complete search history.

(56) References Cited

FOREIGN PATENT DOCUMENTS

| CN | 108026177 A | 5/2018 | |
|---|---|---|---|
| WO | 2015157286 | 10/2015 | |
| WO | WO-2016016412 A1 * | 2/2016 | ............ A61K 47/60 |
| WO | WO-2016116626 A1 * | 7/2016 | ............ A61P 35/00 |
| WO | 2016187594 | 11/2016 | |
| WO | WO-2017040344 A2 * | 3/2017 | ............ A61P 35/00 |
| WO | 2017194438 | 11/2017 | |

OTHER PUBLICATIONS

Muller et al, The Journal of Biological Chemistry vol. 282, No. 17, pp. 12650-12660, Apr. 27, 2007 (Year: 2007).*
MacCallum et al., 1996, J. Mol. Biol. 262: 732-745 (Year: 1996).*
Vajdos et al., 2002, J. Mol. Biol. 320: 415-428 (Year: 2002).*
Paul, Fundamental Immunology, 2003, 5th Edition, Raven Press, New York, Chapter 3, pp. 109-147 (Year: 2003).*
Casset et al., 2003, Biochemical and Biophysical Research Communications 307:198-205 (Year: 2003).*
Sela-Culang et al., 2013, Frontiers in Immunology 4(302): 1-13 (Year: 2013).*
Feng et al., Antibody Therapeutics, 2019, vol. 2, No. 1 1-11 (Year: 2019).*
Asaadi et al., Biomarker Research (2021) 9:87, 20 pages (Year: 2021).*
Japan Patent Office, Office Action regarding Application No. 2021-518060, 10 pages, dated Apr. 26, 2023.
Chinese Patent Office, Office Action regarding Application No. 201980050411.2, 13 pages, dated Aug. 29, 2024.

* cited by examiner

*Primary Examiner* — Vanessa L. Ford
*Assistant Examiner* — Danaya L Middleton
(74) *Attorney, Agent, or Firm* — McAndrews, Held & Malloy, Ltd.

(57) ABSTRACT

The invention relates to multi-specific binding proteins that bind CD19, CD3, and serum albumin. The invention also relates to pharmaceutical compositions comprising these multi-specific binding proteins, expression vectors and host cells for making these multi-specific binding proteins, and methods of use of these multi-specific binding proteins in treating hematologic cancers.

26 Claims, 2 Drawing Sheets
Specification includes a Sequence Listing.

CD19-binding domain
 HSA-binding domain
 CD3-binding domain

MULTI-SPECIFIC BINDING PROTEINS AND METHODS OF USE THEREOF

CROSS-REFERENCE TO RELATED APPLICATIONS

This application is a U.S. national stage application, filed under 35 U.S.C. § 371, of International Application No. PCT/US2019/036177, filed on Jun. 7, 2019, which claims the benefit of and priority to U.S. Provisional Patent Application No. 62/681,784, filed on Jun. 7, 2018, the disclosure of each of which is incorporated by reference herein in its entirety for all purposes.

INCORPORATION BY REFERENCE OF SEQUENCE LISTING

This application contains a Sequence listing that has been submitted in a computer readable format and is hereby incorporated by reference in its entirety. The ASCII text file, created on Nov. 15, 2023, is named 67254US01_CLN-978_Sequence_Listing.txt, and is 373777 bytes in size.

FIELD OF THE INVENTION

The invention relates to multi-specific binding proteins that bind CD19, CD3, and serum albumin. The invention also relates to pharmaceutical compositions comprising these multi-specific binding proteins, expression vectors and host cells for making these multi-specific binding proteins, and methods of use of these multi-specific binding proteins in treating hematologic cancers.

BACKGROUND

Bispecific molecules available under the trade name BiTE® from Micromet AG (bispecific T-cell engager) constructs are recombinant protein constructs made from two flexibly linked antibody-derived binding domains. One binding domain of BiTE® constructs is specific for a selected tumor-associated surface antigen on target cells, and the second binding domain is specific for CD3, a subunit of the T cell receptor complex on T cells. By this design, BiTE® constructs can transiently connect T cells with target cells and, at the same time, potently activate the inherent cytolytic potential of T cells against target cells.

The CD3 receptor complex is a protein complex composed of four polypeptide chains. In mammals, the complex contains a CD3γ (gamma) chain, a CD3δ (delta) chain, and two CD3ε (epsilon) chains. The CD3γ (gamma), CD3δ (delta), and CD3ε (epsilon) chains are highly related cell-surface proteins of the immunoglobulin superfamily containing a single extracellular immunoglobulin domain. These chains associate with the T cell receptor (TCR) to form a TCR-CD3 complex and to generate an activation signal in T lymphocytes upon antigen engagement. About 95% of T cells express αβ TCR, which contains an a (alpha) chain and a β (beta) chain. Two TCRξ (zeta) chains are also present in the TCR-CD3 complex. The αβ TCR is responsible for recognizing antigens presented by a major histocompatibility complex (MHC). When the TCR engages with antigenic peptide and MHC complex, the T lymphocyte is activated through a series of biochemical events mediated by associated enzymes, co-receptors, specialized adaptor molecules, and activated or released transcription factors.

Earlier BiTE® constructs bind conformational epitopes of CD3 and typically are species-specific (see, PCT Publication No. WO2008119567A2). Improved BiTE® constructs, such as blinatumomab (also called AMG 103; see, PCT Publication No. WO1999054440A1) and solitomab (also called AMG 110; see, PCT Publication No. WO2005040220A1), bind context-independent epitopes at the N-terminus of CD3ε chain (e.g., amino acid residues 1-27 of human CD3ε extracellular domain) and show cross-species specificity for human, *Callithrix jacchus, Saguinus Oedipus*, and *Saimiri sciureus* CD3ε chain (see id.). These constructs do not nonspecifically activate T cells to the same degree as observed with the earlier BiTE® constructs, and are therefore believed to bear a lower risk of side effects (see, Brischwein et al. (2007) J. Immunother., 30 (8): 798-807).

BiTE® constructs are believed to suffer from rapid clearance from the body. Therefore, whilst they are able to rapidly penetrate many areas of the body, and are quick to produce and easier to handle, their in vivo applications may be limited by their brief persistence in vivo. Prolonged administration by continuous intravenous infusions may be required to achieve therapeutic effects of blinatumomab and solitomab because of their short in vivo half-life. However, such continuous intravenous infusions are inconvenient for patients and may increase the costs of treatment.

Although significant developments have been made in constructing multi-specific binding proteins, there remains a need for new and useful multi-specific binding proteins for treating cancer that have adequate therapeutic efficacy, a format straightforward to manufacture, and favorable pharmacokinetic properties such as a longer half-life.

SUMMARY OF THE INVENTION

The multi-specific binding proteins disclosed herein comprise a first domain that binds CD19 (e.g., human CD19), a second domain that binds CD3 (e.g., human and/or Macaca CD3), and a third domain that binds serum albumin (e.g., human serum albumin (HSA)). These domains are linked in certain manners for favorable therapeutic efficacy and in vivo half-life. The multi-specific binding proteins can be used to stimulate an immune response against a cell expressing CD19. As a result, the multi-specific binding proteins can be used to treat a disease or disorder associated with aberrant cells expressing CD19, such as certain hematologic B-cell cancers.

In one aspect, the present disclosure provides a multi-specific binding protein comprising: (a) a first antigen-binding site that binds human CD19; (b) a second antigen-binding site that binds human CD3; and (c) a third antigen-binding site that binds human serum albumin (HSA).

In certain embodiments, the multi-specific binding protein comprises a single polypeptide chain. In certain embodiments, the third antigen-binding site is not positioned between the first antigen-binding site and the second antigen-binding site in the polypeptide chain.

In certain embodiments, the third antigen-binding site is positioned N-terminal to both the first antigen-binding site and the second antigen-binding site in the polypeptide chain. In certain embodiments, the third antigen-binding site is positioned N-terminal to the first antigen-binding site, and the first antigen-binding site is positioned N-terminal to the second antigen-binding site in the polypeptide chain. In certain embodiments, the third antigen-binding site is positioned N-terminal to the second antigen-binding site, and the second antigen-binding site is positioned N-terminal to the first antigen-binding site in the polypeptide chain.

In certain embodiments, the third antigen-binding site is positioned C-terminal to both the first antigen-binding site and the second antigen-binding site in the polypeptide chain. In certain embodiments, the first antigen-binding site is positioned N-terminal to the second antigen-binding site, and the second antigen-binding site is positioned N-terminal to the third antigen-binding site in the polypeptide chain. In certain embodiments, the second antigen-binding site is positioned N-terminal to the first antigen-binding site, and the first antigen-binding site is positioned N-terminal of the third antigen-binding site in the polypeptide chain.

In certain embodiments, the first antigen-binding site is positioned N-terminal to the third antigen-binding site, and the third antigen-binding site is positioned N-terminal to the second antigen-binding site in the polypeptide chain. In certain embodiments, the second antigen-binding site is positioned N-terminal to the third antigen-binding site, and the third antigen-binding site is positioned N-terminal binding protein the first antigen-binding site in the polypeptide chain.

In certain embodiments, the first antigen-binding site comprises a single-chain variable fragment (scFv) or a single-domain antibody (sdAb). In certain embodiments, the first antigen-binding site comprises a single-chain variable fragment (scFv). In certain embodiments, the first antigen-binding site binds human CD19 with a dissociation constant ($K_D$) equal to or lower than 20 nM (namely, binding equal to or stronger than 20 nM). In certain embodiments, the first antigen-binding site has a melting temperature of at least 60° C.

In certain embodiments, the first antigen-binding site comprises a heavy chain variable domain (VH) comprising complementarity determining regions HCDR1, HCDR2, and HCDR3, and a light chain variable domain (VL) comprising complementarity determining regions LCDR1, LCDR2, and LCDR3, wherein (i) the HCDR1, HCDR2, HCDR3, LCDR1, LCDR2, and LCDR3 comprise the amino acid sequences set forth in SEQ ID NOs: 3, 4, 5, 6, 7, and 8, respectively; and/or (ii) the VH comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 1, and the VL comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 2.

In certain embodiments, the VH comprises the amino acid sequence set forth in SEQ ID NO: 1, and the VL comprises the amino acid sequence set forth in SEQ ID NO: 2.

In certain embodiments, the first antigen-binding site comprises a VH comprising complementarity determining regions HCDR1, HCDR2, and HCDR3, and a VL comprising complementarity determining regions LCDR1, LCDR2, and LCDR3, wherein (i) the HCDR1, HCDR2, HCDR3, LCDR1, LCDR2, and LCDR3 comprise the amino acid sequences set forth in SEQ ID NOs: 12, 13, 14, 15, 16, and 17, respectively; and/or (ii) the VH comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 10, and the VL comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 11. In certain embodiments, the VH comprises the amino acid sequence set forth in SEQ ID NO: 10, and the VL comprises the amino acid sequence set forth in SEQ ID NO: 11.

In certain embodiments, the second antigen-binding site comprises an scFv or an sdAb. In certain embodiments, the second antigen-binding site comprises an scFv. In certain embodiments, the second antigen-binding site binds human CD3ε. In certain embodiments, the second antigen-binding site binds human CD3 with a $K_D$ equal to or lower than 10 nM (namely, binding equal to or stronger than 10 nM). In certain embodiments, the second antigen-binding site binds human CD3ε with a $K_D$ equal to or lower than 10 nM. In certain embodiments, the second antigen-binding site has a melting temperature of at least 60° C.

In certain embodiments, the second antigen-binding site comprises a VH comprising complementarity determining regions HCDR1, HCDR2, and HCDR3, and a VL comprising complementarity determining regions LCDR1, LCDR2, and LCDR3, wherein (i) the HCDR1, HCDR2, HCDR3, LCDR1, LCDR2, and LCDR3 comprise the amino acid sequences set forth in SEQ ID NOs: 99, 100, 101, 102, 103, and 104, respectively; and/or (ii) the VH comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 97, and the VL comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 98. In certain embodiments, the VH comprises the amino acid sequence set forth in SEQ ID NO: 97, and the VL comprises the amino acid sequence set forth in SEQ ID NO: 98.

In certain embodiments, the third antigen-binding site comprises an scFv or an sdAb. In certain embodiments, the third antigen-binding site comprises an sdAb. In certain embodiments, the third antigen-binding site binds HSA with a $K_D$ equal to or lower than 20 nM (namely, binding equal to or stronger than 20 nM). In certain embodiments, the third antigen-binding site has a melting temperature of at least 60° C.

In certain embodiments, the third antigen-binding site comprises a VH comprising complementarity determining regions HCDR1, HCDR2, and HCDR3, wherein (i) the HCDR1, HCDR2, and HCDR3 comprise the amino acid sequences set forth in SEQ ID NOs: 122 or 123, 124 or 125, and 126, respectively; and/or (ii) the VH comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 121. In certain embodiments, the VH comprises the amino acid sequence set forth in SEQ ID NO: 121.

In certain embodiments, at least two adjacent antigen-binding sites are connected by a peptide linker. In certain embodiments, each of the adjacent antigen-binding sites in the multi-specific binding protein are connected by a peptide linker. In certain embodiments, the peptide linker comprises the amino acid sequence of SEQ ID NO: 298, 299, or 302. In certain embodiments, the peptide linker consists of the amino acid sequence of SEQ ID NO: 298, 299, or 302.

In certain embodiments, the multi-specific binding protein does not comprise an antibody Fc region.

In certain embodiments, the molecular weight of the multi-specific binding protein is at least 65 kD. In certain embodiments, the molecular weight of the multi-specific binding protein is in the range of 50-90 kD, 50-80 kD, 50-70 kD, 50-60 kD, 60-90 kD, 60-80 kD, 60-70 kD, 65-90 kD, 65-80 kD, 65-70 kD, 70-90 kD, or 70-80 kD.

In certain embodiments, the serum half-life of the multi-specific binding protein is at least 24, 36, 48, or 60 hours.

In another aspect, the present disclosure provides a pharmaceutical composition comprising a multi-specific binding protein disclosed herein and a pharmaceutically acceptable carrier.

In another aspect, the present disclosure provides an isolated polynucleotide encoding a multi-specific binding protein disclosed herein. In another aspect, the present disclosure provides a vector comprising the polynucleotide. In another aspect, the present disclosure provides a recombinant host cell comprising the polynucleotide or the vector.

In another aspect, the present disclosure provides a method of producing a multi-specific binding protein, the method comprising culturing a host cell disclosed herein under suitable conditions that allow expression of the multi-specific binding protein. In certain embodiments, the method further comprises isolating the multi-specific binding protein. In certain embodiments, the method further comprises formulating the isolated multi-specific binding protein with a pharmaceutically acceptable carrier.

In another aspect, the present disclosure provides a method of stimulating an immune response against a cell expressing CD19, the method comprising exposing the cell and a T lymphocyte to a multi-specific binding protein or pharmaceutical composition disclosed herein.

In another aspect, the present disclosure provides a method of treating a hematologic cancer in a subject in need thereof, the method comprising administering to the subject an effective amount of a multi-specific binding protein or pharmaceutical composition disclosed herein. In certain embodiments, the hematologic cancer is a B-cell hematologic malignancy.

In another aspect, the present disclosure provides a complex comprising a T cell expressing CD3, a B cell expressing CD19, and a multi-specific binding protein disclosed herein, wherein the T cell and the B cell are simultaneously bound by the multi-specific binding protein. In certain embodiments, the complex further comprises HSA.

DETAILED DESCRIPTION

Figure 1:
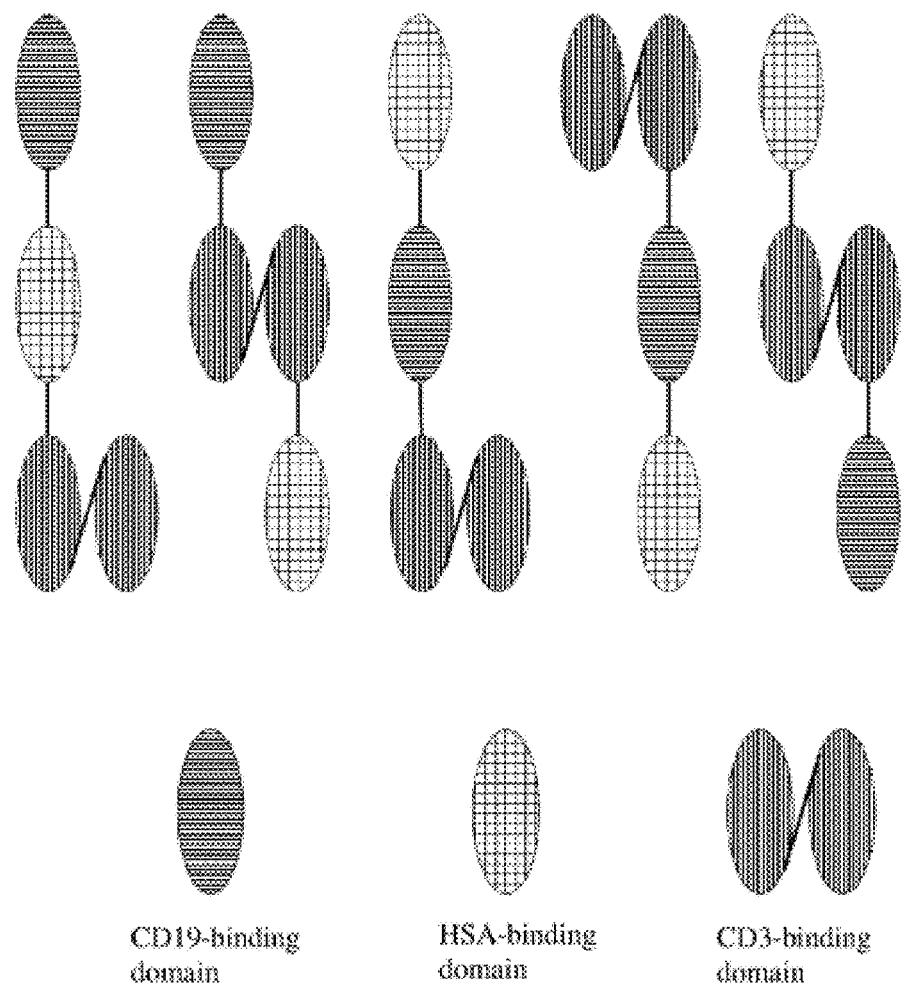
FIG. 1 is a schematic representation of six domain arrangements of single-chain multi-specific binding proteins. The CD19 binding domain in the form of a single-domain antibody (sdAb), the CD3 binding domain in the form of a single-chain variable fragment (scFv), and the HSA binding domain in the form of an sdAb are linked in different orientations. The top of each construct represents the N-terminus and the bottom of each construct represents the C-terminus of a given polypeptide chain.
Figure 2:
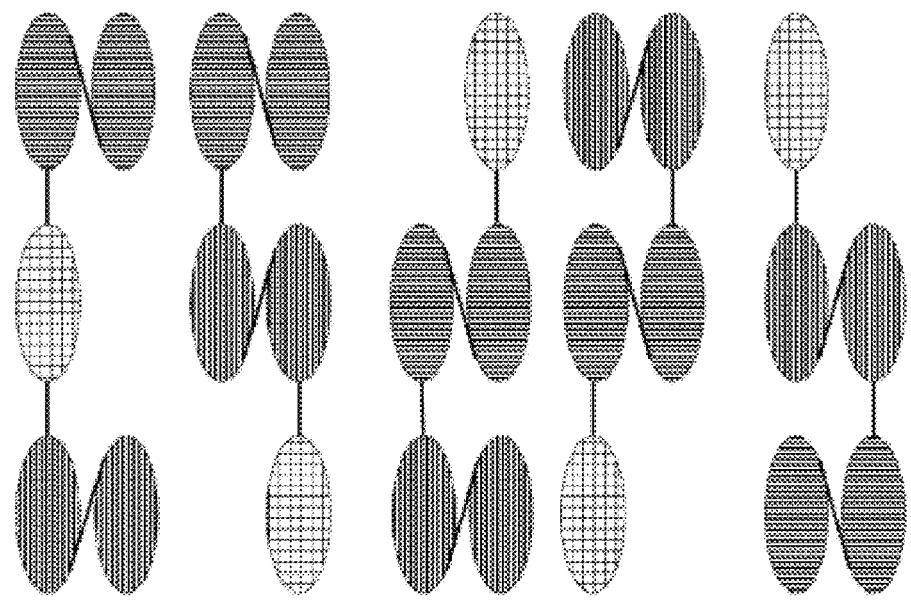
FIG. 2 is a schematic representation of six domain arrangements of single-chain multi-specific binding proteins. The CD19 binding domain in the form of an scFv, the CD3 binding domain in the form of an scFv, and the HSA binding domain in the form of an sdAb are linked in different orientations. The top of each construct represents the N-terminus and the bottom of each construct represents the C-terminus of a given polypeptide chain.
Figure 2:
Figure 2:
Figure 2:
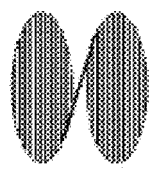

The multi-specific binding proteins disclosed herein comprise a first domain that binds CD19 (e.g., human CD19), a second domain that binds CD3 (e.g., human CD3), and a third domain that binds serum albumin (e.g., HSA). These domains are linked in certain manners for favorable therapeutic efficacy and in vivo half-life. Also provided are pharmaceutical compositions comprising the multi-specific binding proteins, methods of treating a disease or disorder using the multi-specific binding proteins or pharmaceutical compositions, and methods of producing the multi-specific binding proteins. Various aspects of the invention are set forth below in sections; however, aspects of the invention described in one particular section are not to be limited to any particular section.

To facilitate an understanding of the present invention, a number of terms and phrases are defined below.

The term "multi-specific binding protein" refers to a multi-specific molecule in which the structure and/or function is/are based on the structure and/or function of an antibody, e.g., a full-length or whole immunoglobulin molecule, or based on the heavy chain variable domain (VH) and/or light chain variable domain (VL) of an antibody, and/or single chain variants thereof. A multi-specific binding protein is hence capable of binding to its specific target or antigen. Furthermore, any one of the binding domains of a multi-specific binding protein according to the invention comprises the minimum structural requirements of an antibody which allow for the target binding. This minimum requirement may be, e.g., defined by the presence of at least the three heavy chain CDRs (i.e. CDR1, CDR2 and CDR3 of the VH domain) and/or the three light chain CDRs (i.e. CDR1, CDR2 and CDR3 of the VL domain). An alternative approach to defining the minimal structural requirements of an antibody is defining the epitope of a specific target to which the antibody binds, or by referring to a known antibody with which the antibody competes to bind to the same epitope that the known antibody binds. The antibodies on which the constructs according to the invention are based include for example monoclonal, recombinant, chimeric, deimmunized, humanized and human antibodies.

Any one of the binding domains of a multi-specific binding protein according to the invention may comprise the above referred groups of CDRs. Those CDRs may be comprised in the framework of a VH and/or VL. Fd fragments, for example, have two VH domains and often retain some antigen-binding function of the intact antigen-binding domain. Additional examples for formats of antibody fragments, antibody variants or binding domains include: (1) a Fab fragment, a monovalent fragment having the VL, VH, CL and CH1 domains; (2) a F(ab')$_2$ fragment, a bivalent fragment having two Fab fragments linked by a disulfide bridge at the hinge region; (3) an Fd fragment having the two VH and CH1 domains; (4) an Fv fragment having the VL and VH domains of a single arm of an antibody; (5) a dAb fragment (Ward et al., (1989) Nature 341:544-546), which has a VH domain; (6) an isolated complementarity determining region (CDR); and (7) a single chain Fv (scFv), which may be derived, for example, from an scFv-library. Exemplary formats of multi-specific binding proteins according to the invention are described in, e.g., WO2000006605A2, WO2005040220A1, WO2008119567A2, WO2010037838A2, WO2013026837A1, WO 2013026833A1, US20140308285A1, US20140302037A1, WO2014144722A2, WO2014151910A1, and WO2015048272A1.

Multi-specific binding proteins according to the invention may also comprise modified fragments of antibodies, also called antibody variants, such as di-scFv or bi(s)-scFv, scFv-Fc, scFv-zipper, scFab, Fab$_2$, Fab$_3$, diabodies, single chain diabodies, tandem diabodies (Tandab's), tandem di-scFv, tandem tri-scFv, "multibodies" such as triabodies or tetrabodies, or single-domain antibodies such as nanobodies or single variable domain antibodies comprising a single variable domain, which might be VH (also called VHH in the context of an sdAb) or VL, that specifically bind an antigen or epitope independently of other V regions or domains.

As used herein, the terms "single-chain Fv," "single-chain antibody," and "scFv" refer to a single-polypeptide-chain antibody fragment that comprise the variable regions from both the heavy and light chains, but lack the constant regions. Generally, a single-chain antibody further comprises a peptide linker connecting the VH and VL domains which enables it to form the desired structure to bind to antigen. Single chain antibodies are discussed in detail by Pluckthun in The Pharmacology of Monoclonal Antibodies, vol. 113, Rosenburg and Moore eds. Springer-Verlag, New York, pp. 269-315 (1994). Various methods of generating single chain antibodies are known, including those described in U.S. Pat. Nos. 4,694,778 and 5,260,203; International Patent Application Publication No. WO 88/01649; Bird (1988) Science 242:423-442; Huston et al. (1988) Proc. Natl. Acad. Sci. USA 85:5879-5883; Ward et al. (1989) Nature 334:54454; Skerra et al. (1988) Science 242:1038-1041. In specific embodiments, single-chain antibodies can also be bispecific, multispecific, human, humanized and/or synthetic.

Furthermore, the "multi-specific binding protein" described herein can be a monovalent, bivalent or polyvalent/multivalent construct. Moreover, the "multi-specific binding protein" described herein can include a molecule consisting of only one polypeptide chain, or a molecules consisting of more than one polypeptide chain, wherein the chains can be either identical (homodimers, homotrimers or homo oligomers) or different (heterodimer, heterotrimer or heterooligomer). Examples for the above identified antibodies and the variants or derivatives thereof are described, for example, in Harlow and Lane, Antibodies a laboratory manual, CSHL Press (1988); Using Antibodies: a laboratory manual, CSHL Press (1999); Kontermann and Dibel, Antibody Engineering, Springer, 2nd ed. 2010; and Little, Recombinant Antibodies for Immunotherapy, Cambridge University Press 2009.

The domains of the multi-specific binding protein of the present invention may be connected through one or more peptide bonds and/or peptide linkers. The term "peptide linker" comprises in accordance with the present invention an amino acid sequence linking two domains. The peptide linkers can also be used to fuse the third domain to the other domains of the multi-specific binding protein of the invention. An essential technical feature of such peptide linker is that it does not comprise any polymerization activity. Among the suitable peptide linkers are those described in U.S. Pat. Nos. 4,751,180 and 4,935,233 or WO198809344A1.

The multi-specific binding proteins of the present invention may be in vitro generated multi-specific binding proteins. The term "in vitro generated multi-specific binding protein" refers to a multi-specific binding protein according to the above definition where all or part of the variable region (e.g., at least one CDR) is generated by non-immune cell selection, e.g., an in vitro phage display, protein chip or any other method in which candidate sequences can be tested for their ability to bind to an antigen. The multi-specific binding proteins of the present invention may also be generated by genomic rearrangement in an immune cell in an animal. A "recombinant antibody" is an antibody made through the use of recombinant DNA technology or genetic engineering.

The multi-specific binding protein of the invention may be monoclonal. The term "monoclonal," as used herein, means that the proteins obtained from a population are substantially homogeneous, i.e., the individual proteins in the population are identical except for naturally occurring mutations and/or post-translation modifications (e.g., isomerizations, amidations) that may be present. In the context of antibodies, monoclonal antibodies are highly specific, being directed against a single antigenic side or determinant on the antigen, in contrast to conventional (polyclonal) antibody preparations which typically include different antibodies directed against different determinants (or epitopes). The modifier "monoclonal" indicates the character of the antibody as being obtained from a substantially homogeneous population of antibodies, and is not to be construed as requiring production of the antibody by any particular method.

The multi-specific binding protein of the invention or one or more antigen-binding site thereof may be affinity matured. In immunology, affinity maturation is the process by which B cells produce antibodies with increased affinity for antigen during the course of an immune response. With repeated exposures to the same antigen, a host will produce antibodies of successively greater affinities. Like the natural prototype, the in vitro affinity maturation is based on the principles of mutation and selection. Two or three rounds of mutation and selection using display methods such as phage display can result in antibody fragments with affinities in the low nanomolar range.

An amino acid substitution variation can be introduced into the multi-specific binding proteins by substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sides (e.g., 6-7 sides) are mutated to generate all possible amino acid substitutions at each side. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sides for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the binding domains. Such contact residues and neighboring residues are candidates for substitution according to the techniques elaborated herein. Once such variants are generated, the panel of variants is subjected to screening as described herein and antibodies with superior properties in one or more relevant assays may be selected for further development.

The multi-specific binding proteins of the present invention specifically can comprise "chimeric" antibodies (immunoglobulins) or fragments thereof in which a portion of the heavy and/or light chain is identical with or homologous to corresponding sequences in antibodies derived from a particular species or belonging to a particular antibody class or subclass, while the remainder of the chain(s) is/are identical with or homologous to corresponding sequences in antibodies derived from another species or belonging to another antibody class or subclass, so long as they exhibit the desired biological activity (U.S. Pat. No. 4,816,567; Morrison et al. (1984) Proc. Natl. Acad. Sci. U.S.A., 81:6851-55). Chimeric antibodies of interest herein include "primatized" antibodies comprising variable domain antigen-binding sequences derived from a non-human primate (e.g., Old World Monkey, Ape etc.) or human constant region sequences. A variety of approaches for making chimeric antibodies have been described. See e.g., Morrison et al. (1985) Proc. Natl. Acad. Sci. U.S.A., 81:6851; Takeda et al. (1985) Nature, 314:452; U.S. Pat. Nos. 4,816,567; 4,816,397; European Patent No. EP0171496; European Patent Application Publication No. EP0173494; and U.K. Patent No. GB2177096.

The term "binding domain" or "domain that binds (an antigen)" characterizes in connection with the present invention a domain which (specifically) binds to or interacts with a given target epitope or a given target side on the target molecules (antigens), e.g. CD19, serum albumin, and CD3, respectively. The structure and function of the first binding domain, the second binding domain, and/or the third binding domain can be based on the structure and/or function of an antibody, e.g. of a full-length or whole immunoglobulin molecule. A binding domain can be drawn from the VH and/or VL or VHH domain of an antibody or fragment thereof. For example, a binding domain can include three light chain CDRs (i.e., CDR1, CDR2 and CDR3 of the VL domain) and/or three heavy chain CDRs (i.e., CDR1, CDR2 and CDR3 of the VH domain). A binding domain can also include VHH CDRs (i.e., CDR1, CDR2 and CDR3 of the VHH region).

The terms "variable domain" and "variable region" are used interchangeably and refer to the portions of the antibody or immunoglobulin domains that exhibit variability in their sequence and that are involved in determining the specificity and binding affinity of a particular antibody. Variability is not evenly distributed throughout the variable domains of antibodies; it is concentrated in sub-domains of each of the heavy and light chain variable regions. These sub-domains are called "hypervariable regions" or "complementarity determining regions" (CDRs). The more conserved (i.e., non-hypervariable) portions of the variable domains are called the "framework" regions (FRM or FR) and provide a scaffold for the six CDRs in three dimensional space to form an antigen-binding surface.

In the present invention, any one of the binding domains of the multi-specific binding protein may comprise a single domain antibody (sdAb). A single domain antibody comprises a single, monomeric antibody variable domain which is able to bind selectively to a specific antigen, independently of other variable regions or domains. The first single domain antibodies were engineered from heavy chain antibodies found in camelids, and these are called VHH fragments. Cartilaginous fishes also have heavy chain antibodies (IgNAR) from which single domain antibodies called $V_{NAR}$ fragments can be obtained. An alternative approach is to split the dimeric variable domains from common immunoglobulins e.g., from humans or rodents into monomers, hence obtaining VH or VL as a single domain antibody. Although most research into single domain antibodies is currently based on heavy chain variable domains, nanobodies derived from light chains have also been shown to bind specifically to target epitopes. Examples of single domain antibodies include nanobodies and single variable domain antibodies.

As used herein, the term "antigen-binding site" refers to the part of an immunoglobulin molecule or a derivative or variant thereof that participates in antigen binding. In human antibodies, the antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FR." Thus the term "FR" refers to amino acid sequences which are naturally found between and adjacent to hypervariable regions in immunoglobulins. In a human antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." In certain animals, such as camels and cartilaginous fish, the antigen-binding site is formed by a single antibody chain providing a "single domain antibody." Antigen-binding sites can exist in an intact antibody, in an antigen-binding fragment of an antibody that retains the antigen-binding surface, or in a recombinant polypeptide such as an scFv, using a peptide linker to connect the heavy chain variable domain to the light chain variable domain in a single polypeptide.

The terms "a" and "an" as used herein mean "one or more" and include the plural unless the context is inappropriate.

As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably include humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA (1975).

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

I. Multi-Specific Binding Proteins

In one aspect, the present disclosure provides a multi-specific binding protein that comprises a first domain that binds CD19 (e.g., human CD19); a second domain that binds CD3 (e.g., human and/or Macaca CD3), such as CD3ε (epsilon), CD3δ (delta), and/or CD3γ (gamma); and a third domain that binds serum albumin (e.g., HSA).

In certain embodiments, the first domain is a first antigen-binding site that binds CD19. In certain embodiments, the first antigen-binding site comprises an antibody heavy chain variable domain (VH). In certain embodiments, the first antigen-binding site comprises an antibody light chain variable domain (VL). In certain embodiments, the first antigen-binding site comprises a VH and a VL. In certain embodiments, the first antigen-binding site comprises an sdAb. In certain embodiments, the first antigen-binding site comprises an scFv.

In certain embodiments, the second domain is a second antigen-binding site that binds CD3. In certain embodiments, the second antigen-binding site comprises a VH. In certain embodiments, the second antigen-binding site comprises a VL. In certain embodiments, the second antigen-binding site comprises a VH and a VL. In certain embodiments, the second antigen-binding site comprises an sdAb. In certain embodiments, the second antigen-binding site comprises an scFv.

In certain embodiments, the third domain is a third antigen-binding site that binds serum albumin. In certain embodiments, the third antigen-binding site comprises a VH. In certain embodiments, the third antigen-binding site comprises a VL region. In certain embodiments, the third antigen-binding site comprises a VH region and a VL region. In certain embodiments, the third antigen-binding site comprises an sdAb. In certain embodiments, the third antigen-binding site comprises an scFv.

Alternatively, it is also contemplated that one or more of the binding domains may not comprise an antigen-binding site. For example, U.S. Patent Application Publication No. US20130316952A1 discloses a polypeptide that binds serum albumin having the amino acid sequence of LKEAKEKAIEELKKAGITSDYYFDLINKAKTVEG-VNALKDEILKA (SEQ ID NO: 282). Additional exemplary polypeptides that bind HSA are described in Dennis et al. (2002) J. Biol. Chem., 277:35035-43; Jacobs et al. (2015) Protein Eng. Des. Sel., 28:385-93; and Zorzi et al. (2017) Nat. Commun., 8: 16092.

In certain embodiments, the multi-specific binding protein further comprises an antibody Fc region. The presence of an Fc region may increase the serum half-life of the multi-specific binding protein. Depending on the specific Fc subtype and variant used, the Fc region may also alter the activity (e.g., cytotoxic activity) of the multi-specific binding protein.

In other embodiments, the multi-specific binding protein does not comprise an antibody Fc region. The absence of Fc contributes to a smaller size of the multi-specific binding protein, which can exhibit improved tissue penetration and pharmacokinetic properties. In certain embodiments, the multi-specific binding proteins consists of or consists essentially of the first, second, and third antigen-binding sites and the linkers between them. In certain embodiments, the multi-specific binding proteins consists essentially of the first, second, and third antigen-binding sites.

In certain embodiments, the multi-specific binding protein binds CD19, CD3, and/or serum albumin monovalently. The exclusion of additional binding domains reduces the risk of non-specific immune cell activation and decreases the size of the multi-specific binding protein.

A. First Antigen-Binding Site

The first antigen-binding site of the multi-specific binding protein binds CD19 (e.g., human CD19).

CD19, also known as B-cell surface antigen B4 or Leu-12, is a transmembrane protein expressed on B lymphocytes and follicular dendritic cells. CD19 is a co-receptor for the B-cell antigen receptor complex on B lymphocytes (see, Carter et al. (2002) Science, 256:105-07; van Zelm et al. (2006) N. Eng. J. Med., 354:1901-12). It associates with CD21, CD81, and Leu-13 and potentiates B cell receptor (BCR) signaling. Together with the BCR, CD19 modulates intrinsic and antigen receptor-induced signaling thresholds critical for clonal expansion of B cells and humoral immunity. Upon activation, the cytoplasmic tail of CD19 becomes phosphorylated, which leads to binding by Src-family kinases and recruitment of PI-3 kinase.

CD19 is a human B-cell surface marker that is expressed from early stages of pre-B cell development through terminal differentiation into plasma cells. It is also expressed on many non-Hodgkin lymphoma (NHL) cells and certain leukemias. Antibodies that bind CD19 have been developed and tested in clinical studies against cancers of lymphoid origin such as B-cell malignancies (see, e.g., Hekman et al. (1991) Cancer Immunol. Immunother., 32:364-72; Vlasfeld et al. (1995) Cancer Immunol. Immunother., 40:37-47; Corny et al. (1995) J. Immunother. Emphasis Tumor Immunol., 18:231-41; and Manzke et al. (2001) Int. J. Cancer, 91:516-22). Furthermore, a BiTE® construct called blinatumomab has been developed for clinical use.

The first antigen-binding site that binds CD19 can be derived from, for example, MT-103 (a single-chain bispecific CD19/CD3 antibody; see, Hoffman et al. (2005) Int. J. Cancer, 115:98-104; Schlereth et al. (2006) Cancer Immunol. Immunother. 55:503-14), a CD19/CD16 diabody (see, Schlenzka et al. (2004) Anti-cancer Drugs 15:915-19; Kipriyanov et al. (2002) J. Immunol. 169:137-44), BU12-saporin (see, Flavell et al. (1995) Br. J. Cancer 72:1373-79), and anti-CD19-idarubicin (see, Rowland et al. (1993) Cancer Immunol. Immunother. 55:503-14). Additional exemplary antigen-binding sites that bind CD19, from which the instant first antigen-binding site may be derived, are disclosed in U.S. Patent Application Publication Nos. US20170174786A1, US20090042291A1, US20160046730A1, US20070154473A1, US20090142349A1, US20180142018A1, US20090136526A1, US20060257398A1, and US20180230225A1, and PCT Publication No. WO2019057100A1.

A first antigen-binding site that binds CD19 can include a VH comprising three complementarity regions (HCDR1, HCDR2, and HCDR3) and/or a VL comprising three complementarity regions (LCDR1, LCDR2, and LCDR3). Table 1 summarizes, for each variable region, the CDRs of the variable region and scFv constructs based on the given heavy and light chain variable regions. The first antigen-binding site can be derived from the exemplary variable domain and CDR sequences as listed in Table 1.

TABLE 1

Sequences of Exemplary First Antigen-Binding Sites

| Antigen-Binding Site | VH and HCDRs | VL and LCDRs |
|---|---|---|
| Roche mAb | QVQLVQSGAEVKKPGASVKVSCKASGY TFTDYIMHWVRQAPGQGLEWMGYINPY NDGSKYTEKFQGRVTMTSDTSISTAYME LSRLRSDDTAVYYCARGTYYYGPQLFD YWGQGTTVTVSS (SEQ ID NO: 1)<br>HCDR1: DYIMH (SEQ ID NO: 3)<br>HCDR2: YINPYNDGSKYTEKFOG (SEQ ID NO: 4)<br>HCDR3: GTYYYGPQLEDY (SEQ ID NO: 5)<br>scFv:<br>QVQLVQSGAEVKKPGASVKVSCKASGYTFTDYIMHWVRQAPGQGLEWMGYIN PYNDGSKYTEKFQGRVTMTSDTSISTAYMELSRLRSDDTAVYYCARGTYYYGPQ LFDYWGQGTTVTVSSGGGGSGGGGSGGGGSDIVMTQTPLSLSVTPGQPASISCKS SQSLETSTGTTYLNWYLQKPGQSPQLLIYRVSKRFSGVPDRFSGSGSGTDFTLKIS RVEAEDVGVYYCLQLLEDPYTFGQGTKLEIK (SEQ ID NO: 9) | DIVMTQTPLSLSVTPGQPASISCKSS QSLETSTGTTYLNWYLQKPGQSPQ LLIYRVSKRFSGVPDRFSGSGSGTDF TLKISRVEAEDVGVYYCLQLLEDPY TFGQGTKLEIK (SEQ ID NO: 2)<br>LCDR1: KSSQSLETSTGTTYLN (SEQ ID NO: 6)<br>LCDR2: RVSKRFS (SEQ ID NO: 7)<br>LCDR3: LQLLEDPYT (SEQ ID NO: 8) |
| SG mAb | QVQLQESGPGLVKPSQTLSLTCTVSGGSI STSGMGVGWIRQHPGKGLEWIGHIWWD DDKRYNPALKSRVTISVDTSKNQFSLKL SSVTAADTAVYYCARMELWSYYFDYW GQGTLVTVSS (SEQ ID NO: 10)<br>HCDR1: TSGMGVG (SEQ ID NO: 12)<br>HCDR2: HIWWDDDKRYNPALKS (SEQ ID NO: 13)<br>HCDR3: MELWSYYFDY (SEQ ID NO: 14)<br>scFv:<br>QVQLQESGPGLVKPSQTLSLTCTVSGGSISTSGMGVGWIRQHPGKGLEWIGHIW WDDDKRYNPALKSRVTISVDTSKNQFSLKLSSVTAADTAVYYCARMELWSYYF DYWGQGTLVTVSSGGGGSGGGGSGGGGSEIVLTQSPATLSLSPGERATLSCSASS SVSYMHWYQQKPGQAPRLLIYDTSKLASGIPARFSGSGSGTDFTLTISSLEPEDFA VYYCFQGSVYPFTFGQGTKLEIKR (SEQ ID NO: 18) | EIVLTQSPATLSLSPGERATLSCSAS SSVSYMHWYQQKPGQAPRLLIYDT SKLASGIPARFSGSGSGTDFTLTISSL EPEDFAVYYCFQGSVYPFTFGQGTK LEIKR (SEQ ID NO: 11)<br>LCDR1: SASSSVSYMH (SEQ ID NO: 15)<br>LCDR2: DTSKLAS (SEQ ID NO: 16)<br>LCDR3: FQGSVYPFT (SEQ ID NO: 17) |
| Xencor mAb | EVQLVESGGGLVKPGGSLKLSCAASGYT FTSYVMHWVRQAPGKGLEWIGYINPYN DGTKYNEKFQGRVTISSDKSISTAYMELS SLRSEDTAMYYCARGTYYYGTRVFDYW GQGTLVTVSS (SEQ ID NO: 19)<br>HCDR1: SYVMH (SEQ ID NO: 21)<br>HCDR2: WIGYINPYNDGTKY (SEQ ID NO: 22)<br>HCDR3: GTYYYGTRVEDY (SEQ ID NO: 23) | DIVMTQSPATLSLSPGERATLSCRSS KSLQNVNGNTYLYWYQQKPGQSPQ LLIYRMSNLNSGVPDRFSGSGSGTE FTLTISSLEPEDFAVYYCMQHLEYPI TFGAGTKLEIK (SEQ ID NO: 20)<br>LCDR1: RSSKSLQNVNGNTYLY (SEQ ID NO: 24)<br>LCDR2: RMSNLNS (SEQ ID NO: 25)<br>LCDR3: MQHLEYPIT (SEQ ID NO: 26) |
| Abbvie mAb | QVQLQQSGAELVRPGSSVKISCKASGYA FSSYWMNWVKQRPGQGLEWIGQIWPG DGDTNYNGKFKGKATLTADESSSTAYM QLSSLASEDSAVYFCARRETTTVGRYYY AMDYWGQGTSVTVSS (SEQ ID NO: 27)<br>HCDR1: SYWMN (SEQ ID NO: 29)<br>HCDR2: QIWPGDGDTNYNGKFKG (SEQ ID NO: 30)<br>HCDR3: RETTTVGRYYYAMDY (SEQ ID NO: 31) | DILLTQTPASLAVSLGQRATISCKAS QSVDYDGDSYLNWYQQIPGQPPKL LIYDASNLVSGIPPRFSGSGSGTDFT LNIHPVEKVDAATYHCQQSTEDPW TFGGGTKLEIK (SEQ ID NO: 28)<br>LCDR1: KASQSVDYDGDSYLN (SEQ ID NO: 32)<br>LCDR2: DASNLVS (SEQ ID NO: 33)<br>LCDR3: QQSTEDPWT (SEQ ID NO: 34) |
| Immunomedics mAb | QVQLQQSGAEVKKPGSSVKVSCKASGY AFSSYWMNWVRQRPGQGLEWIGQIWPG DGDTNYNGKFKGRATITADESTNTAYM ELSSLRSEDTAFYSCARRETTTVGRYYY AMDYWGQGTTVTVSS (SEQ ID NO: 35)<br>HCDR1: SYWMN (SEQ ID NO: 29)<br>HCDR2: QIWPGDGDTNYNGKFKG (SEQ ID NO: 30)<br>HCDR3: RETTTVGRYYYAMDY (SEQ ID NO: 31) | DIQLTQSPSSLSASVGDRVTITCKAS QSVDYDGDSYLNWYQQIPGKAPKL LIYDASNLVSGIPPRFSGSGSGTDYT FTISSLQPEDIATYHCQQSTEDPWTF GGGTKLQIKR (SEQ ID NO: 36)<br>LCDR1: KASQSVDYDGDSYLN (SEQ ID NO: 32)<br>LCDR2: DASNLVS (SEQ ID NO: 33)<br>LCDR3: QQSTEDPWT (SEQ ID NO: 34) |
| Merck mAb | QVQLEQPGAEVVKPGASVKVSCKTSGY TFTSNWMHWVKQTPGKGLEWIGEIDPS DSYTNYNQKFDGKAKLTVDKSSSTAYM EVSDLTAEDSATYYCARGSNPYYYAMD YWGQGTSVTVSS (SEQ ID NO: 37)<br>HCDR1: SNWMH (SEQ ID NO: 39)<br>HCDR2: EIDPSDSYTN (SEQ ID NO: 40) | QIVLTQSPATLSASPGEKATMTCSA SSGVNYMHWYQQKPGTSPKRWIY DTDKTASGVPARFSGSGSGTSYSLT ISSMEADAATYHCQRGSYTFGG GTKLEIK (SEQ ID NO: 38)<br>LCDR1: SASSGVNYMH (SEQ ID NO: 42) |

TABLE 1-continued

Sequences of Exemplary First Antigen-Binding Sites

| Antigen-Binding Site | VH and HCDRs | VL and LCDRs |
|---|---|---|
| | HCDR3: GSNPYYYAMDY (SEQ ID NO: 41) | LCDR2: DTDKTAS (SEQ ID NO: 43)<br>LCDR3: HQRGSYT (SEQ ID NO: 44) |
| Medarex mAb 21D4a | EVQLVQSGAEVKKPGESLKISCKGSGYS FSSSWIGWVRQMPGKGLEWMGIIYPDDS DTRYSPSFQGQVTISADKSIRTAYLQWSS LKASDTAMYYCARHVTMIWGVIIDFWG QGTLVTVSS (SEQ ID NO: 45)<br>HCDR1: SSWIG (SEQ ID NO: 47)<br>HCDR2: IIYPDDSDTRYSPSFQG (SEQ ID NO: 48)<br>HCDR3: HVTMIWGVIIDF (SEQ ID NO: 49) | AIQLTQSPSSLSASVGDRVTITCRAS QGISSALAWYQQKPGKAPKLLIYD ASSLESGVPSRFSGSGSGTDFTLTISS LQPEDFATYYCQQFNSYPFTFGPGT KVDIK (SEQ ID NO: 46)<br>LCDR1: RASQGISSALA (SEQ ID NO: 50)<br>LCDR2: DASSLES (SEQ ID NO: 51)<br>LCDR3: QQFNSYPFT (SEQ ID NO: 52) |
| Medarex mAb 21D4 | EVQLVQSGAEVKKPGESLKISCKGSGYS FSSSWIGWVRQMPGKGLEWMGIIYPDDS DTRYSPSFQGQVTISADKSIRTAYLQWSS LKASDTAMYYCARHVTMIWGVIIDFWG QGTLVTVSS (SEQ ID NO: 45)<br>HCDR1: SSWIG (SEQ ID NO: 47)<br>HCDR2: IIYPDDSDTRYSPSFQG (SEQ ID NO: 48)<br>HCDR3: HVTMIWGVIIDF (SEQ ID NO: 49) | AIQLTQSPSSLSASVGDRVTITCRAS QGISSALAWYQQKPGKAPKLLIYD ASSLESGVPSRFSGSGSGTDFTLTISS LQPEDFATYYCQQFNSYPYTFGQG TKLEIK (SEQ ID NO: 53)<br>LCDR1: RASQGISSALA (SEQ ID NO: 50)<br>LCDR2: DASSLES (SEQ ID NO: 51)<br>LCDR3: QQFNSYPYT (SEQ ID NO: 54) |
| Medarex mAb 47G4 | QVQLVQSGAEVKKPGSSVKVSCKDSGG TFSSY AISWVRQAPGQGLEWMGGIIPIFG TTNYAQQFQGRVTITADESTSTAYMELS SLRSEDTAVYYCAREAVAADWLDPWG QGTLVTVSS (SEQ ID NO: 55)<br>HCDR1: SYAIS (SEQ ID NO: 57)<br>HCDR2: GIIPIFGTTNYAQQFQG (SEQ ID NO: 58)<br>HCDR3: EAVAADWLDP (SEQ ID NO: 59) | EIVLTQSPGTLSLSPGERATLSCRAS QSVSSSYLAWYQQKPGQAPRLLIY GASSRATGIPDRFSGSGSGTDFTLTI SRLEPEDFAVYYCQQYGSSRFTFGP GTKVDIK (SEQ ID NO: 56)<br>LCDR1: RASQSVSSSYLA (SEQ ID NO: 60)<br>LCDR2: GASSRAT (SEQ ID NO: 61)<br>LCDR3: QQYGSSRFT (SEQ ID NO: 62) |
| Medarex mAb 27F3 | EVQLVQSGAEVKKPGESLKISCKGSGYS FTSYWIAWVRQMPGKGLEWMGIIYPGD SDTRYSPSFQGQVTISADKSISTAYLQWS SLKASDTAMYYCARQGYSSGWDSYYG MGVWGQGTTVTVSS (SEQ ID NO: 63)<br>HCDR1: SYWIA (SEQ ID NO: 65)<br>HCDR2: IIYPGDSDTRYSPSFQG (SEQ ID NO: 66)<br>HCDR3: QGYSSGWDSYYGMGV (SEQ ID NO: 67) | AIQLTQSPSSLSASVGDRVTITCRAS QGISSALAWYQQKPGKAPKLLIYD ASSLESGVPSRFSGSGSGTDFTLTISS LQPEDFATYYCQQFNSYPYTFGQG TKLEIK (SEQ ID NO: 64)<br>LCDR1: RASQGISSALA (SEQ ID NO: 50)<br>LCDR2: DASSLES (SEQ ID NO: 51)<br>LCDR3: QQFNSYPYT (SEQ ID NO: 54) |
| Medarex mAb 3C10 | QVQLVQSGAEVKKPGSSVKVSCKASGG TFSSYTINWVRQAPGQGLEWMGGIIPIFG IPNYAQKFQGRVTITADESTNTAYMELS SLRAEDTAVYYCARASGGSADYSYGMD VWGQGTAVTVSS (SEQ ID NO: 68)<br>HCDR1: SYTIN (SEQ ID NO: 70)<br>HCDR2: GIIPIFGIPNYAQKFQG (SEQ ID NO: 71)<br>HCDR3: ASGGSADYSYGMDV (SEQ ID NO: 72) | DIQMTQSPSSLSASVGDRVTITCRAS QGISSWLAWYQQKPEKAPKSLIYA ASSLQSGVPSRFSGSGSGTDFTLTIS SLQPEDFATYYCQQYKRYPYTFGQ GTKLEIK (SEQ ID NO: 69)<br>LCDR1: RASQGISSWLA (SEQ ID NO: 73)<br>LCDR2: AASSLQS (SEQ ID NO: 74)<br>LCDR3: QQYKRYPYT (SEQ ID NO: 75) |
| Medarex mAb 5G7 | EVQLVQSGAEVKKPGESLNISCKGSGYS FTSYWIGWVRQMPGKGLEWMGIIYPGD SDTRYSPSFQGQVTISADKSINTAYLQWS SLKASDTAMYYCARGVSMIWGVIMDV WGQGTTVTVSS (SEQ ID NO: 76)<br>HCDR1: SYWIG (SEQ ID NO: 78)<br>HCDR2: IIYPGDSDTRYSPSFQG (SEQ ID NO: 66)<br>HCDR3: GVSMIWGVIMDV (SEQ ID NO: 79) | AIQLTQSPSSLSASVGDRVTITCRAS QGISSALAWYQQKPGKAPKLLIYD ASSLESGVPSRFSGSGSGTDFTLTISS LQPEDFATYYCQQFNSYPWTFGQG TKVEIK (SEQ ID NO: 77)<br>LCDR1: RASQGISSALA (SEQ ID NO: 50)<br>LCDR2: DASSLES (SEQ ID NO: 51)<br>LCDR3: QQFNSYPWT (SEQ ID NO: 80) |
| Medarex mAb 13F1 | EVQLVQSGAEVKKPGESLQISCKGSGYT FTNYWIAWVRQMPGKGLEWMGIIYPGD SDTRYSPSFQGQVTISADKSISTAYLQWS GLKASDTAMYYCARQGYSSGWRSYYG MGVWGQGTTVTVSS (SEQ ID NO: 81) | AIQLTQSPSSLSASVGDRVTITCRAS QGISSALAWYQQKPGKAPKLLIYD ASSLESGVPSRFSGSGSGTDFTLTISS LQPEDFATYYCQQFNSYPHTFGQG TKLEIK (SEQ ID NO: 82) |

TABLE 1-continued

Sequences of Exemplary First Antigen-Binding Sites

| Antigen-Binding Site | VH and HCDRs | VL and LCDRs |
|---|---|---|
|  | HCDR1: NYWIA (SEQ ID NO: 83)<br>HCDR2: IIYPGDSDTRYSPSFQG (SEQ ID NO: 66)<br>HCDR3: QGYSSGWRSYYGMGV (SEQ ID NO: 84) | LCDR1: RASQGISSALA (SEQ ID NO: 50)<br>LCDR2: DASSLES (SEQ ID NO: 51)<br>LCDR3: QQFNSYPHT (SEQ ID NO: 85) |
| Medarex mAb 46E8 | EVQLVQSGAEVKKPGESLQISCKGSGYT FTNYWIAWVRQMPGKGLEWMGIIYPGD SDTRYSPSFQGQVTISADKSISTAYLQWS GLKASDTAMYYCARQGYSSGWRSYYG MGVWGQGTTVTVSS (SEQ ID NO: 314)<br>HCDR1: NYWIA (SEQ ID NO: 83)<br>HCDR2: IIYPGDSDTRYSPSFQG (SEQ ID NO: 66)<br>HCDR3: QGYSSGWRSYYGMGV (SEQ ID NO: 84) | AIQLTQSPSSLSASVGDRVTITCRAS QGISSALAWYQQKPGKAPKLLIYD ASSLESGVPSRFSGSGSGTDFTLTISS LQPEDFATYYCQQFNSYPHTFGQG TKLEIK (SEQ ID NO: 315)<br>LCDR1: RASQGISSALA (SEQ ID NO: 50)<br>LCDR2: DASSLES (SEQ ID NO: 51)<br>LCDR3: QQFNSYPHT (SEQ ID NO: 85) |
| Novimmune mAb | EVQLVQSGAEVKKPGESLKISCKGSGYS FTSYWIGWVRQMPGKGLEWMGIIYPGD SDTRYSPSFQGQVTISADKSISTAYLQWS SLKASDTAMYYCARGVSGIYNLHGFDI WGQGTLVTVSS (SEQ ID NO: 86)<br>HCDR1: GYSFTSYW (SEQ ID NO: 88)<br>HCDR2: IYPGDSDT (SEQ ID NO: 89)<br>HCDR3: ARGVSGIYNLHGFDI (SEQ ID NO: 90) | DIQMTQSPSSLSASVGDRVTITCRAS QSISSYLNWYQQKPGKAPKLLIYAA SSLQSGVPSRFSGSGSGTDFTLTISSL QPEDFATYYCQQGRFGSPFTFGQGT KVEIK (SEQ ID NO: 87)<br>LCDR1: QSISSY (SEQ ID NO: 91)<br>LCDR2: AAS (SEQ ID NO: 92)<br>LCDR3: QQGRFGSPFT (SEQ ID NO: 93) |
| Eureka mAb-1 | QVQLVETGGGLVQPGGSLRLSCAASGFT FSSYAMSWVRQAPGKGLEWVSAISGSG GSTYYADSVKGRFTISRDNSKNTLYLQM NSLRAEDTAVYYCARYYYSRLDYWGQ GTLVTVSS (SEQ ID NO: 94)<br>scFv:<br>QTVVTQEPSVSAAPGQKVTISCSGSSSNIGNNYVSWYQQLPGTAPKLLIYDNNKR PSGIPDRESGSKSGTSATLGITGLQTGDEADYYCGTWDSSLSAGVFGTGTKLTVL GSRGGGGSGGGGSGGGGSLEMAQVQLVETGGGLVQPGGSLRLSCAASGFTFSSY AMSWVRQAPGKGLEWVSAISGSGGSTYYADSVKGRFTISRDNSKNTLYLQMNS LRAEDTAVYYCARYYYSRLDYWGQGTLVTVSS (SEQ ID NO: 96) | QTVVTQEPSVSAAPGQKVTISCSGS SSNIGNNYVSWYQQLPGTAPKLLIY DNNKRPSGIPDRFSGSKSGTSATLGI TGLQTGDEADYYCGTWDSSLSAGV FGTGTKLTVLGSR (SEQ ID NO: 95) |
| Eureka mAb-2 | QVQLVESGGGLVQPGGSLRLSCAASGFT FSSYAMSWVRQAPGKGLEWVSGISASG GSTYYADSVKGRFTISRDNSKNTLYLQM NSLRAEDTAVYYCARYYLSQIDSWGQG TLVTVSS (SEQ ID NO: 210)<br>scFv:<br>QSVLTQPPSVSAAPGQKVTISCSGSSSNIGNNYVSWYRQLPGTAPKLLIYENNKRP SGIPDRFSGSKSGTSATLGITGLQTGDEADYYCGTWDSSLRAGVFGTGTKVTVLG SRGGGGSGGGGSGGGGSLEMAQVQLVESGGGLVQPGGSLRLSCAASGFTFSSYA MSWVRQAPGKGLEWVSGISASGGSTYYADSVKGRFTISRDNSKNTLYLQMNSL RAEDTAVYYCARYYLSQIDSWGQGTLVTVSS (SEQ ID NO: 212) | QSVLTQPPSVSAAPGQKVTISCSGSS SNIGNNYVSWYRQLPGTAPKLLIYE NNKRPSGIPDRFSGSKSGTSATLGIT GLQTGDEADYYCGTWDSSLRAGVF GTGTKVTVL (SEQ ID NO: 211) |
| Eureka mAb-3 | EVQLVQSGAEVKKPGATVKISCKVSGYT FTDYYMHWVQQAPGKGLEWMGLVDPE DGETIYAEKFQGRVTITADTSTDTAYME LSSLRSEDTAVYYCATGIYSRPLGYWGQ GTLVTVSS (SEQ ID NO: 213)<br>scFv:<br>QSVLTQPPSASGTPGQRVTISCSGSSSNIGSNTVNWYQQLPGTAPKLLIYSNNQRP SGVPDRFSGSKSGTSASLAISGLQSEDEADYYCAAWDDSLNGHVVFGGGTKLTV LGSRGGGGSGGGGSGGGGSLEMAEVQLVQSGAEVKKPGATVKISCKVSGYTFT DYYMHWVQQAPGKGLEWMGLVDPEDGETIYAEKFQGRVTITADTSTDTAYME LSSLRSEDTAVYYCATGIYSRPLGYWGQGTLVTVSS (SEQ ID NO: 215) | QSVLTQPPSASGTPGQRVTISCSGSS SNIGSNTVNWYQQLPGTAPKLLIYS NNQRPSGVPDRFSGSKSGTSASLAIS GLQSEDEADYYCAAWDDSLNGHV VFGGGTKLTVL (SEQ ID NO: 214) |
| Eureka mAb-4 | EVQLVETGGGLVQPGGSLRLSCAASGFT FSSYAMSWVRQAPGKGLEWVSAISGSG GSTYYADSVKGRFTISRDNSKNTLYLQM NSLRAEDTAVYYCARSDGKHFWQQYD AWGQGTLVTVSS (SEQ ID NO: 216)<br>scFv:<br>SYVLTQPPSASGTPGQRVTISCSGSSSNIGSHTVNWYQQLPGTAPKLLIYSNNQRP SGVPDRFSGSKSGTSASLAISGLQSEDEADYYCAAWDDSLNGYVFGTGTKVTVL GSRGGGGSGGGGSGGGGSLEMAEVQLVETGGGLVQPGGSLRLSCAASGFTFSSY AMSWVRQAPGKGLEWVSAISGSGGSTYYADSVKGRFTISRDNSKNTLYLQMNS LRAEDTAVYYCARSDGKHFWQQYDAWGQGTLVTVSS (SEQ ID NO: 218) | SYVLTQPPSASGTPGQRVTISCSGSS SNIGSHTVNWYQQLPGTAPKLLIYS NNQRPSGVPDRFSGSKSGTSASLAIS GLQSEDEADYYCAAWDDSLNGYV FGTGTKVTVL (SEQ ID NO: 217) |

TABLE 1-continued

Sequences of Exemplary First Antigen-Binding Sites

| Antigen-Binding Site | VH and HCDRs | VL and LCDRs |
| --- | --- | --- |
| Eureka mAb-5 | EVQLVESGGGLVQPGGSLRLSCAASGFT VSSNYMSWVRQAPGKGLEWVSAISGSG GSTYYADSVKGRFTISRDNSKNTLYLQM NSLRAEDTAVYYCARMNIDYWGQGTLV TVSS (SEQ ID NO: 219) scFv: DIQLTQSPSSLSAYVGDRVTITCRASQGITNSLAWYQQKPGKAPKLLLHAASRLE SGVPSRFSGSGFGTDFTLTISSLQPEDFAVYYCQHYLGTPYSFGQGTKVEIKRSRG GGGSGGGGSGGGGSLEMAEVQLVESGGGLVQPGGSLRLSCAASGFTVSSNYMS WVRQAPGKGLEWVSAISGSGGSTYYADSVKGRFTISRDNSKNTLYLQMNSLRAE DTAVYYCARMNIDYWGQGTLVTVSS (SEQ ID NO: 221) | DIQLTQSPSSLSAYVGDRVTITCRAS QGITNSLAWYQQKPGKAPKLLLHA ASRLESGVPSRFSGSGFGTDFTLTIS SLQPEDFAVYYCQHYLGTPYSFGQ GTKVEIK (SEQ ID NO: 220) |
| Eureka mAb-6 | EVQLVQSGAEVKRPGESLTISCKGSEYSF ASYWITWVRQMPGKGLEWMGRIDPSDS YTNYSPSFQGHVTISADKSISTAYLQWSS LKASDTAIYYCARPFQYDYGGYSDAFDI WGQGTMVTVSS (SEQ ID NO: 222) scFv: EIVLTQSPSSLSASVGDRVTISCRASQSVSRFLNWYQQKPGKAPKLLIYGVSTLER GVPSRFSGSGSGTDFTLTISSLQPEDFATYYCQESYIIPLTFGGGTKLEIKRSRGGG GSGGGGSGGGGSLEMAEVQLVQSGAEVKRPGESLTISCKGSEYSFASYWITWVR QMPGKGLEWMGRIDPSDSYTNYSPSFQGHVTISADKSISTAYLQWSSLKASDTAI YYCARPFQYDYGGYSDAFDIWGQGTMVTVSS (SEQ ID NO: 224) | EIVLTQSPSSLSASVGDRVTISCRAS QSVSRFLNWYQQKPGKAPKLLIYG VSTLERGVPSRFSGSGSGTDFTLTIS SLQPEDFATYYCQESYIIPLTFGGGT KLEIK (SEQ ID NO: 223) |
| Eureka mAb-7 | QMQLVQSGAEVKKAGSSVKVSCETSGG TFSSSSVNWVRQAPGQGLEWMGGIIPIV GTPNYAQKFQDRVTITA VESTFTA YMEL SGLRSEDTAVYYCARGGYRDYMDVWG RGTTVTVSS (SEQ ID NO: 225) scFv: EIVMTQSPLSLSVTPGEPASISCRSSQSLLDSNGFNSLDWYLQKPGQSPQLLIHLGS DRASGVPDRESGSGSGTDFTLKISRVEAEDVGIYYCMQSLQIPTFGQGTKVEIKRS RGGGGSGGGGSGGGGSLEMAQMQLVQSGAEVKKAGSSVKVSCETSGGTFSSSS VNWVRQAPGQGLEWMGGIIPIVGTPNYAQKFQDRVTITAVESTFTAYMELSGLR SEDTAVYYCARGGYRDYMDVWGRGTTVTVSS (SEQ ID NO: 227) | EIVMTQSPLSLSVTPGEPASISCRSS QSLLDSNGFNSLDWYLQKPGQSPQ LLIHLGSDRASGVPDRFSGSGSGTD FTLKISRVEAEDVGIYYCMQSLQIPT FGQGTKVEIK (SEQ ID NO: 226) |
| Eureka mAb-8 | EVQLVESGGGLIQPGGSLRLSCAASGFT VSSNYMSWVRQAPGKGLEWVSVIYSGG STYYADSVKGRFTISRDNSKNTLYLQMN SLRAEDTAVYYCARGGFGAEFDYWGQG TLVTVSS (SEQ ID NO: 228) scFv: SYELTQPPSASGTPGQRVTISCSGSSSNIGSNYVYWYQQLPGTAPKLLIYRNNQRP SGVPDRFSGSKSGTSASLAISGLRSEDEADYYCAAWDDSLSGYVFGTGTKVTVL GSRGGGGSGGGGSGGGGSLEMAEVQLVESGGGLIQPGGSLRLSCAASGFTVSSN YMSWVRQAPGKGLEWVSVIYSGGSTYYADSVKGRFTISRDNSKNTLYLQMNSL RAEDTAVYYCARGGFGAEFDYWGQGTLVTVSS (SEQ ID NO: 230) | SYELTQPPSASGTPGQRVTISCSGSS SNIGSNYVYWYQQLPGTAPKLLIYR NNQRPSGVPDRFSGSKSGTSASLAIS GLRSEDEADYYCAAWDDSLSGYVF GTGTKVTVL (SEQ ID NO: 229) |
| Eureka mAb-9 | EVQLVESGGGLIQPGGSLRLSCAASGFT VSSNYMSWVRQAPGKGLEWVSVIYSGG STYYADSVKGRFTISRDNSKNTLYLQMN SLRAEDTAVYYCARGGISDDYYGSGSY DNWGQGTLVTVSS (SEQ ID NO: 231) scFv: SYVLTQPPSVSVSPGQTASITCSGDKLGDKYASWYQQKPGQSPVLVIYQDNKRPS GIPERFSGSNSGNTATLTISGTQAMDEADYYCQAWDSSTEDVFGPGTKVTVLGSR GGGGSGGGGSGGGGSLEMAEVQLVESGGGLIQPGGSLRLSCAASGFTVSSNYMS WVRQAPGKGLEWVSVIYSGGSTYYADSVKGRFTISRDNSKNTLYLQMNSLRAE DTAVYYCARGGISDDYYGSGSYDNWGQGTLVTVSS (SEQ ID NO: 233) | SYVLTQPPSVSVSPGQTASITCSGDK LGDKYASWYQQKPGQSPVLVIYQD NKRPSGIPERFSGSNSGNTATLTISG TQAMDEADYYCQAWDSSTEDVFG PGTKVTVL (SEQ ID NO: 232) |
| Eureka mAb-10 | EVQLVESGGGLVQPGGSLRLSCAASGFT VSSNYMSWVRQAPGKGLEWVSVIYSGG STYYADSVKGRFTISRDNSKNTLYLQMN SLRAEDTAVYYCARERGMGYAFDIWGQ GTMVTVSS (SEQ ID NO: 234) scFv: DIQLTQSPSSLSASVGDRVTITCRASQSISSYLNWYQQKPGKAPKLLIYAASSLQS GVPSRFSGSGSGTDFTLTISSLQPEDFATYYCQQSYSTPFTFGGGTKVEIKRSRGG GGSGGGGSGGGGSLEMAEVQLVESGGGLVQPGGSLRLSCAASGFTVSSNYMSW VRQAPGKGLEWVSVIYSGGSTYYADSVKGRFTISRDNSKNTLYLQMNSLRAEDT AVYYCARERGMGYAFDIWGQGTMVTVSS (SEQ ID NO: 236) | DIQLTQSPSSLSASVGDRVTITCRAS QSISSYLNWYQQKPGKAPKLLIYAA SSLQSGVPSRFSGSGSGTDFTLTISSL QPEDFATYYCQQSYSTPFTFGGGTK VEIK (SEQ ID NO: 235) |

TABLE 1-continued

Sequences of Exemplary First Antigen-Binding Sites

| Antigen-Binding Site | VH and HCDRs | VL and LCDRs |
|---|---|---|
| Eureka mAb-11 | QLQLQESGPGLVKPSETLSLTCSVSGVS MSENYWSWIRQPPGKRLEWIGCAHYTG DTHYNPSLKGRVTISLDTSMNQFSLRLN SVTAADTAVYYCASYHPFNYWGQGTLV TVSS (SEQ ID NO: 237) scFv: DIQMTQSPSSLSASVGDRVTITCRASQGIGSYLA WYQQKPGKAPKLLIYPASTLQS GVPSRFSGSGSGTEFTLTISSLQPEDFATYYCQQLNSLFGQGTRLEIKRSRGGGGS GGGGSGGGGSLEMAQLQLQESGPGLVKPSETLSLTCSVSGVSMSENYWSWIRQP PGKRLEWIGCAHYTGDTHYNPSLKGRVTISLDTSMNQFSLRLNSVTAADTAVYY CASYHPFNYWGQGTLVTVSS (SEQ ID NO: 239) | DIQMTQSPSSLSASVGDRVTITCRAS QGIGSYLAWYQQKPGKAPKLLIYP ASTLQSGVPSRFSGSGSGTEFTLTIS SLQPEDFATYYCQQLNSLFGQGTRL EIK (SEQ ID NO: 238) |
| Eureka mAb-12 | EVQLVQSGAEVRRPGATVKISCKVSGYT FNDFYLHWVRQAPGKGLEWMGRIDPED GKTRYAEKFQGRLTITADTSTDTLYMQL GGLTSDDTAVYYCTTDWGYSSSLREEDI WYDCWGQGTLVTVSS (SEQ ID NO: 240) scFv: QAVLTQPPSASGTPGQRVTISCSGSSSNIGTKTVNWYQVLPGTAPKLLIYSNYRRP SGVPDRFSGSKSGTSASLAISGLQSDDEADYYCALWDDSLDGYVFGTGTKVTVL GSRGGGGSGGGGSGGGGSLEMAEVQLVQSGAEVRRPGATVKISCKVSGYTEND FYLHWVRQAPGKGLEWMGRIDPEDGKTRYAEKFQGRLTITADTSTDTLYMQLG GLTSDDTAVYYCTTDWGYSSSLREEDIWYDCWGQGTLVTVSS (SEQ ID NO: 242) | QAVLTQPPSASGTPGQRVTISCSGSS SNIGTKTVNWYQVLPGTAPKLLIYS NYRRPSGVPDRFSGSKSGTSASLAIS GLQSDDEADYYCALWDDSLDGYV FGTGTKVTVL (SEQ ID NO: 241) |
| Eureka mAb-13 | EVQLVQSGAEVKKPGSSVKVSCKASGG TFSSYAISWVRQAPGQGLEWMGGIIPIFG TANYAQKFQGRVTITADESTSTAYMELS SLRSEDTAVYYCARDYGYGDYGDAFDI WGQGTMVTVSS (SEQ ID NO: 243) scFv: SYELTQPPSVSVAPGKTARITCGGNNIGSKSVHWYQQKPGQAPVLVIYYDSDRPS GIPERFSGSNSGNTATLTISRVEAGDEADYYCQVWDSSSDHYVFGTGTKVTVLGS RGGGGSGGGGSGGGGSLEMAEVQLVQSGAEVKKPGSSVKVSCKASGGTFSSYAI SWVRQAPGQGLEWMGGIIPIFGTANYAQKFQGRVTITADESTSTAYMELSSLRSE DTAVYYCARDYGYGDYGDAFDIWGQGTMVTVSS (SEQ ID NO: 245) | SYELTQPPSVSVAPGKTARITCGGN NIGSKSVHWYQQKPGQAPVLVIYY DSDRPSGIPERFSGSNSGNTATLTIS RVEAGDEADYYCQVWDSSSDHYV FGTGTKVTVL (SEQ ID NO: 244) |
| Eureka mAb-14 | EVQLVQSGAEVKKPGESLKISCKGSGYS FTSYWIGWVRQMPGKGLEWMGIIYPGD SDTRYSPSFQGQVTISADKSISTAYLQWS SLKASDTAMYYCARVVGTIYSMQYDV WGQGTLVTVSS (SEQ ID NO: 246) scFv: SYVLTQPPSVSVAPGKTARITCGGNNIGSKSVHWYQQRPGQAPVLVVYDDSDRP SGIPERFSGSNSGNTATLTISRVEAGDEADYSCQVWDSSSDHYVFGPGTKVTVLG SRGGGGSGGGGSGGGGSLEMAEVQLVQSGAEVKKPGESLKISCKGSGYSFTSYW IGWVRQMPGKGLEWMGIIYPGDSDTRYSPSFQGQVTISADKSISTAYLQWSSLKA SDTAMYYCARVVGTIYSMQYDVWGQGTLVTVSS (SEQ ID NO: 248) | SYVLTQPPSVSVAPGKTARITCGGN NIGSKSVHWYQQRPGQAPVLVVYD DSDRPSGIPERFSGSNSGNTATLTIS RVEAGDEADYSCQVWDSSSDHYVF GPGTKVTVL (SEQ ID NO: 247) |
| Eureka mAb-15 | EVQLVQSGAEVKKPGESLKISCKGSGYS FTSYWIGWVRQMPGKGLEWMGIIYPGD SDTRYSPSFQGQVTISADKSISTAYLQWS SLKASDTAMYYCARQVWGWQGGMYP RSNWWYNMDSWGQGTLVTVSS (SEQ ID NO: 249) scFv: LPVLTQPPSVSVAPGKTARITCGGNNIGSKSVHWYQQKPGQAPVLVVYDDSDRP SGIPERFSGSNSGNTATLTISRVEAGDEADYYCQVWDSSSDYVVFGGGTKLTVLG SRGGGGSGGGGSGGGGSLEMAEVQLVQSGAEVKKPGESLKISCKGSGYSFTSYW IGWVRQMPGKGLEWMGIIYPGDSDTRYSPSFQGQVTISADKSISTAYLQWSSLKA SDTAMYYCARQVWGWQGGMYPRSNWWYNMDSWGQGTLVTVSS (SEQ ID NO: 251) | LPVLTQPPSVSVAPGKTARITCGGN NIGSKSVHWYQQKPGQAPVLVVYD DSDRPSGIPERFSGSNSGNTATLTIS RVEAGDEADYYCQVWDSSSDYVV FGGGTKLTVL (SEQ ID NO: 250) |
| Eureka mAb-16 | EVQLVQSGAEVKKPGESLKISCKGSGYS FTSYWIGWVRQMPGKGLEWMGIIYPGD SDTRYSPSFQGQVTISADKSISTAYLQWS SLKASDTAMYYCARWSSTWDSMYMDY WGQGTLVTVSS (SEQ ID NO: 252) scFv: QAVLTQPPSVSEAPRQRVTISCSGSSSNVGNNAVNWYQQVPGKAPKLLIYYDDL LSSGVSDRFSGSKSGTSASLAISGLQSEDEADYYCAAWDDSLNGPVFGGGTKLTV LGSRGGGGSGGGGSGGGGSLEMAEVQLVQSGAEVKKPGESLKISCKGSGYSFTS YWIGWVRQMPGKGLEWMGIIYPGDSDTRYSPSFQGQVTISADKSISTAYLQWSS LKASDTAMYYCARWSSTWDSMYMDYWGQGTLVTVSS (SEQ ID NO: 254) | QAVLTQPPSVSEAPRQRVTISCSGSS SNVGNNAVNWYQQVPGKAPKLLI YYDDLLSSGVSDRFSGSKSGTSASL AISGLQSEDEADYYCAAWDDSLNG PVFGGGTKLTVL (SEQ ID NO: 253) |

TABLE 1-continued

Sequences of Exemplary First Antigen-Binding Sites

| Antigen-Binding Site | VH and HCDRs | VL and LCDRs |
|---|---|---|
| Eureka mAb-17 | EVQLVQSGAEVKKPGESLRISCKGSGYS FTSYWIGWVRQMPGKGLEWMGIIYPGD SDTRYSPSFQGQVTISADKSISTAYLQWS SLKASDTAMYYCARVTYSMDSYYFDSW GQGTLVTVSS (SEQ ID NO: 255) scFv: QPVLTQPPSVSVAPGKTARITCGGNNIGSESVHWYQQKPGQAPMVVIYYDSNRP SGIPERFSGSNSGNTATLTVSRVEAEDEADYYCQVWNSSSDHRGVFGGGTKLTV LGSRGGGGSGGGGSGGGGSLEMAEVQLVQSGAEVKKPGESLRISCKGSGYSFTS YWIGWVRQMPGKGLEWMGIIYPGDSDTRYSPSFQGQVTISADKSISTAYLQWSS LKASDTAMYYCARVTYSMDSYYFDSWGQGTLVTVSS (SEQ ID NO: 257) | QPVLTQPPSVSVAPGKTARITCGGN NIGSESVHWYQQKPGQAPMVVIYY DSNRPSGIPERFSGSNSGNTATLTVS RVEAEDEADYYCQVWNSSSDHRG VFGGGTKLTV (SEQ ID NO: 256) |
| WuXi WBP701 1-4.34.11 | EVQLQQSGPELVKPGASVKMSCKASGY TFTNYVIHWVKQKPGQGLEWIGYFNPY NDGTEYNEKFKAKATLTSDKSSTAYM ELSSLTSEDSAVYYCAKGPYYYGSSPFD YWGQGTTLTVSS (SEQ ID NO: 316) HCDR1: GYTFTNYVIH (SEQ ID NO: 318) HCDR2: YFNPYNDGTEYNEKFKA (SEQ ID NO: 319) HCDR3: GPYYYGSSPFDY (SEQ ID NO: 320) | DAVMTQTPLSLPVSLGDQASISCRS SQSLENSNGNTYLNWYLQKPGQSP QLLIYRVSNRFSGVLDRFSGSGSGT DFTLKISRVEAEDLGVYFCLQVTHV PYTFGGGTKLEIK (SEQ ID NO: 317) LCDR1: RSSQSLENSNGNTYLN (SEQ ID NO: 321) LCDR2: RVSNRFS (SEQ ID NO: 322) LCDR3: RVSNRFS (SEQ ID NO: 323) |
| WuXi WBP701 1-4.87.6 | QVQLQQSGAELVRPGSSVKISCKASGYA FSTYWMNWVKQRPGQGLEWIGQIYPGD DDTKYNGKFKGKASLTADKSSSTAYMQ LISLTSEDSAVYFCARRYFRYDYWYSDV WGAGTTVTVTS (SEQ ID NO: 324) HCDR1: GYAFSTYWMN (SEQ ID NO: 326) HCDR2: QIYPGDDDTKYNGKFKG (SEQ ID NO: 327) HCDR3: RYFRYDYWYSDV (SEQ ID NO: 328) | DIQMTQTTSSLSASLGDRVTISCRAS QDISNYLNWYQQKPDGTVKLLIYY TSRLHSGVPARFSGSGSGTDYSLTIS NLEQEDIATYFCHQGNTLPLTFGAG TKLELK (SEQ ID NO: 325) LCDR1: RASQDISNYLN (SEQ ID NO: 329) LCDR2: YTSRLHS (SEQ ID NO: 330) LCDR3: HQGNTLPLT (SEQ ID NO: 331) |
| WuXi WBP701 1_4.155.8 | EIQLQQSGPELVKPGASVKVSCKASGYA FTSYNMYWVKQSHGKSLEWIGYIDPYN GDTTYNQKFKGKATLTVDKSSSTAYMH LNSLTSEDSAVYYCLTTAYAMDYWGQG TSVTVSS (SEQ ID NO: 332) HCDR1: GYAFTSYNMY (SEQ ID NO: 334) HCDR2: YIDPYNGDTTYNQKFKG (SEQ ID NO: 335) HCDR3: TAYAMDY (SEQ ID NO: 336) | QIVLTQSPAIMSASLGEEITLTCSASS TVNYMHWYQQKSGTSPKLLIYSTS NLASGVPSRFSGSGSGTFYSLTIRSV EAEDAADYYCHQWSSYPYTFGGGT KLEIK (SEQ ID NO: 333) LCDR1: SASSTVNYMH (SEQ ID NO: 337) LCDR2: STSNLAS (SEQ ID NO: 338) LCDR3: HQWSSYPYT (SEQ ID NO: 339) |
| WuXi WBP701 1-4.34.11-z1-m5 | QVQLVQSGAEVKKPGSSVKVSCKASGY TFTDYVIHWVRQAPGQGLEWMGYFNPY NDGTEYNEKFKARVTITADKSTSTAYME LSSLRSEDTA VYYCARGPYYYGSSPFDY WGQGTTVTVSS (SEQ ID NO: 340) HCDR1: GYTFTNYVIH (SEQ ID NO: 341) HCDR2: YFNPYNDGTEYNEKFKA (SEQ ID NO: 342) HCDR3: GPYYYGSSPFDY (SEQ ID NO: 343) | DIVMTQTPLSLPVTPGEPASISCRSS QSLENSNHNTYINWYLQKPGQSPQ LLIYRVSKRFSGVPDRFSGSGSGTDF TLKISRVEAEDVGVYYCHQVTHVP YTFGQGTKLEIK (SEQ ID NO: 344) LCDR1: RSSQSLENSNHNTYIN (SEQ ID NO: 345) LCDR2: RVSKRFS (SEQ ID NO: 346) LCDR3: HQVTHVPYT (SEQ ID NO: 347) |
| WuXi WBP701 1-4.87.6-z1(N-S) | QVQLVQSGAEVKKPGASVKVSCKASGY AFSTYWMNWVRQAPGQGLEWMGQIYP GDDDTKYSGKFKGRVTITADKSTSTAY MELSSLRSEDTAVYYCARRYFRYDYWY SDVWGQGTTVTVSS (SEQ ID NO: 348) HCDR1: GYAFSTYWMN (SEQ ID NO: 350) HCDR2: QIYPGDDDTKYSGKFKG (SEQ ID NO: 351) HCDR3: RYFRYDYWYSDV (SEQ ID NO: 352) | DIQMTQSPSSLSASVGDRVTITCRAS QDISNYLNWYQQKPGKVPKLLIYY TSRLHSGVPSRFSGSGSGTDFTLTIS SLQPEDVATYYCHQGNTLPLTFGQ GTKLEIK (SEQ ID NO: 349) LCDR1: RASQDISNYLN (SEQ ID NO: 353) LCDR2: YTSRLHS (SEQ ID NO: 354) LCDR3: HQGNTLPLT (SEQ ID NO: 355) |
| WuXi WBP701 1_4.155.8-z1-P15 | QMQLVQSGPEVKKPGTSVKVSCKASGY AFTSYNMYWVRQARGQRLEWIGYIDPY NADTTYNQKFKGRVTITRDMSTSTAYM ELSSLRSEDTAVYYCLTTAYAMDYWGQ | DIQLTQSPSFLSASVGDRVTITCSAS STVNYMHWYQQKPGKAPKLLIYST SNLASGVPSRFSGSGSGTEFTLTISS LQPEDFATYYCHQWSSYPYTFGQG |

TABLE 1-continued

Sequences of Exemplary First Antigen-Binding Sites

| Antigen-Binding Site | VH and HCDRs | VL and LCDRs |
|---|---|---|
| | GTLVTVSS (SEQ ID NO: 356)<br>HCDR1: GYAFTSYNMY (SEQ ID NO: 358)<br>HCDR2: YIDPYNADTTYNQKFKG (SEQ ID NO: 359)<br>HCDR3: TAYAMDY (SEQ ID NO: 360) | TKLEIK (SEQ ID NO: 357)<br>LCDR1: SASSTVNYMH (SEQ ID NO: 361)<br>LCDR2: STSNLAS (SEQ ID NO: 362)<br>LCDR3: HQWSSYPYT (SEQ ID NO: 363) |
| Legend mAb | QVKLEESGGELVQPGGPLRLSCAASGNIFSINRMGWYRQAPGKQRAFVASITVRGITNYADSVKGRFTISVDKSKNTIYLQMNALKPEDTAVYYCNAVSSNRDPDYWGQGTQVTVSS (SEQ ID NO: 364)<br>HCDR1: INRMG (SEQ ID NO: 365)<br>HCDR2: SITVRGITNYADSVKG (SEQ ID NO: 366)<br>HCDR3: VSSNRDPDY (SEQ ID NO: 367) | N/A |

Where the VL and LCDR sequences are noted as "N/A," the antigen-binding site is an sdAb having a VH (e.g., VHH) only.

In certain embodiments, the first antigen-binding site comprises a VH comprising complementarity determining regions HCDR1, HCDR2, and HCDR3, and a VL comprising complementarity determining regions LCDR1, LCDR2, and LCDR3. In certain embodiments, the VH comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to the VH of an antibody provided in Table 1, and the VL comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to the VL of the antibody provided in Table 1. In certain embodiments, the VH comprises the HCDR1, HCDR2, and HCDR3 sequences of the antibody provided in Table 1, and the VL comprises the LCDR1, LCDR2, and LCDR3 sequences of the antibody provided in Table 1. In certain embodiments, the VH comprises the amino acid sequence of the VH of an antibody provided in Table 1, and the VL comprises the amino acid sequence of the VL of the antibody provided in Table 1.

In certain embodiments, the VH of the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 1, and the VL of the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 2. In certain embodiments, the VH comprises HCDR1, HCDR2, and HCDR3 sequences set forth in SEQ ID NOs: 3, 4, and 5, respectively, and the VL comprises LCDR1, LCDR2, and LCDR3 sequences set forth in SEQ ID NOs: 6, 7, and 8, respectively. In certain embodiments, the VH comprises the amino acid sequence set forth in SEQ ID NO: 1, and the VL comprises the amino acid sequence set forth in SEQ ID NO: 2.

In certain embodiments, the VH of the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 10, and the VL of the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 11. In certain embodiments, the VH comprises HCDR1, HCDR2, and HCDR3 sequences set forth in SEQ ID NOs: 12, 13, and 14, respectively, and the VL comprises LCDR1, LCDR2, and LCDR3 sequences set forth in SEQ ID NOs: 15, 16, and 17, respectively. In certain embodiments, the VH comprises the amino acid sequence set forth in SEQ ID NO: 10, and the VL comprises the amino acid sequence set forth in SEQ ID NO: 11.

In certain embodiments, the VH of the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 19, and the VL of the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 20. In certain embodiments, the VH comprises HCDR1, HCDR2, and HCDR3 sequences set forth in SEQ ID NOs: 21, 22, and 23, respectively, and the VL comprises LCDR1, LCDR2, and LCDR3 sequences set forth in SEQ ID NOs: 24, 25, and 26, respectively. In certain embodiments, the VH comprises the amino acid sequence set forth in SEQ ID NO: 19, and the VL comprises the amino acid sequence set forth in SEQ ID NO: 20.

In certain embodiments, the VH of the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 27, and the VL of the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 28. In certain embodiments, the VH comprises HCDR1, HCDR2, and HCDR3 sequences set forth in SEQ ID NOs: 29, 30, and 31, respectively, and the VL comprises LCDR1, LCDR2, and LCDR3 sequences set forth in SEQ ID NOs: 32, 33, and 34, respectively. In certain embodiments, the VH comprises the amino acid sequence set forth in SEQ ID NO: 27, and the VL comprises the amino acid sequence set forth in SEQ ID NO: 28.

In certain embodiments, the VH of the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 35, and the VL of the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 36. In certain embodiments, the VH comprises HCDR1, HCDR2, and HCDR3 sequences set forth in SEQ ID NOs: 29, 30, and 31, respectively, and the VL comprises LCDR1, LCDR2, and LCDR3 sequences set forth in SEQ ID NOs: 32, 33, and 34, respectively. In certain embodiments, the VH comprises the amino acid sequence set forth in SEQ ID NO: 35, and the VL comprises the amino acid sequence set forth in SEQ ID NO: 36.

In certain embodiments, the VH of the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 37, and the VL of the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 38. In certain embodiments, the VH comprises HCDR1, HCDR2, and HCDR3 sequences set forth in SEQ ID NOs: 39, 40, and 41, respectively, and the VL comprises LCDR1, LCDR2, and LCDR3 sequences set forth in SEQ ID NOs: 42, 43, and 44, respectively. In certain embodiments, the VH comprises the amino acid sequence set forth in SEQ ID NO: 37, and the VL comprises the amino acid sequence set forth in SEQ ID NO: 38.

In certain embodiments, the VH of the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 45, and the VL of the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 46. In certain embodiments, the VH comprises HCDR1, HCDR2, and HCDR3 sequences set forth in SEQ ID NOs: 47, 48, and 49, respectively, and the VL comprises LCDR1, LCDR2, and LCDR3 sequences set forth in SEQ ID NOs: 50, 51, and 52, respectively. In certain embodiments, the VH comprises the amino acid sequence set forth in SEQ ID NO: 45, and the VL comprises the amino acid sequence set forth in SEQ ID NO: 46.

In certain embodiments, the VH of the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 86, and the VL of the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 87. In certain embodiments, the VH comprises HCDR1, HCDR2, and HCDR3 sequences set forth in SEQ ID NOs: 88, 89, and 90, respectively, and the VL comprises LCDR1, LCDR2, and LCDR3 sequences set forth in SEQ ID NOs: 91, 92, and 93, respectively. In certain embodiments, the VH comprises the amino acid sequence set forth in SEQ ID NO: 86, and the VL comprises the amino acid sequence set forth in SEQ ID NO: 87.

Such antigen-binding site may take the form of scFv. In certain embodiments, the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to an scFv sequence provided in Table 1. In certain embodiments, the first antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 9, 18, 96, 212, 215, 218, 221, 224, 227, 230, 233, 236, 239, 242, 245, 248, 251, 254, or 257.

In other embodiments, the first antigen-binding site comprises an sdAb comprising a VH comprising complementarity determining regions HCDR1, HCDR2, and HCDR3. In certain embodiments, the VH comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to the VH of an sdAb antibody provided in Table 1. In certain embodiments, the VH comprises the HCDR1, HCDR2, and HCDR3 sequences of the antibody provided in Table 1. In certain embodiments, the VH comprises the amino acid sequence of the VH of an sdAb provided in Table 1.

In certain embodiments, the first antigen-binding site competes for binding CD19 (e.g., human CD19) with an antibody or antigen-binding fragment thereof comprising the VH, VL and/or scFv sequences provided in Table 1.

In certain embodiments, the first antigen-binding site of the multi-specific binding protein binds CD19 (e.g., human CD19) with a dissociation constant ($K_D$) of about 10 pM-about 1 μM. The $K_D$ can be measured by a method known in the art. In certain embodiments, the $K_D$ is measured by SPR to CD19 or an extracellular fragment thereof immobilized on a chip. In certain embodiments, the $K_D$ is measured by flow cytometry to CD19 expressed on the surface of cells, for example, following the method described in Example 5 below.

In certain embodiments, the first antigen-binding site binds CD19 with a $K_D$ of lower than or equal to 20 nM, 15 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 90 pM, 80 pM, 70 pM, 60 pM, 50 pM, 40 pM, 30 pM, 20 pM, or 10 pM. For example, in certain embodiments, the first antigen-binding site binds CD19 with a $K_D$ of about 10 pM-about 1 nM, about 10 pM-about 0.9 nM, about 10 pM-about 0.8 nM, about 10 pM-about 0.7 nM, about 10 pM-about 0.6 nM, about 10 pM nM-about 0.5 nM, about 10 pM-about 0.4 nM, about 10 pM-about 0.3 nM, about 10 pM-about 0.2 nM, about 10 pM-about 0.1 nM, about 10 pM-about 50 pM, 0.1 nM-about 10 nM, about 0.1 nM-about 9 nM, about 0.1 nM-about 8 nM, about 0.1 nM-about 7 nM, about 0.1 nM-about 6 nM, about 0.1 nM-about 5 nM, about 0.1 nM-about 4 nM, about 0.1 nM-about 3 nM, about 0.1 nM-about 2 nM, about 0.1 nM-about 1 nM, about 0.1 nM-about 0.5 nM, about 0.5 nM-about 10 nM, about 1 nM-about 10 nM, about 2 nM-about 10 nM, about 3 nM-about 10 nM, about 4 nM-about 10 nM, about 5 nM-about 10 nM, about 6 nM-about 10 nM, about 7 nM-about 10 nM, about 8 nM-about 10 nM, or about 9 nM-about 10 nM.

In certain embodiments, the first antigen-binding site binds CD19 with a $K_D$ greater than or equal to 10 nM, 20 nM, 30 nM, 40 nM, 50 nM, 60 nM, 70 nM, 80 nM, 90 nM, or 100 nM. In certain embodiments, the first antigen-binding site binds CD19 with a $K_D$ of about 10 nM-about 1000 nM, about 10 nM-about 900 nM, about 10 nM-about 800 nM, about 10 nM-about 700 nM, about 10 nM-about 600 nM, about 10 nM-about 500 nM, about 10 nM-about 400 nM, about 10 nM-about 300 nM, about 10 nM-about 200 nM, about 10 nM-about 100 nM, about 10 nM-about 50 nM, about 50 nM-about 1000 nM, about 100 nM-about 1000 nM, about 200 nM-about 1000 nM, about 300 nM-about 1000 nM, about 400 nM-about 1000 nM, about 500 nM-about 1000 nM, about 600 nM-about 1000 nM, about 700 nM-about 1000 nM, about 800 nM-about 1000 nM, or about 900 nM-about 1000 nM.

It is understood that the binding affinity to CD19 of the first antigen-binding site alone may be different from the binding affinity of the same antigen-binding site in the context of the multi-specific binding protein disclosed herein, possibly due to the conformational restraint from the other domains. The context-dependent binding affinity is described in subsection I.G titled "Binding Affinity."

Melting temperature represents the thermostability of the antigen-binding site and can be measured by differential scanning fluorimetry, for example, as described in Durowoju et al. (2017) J. Vis. Exp. (121): 55262. The thermostability of an antibody or fragment thereof may be enhanced by grafting CDRs onto stable frameworks, introducing non-canonical disulfide bonds, and other mutagenesis, as described in McConnell et al. (2014) MAbs, 6 (5): 1274-82; and Goldman et al. (2017) Front. Immunol., 8:865.

In certain embodiments, the first antigen-binding site has a melting temperature of at least 50° C., at least 55° C., at least 56° C., at least 57° C., at least 58° C., at least 59° C., at least 60° C., at least 61° C., at least 62° C., at least 63° C., at least 64° C., at least 65° C., at least 70° C., at least 75° C., or at least 80° C. In certain embodiments, the first antigen-binding site has a melting temperature in the range of 50-80° C., 50-70° C., 50-65° C., 50-60° C., 50-55° C., 55-70° C., 55-65° C., 55-60° C., 56-65° C., 56-60° C., 57-65° C., 57-60° C., 58-65° C., 58-60° C., 59-65° C., 59-60° C., 60-80° C., 60-75° C., 60-70° C., 60-65° C., 65-80° C., 65-75° C., 65-70° C., 70-80° C., or 70-75° C.

B. Second Antigen-Binding Site

The second antigen-binding site of the multi-specific binding protein binds CD3 (e.g., human CD3 and/or Macaca CD3). In certain embodiments, the second antigen-binding site binds CD3ε (epsilon). In certain embodiments, the second antigen-binding site binds CD3δ (delta). In certain embodiments, the second antigen-binding site binds CD3γ (gamma).

In certain embodiments, the second antigen-binding site of the multi-specific binding protein binds an epitope at the N-terminus of CD3ε chain. In certain embodiments, the second antigen-binding site binds an epitope localized in amino acid residues 1-27 of human CD3ε extracellular domain. This epitope or a homologous variant thereof is also present in certain non-human primates. Accordingly, in certain embodiments, the second antigen-binding site binds CD3 in different primates, for example, human, new world primates (such as *Callithrix jacchus*, *Saguinus Oedipus*, or *Saimiri sciureus*), old world primates (such as baboons and macaques), gibbons, and non-human homininae. *Callithrix jacchus* and *Saguinus oedipus* are new world primates belonging to the family of Callitrichidae, while *Saimiri sciureus* is a new world primate belonging to the family of Cebidae. In certain embodiments, the second antigen-binding site binds human CD3ε and/or Macaca CD3ε. In certain embodiments, the second antigen-binding site further binds *Callithrix jacchus*, *Saguinus Oedipus*, and/or *Saimiri sciureus* CD3ε.

The second antigen-binding site that binds an extracellular epitope of human and/or Macaca CD3 can be derived from, for example, muromonab-CD3 (OKT3), otelixizumab (TRX4), teplizumab (MGA031), visilizumab (Nuvion), SP34, X35, VIT3, BMA030 (BW264/56), CLB-T3/3, CRIS7, YTH12.5, Fl 11-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1, WT-31, and the antibodies described in WO2008119567A2. For example, the second binding domain optionally can include a VL domain comprising CDR-L1, CDR-L2 and CDR-L3 selected from: (a) CDR-L1 as depicted in SEQ ID NO: 27 of WO2008119567A2, CDR-L2 as depicted in SEQ ID NO: 28 of WO2008119567A2 and CDR-L3 as depicted in SEQ ID NO: 29 of WO2008119567A2; (b) CDR-L1 as depicted in SEQ ID NO: 117 of WO2008119567A2, CDR-L2 as depicted in SEQ ID NO: 118 of WO2008119567A2 and CDR-L3 as depicted in SEQ ID NO: 119 of WO2008119567A2; and (c) CDR-L1 as depicted in SEQ ID NO: 153 of WO2008119567A2, CDR-L2 as depicted in SEQ ID NO: 154 of WO2008119567A2 and CDR-L3 as depicted in SEQ ID NO: 155 of WO2008119567A2. Alternatively, one or more amino acid mutations can be introduced in (a), (b) or (c) group of CDR-L1, CDR-L2 and CDR-L3, and the second binding domain can include any of the mutated groups of CDR-L1, CDR-L2 and CDR-L3.

For example, the second binding domain can include a VL domain comprising CDR-L1, CDR-L2 and CDR-L3 selected from: (a) CDR-H1 as depicted in SEQ ID NO: 12 of WO2008119567A2, CDR-H2 as depicted in SEQ ID NO: 13 of WO2008119567A2 and CDR-H3 as depicted in SEQ ID NO: 14 of WO2008119567A2; (b) CDR-H1 as depicted in SEQ ID NO: 30 of WO2008119567A2, CDR-H2 as depicted in SEQ ID NO: 31 of WO2008119567A2 and CDR-H3 as depicted in SEQ ID NO: 32 of WO2008119567A2; (c) CDR-H1 as depicted in SEQ ID NO: 48 of WO2008119567A2, CDR-H2 as depicted in SEQ ID NO: 49 of WO2008119567A2 and CDR-H3 as depicted in SEQ ID NO: 50 of WO2008119567A2; (d) CDR-H1 as depicted in SEQ ID NO: 66 of WO2008119567A2, CDR-H2 as depicted in SEQ ID NO: 67 of WO2008119567A2 and CDR-H3 as depicted in SEQ ID NO: 68 of WO2008119567A2; (e) CDR-H1 as depicted in SEQ ID NO: 84 of WO2008119567A2, CDR-H2 as depicted in SEQ ID NO: 85 of WO2008119567A2 and CDR-H3 as depicted in SEQ ID NO: 86 of WO2008119567A2; (f) CDR-H1 as depicted in SEQ ID NO: 102 of WO2008119567A2, CDR-H2 as depicted in SEQ ID NO: 103 of WO2008119567A2 and CDR-H3 as depicted in SEQ ID NO: 104 of WO2008119567A2; (g) CDR-H1 as depicted in SEQ ID NO: 120 of WO2008119567A2, CDR-H2 as depicted in SEQ ID NO: 121 of WO2008119567A2 and CDR-H3 as depicted in SEQ ID NO: 122 of WO2008119567A2; (h) CDR-H1 as depicted in SEQ ID NO: 138 of WO2008119567A2, CDR-H2 as depicted in SEQ ID NO: 139 of WO2008119567A2 and CDR-H3 as depicted in SEQ ID NO: 140 of WO2008119567A2; (i) CDR-H1 as depicted in SEQ ID NO: 156 of WO2008119567A2, CDR-H2 as depicted in SEQ ID NO: 157 of WO2008119567A2 and CDR-H3 as depicted in SEQ ID NO: 158 of WO2008119567A2; and (j) CDR-H1 as depicted in SEQ ID NO: 174 of WO2008119567A2, CDR-H2 as depicted in SEQ ID NO: 175 of WO2008119567A2 and CDR-H3 as depicted in SEQ ID NO: 176 of WO2008119567A2. Alternatively, one or more amino acid mutations can be introduced in (a), (b), (c), (d), (e), (f), (g), (h), (i), and (j) group of CDR-H1, CDR-H2 and CDR-H3, and the second binding domain can include any of the mutated groups of CDR-H1, CDR-H2 and CDR-H3. The referenced sequences disclosed in WO2008119567A2 are incorporated by reference herein.

Alternatively, the second domain can be derived from existing CD3 antibodies, for example, muromonab-CD3 (OKT3) as depicted in WO2008101154, otelixizumab (TRX4) as depicted in WO2007145941A2, teplizumab (MGA031) as depicted in WO2013040164A1, visilizumab (Nuvion) as depicted in WO2004052397A1, SP34 as depicted in WO2015181098A1, X35 as depicted in WO2015006749A2, VIT3 as depicted in WO2015006749A2, BMA030 (BW264/56) as depicted in WO2015006749A2, CLB-T3/3 as depicted in WO2004106381A1, CRIS7 as depicted in WO2004106381A1, YTH12.5 as depicted in WO2004106383A1, F1 11-409 as depicted in WO2012084895A2, CLB-T3.4.2 as depicted in WO2004106381A1, TR-66 as depicted in WO2013158856A2, WT32 as depicted in WO2004106381A1, SPv-T3b as depicted in WO2004106383A1, 11D8 as depicted in WO2004106381A1, XIII-141 as depicted in WO2004106381A1, XIII-46 as depicted in WO 2004106381A1, XIII-87 as depicted in WO2004106381A1, 12F6 as depicted in WO 2004106381A1, T3/RW2-8C8 as depicted in WO2004106381A1, T3/RW2-4B6 as depicted in WO 2004106381A1, OKT3D as depicted in WO2004106381A1, M-T301 as depicted in WO2004106381A1, SMC2 as depicted in WO2004106381A1, F101.01 as depicted in WO2004106381A1, UCHT-1 as depicted in WO2000041474A2 and WT-31 as depicted in WO2016085889A1. The referenced sequences above disclosed in WO2008101154, WO2007145941A2, WO2013040164A1, WO2004052397A1, WO2015181098A1, WO2015006749A2, WO2004106381A1, WO2004106383A1, WO2012084895A2, WO2013158856A2, WO2000041474A2 and WO2016085889A1, are incorporated by reference herein.

A second antigen-binding site that binds CD3 can include a VH comprising three complementarity regions (HCDR1, HCDR2, and HCDR3) and/or a VL comprising three complementarity regions (LCDR1, LCDR2, and LCDR3). Table 2 summarizes, for each variable region, the CDRs of the variable region and scFv constructs based on the given heavy and light chain variable regions. The second antigen-binding site can be derived from the exemplary variable domain and CDR sequences as listed in Table 2.

TABLE 2

Sequences of Exemplary Second Antigen-Binding Sites

| Antigen-Binding Site | VH and HCDRs | VL and LCDRs |
| --- | --- | --- |
| Adimab Ab325 | QVQLVQSGAEVKKPGASVKVSCKASGF NIKDYYMHWVRQAPGQRLEWMGWIDL ENANTIYDAKFQGRVTITRDTSASTAYM ELSSLRSEDTAVYYCARDAYGRYFYDV WGQGTLVTVSS (SEQ ID NO: 97) HCDR1: FNIKDYYMH (SEQ ID NO: 99) HCDR2: WIDLENANTIYDAKFQG (SEQ ID NO: 100) HCDR3: ARDAYGRYFYDV (SEQ ID NO: 101) scFv: DIVMTQSPDSLAVSLGERATINCKSSQSLLNARTGKNYLAWYQQKPGQPPKLLIY WASTRESGVPDRFSGSGSGTDFTLTISSLQAEDVAVYYCKQSYSRRTFGGGTKVE IKGGGGSGGGGSGGGGSGGGGSQVQLVQSGAEVKKPGASVKVSCKASGFNIKD YYMHWVRQAPGQRLEWMGWIDLENANTIYDAKFQGRVTITRDTSASTAYMELS SLRSEDTAVYYCARDAYGRYFYDVWGQGTLVTVSS (SEQ ID NO: 105) | DIVMTQSPDSLAVSLGERATINCKS SQSLLNARTGKNYLAWYQQKPGQP PKLLIYWASTRESGVPDRFSGSGSG TDFTLTISSLQAEDVAVYYCKQSYS RRTFGGGTKVEIK (SEQ ID NO: 98) LCDR1: KSSQSLLNARTGKNYLA (SEQ ID NO: 102) LCDR2: WASTRES (SEQ ID NO: 103) LCDR3: KQSYSRRT (SEQ ID NO: 104) |
| Harpoon Ab 2B2 | EVQLVESGGGLVQPGGSLKLSCAASGFT FNKYAINWVRQAPGKGLEWVARIRSKY NNYATYYADQVKDRFTISRDDSKNTAY LQMNNLKTEDTAVYYCVRHANFGNSYI SYWAYWGQGTLVTVSS (SEQ ID NO: 106) HCDR1: GFTFNKYAIN (SEQ ID NO: 108) HCDR2: RIRSKYNNYATYYADQVK (SEQ ID NO: 109) HCDR3: HANFGNSYISYWAY (SEQ ID | QTVVTQEPSLTVSPGGTVTLTCASS TGAVTSGNYPNWVQQKPGQAPRG LIGGTKFLVPGTPARFSGSLLGGKA ALTLSGVQPEDEAEYYCTLWYSNR WVFGGGTKLTVL (SEQ ID NO: 107) LCDR1: ASSTGAVTSGNYPN (SEQ ID NO: 111) LCDR2: GTKFLVP (SEQ ID NO: 112) LCDR3: TLWYSNRWV (SEQ ID NO: 113) |

TABLE 2-continued

Sequences of Exemplary Second Antigen-Binding Sites

| Antigen-Binding Site | VH and HCDRs | VL and LCDRs |
|---|---|---|
| | NO: 110)<br>scFv:<br>EVQLVESGGGLVQPGGSLKLSCAASGFTFNKYAINWVRQAPGKGLEWVARIRSK<br>YNNYATYYADQVKDRFTISRDDSKNTAYLQMNNLKTEDTAVYYCVRHANFGN<br>SYISYWAYWGQGTLVTVSSGGGGSGGGGSGGGGSQTVVTQEPSLTVSPGGTVTL<br>TCASSTGAVTSGNYPNWVQQKPGQAPRGLIGGTKFLVPGTPARFSGSLLGGKAA<br>LTLSGVQPEDEAEYYCTLWYSNRWVFGGGTKLTVL (SEQ ID NO: 114) | |
| Adimab mAb393 | QVQLVQSGAEVKKPGASVKVSCKASGF<br>NIKDYYMHWVRQAPGQRLEWMGWIDL<br>ENANTIYDAKFQGRVTITRDTSASTAYM<br>ELSSLRSEDTAVYYCARDSYGRYFYDV<br>WGQGTLVTVSS (SEQ ID NO: 115)<br>HCDR1: FNIKDYYMH (SEQ ID NO: 99)<br>HCDR2: WIDLENANTIYDAKFQG (SEQ ID NO: 100)<br>HCDR3: ARDSYGRYFYDV (SEQ ID NO: 368) | DIVMTQSPDSLAVSLGERATINCKS<br>SQSLLNSRTGKNYLAWYQQKPGQP<br>PKLLIYWASTRESGVPDRFSGSGSG<br>TDFTLTISSLQAEDVAVYYCKQSYS<br>RRTFGGGTKVEIK (SEQ ID NO: 116)<br>LCDR1: KSSQSLLNARTGKNYLA (SEQ ID NO: 102)<br>LCDR2: WASTRES (SEQ ID NO: 103)<br>LCDR3: KQSYSRRT (SEQ ID NO: 104) |
| Adimab mAb333 | QVQLVQSGAEVKKPGASVKVSCKASGF<br>NIKDYYMHWVRQAPGQRLEWMGWIDL<br>ENANTIYDAKFQGRVTITRDTSASTAYM<br>ELSSLRSEDTA VYYCARDVYGRYFYDL<br>WGQGTLVTVSS (SEQ ID NO: 117)<br>HCDR1: FNIKDYYMH (SEQ ID NO: 99)<br>HCDR2: WIDLENANTIYDAKFOG (SEQ ID NO: 100)<br>HCDR3: ARDVYGRYFYDL (SEQ ID NO: 369) | DIVMTQSPDSLAVSLGERATINCKS<br>SQSLLESRTGKNYLAWYQQKPGQP<br>PKLLIYWASTRESGVPDRFSGSGSG<br>TDFTLTISSLQAEDVAVYYCKQSYS<br>RRTFGGGTKVEIK (SEQ ID NO: 118)<br>LCDR1: KSSQSLLNARTGKNYLA (SEQ ID NO: 102)<br>LCDR2: WASTRES (SEQ ID NO: 103)<br>LCDR3: KQSYSRRT (SEQ ID NO: 104) |
| Adimab mAb334 | QVQLVQSGAEVKKPGASVKVSCKASGF<br>NIKDYYMHWVRQAPGQRLEWMGWIDL<br>ENANTIYDAKFQGRVTITRDTSASTAYM<br>ELSSLRSEDTAVYYCARDAYGGYFYDV<br>WGQGTLVTVSS (SEQ ID NO: 186)<br>HCDR1: FNIKDYYMH (SEQ ID NO: 99)<br>HCDR2: WIDLENANTIYDAKFQG (SEQ ID NO: 100)<br>HCDR3: ARDAYGGYFYDV (SEQ ID NO: 370) | DIVMTQSPDSLAVSLGERATINCKS<br>SQSLLNSRTGKNYLAWYQQKPGQP<br>PKLLIYWASTRESGVPDRFSGSGSG<br>TDFTLTISSLQAEDVAVYYCKQSYS<br>RRTFGCGTKVEIK (SEQ ID NO: 187)<br>LCDR1: KSSQSLLNARTGKNYLA (SEQ ID NO: 102)<br>LCDR2: WASTRES (SEQ ID NO: 103)<br>LCDR3: KQSYSRRT (SEQ ID NO: 104) |
| Adimab mAb404 | EVQLLESGGGLVQPGGSLRLSCAASGFT<br>FDTYAMNWVRQAPGKGLEWVARIRSK<br>YNNYATYYADSVKDRFTISRDDSKSTLY<br>LQMESLRAEDTAVYYCVRHGNFGNYAV<br>SWFAHWGQGTLVTVSS (SEQ ID NO: 371)<br>HCDR1: FTFDTYAMN (SEQ ID NO: 373)<br>HCDR2: RIRSKYNNYATYYADSVKD (SEQ ID NO: 374)<br>HCDR3: VRHGNFGNYAVSWFAH (SEQ ID NO: 375) | QTVVTQEPSLSVSPGGTVTLTCGSS<br>TGAVTTSNYANWVQQTPGQAPRG<br>LIGGTDKRAPGVPDRFSGSLLGDKA<br>ALTITGAQAEDEADYYCALWYSNH<br>WVFGGGTKLTVL (SEQ ID NO: 372)<br>LCDR1: GSSTGAVTTSNYAN (SEQ ID NO: 376)<br>LCDR2: GTDKRAP (SEQ ID NO: 377)<br>LCDR3: ALWYSNHWV (SEQ ID NO: 378) |
| Adimab mAb405 | EVQLLESGGGLVQPGGSLRLSCAASGFT<br>FDTYAMNWVRQAPGKGLEWVARIRSK<br>YNNYATYYADSVKDRFTISRDDSKSTLY<br>LQMESLRAEDTAVYYCVRHGSFGNHIVS<br>WFAHWGQGTLVTVSS (SEQ ID NO: 379)<br>HCDR1: FTFDTYAMN (SEQ ID NO: 373)<br>HCDR2: RIRSKYNNYATYYADSVKD (SEQ ID NO: 374)<br>HCDR3: VRHGSFGNHIVSWFAH (SEQ ID NO: 399) | QTVVTQEPSLSVSPGGTVTLTCGSS<br>TGAVTTSNYANWVQQTPGQAPRG<br>LIGGTDKRAPGVPDRFSGSLLGDKA<br>ALTITGAQAEDEADYYCALWYSNH<br>WVFGGGTKLTVL (SEQ ID NO: 372)<br>LCDR1: GSSTGAVTTSNYAN (SEQ ID NO: 376)<br>LCDR2: GTDKRAP (SEQ ID NO: 377)<br>LCDR3: ALWYSNHWV (SEQ ID NO: 378) |
| Adimab mAb-1 | QVQLVQSGAEVKKPGASVKVSCKASGF<br>NIKDYYMHWVRQAPGQRLEWMGWIDL<br>ENGNTIYDAKFQGRVTITRDTSASTAYM<br>ELSSLRSEDTAVYYCARDGYGRYFYDV<br>WGQGTLVTVIS (SEQ ID NO: 188) | DIVMTQSPDSLAVSLGERATINCKS<br>SQSLLNSRTRKNYLAWYQQKPGQP<br>PKLLIYWASTRESGVPDRFSGSGSG<br>TDFTLTISSLQAEDVAVYYCKQSYS<br>RRTFGGGTKVEIK (SEQ ID NO: 189) |

TABLE 2-continued

Sequences of Exemplary Second Antigen-Binding Sites

| Antigen-Binding Site | VH and HCDRs | VL and LCDRs |
|---|---|---|
| Adimab mAb-2 | QVQLVQSGAEVKKPGASVKVSCKASGF NIKDYYMHWVRQAPGQRLEWMGWIDL ENANTIYDAKFQGRVTITRDTSASTAYM ELSSLRSEDTAVYYCARDVYGRYLYDV WGQGTLVTVSS (SEQ ID NO: 190) | DIVMTQSPDSLAVSLGERATINCKS SQSLLNNRTRKNYLAWYQQKPGQP PKLLIYWASTRESGVPDRFSGSGSG TDFTLTISSLQAEDVAVYYCKQSYS RRTFGGGTKVEIK (SEQ ID NO: 191) |
| Adimab mAb-3 | QVQLVQSGAEVKKPGASVKVSCKASGF NIKDYYMHWVRQAPGQRLEWMGWIDL ENGNTIYDPKFQGRVTITRDTSASTAYM ELSSLRSEDTAVYYCARDAYGRYFYDV WGQGTLVTVSS (SEQ ID NO: 192) | DIVMTQSPDSLAVSLGERATINCRS SQSLLNSRTRKNYLAWYQQKPGQP PKLLIYWASTRESGVPDRFSGSGSG TDFTLTISSLQAEDVAVYYCKQSYS RRTFGGGTKVEIK (SEQ ID NO: 193) |
| Adimab mAb-4 | QVQLVQSGAEVKKPGASVKVSCKASGF NIKDYYMHWVRQAPGQRLEWMGWIDL EEGNTIYDAKFQGRVTITRDTSASTAYM ELSSLRSEDTAVYYCARDAYGRYFYDV WGQGTLVTVSS (SEQ ID NO: 194) | DIVMTQSPDSLAVSLGERATINCKS SQSLLNGRTRKNYLAWYQQKPGQP PKLLIYWASTRESGVPDRFSGSGTG TDFTLTISSLQAEDVAVYYCKQSYS RRTFGGGTKVEIK (SEQ ID NO: 195) |
| Adimab mAb-5 | QVQLVQSGAEVKKPGASVKVSCKASGF NIKDYYMHWVRQAPGQRLEWMGWIDL ENANTIYDAKFQGRVTITRDTSASTAYM ELSSLRSEDTAVYYCARDNYGGYFYDV WGQGTLVTVSS (SEQ ID NO: 196) | DIVMTQSPDSLAVPLGERATINCKS SQSLLNSRTRKNYLAWYQQKPGQP PKLLIYWASTRESGVPDRFSGSGSG TDFTLTISSLQAEDVAVYYCKQSYS RRTFGGGTKVEIK (SEQ ID NO: 197) |
| Adimab mAb-6 | QVQLVQSGAEVKKPGASVKVSCKASGF NIKDYYMHWVRQAPGQRLEWMGWIDL ENGNTIYDPKFQGRVTITRDTSASTAYM ELSSLRSEDTA VYYCARDGYGRYFYDV WGQGTLVTVSS (SEQ ID NO: 198) | DIVMTQSPDSLAVSLGERATINCKS SQSLLNSRTRKNYLAWYQQKPGQP PKLLIYWASTRESGVPDRFSGSGSG TDFTLTISSLQAEDVAVYYCKQSYS LRTFGGGTKVEIK (SEQ ID NO: 199) |
| Adimab mAb-7 | QVQLVQSGAEVKKPGASVKVSCKASGF NIKDYYMHWVRQAPGQRLEWMGWIDL ENGNTIYDPKFQGRVTITRDTSASTAYM ELSSLRSEDTAVYYCARDGYGRYFFDV WGQGTLVTVSS (SEQ ID NO: 200) | DIVMTQSPDSLAVSLGERATINCKS SQSLLNSRTRKNYLAWYQQKPGQP PKLLIYWASTRESGVPDRFSGSGSG TDFTLTISSLQAEDVAVYYCKQSYN LRTFGGGTKVEIK (SEQ ID NO: 201) |
| Adimab mAb-8 | QVQLVQSGAEVKKPGASVKVSCKASGF NIKDYYMHWVRQAPGQRLEWMGWIDL ENGNTIYDPKFQGRVTITRDTSASTAYM ELSSLRSEDTAVYYCAREGYGRYFYDV WGQGTLVTVSS (SEQ ID NO: 202) | DIVMTQSPDSLAVSLGERATINCKS SQSLLNSRTRKNYLAWYQQKPGQP PKLLIYWASTRESGVPDRFSGSGSG TDFTLTISSLQAEDVAVYYCKQSYF RRAFGGGTKVEIK (SEQ ID NO: 203) |
| Adimab mAb-9 | QVQLVQSGAEVKKPGASVKVSCKASGF NIKDYYMHWVRQAPGQRLEWMGWIDL ENGNTIYDPKFQGRVTITRDTSASTAYM ELSSLRSEDTAVYYCARDGYGRYYYDV WGQGTLVTVSS (SEQ ID NO: 204) | DIVMTQSPDSLAVSLGERATINCKS SQSLLNSRTRKNYLAWYQQKPGQP PKLLIYWASTRESGVPDRFSGSGSG TDFTLTISSLQAEDVAVYYCKQSYN LRTFGGGTKLEIK (SEQ ID NO: 205) |
| Adimab mAb-10 | QVQLVQSGAEVKKPGASVKVSCKASGF NIKDYYMHWVRQAPGQRLEWMGWIDL ENGNTIYQPKFQGRVTITRDTSASTAYM ELSSLRSEDTAVYYCARDGYGRYFYDV WGQGTLVTVSS (SEQ ID NO: 206) | DIVMTQSPDSLAVSLGERATINCKS SQSLLNSRTRKNYLAWYQQKPGQS PKLLIYWASTRESGVPDRFTGSGSG TDFTLTISSLQAEDVAVYYCKQSYS LRTFGGGTKVEIK (SEQ ID NO: 207) |
| Adimab mAb-11 | QVQLVQSGAEVKKPGASVKVSCKASGF NIKDYYMHWVRQAPGQRLEWMGWIDL ENGNTIYDPKFQGRVTITRDTSASTAYM ELSSLRSEDTAVYYCARDGYGRYFYDY WGQGTLVTVSS (SEQ ID NO: 208) | DIVMTQSPDSLAVSLGERATINCKS SQSLLESRTGKNYLAWYQQKPGQP PKLLIYWASTRESGVPDRFSGSGSG TDFTLTISSLQAEDVAVYYCKQSYS LRTFGGGTKVEIK (SEQ ID NO: 209) |
| CD3 binding domain in blinatumomab | DIKLQQSGAELARPGASVKMSCKTSGYT FTRYTMHWVKQRPGQGLEWIGYINPSR GYTNYNQKFKDKATLTTDKSSSTAYMQ LSSLTSEDSAVYYCARYYDDHYCLDYW GQGTTLTVSSVE (SEQ ID NO: 119) scFv: DIKLQQSGAELARPGASVKMSCKTSGYTFTRYTMHWVKQRPGQGLEWIGYINPS RGYTNYNQKFKDKATLTTDKSSSTAYMQLSSLTSEDSAVYYCARYYDDHYCLD YWGQGTTLTVSSVEGGSGSGGSGGSGGVDDIQLTQSPAIMSASPGEKVTMTCR ASSSVSYMNWYQQKSGTSPKRWIYDTSKVASGVPYRFSGSGSGTSYSLTISSMEA EDAATYYCQQWSSNPLTFGAGTKLELK (SEQ ID NO: 258) | VDDIQLTQSPAIMSASPGEKVTMTC RASSSVSYMNWYQQKSGTSPKRWI YDTSKVASGVPYRFSGSGSGTSYSL TISSMEAEDAATYYCQQWSSNPLTF GAGTKLELK (SEQ ID NO: 120) |

TABLE 2-continued

Sequences of Exemplary Second Antigen-Binding Sites

| Antigen-Binding Site | VH and HCDRs | VL and LCDRs |
|---|---|---|
| Novimmune 28F11 | QVQLVESGGGVVQPGRSLRLSCAASGFK FSGYGMHWVRQAPGKGLEWVAVIWYD GSKKYYVDSVKGRFTISRDNSKNTLYLQ MNSLRAEDTAVYYCARQMGYWHFDLW GRGTLVTVSS (SEQ ID NO: 259) HCDR1: GYGMH (SEQ ID NO: 261) HCDR2: VIWYDGSKKYYVDSVKG (SEQ ID NO: 262) HCDR3: QMGYWHFDL (SEQ ID NO: 263) | EIVLTQSPATLSLSPGERATLSCRAS QSVSSYLAWYQQKPGQAPRLLIYD ASNRATGIPARFSGSGSGTDFTLTIS SLEPEDFAVYYCQQRSNWPPLTFG GGTKVEIK (SEQ ID NO: 260) LCDR1: RASQSVSSYLA (SEQ ID NO: 264) LCDR2: DASNRAT (SEQ ID NO: 265) LCDR3: QQRSNWPPLT (SEQ ID NO: 266) |
| Novimmune 27H5 | EVQLLESGGGLVQPGGSLRLSCAASGFT FSSFPMAWVRQAPGKGLEWVSTISTSGG RTYYRDSVKGRFTISRDNSKNTLYLQMN SLRAEDTAVYYCAKFRQYSGGFDYWGQ GTLVTVSS (SEQ ID NO: 267) | DFMLTQPHSVSESPGKTVIISCWYQ QRPGRAPTTVIFGVPDRFSGSIDRSS NSASLTISGLQTEDEADYYCFGGGT KLTVLGQPKAAPSVTLFPPSSEELQ (SEQ ID NO: 268) |
| Glaxo mAb | EVQLLESGGGLVQPGGSLRLSCAASGFT FSSFPMAWVRQAPGKGLEWVSTISTSGG RTYYRDSVKGRFTISRDNSKNTLYLQMN SLRAEDTAVYYCAKFRQYSGGFDYWGQ GTLVTVSS (SEQ ID NO: 269) | DIQLTQPNSVSTSLGSTVKLSCTLSS GNIENNYVHWYQLYEGRSPTTMIY DDDKRPDGVPDRFSGSIDRSSNSAF LTIHNVAIEDEAIYFCHSYVSSFNVF GGGTKLTVLR (SEQ ID NO: 270) |
| Eureka mAb | DVQLVQSGAEVKKPGASVKVSCKASGY TFTRYTMHWVRQAPGQGLEWIGYINPS RGYTNYADSVKGRFTITTDKSTSTAYME LSSLRSEDTATYYCARYYDDHYCLDYW GQGTTVTVSS (SEQ ID NO: 271) scFv: DVQLVQSGAEVKKPGASVKVSCKASGYTFTRYTMHWVRQAPGQGLEWIGYINP SRGYTNYADSVKGRFTITTDKSTSTAYMELSSLRSEDTATYYCARYYDDHYCLD YWGQGTTVTVSSGEGTSTGSGGSGGSGGADDIVLTQSPATLSLSPGERATLSCRA SQSVSYMNWYQQKPGKAPKRWIYDTSKVASGVPARFSGSGSGTDYSLTINSLEA EDAATYYCQQWSSNPLTFGGGTKVEIK (SEQ ID NO: 273) | DIVLTQSPATLSLSPGERATLSCRAS QSVSYMNWYQQKPGKAPKRWIYD TSKVASGVPARFSGSGSGTDYSLTI NSLEAEDAATYYCQQWSSNPLTFG GGTKVEIK (SEQ ID NO: 272) |
| Muromon ab | QVQLVQSGGGVVQPGRSLRLSCKASGY TFTRYTMHWVRQAPGKGLEWIGYINPS RGYTNYNQKVKDRFTISRDNSKNTAFLQ MDSLRPEDTGVYFCARYYDDHYCLDY WGQGTPVTVSS (SEQ ID NO: 274) | DDIQMTQSPSSLSASVGDRVTITCS ASSSVSYMNWYQQTPGKAPKRWIY DTSKLASGVPSRFSGSGSGTDYTFTI SSLQPEDIATYYCQQWSSNPFTFGQ GTKLQIT (SEQ ID NO: 275) |
| MacroGenics mAb humanized OKT3 | QVQLVQSGGGVVQPGRSLRLSCKASGY TFTRYTMHWVRQAPGKGLEWIGYINPS RGYTNYNQKFKDRFTISTDKSKSTAFLQ MDSLRPEDTAVYYCARYYDDHYCLDY WGQGTPVTVSS (SEQ ID NO: 276) | DIQMTQSPSSLSASVGDRVTITCSAS SSVSYMNWYQQTPGKAPKRWIYD TSKLASGVPSRFSGSGSGTDYTFTIS SLQPEDIATYYCQQWSSNPFTFGQG TKLQITR (SEQ ID NO: 277) |
| Roche CH2527 | EVQLLESGGGLVQPGGSLRLSCAASGFT FSTYAMNWVRQAPGKGLEWVSRIRSKY NNYATYYADSVKGRFTISRDDSKNTLYL QMNSLRAEDTAVYYCVRHGNFGNSYVS WFAYWGQGTLVTVSS (SEQ ID NO: 278) | QAVVTQEPSLTVSPGGTVTLTCGSS TGAVTTSNYANWVQEKPGQAFRG LIGGTNKRAPGTPARFSGSLLGGKA ALTLSGAQPEDEAEYYCALWYSNL WVFGGGTKLTVL (SEQ ID NO: 279) |
| Regeneron mAb (anti-CD3/anti-CD20) | EVQLVESGGGLVQPGRSLRLSCAASGFT FDDYTMHWVRQAPGKGLEWVSGISWN SGSIGYADSVKGRFTISRDNAKKSLYLQ MNSLRAEDTALYYCAKDNSGYGHYYY GMDVWGQGTTVTVAS (SEQ ID NO: 280) | AEIVMTQSPATLSVSPGERATLSCR ASQSVSSNLAWYQQKPGQAPRLLI YGASTRATGIPARFSGSGSGTEFTLT ISSLQSEDFAVYYCQHYINWPLTFG GGTKVEIK (SEQ ID NO: 281) |
| WuXi WBP331 1_2.166.4 8-z1 | QVQLVQSGAEVKKPGSSVKVSCKASGY SFTTYYIHWVRQAPGQGLEWMGWIFPG NDNIKYSEKFKGRVTITADKSTSTAYME LSSLRSEDTAVYYCAIDSVSIYYFDYWG QGTLVTVSS (SEQ ID NO: 380) HCDR1: GYSFTTYYIH (SEQ ID NO: 382) HCDR2: WIFPGNDIKYSEKFKG (SEQ ID NO: 383) HCDR3: DSVSIYYFDY (SEQ ID NO: 384) | DIVMTQSPDSLAVSLGERATINCKS SQSLLNSRTRKNYLAWYQQKPGQP PKLLIYWASTRKSGVPDRFSGSGSG TDFTLTISSLQAEDVAVYYCTQSFIL RTFGGGTKVEIK (SEQ ID NO: 381) LCDR1: KSSQSLLNSRTRKNYLA (SEQ ID NO: 385) LCDR2: WASTRKS (SEQ ID NO: 386) LCDR3: TQSFILRT (SEQ ID NO: 387) |
| WuXi WBP331 1_2.306.4-z1 | QVQLVQSGAEVKKPGSSVKVSCKASGF AFTDYYIHWVRQAPGQGLEWMGWISPG NVNTKYNENFKGRVTITADKSTSTAYM ELSSLRSEDTAVYYCARDGYSLYYFDY | DIVMTQSPDSLAVSLGERATINCKS SQSLLNSRTRKNYLAWYQQKPGQP PKLLIYWASTRQSGVPDRFSGSGSG TDFTLTISSLQAEDVAVYYCTQSHT |

TABLE 2-continued

Sequences of Exemplary Second Antigen-Binding Sites

| Antigen-Binding Site | VH and HCDRs | VL and LCDRs |
|---|---|---|
| | WGQGTLVTVSS (SEQ ID NO: 388)<br>HCDR1: GFAFTDYYIH (SEQ ID NO: 390)<br>HCDR2: WISPGNVNTKYNENFKG (SEQ ID NO: 391)<br>HCDR3: DGYSLYYFDY (SEQ ID NO: 392) | LRTFGGGTKVEIK (SEQ ID NO: 389)<br>LCDR1: KSSQSLLNSRTRKNYLA (SEQ ID NO: 385)<br>LCDR2: WASTRQS (SEQ ID NO: 393)<br>LCDR3: TQSHTLRT (SEQ ID NO: 394) |
| ADLQ mAb-1 | MAESGGGSVQTGGSLRLSCAYTASSVC<br>MAWFRQAPGKEREGVAVTREGLTKTGY<br>ADSVKGRFAISQDYAKKTLYLQMSSLKP<br>EDTARYYCAARPTSPCTVDGELLASTYN<br>YWGQGTQVTV (SEQ ID NO: 395) | N/A |
| ADLQ mAb-2 | MAESGGGSVQTGGSLRLSCAYTASSVC<br>MAWFRQAPGKEREGVAVTREGLTKTGY<br>ADSVKGRFAISQDYAKKTLYLQMSSLKP<br>EDTARYYCAARPTSPCTVDGELLASTYD<br>YWGQGTQVTV (SEQ ID NO: 396) | N/A |
| ADLQ mAb-3 | MAESGGGSVQTGGSLRLSCAYTASSVC<br>MAWFRQAPGKEREGVAVTREGLTQTGY<br>ADSVKGRFAISQDYAKKTLYLQMSSLKP<br>EDTARYYCAARPTSPCTVDGELLASTYN<br>YWGQGTQVTV (SEQ ID NO: 397) | N/A |
| ADLQ mAb-4 | MAESGGGSVQTGGSLRLSCAYTASSVC<br>MAWFRQAPGKEREGVAVTREGLTQTGY<br>ADSVKGRFAISQDYAKKTLYLQMSSLKP<br>EDTARYYCAARPTSPCTVDGELLASTYD<br>YWGQGTQVTV (SEQ ID NO: 398) | N/A |

Where the VL and LCDR sequences are noted as "N/A," the antigen-binding site is an sdAb having a VH (e.g., VHH) only.

In certain embodiments, the second antigen-binding site comprises a VH comprising complementarity determining regions HCDR1, HCDR2, and HCDR3, and a VL comprising complementarity determining regions LCDR1, LCDR2, and LCDR3. In certain embodiments, the VH comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to the VH of an antibody provided in Table 2, and the VL comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to the VL of the antibody provided in Table 2. In certain embodiments, the VH comprises the HCDR1, HCDR2, and HCDR3 sequences of the antibody provided in Table 2, and the VL comprises the LCDR1, LCDR2, and LCDR3 sequences of the antibody provided in Table 2. In certain embodiments, the VH comprises the amino acid sequence of the VH of an antibody provided in Table 2, and the VL comprises the amino acid sequence of the VL of the antibody provided in Table 2.

In certain embodiments, the VH of the second antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 97, and the VL of the second antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 98. In certain embodiments, the VH comprises HCDR1, HCDR2, and HCDR3 sequences set forth in SEQ ID NOs: 99, 100, 101, respectively, and the VL comprises LCDR1, LCDR2, and LCDR3 sequences set forth in SEQ ID NOs: 102, 103, and 104, respectively. In certain embodiments, the VH comprises the amino acid sequence set forth in SEQ ID NO: 97, and the VL comprises the amino acid sequence set forth in SEQ ID NO: 98.

In certain embodiments, the VH of the second antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 106, and the VL of the second antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 107. In certain embodiments, the VH comprises HCDR1, HCDR2, and HCDR3 sequences set forth in SEQ ID NOs: 108, 109, and 110, respectively, and the VL comprises LCDR1, LCDR2, and LCDR3 sequences set forth in SEQ ID NOs: 111, 112, and 113, respectively. In certain embodiments, the VH comprises the amino acid sequence set forth in SEQ ID NO: 106, and the VL comprises the amino acid sequence set forth in SEQ ID NO: 107.

Such antigen-binding site may take the form of scFv. In certain embodiments, the second antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to an scFv sequence provided in Table 2. In certain embodiments, the second antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 105 or 114.

In other embodiments, the second antigen-binding site comprises an sdAb comprising a VH comprising complementarity determining regions HCDR1, HCDR2, and HCDR3. In certain embodiments, the VH comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to the VH of an sdAb antibody provided in Table 2. In certain embodiments, the VH comprises the HCDR1, HCDR2, and HCDR3 sequences of the antibody provided in Table 2. In certain embodiments, the VH comprises the amino acid sequence of the VH of an sdAb provided in Table 2.

In certain embodiments, the second antigen-binding site competes for binding CD3 (e.g., human CD3 and/or Macaca CD3) with an antibody or antigen-binding fragment thereof comprising the VH, VL and/or scFv sequences provided in Table 2.

In certain embodiments, the second antigen-binding site of the multi-specific binding protein binds CD3 (e.g., human CD3 and/or Macaca CD3) with a dissociation constant ($K_D$) of about 0.1 nM-about 1 µM. The $K_D$ can be measured by a method known in the art. In certain embodiments, the $K_D$ is measured by SPR to CD3 or an extracellular fragment thereof immobilized on a chip. In certain embodiments, the $K_D$ is measured by flow cytometry to CD3 expressed on the surface of cells, for example, following the method described in Example 5 below.

In certain embodiments, the second antigen-binding site binds CD3 with a $K_D$ of lower than or equal to 20 nM, 15 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 90 pM, 80 pM, 70 pM, 60 pM, 50 pM, 40 pM, 30 pM, 20 pM, or 10 pM. For example, in certain embodiments, the first antigen-binding site binds CD3 with a $K_D$ of about 10 pM-about 1 nM, about 10 pM-about 0.9 nM, about 10 pM-about 0.8 nM, about 10 pM-about 0.7 nM, about 10 pM-about 0.6 nM, about 10 pM-about 0.5 nM, about 10 pM-about 0.4 nM, about 10 pM-about 0.3 nM, about 10 pM-about 0.2 nM, about 10 pM-about 0.1 nM, about 10 pM-about 50 pM, 0.1 nM-about 10 nM, about 0.1 nM-about 9 nM, about 0.1 nM-about 8 nM, about 0.1 nM-about 7 nM, about 0.1 nM-about 6 nM, about 0.1 nM-about 5 nM, about 0.1 nM-about 4 nM, about 0.1 nM-about 3 nM, about 0.1 nM-about 2 nM, about 0.1 nM-about 1 nM, about 0.1 nM-about 0.5 nM, about 0.5 nM-about 10 nM, about 1 nM-about 10 nM, about 2 nM-about 10 nM, about 3 nM-about 10 nM, about 4 nM-about 10 nM, about 5 nM-about 10 nM, about 6 nM-about 10 nM, about 7 nM-about 10 nM, about 8 nM-about 10 nM, or about 9 nM-about 10 nM.

In certain embodiments, the second antigen-binding site binds CD3 with a $K_D$ greater than or equal to 10 nM, 20 nM, 30 nM, 40 nM, 50 nM, 60 nM, 70 nM, 80 nM, 90 nM, or 100 nM. In certain embodiments, the second antigen-binding site binds CD3 with a $K_D$ of about 10 nM-about 1000 nM, about 10 nM-about 900 nM, about 10 nM-about 800 nM, about 10 nM-about 700 nM, about 10 nM-about 600 nM, about 10 nM-about 500 nM, about 10 nM-about 400 nM, about 10 nM-about 300 nM, about 10 nM-about 200 nM, about 10 nM-about 100 nM, about 10 nM-about 50 nM, about 50 nM-about 1000 nM, about 100 nM-about 1000 nM, about 200 nM-about 1000 nM, about 300 nM-about 1000 nM, about 400 nM-about 1000 nM, about 500 nM-about 1000 nM, about 600 nM-about 1000 nM, about 700 nM-about 1000 nM, about 800 nM-about 1000 nM, or about 900 nM-about 1000 nM.

It is understood that the binding affinity to CD3 of the second antigen-binding site alone may be different from the binding affinity of the same antigen-binding site in the context of the multi-specific binding protein disclosed herein, possibly due to the conformational restraint from the other domains. The context-dependent binding affinity is described in the subsection I.G titled "Binding Affinity."

In certain embodiments, the second antigen-binding site has a melting temperature of at least 50° C., at least 55° C., at least 56° C., at least 57° C., at least 58° C., at least 59° C., at least 60° C., at least 61° C., at least 62° C., at least 63° C., at least 64° C., at least 65° C., at least 70° C., at least 75° C., or at least 80° C. In certain embodiments, the second antigen-binding site has a melting temperature in the range of 50-80° C., 50-70° C., 50-65° C., 50-60° C., 50-55° C., 55-70° C., 55-65° C., 55-60° C., 56-65° C., 56-60° C., 57-65° C., 57-60° C., 58-65° C., 58-60° C., 59-65° C., 59-60° C., 60-80° C., 60-75° C., 60-70° C., 60-65° C., 65-80° C., 65-75° C., 65-70° C., 70-80° C., or 70-75° C.

C. Third Antigen-Binding Site

The third antigen-binding site of the multi-specific binding protein binds serum albumin (e.g., HSA). In certain embodiments, the third antigen-binding site has a higher binding affinity to a human serum albumin than to a mouse serum albumin. In certain embodiments, the third antigen-binding site does not bind the D-III domain of HSA. In certain embodiments, the third antigen-binding site extends the serum half-life of the multi-specific binding protein.

The third antigen-binding site that binds serum albumin can be derived from, for example, the antigen-binding sites disclosed in U.S. Pat. No. 8,188,223, and PCT Publication Nos. WO2017085172, and WO2018050833.

A third antigen-binding site that binds HSA can include a VH comprising three complementarity regions (HCDR1, HCDR2, and HCDR3) and/or a VL comprising three complementarity regions (LCDR1, LCDR2, and LCDR3). Table 3 summarizes, for each variable region, the CDRs of the variable region and scFv constructs based on the given heavy and light chain variable regions. The third antigen-binding site can be derived from the exemplary variable domain and CDR sequences as listed in Table 3.

TABLE 3

Sequences of Exemplary Third Antigen-Binding Sites

| Antigen-Binding Site | VH and HCDRs | VL and LCDRs |
|---|---|---|
| Ablynx ALB8 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS (SEQ ID NO: 121)<br>HCDR1: SFGMS (SEQ ID NO: 122) or GFTFSSFGMS (SEQ ID NO: 123)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx ALB3 | EVQLVESGGGLVQPGGSLRLSCAASGFTFRSFGMSWVRQAPGKEPEWVSSISGSGSDTLYADSVKGRFTISRDNAKTTLYLQMNSLKPEDTAVYYCTIGGSLSRSSQGTQVTVSS (SEQ ID NO: 127)<br>HCDR1: SFGMS (SEQ ID NO: 122) or GFTFRSFGMS (SEQ ID NO: 128)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx ALB4 | EVQLVESGGGLVQPGGSLRLSCAASGFTFSSFGMSWVRQAPGKEPEWVSSISGSGSDTLYADSVKGRFTISRDNAKTTLYLQMNSLKPEDTAVYYCTIGGSLSRSSQGTQVTVSS (SEQ ID NO: 129)<br>HCDR1: SFGMS (SEQ ID NO: 122) or GFTFSSFGMS (SEQ ID NO: 123)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx ALB5 | EVQLVESGGGLVQPGGSLRLSCAASGFTFRSFGMSWVRQAPGKGLEWVSSISGSGSDTLYADSVKGRFTISRDNAKTTLYLQMNSLKPEDTAVYYCTIGGSLSRSSQGTQVTVSS (SEQ ID NO: 130)<br>HCDR1: SFGMS (SEQ ID NO: 122) or GFTFRSFGMS (SEQ ID NO: 128)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx ALB6 | EVQLVESGGGLVQPGNSLRLSCAASGFTFRSFGMSWVRQAPGKGLEWVSSISGSGSDTLYADSVKGRFTISRDNAKTTLYLQMNSLKPEDTAVYYCTIGGSLSRSSQGTLVTVSS (SEQ ID NO: 131)<br>HCDR1: SFGMS (SEQ ID NO: 122) or GFTFRSFGMS (SEQ ID NO: 128)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx ALB7 | EVQLVESGGGLVQPGNSLRLSCAASGFTFRSFGMSWVRQAPGKGLEWVSSISGSGSDTLYADSVKGRFTISRDNAKTTLYLQMNSLRPEDTAVYYCTIGGSLSRSSQGTLVTVSS (SEQ ID NO: 132)<br>HCDR1: SFGMS (SEQ ID NO: 122) or GFTFRSFGMS (SEQ ID NO: 128)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx ALB9 | EVQLVESGGGLVQPGNSLRLSCAASGFTFSSFGMSWVRQAPGKGLEWVSSISGSGS | N/A |

TABLE 3-continued

Sequences of Exemplary Third Antigen-Binding Sites

| Antigen-Binding Site | VH and HCDRs | VL and LCDRs |
|---|---|---|
| | DTLYADSVKGRFTISRDNAKNTLYLQM NSLRPEDTAVYYCTIGGSLSRSSQGTLVT VSS (SEQ ID NO: 133)<br>HCDR1: SFGMS (SEQ ID NO: 122) or GFTFSSFGMS (SEQ ID NO: 123)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | |
| Ablynx ALB10 | EVQLVESGGGLVQPGNSLRLSCAASGFT FSSFGMSWVRQAPGKGLEWVSSISGSGS DTLYADSVKGRFTISRDNAKNTLYLQM NSLRPEDTAVYYCTIGGSLSRSGQGTLV TVSS (SEQ ID NO: 134)<br>HCDR1: SFGMS (SEQ ID NO: 122) or GFTFSSFGMS (SEQ ID NO: 123)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx ALB23 | EVQLLESGGGLVQPGGSLRLSCAASGFT FRSFGMSWVRQAPGKGPEWVSSISGSGS DTLYADSVKGRFTISRDNSKNTLYLQMN SLRPEDTAVYYCTIGGSLSRSSQGTLVTV SS (SEQ ID NO: 135)<br>HCDR1: SFGMS (SEQ ID NO: 122) or GFTFRSFGMS (SEQ ID NO: 128)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx mAb-1 | EVQLVESGGGVVQPGNSLRLSCAASGFT FSSFGMSWVRQAPGKGLEWVSSISGSGS DTLYADSVKGRFTISRDNAKTTLYLQMN SLRPEDTATYYCTIGGSLSRSSQGTLVTV SSA (SEQ ID NO: 167)<br>HCDR1: SFGMS (SEQ ID NO: 122) or GFTFSSFGMS (SEQ ID NO: 123)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx mAb-2 | EVQLVESGGGVVQPGGSLRLSCAASGFT FRSFGMSWVRQAPGKGPEWVSSISGSGS DTLYADSVKGRFTISRDNSKNTLYLQMN SLRPEDTATYYCTIGGSLSRSSQGTLVTV SSA (SEQ ID NO: 168)<br>HCDR1: SFGMS (SEQ ID NO: 122) or GFTFRSFGMS (SEQ ID NO: 128)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx mAb-3 | EVQLVESGGGLVQPGNSLRLSCAASGFT FSSFGMSWVRQAPGKGLEWVSSISGSGS DTLYADSVKGRFTISRDNAKTTLYLQMN SLRPEDTAVYYCTIGGSLSRSSQGTLVKV SSA (SEQ ID NO: 169)<br>HCDR1: SFGMS (SEQ ID NO: 122) or GFTFSSFGMS (SEQ ID NO: 123)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx mAb-4 | EVQLVESGGGVVQPGNSLRLSCAASGFT FSSFGMSWVRQAPGKGLEWVSSISGSGS DTLYADSVKGRFTISRDNAKTTLYLQMN SLRPEDTALYYCTIGGSLSRSSQGTLVTV | N/A |

TABLE 3-continued

Sequences of Exemplary Third Antigen-Binding Sites

| Antigen-Binding Site | VH and HCDRs | VL and LCDRs |
|---|---|---|
| | SS (SEQ ID NO: 170)<br>HCDR1: SFGMS (SEQ ID NO: 122) or GFTFSSFGMS (SEQ ID NO: 123)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | |
| Ablynx mAb-5 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSA (SEQ ID NO: 171)<br>HCDR1: SFGMS (SEQ ID NO: 122) or GFTFSSFGMS (SEQ ID NO: 123)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx mAb-6 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSAA (SEQ ID NO: 172)<br>HCDR1: SFGMS (SEQ ID NO: 122) or GFTFSSFGMS (SEQ ID NO: 123)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx mAb-7 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSAAA (SEQ ID NO: 173)<br>HCDR1: SFGMS (SEQ ID NO: 122) or GFTFSSFGMS (SEQ ID NO: 123)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx mAb-8 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSG (SEQ ID NO: 174)<br>HCDR1: SFGMS (SEQ ID NO: 122) or GFTFSSFGMS (SEQ ID NO: 123)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx mAb-9 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSGG (SEQ ID NO: 175)<br>HCDR1: SFGMS (SEQ ID NO: 122) or GFTFSSFGMS (SEQ ID NO: 123)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx mAb-10 | EVQLVESGGGVVQPGNSLRLSCAASGFTFSSFGMSWVRQAPGKGLEWVSSISGSGSDTLYADSVKGRFTISRDNAKTTLYLQMNSLRPEDTALYYCTIGGSLSRSSQGTLVTVSSGGG (SEQ ID NO: 176)<br>HCDR1: SFGMS (SEQ ID NO: 122) or | N/A |

TABLE 3-continued

Sequences of Exemplary Third Antigen-Binding Sites

| Antigen-Binding Site | VH and HCDRs | VL and LCDRs |
|---|---|---|
| | GFTFSSFGMS (SEQ ID NO: 123)<br>HCDR2: SISGSGSDTL (SEQ ID NO: 124)<br>or SISGSGSDTLYADSVKG (SEQ ID NO: 125)<br>HCDR3: GGSLSR (SEQ ID NO: 126) | |
| Ablynx PMP6A6 | AVQLVESGGGLVQPGNSLRLSCAASGFT FRSFGMSWVRQAPGKEPEWVSSISGSGS DTLYADSVKGRFTISRDNAKTTLYLQMN SLKPEDTAVYYCTIGGSLSRSSQGTQVT VSS (SEQ ID NO: 136)<br>HCDR1: SFGMS (SEQ ID NO: 122) or GFTFRSFGMS (SEQ ID NO: 128)<br>HCDR2: SISGSGSDTL (SEQ ID NO: 124) or SISGSGSDTLYADSVKG (SEQ ID NO: 125)<br>HCDR3: GGSLSR (SEQ ID NO: 126) | N/A |
| Ablynx PMP6C1 | AVQLVDSGGGLVQPGGSLRLSCAASGFS FGSFGMSWVRQYPGKEPEWVSSINGRG DDTRYADSVKGRFSISRDNAKNTLYLQ MNSLKPEDTAEYYCTIGRSVSRSRTQGT QVTVSS (SEQ ID NO: 137)<br>HCDR1: SFGMS (SEQ ID NO: 122) or GFSFGSFGMS (SEQ ID NO: 138)<br>HCDR2: SINGRGDDTR (SEQ ID NO: 139) or SINGRGDDTRYADSVKG (SEQ ID NO: 140)<br>HCDR3: GRSVSRS (SEQ ID NO: 141) | N/A |
| Ablynx PMP6G8 | AVQLVESGGGLVQPGGSLRLTCTASGFT FRSFGMSWVRQAPGKDQEWVSAISADS STKNYADSVKGRFTISRDNAKKMLYLE MNSLKPEDTAVYYCVIGRGSPSSPGTQV TVSS (SEQ ID NO: 142)<br>HCDR1: SFGMS (SEQ ID NO: 122) or GFTFRSFGMS (SEQ ID NO: 128)<br>HCDR2: AISADSSTKN (SEQ ID NO: 143) or AISADSSTKNYADSVKG (SEQ ID NO: 144)<br>HCDR3: GRGSP (SEQ ID NO: 145) | N/A |
| Ablynx PMP6A5 | QVQLAESGGGLVQPGGSLRLTCTASGFT FGSFGMSWVRQAPGEGLEWVSAISADSS DKRYADSVKGRFTISRDNAKKMLYLEM NSLKSEDTAVYYCVIGRGSPASQGTQVT VSS (SEQ ID NO: 146)<br>HCDR1: SFGMS (SEQ ID NO: 122) or GFTFGSFGMS (SEQ ID NO: 147)<br>HCDR2: AISADSSDKR (SEQ ID NO: 148) or AISADSSDKRYADSVKG (SEQ ID NO: 149)<br>HCDR3: GRGSP (SEQ ID NO: 145) | N/A |
| Ablynx PMP6G7 | QVQLVESGGGLVQPGGSLRLSCAASGFT FSNYWMYWVRVAPGKGLERISRDISTG GGYSYYADSVKGRFTISRDNAKNTLYLQ MNSLKPEDTALYYCAKDREAQVDTLDF DYRGQGTQVTVSS (SEQ ID NO: 150)<br>HCDR1: NYWMY (SEQ ID NO: 151) or GFTFSNYWMY (SEQ ID NO: 152)<br>HCDR2: RDISTGGGYSY (SEQ ID NO: 153) or RDISTGGGYSYYADSVKG (SEQ ID NO: 154)<br>HCDR3: DREAQVDTLDFDY (SEQ ID NO: 155) | N/A |
| Ablynx PMP6A8 | AVQLVESGGGLVQGGGSLRLACAASERI FDLNLMGWYRQGPGNERELVATCITVG DSTNYADSVKGRFTISMDYTKQTVYLH MNSLRPEDTGLYYCKIRRTWHSELWGQ GTQVTVSS (SEQ ID NO: 156)<br>HCDR1: LNLMG (SEQ ID NO: 157) or SERIFDLNLMG (SEQ ID NO: 158) | N/A |

TABLE 3-continued

Sequences of Exemplary Third Antigen-Binding Sites

| Antigen-Binding Site | VH and HCDRs | VL and LCDRs |
|---|---|---|
| | HCDR2: TCITVGDSTN (SEQ ID NO: 159) or TCITVGDSTNYADSVKG (SEQ ID NO: 160)<br>HCDR3: RRTWHSEL (SEQ ID NO: 161) | |
| Ablynx PMP6C1 | EVQLVESGGGLVQEGGSLRLACAASERI WDINLLGWYRQGPGNERELVATITVGD STSYADSVKGRFTISRDYDKNTLYLQMN SLRPEDTGLYYCKIRRTWHSELWGQGT QVTVSS (SEQ ID NO: 162)<br>HCDR1: INLLG (SEQ ID NO: 163) or SERIWDINLLG (SEQ ID NO: 164)<br>HCDR2: TITVGDSTS (SEQ ID NO: 165) or TITVGDSTSYADSVKG (SEQ ID NO: 166)<br>HCDR3: RRTWHSEL (SEQ ID NO: 161) | N/A |
| Harpoon mAb-1 | EVQLVESGGGLVQPGNSLRLSCAASGFT FSKFGMSWVRQAPGKGLEWVSSISGSGR DTLYAESVKGRFTISRDNAKTTLYLQMN SLRPEDTAVYYCTIGGSLSVSSQGTLVTV SS (SEQ ID NO: 177)<br>HCDR1: GFTFSKFGMS (SEQ ID NO: 178)<br>HCDR2: SISGSGRDTLYAESVK (SEQ ID NO: 179)<br>HCDR3: GGSLSV (SEQ ID NO: 180) | N/A |
| Harpoon mAb-2 | EVQLVESGGGLVQPGNSLRLSCAASGFT FSRFGMSWVRQAPGKGLEWVSSISGSGS DTLYAESVKGRFTISRDNAKTTLYLQMN SLRPEDTAVYYCTIGGSLSRSSQGTLVTV SS (SEQ ID NO: 181)<br>HCDR1: GFTFSRFGMS (SEQ ID NO: 182)<br>HCDR2: SISGSGSDTLYAESVK (SEQ ID NO: 183)<br>HCDR3: GGSLSR (SEQ ID NO: 126) | N/A |
| Harpoon mAb-3 | EVQLVESGGGLVQPGNSLRLSCAASGFT FSKFGMSWVRQAPGKGLEWVSSISGSGT DTLYAESVKGRFTISRDNAKTTLYLQMN SLRPEDTAVYYCTIGGSLSRSSQGTLVTV SS (SEQ ID NO: 184)<br>HCDR1: GFTFSKFGMS (SEQ ID NO: 178)<br>HCDR2: SISGSGTDTLYAESVK (SEQ ID NO: 185)<br>HCDR3: GGSLSR (SEQ ID NO: 126) | N/A |
| Domantis DOM7h-22 | EVQLLESGGGLVQPGGSLRLSCAASGFT FSKYWMSWVRQAPGKGLEWVSSIDFM GPHTYYADSVKGRFTISRDNSKNTLYLQ MNSLRAEDTAVYYCAKGRTSMLPMKG KFDYWGQGTLVTVSS (SEQ ID NO: 283) | N/A |
| Domantis DOM7h-26 | EVQLLESGGGLVQPGGSLRLSCTASGFT FDEYNMSWVRQAPGKGLEWVSTILPHG DRTYYADSVKGRFTISRDNSKNTLYLQM NSLRAEDTAVYYCAKQDPLYRFDYWGQ GTLVTVSS (SEQ ID NO: 284) | |
| Domantis DOM7h-2 | N/A | DIQMTQSPSSLSASVGDRVTITCRAS QKIATYLNWYQQKPGKAPKLLIYR SSSLQSAVPSRFSGSGSGTVFTLTISS LQPEDFATYYCQQTYAVPPTFGQG TKVEIKR (SEQ ID NO: 285) |
| Domantis DOM7h-8 | N/A | DIQMTQSPSSLSASVGDRVTITCRAS QSISSYLNWYQQKPGKAPKLLIYRN SPLQSGVPSRFSGSGSGTDFTLTISSL QPEDFATYYCQQTYRVPPTFGQGT KVEIKR (SEQ ID NO: 286) |

TABLE 3-continued

Sequences of Exemplary Third Antigen-Binding Sites

| Antigen-Binding Site | VH and HCDRs | VL and LCDRs |
|---|---|---|
| MSA21 | QVQLQESGGGLVQPGGSLRLSCEASGFT FSRFGMTWVRQAPGKGVEWVSGISSLG DSTLYADSVKGRFTISRDNAKNTLYLQM NSLKPEDTAVYYCTIGGSLNPGGQGTQV TVSS (SEQ ID NO: 287) | N/A |
| UCB mAb-1 | EVQLLESGGGLVQPGGSLRLSCAVSGID LSNYAINWVRQAPGKCLEWIGIIWASGT TFYATWAKGRFTISRDNSKNTVYLQMN SLRAEDTAVYYCARTVPGYSTAPYFDL WGQGTLVTVSS (SEQ ID NO: 288) | DIQMTQSPSSVSASVGDRVTITCQSS PSVWSNFLSWYQQKPGKAPKLLIY EASKLTSGVPSRFSGSGSGTDFTLTI SSLQPEDFATYYCGGGYSSISDTTF GCGTKVEIKRT (SEQ ID NO: 289) |
| UCB mAb-2 | EVQLLESGGGLVQPGGSLRLSCAVSGID LSNYAINWVRQAPGKGLEWIGIIWASGT TFYATWAKGRFTISRDNSKNTVYLQMN SLRAEDTAVYYCARTVPGYSTAPYFDL WGQGTLVTVSS (SEQ ID NO: 290) | DIQMTQSPSSVSASVGDRVTITCQSS PSVWSNFLSWYQQKPGKAPKLLIY EASKLTSGVPSRFSGSGSGTDFTLTI SSLQPEDFATYYCGGGYSSISDTTF GGGTKVEIKRT (SEQ ID NO: 291) |

Where the VL and LCDR sequences are noted as "N/A," the antigen-binding site is an sdAb having a VH (e.g., VHH) only. Where the VH and HCDR sequences are noted as "N/A," the antigen-binding site is an sdAb having a VL only.

In certain embodiments, the third antigen-binding site comprises a VH comprising complementarity determining regions HCDR1, HCDR2, and HCDR3, and a VL comprising complementarity determining regions LCDR1, LCDR2, and LCDR3. In certain embodiments, the VH comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to the VH of an antibody provided in Table 3, and the VL comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to the VL of the antibody provided in Table 3. In certain embodiments, the VH comprises the HCDR1, HCDR2, and HCDR3 sequences of the antibody provided in Table 3, and the VL comprises the LCDR1, LCDR2, and LCDR3 sequences of the antibody provided in Table 3. In certain embodiments, the VH comprises the amino acid sequence of the VH of an antibody provided in Table 3, and the VL comprises the amino acid sequence of the VL of the antibody provided in Table 3.

In other embodiments, the third antigen-binding site comprises an sdAb comprising a VH comprising complementarity determining regions HCDR1, HCDR2, and HCDR3. In certain embodiments, the VH comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to the VH of an sdAb antibody provided in Table 3. In certain embodiments, the VH comprises the HCDR1, HCDR2, and HCDR3 sequences of the antibody provided in Table 3. In certain embodiments, the VH comprises the amino acid sequence of the VH of an sdAb provided in Table 3.

In certain embodiments, the VH of the third antigen-binding site comprises an amino acid sequence at least 60% (e.g., at least 70%, at least 80%, at least 85%, at least 90%, at least 91%, at least 92%, at least 93%, at least 94%, at least 95%, at least 96%, at least 97%, at least 98%, or at least 99%) identical to SEQ ID NO: 121. In certain embodiments, the VH comprises HCDR1, HCDR2, and HCDR3 sequences set forth in SEQ ID NOs: 122 or 123, 124 or 125, and 126, respectively. In certain embodiments, the VH comprises HCDR1, HCDR2, and HCDR3 sequences set forth in SEQ ID NOs: 122, 125, and 126, respectively. In certain embodiments, the VH comprises HCDR1, HCDR2, and HCDR3 sequences set forth in SEQ ID NOs: 123, 124, and 126, respectively. In certain embodiments, the VH comprises the amino acid sequence set forth in SEQ ID NO: 121.

In certain embodiments, the third antigen-binding site competes for binding serum albumin (e.g., HSA) with an antibody or antigen-binding fragment thereof comprising the VH, VL and/or scFv sequences provided in Table 3.

In certain embodiments, the third antigen-binding site of the multi-specific binding protein binds serum albumin (e.g., HSA) with a dissociation constant ($K_D$) of about 0.1 nM-about 100 μM. The $K_D$ can be measured by a method known in the art. In certain embodiments, the $K_D$ is measured by SPR to serum albumin or a fragment thereof immobilized on a chip.

In certain embodiments, the third antigen-binding site binds serum albumin with a $K_D$ of lower than or equal to 20 nM, 15 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 90 pM, 80 pM, 70 pM, 60 pM, 50 pM, 40 pM, 30 pM, 20 pM, or 10 pM. For example, in certain embodiments, the third antigen-binding site binds serum albumin with a $K_D$ of about 10 pM-about 1 nM, about 10 pM-about 0.9 nM, about 10 pM-about 0.8 nM, about 10 pM-about 0.7 nM, about 10 pM-about 0.6 nM, about 10 pM-about 0.5 nM, about 10 pM-about 0.4 nM, about 10 pM-about 0.3 nM, about 10 pM-about 0.2 nM, about 10 pM-about 0.1 nM, about 10 pM-about 50 pM, 0.1 nM-about 10 nM, about 0.1 nM-about 9 nM, about 0.1 nM-about 8 nM, about 0.1 nM-about 7 nM, about 0.1 nM-about 6 nM, about 0.1 nM-about 5 nM, about 0.1 nM-about 4 nM, about 0.1 nM-about 3 nM, about 0.1 nM-about 2 nM, about 0.1 nM-about 1 nM, about 0.1 nM-about 0.5 nM, about 0.5 nM-about 10 nM, about 1 nM-about 10 nM, about 2 nM-about 10 nM, about 3 nM-about 10 nM, about 4 nM-about 10 nM, about 5 nM-about 10 nM, about 6 nM-about 10 nM, about 7 nM-about 10 nM, about 8 nM-about 10 nM, about 9 nM-about 10 nM, about 1 nM-about 15 nM, about 2 nM-about 15 nM, about 3 nM-about 15 nM, about 4 nM-about 15 nM, about 5 nM-about 15 nM, about 6 nM-about 15 nM, about 7 nM-about 15 nM, about 8 nM-about 15 nM, about 9 nM-about 15 nM, about 10 nM-about 15 nM, about 11 nM-about 15 nM, about 12 nM-about 15 nM, about 13 nM-about 15 nM, about 14 nM-about 15 nM, about 1 nM-about 20 nM, about 2 nM-about 20 nM, about 3 nM-about 20 nM, about 4 nM-about 20 nM, about 5 nM-about 20 nM, about 6 nM-about 20 nM, about 7 nM-about 20 nM, about 8 nM-about 20 nM, about 9 nM-about 20 nM, about 10 nM-about 20 nM, about 11 nM-about 20 nM, about 12 nM-about 20 nM, about 13 nM-about 20 nM, about 14 nM-about 20 nM, about 15 nM-about 20 nM, about 16 nM-about 20 nM, about 17 nM-about 20 nM, about 18 nM-about 20 nM, or about 19 nM-about 20 nM.

In certain embodiments, the third antigen-binding site binds serum albumin with a $K_D$ greater than or equal to 10 nM, 20 nM, 30 nM, 40 nM, 50 nM, 60 nM, 70 nM, 80 nM, 90 nM, or 100 nM. In certain embodiments, the third antigen-binding site binds serum albumin with a $K_D$ of about 10 nM-about 1000 nM, about 10 nM-about 900 nM, about 10 nM-about 800 nM, about 10 nM-about 700 nM, about 10 nM-about 600 nM, about 10 nM-about 500 nM, about 10 nM-about 400 nM, about 10 nM-about 300 nM, about 10 nM-about 200 nM, about 10 nM-about 100 nM, about 10 nM-about 50 nM, about 50 nM-about 1000 nM, about 100 nM-about 1000 nM, about 200 nM-about 1000 nM, about 300 nM-about 1000 nM, about 400 nM-about 1000 nM, about 500 nM-about 1000 nM, about 600 nM-about 1000 nM, about 700 nM-about 1000 nM, about 800 nM-about 1000 nM, or about 900 nM-about 1000 nM.

It is understood that the binding affinity to serum albumin of the third antigen-binding site alone may be different from the binding affinity of the same antigen-binding site in the context of the multi-specific binding protein disclosed herein, possibly due to the conformational restraint from the other domains. The context-dependent binding affinity is described in subsection I.G titled "Binding Affinity."

In certain embodiments, the third antigen-binding site has a melting temperature of at least 50° C., at least 55° C., at least 56° C., at least 57° C., at least 58° C., at least 59° C., at least 60° C., at least 61° C., at least 62° C., at least 63° C., at least 64° C., at least 65° C., at least 70° C., at least 75° C., or at least 80° C. In certain embodiments, the third antigen-binding site has a melting temperature in the range of 50-80° C., 50-70° C., 50-65° C., 50-60° C., 50-55° C., 55-70° C., 55-65° C., 55-60° C., 56-65° C., 56-60° C., 57-65° C., 57-60° C., 58-65° C., 58-60° C., 59-65° C., 59-60° C., 60-80° C., 60-75° C., 60-70° C., 60-65° C., 65-80° C., 65-75° C., 65-70° C., 70-80° C., or 70-75° C.

D. Humanization and Deimmunization

The first, second, and/or third antigen-binding sites of the multi-specific binding protein disclosed herein may be humanized, for example, from one or more antigen-binding sites disclosed above, to optimize the immunogenicity and binding properties of the multi-specific binding protein, thereby enhancing the therapeutic index of the multi-specific binding protein.

"Humanized" antibodies or fragments thereof (e.g., Fv, Fab, Fab', F(ab')2, sdAb, scFv or other antigen-binding subsequences of antibodies) contain mostly human sequences but also (a) minimal sequence(s) derived from non-human immunoglobulin(s). For the most part, humanized antibodies are human immunoglobulins (recipient antibody) in which residues from one or more hypervariable regions (CDRs) of the recipient are replaced by residues from one or more hypervariable region of a non-human species (donor antibody) such as rodent (e.g., mouse, rat, or hamster), rabbit, or camelid (e.g., llama) having the desired specificity, affinity, and capacity. In some instances, Fv framework region (FR) residues of the human immunoglobulin are replaced by corresponding non-human residues. Furthermore, "humanized antibodies" as used herein may also comprise residues which are found neither in the recipient antibody nor the donor antibody. These modifications are made to further refine and optimize antibody performance. The humanized antibody may also comprise at least a portion of an immunoglobulin constant region (Fc), typically that of a human immunoglobulin. For further details, see Jones et al. (1986) Nature, 321:522-25; Reichmann et al. (1988) Nature, 332:323-29; and Presta (1992) Curr. Op. Struct. Biol., 2:593-96.

Humanized antibodies may be produced using transgenic animals such as mice that express human heavy and light chain genes, but are incapable of expressing the endogenous mouse immunoglobulin heavy and light chain genes. Winter describes an exemplary CDR grafting method that may be used to prepare the humanized antibodies described herein (see, U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

A humanized antibody can be optimized by the introduction of conservative substitutions, consensus sequence substitutions, germline substitutions and/or back mutations. Such altered immunoglobulin molecules can be made by any of several techniques known in the art, (e.g., Teng et al., Proc. Natl. Acad. Sci. U.S.A., 80:7308-7312, 1983; Kozbor et al., Immunology Today, 4:7279, 1983; Olsson et al., Meth. Enzymol, 92:3-16, 1982, and EP 239 400).

An antibody or fragment thereof may also be modified by specific deletion of human T cell epitopes in a process called "deimmunization." Methods of deimmunization have been disclosed, for example, in WO1998052976A1 or WO2000034317A2. Briefly, the heavy and light chain variable domains of an antibody can be analyzed for peptides that bind to MHC class II; these peptides represent potential T cell epitopes. For detection of potential T cell epitopes, a computer modeling approach termed "peptide threading" can be applied, and in addition a database of human MHC class II binding peptides can be searched for motifs present in the VH and VL sequences. These motifs bind to any of the 18 major MHC class II DR allotypes, and thus constitute potential T cell epitopes. Potential T cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. Human germline sequences are disclosed e.g., in Tomlinson, et al. (1992) J. Mol. Biol. 227:776-798; Cook, G. P. et al. (1995) Immunol. Today Vol. 16 (5): 237-242; and Tomlinson et al. (1995) EMBO J. 14:4628-38. The V BASE directory provides a comprehensive directory of human immunoglobulin variable region sequences (compiled by Tomlinson, L A. et al. MRC Centre for Protein Engineering, Cambridge, UK). These sequences can be used as a source of human sequence, e.g., for framework regions and CDRs. Consensus human framework regions can also be used, for example as described in U.S. Pat. No. 6,300,064.

E. Construct Formats

The first, second, and third antigen-binding sites may take various forms. In certain embodiments, the first, second, and/or third antigen-binding sites comprises two antibody variable domains (e.g., a VH and a VL). The VH and the VL can be mutated to introduce a disulfide bond (e.g., between H44 and L100) that stabilizes the antigen-binding site (see, Zhao et al. (2010) Int. J. Mol. Sci., 12 (1): 1-11). In certain embodiments, the first, second, and/or third antigen-binding sites comprises a single antibody variable domain (e.g., an sdAb).

In an antigen-binding site that contains a VH and a VL, the VH and the VL can be linked to form an scFv. The VH can be positioned N-terminal or C-terminal to the VL. The VH and the VL are typically linked through a linker, such as a peptide linker. Exemplary sequences of peptide linkers are provided in subsection I.F titled "Linkers." In certain embodiments, the VH of an antigen-binding domain is connected to the VL of the antigen-binding domain through a peptide linker having an amino acid sequence listed in Table 4. In particular embodiments, the VH of an antigen-binding domain is connected to the VL of the antigen-binding domain through a peptide linker having the amino acid sequence of SEQ ID NO: 298, 299, or 302, wherein the VH is positioned N-terminal to the VL. In other particular embodiments, the VH of an antigen-binding domain is connected to the VL of the antigen-binding domain through a peptide linker having the amino acid sequence of SEQ ID NO: 298, 299, or 302, wherein the VH is positioned C-terminal to the VL.

Alternatively, the VH and the VL may be present on separate polypeptide chains, and the formation of a VH-VL complex may be facilitated by additional domains, such as antibody constant regions CH1 and CL. Accordingly, in certain embodiments, the multi-specific binding protein comprises an Fab comprising a VH and a VL disclosed herein.

In certain embodiments, a multi-specific binding protein of the present invention comprises a first antigen-binding site comprising a single antibody variable domain, a second antigen-binding site comprising a single antibody variable domain, and a third antigen-binding site comprising a single antibody variable domain. In certain embodiments, the multi-specific binding protein comprises a first antigen-binding site in an sdAb format, a second antigen-binding site in an sdAb format, and a third antigen-binding site in an sdAb format.

In certain embodiments, a multi-specific binding protein of the present invention comprises a first antigen-binding site comprising a single antibody variable domain, a second antigen-binding site comprising a single antibody variable domain, and a third antigen-binding site comprising two antibody variable domains. In certain embodiments, the multi-specific binding protein comprises a first antigen-binding site in an sdAb format, a second antigen-binding site in an sdAb format, and a third antigen-binding site in an scFv format.

In certain embodiments, a multi-specific binding protein of the present invention comprises a first antigen-binding site comprising a single antibody variable domain, a second antigen-binding site comprising two antibody variable domains, and a third antigen-binding site comprising a single antibody variable domain. In certain embodiments, the multi-specific binding protein comprises a first antigen-binding site in an sdAb format, a second antigen-binding site in an scFv format, and a third antigen-binding site in an sdAb format.

In certain embodiments, a multi-specific binding protein of the present invention comprises a first antigen-binding site comprising a single antibody variable domain, a second antigen-binding site comprising two antibody variable domains, and a third antigen-binding site comprising two antibody variable domains. In certain embodiments, the multi-specific binding protein comprises a first antigen-binding site in an sdAb format, a second antigen-binding site in an scFv format, and a third antigen-binding site in an scFv format.

In certain embodiments, a multi-specific binding protein of the present invention comprises a first antigen-binding site comprising two antibody variable domains, a second antigen-binding site comprising a single antibody variable domain, and a third antigen-binding site comprising a single antibody variable domain. In certain embodiments, the multi-specific binding protein comprises a first antigen-binding site in an scFv format, a second antigen-binding site in an sdAb format, and a third antigen-binding site in an sdAb format.

In certain embodiments, a multi-specific binding protein of the present invention comprises a first antigen-binding site comprising two antibody variable domains, a second antigen-binding site comprising a single antibody variable domain, and a third antigen-binding site comprising two antibody variable domains. In certain embodiments, the multi-specific binding protein comprises a first antigen-binding site in an scFv format, a second antigen-binding site in an sdAb format, and a third antigen-binding site in an scFv format.

In certain embodiments, a multi-specific binding protein of the present invention comprises a first antigen-binding site comprising two antibody variable domains, a second antigen-binding site comprising two antibody variable domains, and a third antigen-binding site comprising a single antibody variable domain. In certain embodiments, the multi-specific binding protein comprises a first antigen-binding site in an scFv format, a second antigen-binding site in an scFv format, and a third antigen-binding site in an sdAb format.

In certain embodiments, a multi-specific binding protein of the present invention comprises a first antigen-binding site comprising two antibody variable domains, a second antigen-binding site comprising two antibody variable domains, and a third antigen-binding site comprising two antibody variable domains. In certain embodiments, the multi-specific binding protein comprises a first antigen-binding site in an scFv format, a second antigen-binding site in an scFv format, and a third antigen-binding site in an scFv format.

The three antigen-binding sites of the multi-specific binding protein can be linked in any one of the following orientations in an amino-to-carboxyl direction:
 (i) the first antigen-binding site (CD19 binding domain)-the second antigen-binding site (CD3 binding domain)-the third antigen-binding site (serum albumin binding domain);
 (ii) the first antigen-binding site (CD19 binding domain)-the third antigen-binding site (serum albumin binding domain)-the second antigen-binding site (CD3 binding domain);

(iii) the second antigen-binding site (CD3 binding domain)-the first antigen-binding site (CD19 binding domain)-the third antigen-binding site (serum albumin binding domain);
(iv) the second antigen-binding site (CD3 binding domain)-the third antigen-binding site (serum albumin binding domain)-the first antigen-binding site (CD19 binding domain);
(v) the third antigen-binding site (serum albumin binding domain)-the first antigen-binding site (CD19 binding domain)-the second antigen-binding site (CD3 binding domain); and
(vi) the third antigen-binding site (serum albumin binding domain)-the second antigen-binding site (CD3 binding domain)-the first antigen-binding site (CD19 binding domain), wherein the dashes above represent a peptide bond and/or a linker (e.g., peptide linker).

In certain embodiments, the third antigen-binding site is not positioned between the first antigen-binding site and the second antigen-binding site. In certain embodiments, the third antigen-binding site is positioned N-terminal to both the first antigen-binding site and the second antigen-binding site or C-terminal to both the first antigen-binding site and the second antigen-binding site. In certain embodiments, the third antigen-binding site is positioned N-terminal to both the first antigen-binding site and the second antigen-binding site. In certain embodiments, the third antigen-binding site is positioned C-terminal to both the first antigen-binding site and the second antigen-binding site.

The position (N-terminal or C-terminal) of one antigen-binding site relative to another is determined under the definitions of "N-terminal" and "C-terminal" as known in the art if a single polypeptide chain comprises both antigen-binding sites. It is understood that if an antigen-binding site comprises two separate polypeptide chains, its position (N-terminal or C-terminal) relative to another antigen-binding site (either having a single polypeptide chain or two polypeptide chains) can be similarly determined if a single polypeptide chain comprises at least one polypeptide chain of the former and at least one polypeptide chain of the latter. It is further understood that if antigen-binding site A is N-terminal to antigen-binding site B and antigen-binding site B is N-terminal to antigen-binding site C, it is deemed that antigen-binding site A is positioned N-terminal to antigen-binding site C even if antigen-binding sites A and C are not present in any single, common polypeptide chain. More complex structures of multi-specific binding proteins are also contemplated, some of which may have orientations difficult to characterize using the terms of "N-terminal" and "C-terminal" as described above due to, for example, different relative positions of two antigen-binding sites on one polypeptide chain versus another polypeptide chain, or the presence of a loop structure.

According to the present invention, the multi-specific binding proteins and its constituent binding domains are in the form of one or more polypeptides. Such polypeptides may include proteinaceous parts and non-proteinaceous parts (e.g., chemical linkers or chemical cross-linking agents such as glutaraldehyde). In certain embodiments, a multi-specific binding protein of the present invention includes a first antigen-binding site, a second antigen-binding site, and a third antigen-binding site, all of which are linked together to form a single polypeptide chain. In certain embodiments, the first, second, and third antigen-binding sites take the forms of scFv and/or sdAb, for example, in a combination as described above, to form a single polypeptide chain.

F. Linkers

As noted above, the antigen-binding sites of the multi-specific binding proteins of the present invention can be linked through a peptide bond or a linker (e.g., peptide linker). In certain embodiments, at least two adjacent antigen-binding sites are connected by a linker (e.g., peptide linker). In certain embodiments, each two adjacent antigen-binding sites are connected by a linker (e.g., peptide linker).

In certain embodiments, the three antigen-binding sites of the multi-specific binding protein can be linked by linkers (e.g., peptide linkers) denoted as $L_1$ and $L_2$ in any one of the following orientations in an amino-to-carboxyl direction:
(i) the first antigen-binding site (CD19 binding domain)-$L_1$-the second antigen-binding site (CD3 binding domain)-$L_2$-the third antigen-binding site (serum albumin binding domain);
(ii) the first antigen-binding site (CD19 binding domain)-$L_1$-the third antigen-binding site (serum albumin binding domain)-$L_2$-the second antigen-binding site (CD3 binding domain);
(iii) the second antigen-binding site (CD3 binding domain)-$L_1$-the first antigen-binding site (CD19 binding domain)-$L_2$-the third antigen-binding site (serum albumin binding domain);
(iv) the second antigen-binding site (CD3 binding domain)-$L_1$-the third antigen-binding site (serum albumin binding domain)-$L_2$-the first antigen-binding site (CD19 binding domain);
(v) the third antigen-binding site (serum albumin binding domain)-$L_1$-the first antigen-binding site (CD19 binding domain)-$L_2$-the second antigen-binding site (CD3 binding domain); and
(vi) the third antigen-binding site (serum albumin binding domain)-$L_1$-the second antigen-binding site (CD3 binding domain)-$L_2$-the first antigen-binding site (CD19 binding domain). It is appreciated that in a given construct, either $L_1$ or $L_2$ may be replaced with a peptide bond.

It is understood that if a single polypeptide chain comprises two adjacent antigen-binding sites, the peptide linker connecting the two antigen-binding sites represents the amino acid sequence between them. If an antigen-binding site comprises two separate polypeptide chains, one of which is present in a single, common polypeptide as an adjacent antigen-binding site or a polypeptide chain thereof, the peptide linker connecting the two antigen-binding sites represents the amino acid sequence between them in the common, single polypeptide.

In certain embodiments, the linkers $L_1$ and $L_2$ are peptide linkers. Suitable lengths of $L_1$ and $L_2$ can be independently selected. For example, in certain embodiments, $L_1$ and/or $L_2$ are about 50 or less amino acid residues in length. In certain embodiments, $L_1$ consists of about 50 or less amino acid residues. In certain embodiments, $L_1$ consists of about 20 or less amino acid residues. In certain embodiments, $L_2$ consists of about 50 or less amino acid residues. In certain embodiments, $L_2$ consists of about 20 or less amino acid residues. In certain embodiments, $L_1$ and $L_2$ independently consist of about 50 or less amino acid residues. In certain embodiments, $L_1$ and $L_2$ independently consist of about 20 or less amino acid residues.

In some embodiments, peptide linkers $L_1$ and $L_2$ have an optimized length and/or amino acid composition. In some embodiments, $L_1$ and $L_2$ are of the same length and have the same amino acid composition. In other embodiments, $L_1$ and $L_2$ are different. In certain embodiments, $L_1$ and/or $L_2$ are "short," i.e., consist of 1, 2, 3, 4, 5, 6, 7, 8, 9, 10, 11 or 12 amino acid residues. Thus, in certain instances, the linkers consist of about 12 or less amino acid residues. In certain embodiments, $L_1$ and/or $L_2$ are "long," e.g., consist of 15, 20 or 25 amino acid residues. In some embodiments, $L_1$ and/or $L_2$ consist of about 3 to about 15, for example 8, 9 or 10 contiguous amino acid residues.

Regarding the amino acid composition of $L_1$ and $L_2$, peptides are selected with properties that confer flexibility to multi-specific binding protein of the present invention, do not interfere with the binding domains as well as resist cleavage from proteases. For example, glycine and serine residues generally provide protease resistance. Examples of the linkers suitable for linking the domains in the multi-specific binding protein include but are not limited to $(GS)_n$, $(GGS)_n$, $(GGGS)_n$, $(GGSG)_n$, $(GGSGG)_n$, and $(GGGGS)_n$, wherein n is 1, 2, 3, 4, 5, 6, 7, 8, 9, 10, 11, 12, 13, 14, 15, 16, 17, 18, 19, or 20. In some embodiments, $L_1$ and/or $L_2$ are independently selected from the peptide sequences listed in table 4. In some embodiments, $L_1$ and/or $L_2$ are independently selected from SEQ ID NOs: 292, 293, 294, 295, 296, 297, 298, 299, 300, 301, or 302. In some embodiments, $L_1$ and/or $L_2$ are independently selected from SEQ ID NOs: 298, 299, and 302. In some embodiments, $L_1$ and/or $L_2$ comprise the amino acid sequence of SEQ ID NO: 298, 299, or 302. In some embodiments, $L_1$ and/or $L_2$ consist of the amino acid sequence of 298, 299, or 302. In some embodiments, $L_1$ and $L_2$ each comprise the amino acid sequence of SEQ ID NO: 298, 299, or 302. In some embodiments, $L_1$ and $L_2$ each consist of the amino acid sequence of SEQ ID NO: 298, 299, or 302.

TABLE 4

Sequences of Exemplary Peptide Linkers

| Linker | SEQ ID NO | Length | Amino Acid Sequence |
|---|---|---|---|
| $(GS)_{10}$ | 292 | 20 | GSGSGSGSGSGSGSGSGSGS |
| $(GGS)_{10}$ | 293 | 30 | GGSGGSGGSGGSGGSGGSGGSGGSGGSGGS |
| $(GGGS)_{10}$ | 294 | 40 | GGGSGGGSGGGSGGGSGGGSGGGSGGGSGGGSGGGSGGGS |
| $(GGSG)_{10}$ | 295 | 40 | GGSGGGSGGGSGGGSGGGSGGGSGGGSGGGSGGGSGGGSGGGSG GGSG |
| $(GGSGG)_{10}$ | 296 | 50 | GGSGGGSGGGSGGGSGGGSGGGSGGGSGGGSGGGSGG GGSGGGSGGGSGG |
| $(GGGGS)_{10}$ | 297 | 50 | GGGGSGGGGSGGGGSGGGGSGGGGSGGGGSGGGGSGGGGS GGGGSGGGGSGGGGS |
| $(GGGGS)_4$ | 298 | 20 | GGGGSGGGGSGGGGSGGGGS |
| $(GGGGS)_3$ | 299 | 15 | GGGGSGGGGSGGGGS |
| $(GGGGS)_{20}$ | 300 | 100 | GGGGSGGGGSGGGGSGGGGSGGGGSGGGGSGGGGSGGGGS GGGGSGGGGSGGGGSGGGGSGGGGSGGGGSGGGGSGGGGS GGGGSGGGGSGGGGSGGGGSGGGGSGGGGSGGGGS |
| $(GGSGG)_{20}$ | 301 | 100 | GGSGGGSGGGSGGGSGGGSGGGSGGGSGGGSGGGSGG GGSGGGSGGGSGGGSGGGSGGGSGGGSGGGSGGGSGG GGSGGGSGGGSGGGSGGGSGGGSGGGSGG |
| Assymetrical linker | 302 | 9 | GGGGSGGGS |

A linker, such as a peptide linker disclosed herein, can also be used to connect the VH and VL of an scFv, as mentioned in subsection I.E titled "Construct Formats."

G. Binding Affinity

In certain embodiments, the multi-specific binding protein binds CD19 (e.g., human CD19), CD3 (e.g., human CD3 and/or Macaca CD3), and/or serum albumin (e.g., HSA) with a $K_D$ of about 0.1 nM-about 100 μM. The $K_D$ can be measured by a method known in the art, such as by SPR or by flow cytometry as described in Example 5 below.

In certain embodiments, the multi-specific binding protein binds CD19, CD3, and/or serum albumin with a $K_D$ of lower than or equal to 20 nM, 15 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 90 pM, 80 pM, 70 pM, 60 pM, 50 pM, 40 pM, 30 pM, 20 pM, or 10 pM. For example, in certain embodiments, the multi-specific binding protein binds CD19, CD3, and/or serum albumin with a $K_D$ of about 10 pM-about 1 nM, about 10 pM-about 0.9 nM, about 10 pM-about 0.8 nM, about 10 pM-about 0.7 nM, about 10 pM-about 0.6 nM, about 10 pM nM-about 0.5 nM, about 10 pM-about 0.4 nM, about 10 pM-about 0.3 nM, about 10 pM-about 0.2 nM, about 10 pM-about 0.1 nM, about 10 pM-about 50 pM, 0.1 nM-about 10 nM, about 0.1 nM-about 9 nM, about 0.1 nM-about 8 nM, about 0.1 nM-about 7 nM, about 0.1 nM-about 6 nM, about 0.1 nM-about 5 nM, about 0.1 nM-about 4 nM, about 0.1 nM-about 3 nM, about 0.1 nM-about 2 nM, about 0.1 nM-about 1 nM, about 0.1 nM-about 0.5 nM, about 0.5 nM-about 10 nM, about 1 nM-about 10 nM, about 2 nM-about 10 nM, about 3 nM-about 10 nM, about 4 nM-about 10 nM, about 5 nM-about 10 nM, about 6 nM-about 10 nM, about 7 nM-about 10 nM, about 8 nM-about 10 nM, or about 9 nM-about 10 nM.

In certain embodiments, the multi-specific binding protein binds CD19, CD3, and/or serum albumin with a $K_D$ greater than or equal to 10 nM, 20 nM, 30 nM, 40 nM, 50 nM, 60 nM, 70 nM, 80 nM, 90 nM, or 100 nM. In certain embodiments, the multi-specific binding protein binds CD19, CD3, and/or serum albumin with a $K_D$ of about 10 nM-about 1000 nM, about 10 nM-about 900 nM, about 10 nM-about 800 nM, about 10 nM-about 700 nM, about 10 nM-about 600 nM, about 10 nM-about 500 nM, about 10 nM-about 400 nM, about 10 nM-about 300 nM, about 10 nM-about 200 nM, about 10 nM-about 100 nM, about 10 nM-about 50 nM, about 50 nM-about 1000 nM, about 100 nM-about 1000 nM, about 200 nM-about 1000 nM, about 300 nM-about 1000 nM, about 400 nM-about 1000 nM, about 500 nM-about 1000 nM, about 600 nM-about 1000 nM, about 700 nM-about 1000 nM, about 800 nM-about 1000 nM, or about 900 nM-about 1000 nM.

In certain embodiments, the $K_D$ of binding to CD19 or CD3 is measured in the absence of serum albumin (e.g., HSA). In certain embodiments, the $K_D$ of binding to CD19 or CD3 is measured in substantial absence of serum albumin (e.g., HSA). In certain embodiments, the $K_D$ of binding to CD19 or CD3 is measured in the presence of serum albumin (e.g., HSA), for example, in the presence of about 10 mg/mL, 15 mg/mL, 20 mg/mL, 25 mg/mL, 30 mg/mL, 35 mg/mL, 40 mg/mL, 45 mg/mL, or 50 mg/mL serum albumin (e.g., HSA).

In certain embodiments, the multi-specific binding protein of the present disclosure binds CD19, CD3, and/or serum albumin with a similar $K_D$ value to that of the respective antigen-binding site alone or a monoclonal antibody having the same antigen-binding site. In certain embodiments, the $K_D$ value of the multi-specific binding protein to CD19, CD3, and/or serum albumin is increased by no more than 1.5 fold, 2 fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, or 50 fold compared to that of the respective antigen-binding site alone or a monoclonal antibody having the same antigen-binding site.

In certain embodiments, the multi-specific binding protein of the present disclosure binds CD19 and/or CD3 with a similar $K_D$ value in the presence of serum albumin to that in the absence or substantial absence of serum albumin. In certain embodiments, the $K_D$ value of the multi-specific binding protein for binding CD19 and/or CD3 in the presence of serum albumin is increased by no more than 1.5 fold, 2 fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, or 50 fold compared to that in the absence or substantial absence of serum albumin.

H. Therapeutic Activities of the Constructs

The multi-specific binding protein disclosed herein is designed to simultaneously bind B cells and T cells. Recruitment of T cells facilitates lysis of the B cells involving cytolytic synapse formation and delivery of perforin and granzymes. The engaged T cells are capable of serial target cell lysis, and are not affected by immune escape mechanisms interfering with peptide antigen processing and presentation, or clonal T cell differentiation; see, for example, WO2007042261A2. Accordingly, binding of the multi-specific binding proteins to the target B cells destroys the target cells and/or impairs the progression of B cell related diseases.

Cytotoxicity mediated by multi-specific binding proteins of the invention can be measured in various ways in vitro. Effector cells can be e.g., stimulated enriched (human) CD8 positive T cells or unstimulated (human) peripheral blood mononuclear cells (PBMC). If the target cells are of macaque origin or express or are transfected with macaque target cell surface antigen which is bound by the first domain, the effector cells should also be of macaque origin such as a macaque T cell line, e.g., 4119LnPx. The target cells should express CD19, e.g., human or macaque CD19. The target cells can be a cell line (such as CHO) which is stably or transiently transfected with CD19. Alternatively, the target cells can be a cell line naturally expressing CD19, such as B lymphocytes. The effector to target cell (E:T) ratio is usually about 10:1, but can also vary. Killing of the target cells can be measured in a $^{51}$Cr-release assay (incubation time of about 18 hours) or in a in a FACS-based cytotoxicity assay (incubation time of about 48 hours). Other methods of measuring cell death are well-known to the skilled person, such as MTT or MTS assays, ATP-based assays including bioluminescent assays, the sulforhodamine B (SRB) assay, WST assay, clonogenic assay and the ECIS technology.

In certain embodiments, the cytotoxic activity mediated by the multi-specific binding protein disclosed herein is measured in a cell-based cytotoxicity assay described above. It is represented by the $EC_{50}$ value, which corresponds to the half maximal effective concentration (concentration of the multi-specific binding protein which induces a cytotoxic response halfway between the baseline and maximum). In certain embodiments, the $EC_{50}$ value of the multi-specific binding proteins is ≤5000 pM, for example, ≤4000 pM, ≤3000 pM, ≤2000 pM, ≤1000 pM, ≤500 pM, ≤400 pM, ≤300 pM, ≤200 pM, ≤100 pM, ≤50 pM, ≤20 pM, ≤10 pM, ≤5 pM, ≤4 pM, ≤3 pM, ≤2 pM, or ≤1 pM.

It is understood that an $EC_{50}$ value is generally lower when stimulated/enriched CD8$^+$ T cells are used as effector cells, compared with unstimulated PBMC. It is further understood that the $EC_{50}$ value is generally lower when the target cells express a high level of the target cell surface antigen compared with a low level of the target antigen. For example, when stimulated/enriched human $CD8^+$ T cells are used as effector cells (and either target cell surface antigen transfected cells such as CHO cells or target cell surface antigen positive human cell lines are used as target cells), the $EC_{50}$ value of multi-specific binding protein is ≤1000 pM, for example, ≤500 pM, ≤250 pM, ≤100 pM, 50 pM, ≤10 pM, or ≤5 pM. When human PBMCs are used as effector cells, the $EC_{50}$ value of the multi-specific binding protein is ≤5000 pM, for example, ≤4000 pM, ≤2000 pM, ≤1000 pM, ≤500 pM, ≤200 pM, ≤150 pM, ≤100 pM, ≤50 pM, ≤10 pM, or ≤5 pM. When a macaque T cell line such as LnPx4119 is used as effector cells, and a macaque target cell surface antigen transfected cell line such as CHO cells is used as target cell line, the $EC_{50}$ value of the multi-specific binding protein is ≤2000 pM, for example, ≤1500 pM, ≤1000 pM, ≤500 pM, ≤300 pM, ≤250 pM, ≤100 pM, ≤50 pM, ≤10 pM, or ≤5 pM.

Accordingly, in certain embodiments, the $EC_{50}$ value is measured using stimulated/enriched human $CD8^+$ T cells as effector cells. In certain embodiments, the $EC_{50}$ value is measured using human PBMCs as effector cells. In certain embodiments, the $EC_{50}$ value is measured using a macaque T cell line such as LnPx4119 as effector cells and cells (e.g., CHO cells) engineered to express macaque CD19 as target cells.

In certain embodiments, the multi-specific binding protein of the present invention does not induce or mediate lysis of cells that do not express CD19. The term "does not induce lysis" or "does not mediate lysis," or grammatical equivalents thereof, means that the multi-specific binding protein, at a concentration of up to 500 nM, does not induce or mediate lysis of more than 30%, for example, no more than 30%, 25%, 20%, 15%, 10%, 9%, 8%, 7%, 6% or 5% of cells that do not express CD19, whereby lysis of a cell line that expresses CD19 is set to be 100%.

In certain embodiments, a multi-specific binding protein disclosed herein is more effective in in killing CD19-expressing cells (e.g., cancer cells) than the corresponding respective anti-CD19 or anti-CD3 monoclonal antibody at the same molar concentration. In certain embodiments, the multi-specific binding protein is more effective in killing CD19-expressing cells (e.g., cancer cells) than a combination of the corresponding respective anti-CD19 and anti-CD3 monoclonal antibodies each at the same molar concentration.

The cytotoxic activity of the multi-specific binding protein can be measured in the presence or absence of serum albumin (e.g., HSA). In certain embodiments, the cytotoxic activity disclosed above is measured in the absence of serum albumin (e.g., HSA). In certain embodiments, the cytotoxic activity disclosed above is measured in substantial absence of serum albumin (e.g., HSA). In certain embodiments, the cytotoxic activity disclosed above is measured in the presence of serum albumin (e.g., HSA), for example, in the presence of about 10 mg/mL, 15 mg/mL, 20 mg/mL, 25 mg/mL, 30 mg/mL, 35 mg/mL, 40 mg/mL, 45 mg/mL, or 50 mg/mL serum albumin (e.g., HSA).

In certain embodiments, the multi-specific binding protein of the present disclosure kills CD19-expressing cells with a similar $EC_{50}$ value in the presence of serum albumin to that in the absence or substantial absence of serum albumin. In certain embodiments, the $EC_{50}$ value of the multi-specific binding protein for killing CD19-expressing cells in the presence of serum albumin is increased by no more than 1.5 fold, 2 fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, or 50 fold compared to that in the absence or substantial absence of serum albumin. It is understood that the presence of serum albumin (e.g., about 10 mg/mL, 15 mg/mL, 20 mg/mL, 25 mg/mL, 30 mg/mL, 35 mg/mL, 40 mg/mL, 45 mg/mL, or 50 mg/mL serum albumin) may also alter the $EC_{50}$ value of a multi-specific binding protein nonspecifically. The nonspecific effect can be assessed by comparing the $EC_{50}$ values of a control protein, which does not contain a serum albumin binding domain, in the presence and absence of serum albumin. In certain embodiments, the fold change is offset by the nonspecific effect of serum albumin on a control protein, such as a bispecific protein that binds CD19 and CD3.

I. Construct Size

In certain embodiments, the molecular weight of the multi-specific binding protein is from about 40 kD to about 100 kD. In certain embodiments, the molecular weight of the multi-specific binding protein is at least 60 kD, at least 65 kD, at least 70 kD, at least 75 kD, at least 80 kD, at least 85 kD, at least 90 kD, or at least 95 kD. It is understood that smaller size generally contributes to faster diffusion and tissue penetration, but size reduction may not be as critical for the purpose of treating the indications with substantial presence of target cells (e.g., cancer cells) in the blood.

In certain embodiments, the molecular weight of the multi-specific binding protein is from about 40 kD to about 90 kD, from about 40 kD to about 80 kD, from about 40 kD to about 70 kD, from about 40 kD to about 60 kD, from about 40 kD to about 50 kD, from about 50 kD to about 100 kD, from about 50 kD to about 90 kD, from about 50 kD to about 80 kD, from about 50 kD to about 70 kD, from about 50 kD to about 60 kD, from about 60 kD to about 100 kD, from about 60 kD to about 90 kD, from about 60 kD to about 80 kD, from about 60 kD to about 70 kD, from about 65 kD to about 100 kD, from about 65 kD to about 90 kD, from about 65 kD to about 80 kD, from about 65 kD to about 70 kD, from about 70 kD to about 100 kD, from about 70 kD to about 90 kD, from about 70 kD to about 80 kD, from about 80 kD to about 100 kD, from about 80 kD to about 90 kD, or from about 90 kD to about 100 kD. In certain embodiments, the multi-specific binding protein is lower than 40 kD. In certain embodiments, the multi-specific binding protein is about 50 kD–about 90 kD, about 50 kD–about 80 kD, about 50 kD–about 70 kD, about 50 kD–about 60 kD, about 60 kD–about 90 kD, about 60 kD–about 80 kD, about 60 kD–about 70 kD, about 65 kD–about 90 kD, about 65 kD–about 80 kD, about 65 kD–about 70 kD, about 70 kD–about 90 kD, or about 70 kD–about 80 kD.

J. Serum Half-Life

Fusion proteins have been developed to increase the in vivo half-life of a small protein, particularly an antibody fragment. For example, fusion with a heterodimeric antibody Fc region, such as an Fc with one or more mutations that extend the in vivo half-life, is described in U.S. Patent Application Publication Nos. US20140302037A1, US20140308285A1, and PCT Publication Nos. WO2014144722A2, WO2014151910A1 and WO2015048272A1. An alternative strategy is fusion with human serum albumin (HSA) or an HSA-binding peptide (see, e.g., PCT Publication Nos. WO2013128027A1 and WO2014140358A1). The neonatal Fc receptor (FcRn) appears to be involved in prolonging the life-span of albumin in circulation (see, Chaudhury et al. (2003) J. Exp. Med., 3:315-22). Albumin and IgG bind noncooperatively to distinct sites of FcRn and form a tri-molecular (see id.).

Binding of human FcRn to HSA and to human IgG is pH dependent, stronger at acidic pH and weaker at neutral or physiological pH (see id.). This observation suggests that proteins and protein complexes containing albumin, similar to those containing IgG (particularly Fc), are protected from degradation through pH-sensitive interaction with FcRn (see id.). Using surface plasmon resonance (SPR) to measure the capacity of individual HSA domains to bind immobilized soluble human FcRn, it has been shown that FcRn and albumin interact via the D-III domain of albumin in a pH-dependent manner, on a site distinct from the IgG binding site (see, Chaudhury et al. (2006) Biochemistry 45:4983-90 and PCT Publication No. WO2008068280A1).

The present disclosure provides multi-specific binding proteins with extended half-life. In certain embodiments, the multi-specific binding protein has a serum half-life of at least 24, 36, 48, 60, 72, 84, or 96 hours. In certain embodiments, the multi-specific binding protein has a serum half-life of at least about 50 hours. In certain embodiments, the multi-specific binding protein has a serum half-life of at least about 100 hours. Methods of measuring serum half-life are known in the art, and exemplary methods are described in Example 4. In certain embodiments, the serum half-life is measured in a non-human primate. In certain embodiments, the serum half-life is measured in human.

In certain embodiments, 50 hours after intravenous administration to a subject, the serum concentration of the multi-specific binding protein is at least 10%, at least 20%, at least 30%, at least 40%, at least 50%, at least 60%, at least 70%, at least 80%, or at least 90% of the serum concentration of the multi-specific binding protein 1 hour after the administration in said subject.

In certain embodiments, the multi-specific binding protein has a serum half-life that is at least 20% longer than a control multi-specific binding protein, wherein the control multi-specific binding protein includes a first domain identical to the first antigen-binding site of the multi-specific binding protein, a second domain identical to the second antigen-binding site of the multi-specific binding protein, but not a third domain identical or substantially identical to the third antigen-binding site of the multi-specific binding protein. In certain embodiments, the control multi-specific binding protein is identical to the multi-specific binding protein but for the absence of the third antigen-binding site. In certain embodiments, the serum half-life of the multi-specific binding protein is at least 30%, at least 40%, at least 50%, at least 60%, at least 70%, at least 80%, or at least 90% longer than the serum half-life of the control multi-specific binding protein. In certain embodiments, the serum half-life of the multi-specific binding protein is longer than the serum half-life of the control multi-specific binding protein by at least 2 fold, at least 3 fold, at least 4 fold, at least 5 fold, at least 6 fold, at least 7 fold, at least 8 fold, at least 9 fold, or at least 10 fold.

II. Methods of Preparation

The multi-specific binding proteins described above can be made using recombinant DNA technology well known to a skilled person in the art. For example, one or more isolated polynucleotides encoding the multi-specific binding protein can be ligated to other appropriate nucleotide sequences, including, for example, constant region coding sequences, and expression control sequences, to produce conventional gene expression constructs (i.e., expression vectors) encoding the desired multi-specific binding proteins. Production of defined gene constructs is within routine skill in the art.

Nucleic acids encoding desired multi-specific binding proteins can be incorporated (ligated) into expression vectors, which can be introduced into host cells through conventional transfection or transformation techniques. Exemplary host cells are E. coli cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the multi-specific binding proteins.

Specific expression and purification conditions will vary depending upon the expression system employed. For example, if a gene is to be expressed in E. coli, it is first cloned into an expression vector by positioning the engineered gene downstream from a suitable bacterial promoter, e.g., Trp or Tac, and a prokaryotic signal sequence. The expressed protein may be secreted. The expressed protein may accumulate in refractile or inclusion bodies, which can be harvested after disruption of the cells by French press or sonication. The refractile bodies then are solubilized, and the protein may be refolded and/or cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon. Optionally, the vector or gene construct may contain enhancers and introns. In embodiments involving fusion proteins comprising an antibody or portion thereof, the expression vector optionally contains sequences encoding all or part of a constant region, enabling an entire, or a part of, a heavy or light chain to be expressed. The gene construct can be introduced into eukaryotic host cells using conventional techniques.

The multi-specific binding protein disclosed herein may comprise a single polypeptide chain. In this instance, a host cell can be transfected with a single vector expressing the polypeptide (e.g., containing an expression control sequence operably linked to a nucleotide sequence encoding the polypeptide). Alternatively, multi-specific binding protein disclosed herein may comprise two or more polypeptides. In this instance, a host cell can be co-transfected with more than one expression vector, for example, one expression vector expressing each polypeptide. A host cell can also be transfected with a single expression vector that expresses the two or more polypeptides. For example, the coding sequences of the two or more polypeptides can be operably linked to different expression control sequences (e.g., promoter, enhancer, and/or internal ribosome entry site (IRES)). The coding sequences of the two or more polypeptides can also be separated by a ribosomal skipping sequence or self-cleaving sequence, such as a 2A peptide.

In certain embodiments, in order to express a multi-specific binding protein, an N-terminal signal sequence is included in the protein construct. Exemplary N-terminal signal sequences include signal sequences from interleukin-2, CD-5, IgG kappa light chain, trypsinogen, serum albumin, and prolactin.

After transfection, single clones can be isolated for cell bank generation using methods known in the art, such as limited dilution, ELISA, FACS, microscopy, or Clonepix. Clones can be cultured under conditions suitable for bioreactor scale-up and maintained expression of the multi-specific binding proteins.

The multi-specific binding proteins can be isolated and purified using methods known in the art including centrifugation, depth filtration, cell lysis, homogenization, freezethawing, affinity purification, gel filtration, ion exchange chromatography, hydrophobic interaction exchange chromatography, and mixed-mode chromatography.

III. Pharmaceutical Compositions

The present disclosure also features pharmaceutical compositions that contain a therapeutically effective amount of the multi-specific binding proteins described herein. The composition can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

In certain embodiments, a pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants (see, Remington's *Pharmaceutical Sciences,* 18th ed. (Mack Publishing Company, 1990).

In certain embodiments, a pharmaceutical composition may contain nanoparticles, e.g., polymeric nanoparticles, liposomes, or micelles (See Anselmo et al. (2016) BIOENG. TRANSL. MED. 1:10-29).

In certain embodiments, a pharmaceutical composition may contain a sustained- or controlled-delivery formulation. Techniques for formulating sustained- or controlled-delivery means, such as liposome carriers, bio-erodible microparticles or porous beads and depot injections, are also known to those skilled in the art. Sustained-release preparations may include, e.g., porous polymeric microparticles or semipermeable polymer matrices in the form of shaped articles, e.g., films, or microcapsules. Sustained release matrices may include polyesters, hydrogels, polylactides, copolymers of L-glutamic acid and gamma ethyl-L-glutamate, poly (2-hydroxyethyl-inethacrylate), ethylene vinyl acetate, or poly-D (−)-3-hydroxybutyric acid. Sustained release compositions may also include liposomes that can be prepared by any of several methods known in the art.

Pharmaceutical compositions containing a multi-specific binding protein disclosed herein can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, intrathecal and rectal administration. In certain embodiments, a recombinant human sialidase, a recombinant human sialidase fusion protein, or an antibody conjugate disclosed herein is administered by IV infusion. In certain embodiments, a recombinant human sialidase, a recombinant human sialidase fusion protein, or an antibody conjugate disclosed herein is administered by intratumoral injection. Useful formulations can be prepared by methods known in the pharmaceutical art. For example, see *Remington's Pharmaceutical Sciences,* 18th ed. (Mack Publishing Company, 1990). Formulation components suitable for parenteral administration include a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor® EL™ (BASF®, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

An intravenous drug delivery formulation may be contained in a syringe, pen, or bag. In certain embodiments, the bag may be connected to a channel comprising a tube and/or a needle. In certain embodiments, the formulation may be a lyophilized formulation or a liquid formulation. In certain embodiments, the formulation may freeze-dried (lyophilized) and contained in about 12-60 vials. In certain embodiments, the formulation may be freeze-dried and 45 mg of the freeze-dried formulation may be contained in one vial. In certain embodiments, the about 40 mg-about 100 mg of freeze-dried formulation may be contained in one vial. In certain embodiments, freeze dried formulation from 12, 27, or 45 vials are combined to obtained a therapeutic dose of the protein in the intravenous drug formulation. In certain embodiments, the formulation may be a liquid formulation and stored as about 250 mg/vial to about 1,000 mg/vial. In certain embodiments, the formulation may be a liquid formulation and stored as about 600 mg/vial. In certain embodiments, the formulation may be a liquid formulation and stored as about 250 mg/vial.

These compositions may be sterilized by conventional sterilization techniques, or may be sterile filtered. The resulting aqueous solutions may be packaged for use as-is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents. The composition in solid form can also be packaged in a container for a flexible quantity.

In certain embodiments, the present disclosure provides a formulation with an extended shelf life including the protein of the present disclosure, in combination with mannitol, citric acid monohydrate, sodium citrate, disodium phosphate dihydrate, sodium dihydrogen phosphate dihydrate, sodium chloride, polysorbate 80, water, and sodium hydroxide.

In certain embodiments, an aqueous formulation is prepared including the protein of the present disclosure in a pH-buffered solution. The buffer of this invention may have a pH ranging from about 4 to about 8, e.g., from about 4.5 to about 6.0, or from about 4.8 to about 5.5, or may have a pH of about 5.0 to about 5.2. Ranges intermediate to the above recited pH's are also intended to be part of this disclosure. For example, ranges of values using a combination of any of the above recited values as upper and/or lower limits are intended to be included. Examples of buffers that will control the pH within this range include acetate (e.g. sodium acetate), succinate (such as sodium succinate), gluconate, histidine, citrate and other organic acid buffers.

In certain embodiments, the formulation includes a buffer system which contains citrate and phosphate to maintain the pH in a range of about 4 to about 8. In certain embodiments the pH range may be from about 4.5 to about 6.0, or from about pH 4.8 to about 5.5, or in a pH range of about 5.0 to about 5.2. In certain embodiments, the buffer system includes citric acid monohydrate, sodium citrate, disodium phosphate dihydrate, and/or sodium dihydrogen phosphate dihydrate. In certain embodiments, the buffer system includes about 1.3 mg/ml of citric acid (e.g., 1.305 mg/ml), about 0.3 mg/ml of sodium citrate (e.g., 0.305 mg/ml), about 1.5 mg/ml of disodium phosphate dihydrate (e.g., 1.53 mg/ml), about 0.9 mg/ml of sodium dihydrogen phosphate dihydrate (e.g., 0.86), and about 6.2 mg/ml of sodium chloride (e.g., 6.165 mg/ml). In certain embodiments, the buffer system includes 1-1.5 mg/ml of citric acid, 0.25 to 0.5 mg/ml of sodium citrate, 1.25 to 1.75 mg/ml of disodium phosphate dihydrate, 0.7 to 1.1 mg/ml of sodium dihydrogen phosphate dihydrate, and 6.0 to 6.4 mg/ml of sodium chloride. In certain embodiments, the pH of the formulation is adjusted with sodium hydroxide.

A polyol, which acts as a tonicifier and may stabilize the multi-specific binding protein, may also be included in the formulation. The polyol is added to the formulation in an amount which may vary with respect to the desired isotonicity of the formulation. In certain embodiments, the aqueous formulation may be isotonic. The amount of polyol added may also be altered with respect to the molecular weight of the polyol. For example, a lower amount of a monosaccharide (e.g., mannitol) may be added, compared to a disaccharide (such as trehalose). In certain embodiments, the polyol which may be used in the formulation as a tonicity agent is mannitol. In certain embodiments, the mannitol concentration may be about 5 to about 20 mg/ml. In certain embodiments, the concentration of mannitol may be about 7.5 to 15 mg/ml. In certain embodiments, the concentration of mannitol may be about 10-14 mg/ml. In certain embodiments, the concentration of mannitol may be about 12 mg/ml. In certain embodiments, the polyol sorbitol may be included in the formulation.

A detergent or surfactant may also be added to the formulation. Exemplary detergents include nonionic detergents such as polysorbates (e.g., polysorbates 20, 80 etc.) or poloxamers (e.g., poloxamer 188). The amount of detergent added is such that it reduces aggregation of the formulated antibody and/or minimizes the formation of particulates in the formulation and/or reduces adsorption. In certain embodiments, the formulation may include a surfactant which is a polysorbate. In certain embodiments, the formulation may contain the detergent polysorbate 80 or Tween 80. Tween 80 is a term used to describe polyoxyethylene (20) sorbitanmonooleate (see Fiedler, Lexikon der Hifsstoffe, Editio Cantor Verlag Aulendorf, 4th edi., 1996). In certain embodiments, the formulation may contain between about 0.1 mg/mL and about 10 mg/mL of polysorbate 80, or between about 0.5 mg/mL and about 5 mg/mL. In certain embodiments, about 0.1% polysorbate 80 may be added in the formulation.

In embodiments, the protein product of the present disclosure is formulated as a liquid formulation. The liquid formulation may be presented at a 10 mg/mL concentration in either a USP/Ph Eur type I 50R vial closed with a rubber stopper and sealed with an aluminum crimp seal closure. The stopper may be made of elastomer complying with USP and Ph Eur. In certain embodiments, the liquid formulation may be diluted with 0.9% saline solution.

In certain embodiments, the liquid formulation of the disclosure may be prepared as a 10 mg/mL concentration solution in combination with a sugar at stabilizing levels. In certain embodiments the liquid formulation may be prepared in an aqueous carrier. In certain embodiments, a stabilizer may be added in an amount no greater than that which may result in a viscosity undesirable or unsuitable for intravenous administration. In certain embodiments, the sugar may be disaccharides, e.g., sucrose. In certain embodiments, the liquid formulation may also include one or more of a buffering agent, a surfactant, and a preservative.

In certain embodiments, the pH of the liquid formulation may be set by addition of a pharmaceutically acceptable acid and/or base. In certain embodiments, the pharmaceutically acceptable acid may be hydrochloric acid. In certain embodiments, the base may be sodium hydroxide.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

The multi-specific binding protein may be lyophilized to produce a lyophilized formulation including the proteins and a lyoprotectant. The lyoprotectant may be sugar, e.g., disaccharides. In certain embodiments, the lyoprotectant may be sucrose or maltose. The lyophilized formulation may also include one or more of a buffering agent, a surfactant, a bulking agent, and/or a preservative.

The amount of sucrose or maltose useful for stabilization of the lyophilized drug product may be in a weight ratio of at least 1:2 protein to sucrose or maltose. In certain embodiments, the protein to sucrose or maltose weight ratio may be of from 1:2 to 1:5. In certain embodiments, the pH of the formulation, prior to lyophilization, may be set by addition of a pharmaceutically acceptable acid and/or base. In certain embodiments the pharmaceutically acceptable acid may be hydrochloric acid. In certain embodiments, the pharmaceutically acceptable base may be sodium hydroxide. Before lyophilization, the pH of the solution containing the protein of the present disclosure may be adjusted between 6 to 8. In certain embodiments, the pH range for the lyophilized drug product may be from 7 to 8.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The specific dose can be a uniform dose for each patient, for example, 50-5,000 mg of protein. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., *Clinica Chimica Acta* 308:43-53, 2001; Steimer et al., *Clinica Chimica Acta* 308:33-41, 2001).

In general, dosages based on body weight are from about 0.01 µg to about 100 mg per kg of body weight, such as about 0.01 µg to about 100 mg/kg of body weight, about 0.01 µg to about 50 mg/kg of body weight, about 0.01 µg to about 10 mg/kg of body weight, about 0.01 µg to about 1 mg/kg of body weight, about 0.01 µg to about 100 µg/kg of body weight, about 0.01 µg to about 50 µg/kg of body weight, about 0.01 µg to about 10 µg/kg of body weight, about 0.01 µg to about 1 µg/kg of body weight, about 0.01 µg to about 0.1 µg/kg of body weight, about 0.1 µg to about 100 mg/kg of body weight, about 0.1 µg to about 50 mg/kg of body weight, about 0.1 µg to about 10 mg/kg of body weight, about 0.1 µg to about 1 mg/kg of body weight, about 0.1 µg to about 100 µg/kg of body weight, about 0.1 µg to about 10 µg/kg of body weight, about 0.1 µg to about 1 µg/kg of body weight, about 1 µg to about 100 mg/kg of body weight, about 1 µg to about 50 mg/kg of body weight, about 1 µg to about 10 mg/kg of body weight, about 1 µg to about 1 mg/kg of body weight, about 1 µg to about 100 µg/kg of body weight, about 1 µg to about 50 µg/kg of body weight, about 1 µg to about 10 µg/kg of body weight, about 10 µg to about 100 mg/kg of body weight, about 10 µg to about 50 mg/kg of body weight, about 10 µg to about 10 mg/kg of body weight, about 10 µg to about 1 mg/kg of body weight, about 10 µg to about 100 µg/kg of body weight, about 10 µg to about 50 µg/kg of body weight, about 50 µg to about 100 mg/kg of body weight, about 50 µg to about 50 mg/kg of body weight, about 50 µg to about 10 mg/kg of body weight, about 50 µg to about 1 mg/kg of body weight, about 50 µg to about 100 µg/kg of body weight, about 100 µg to about 100 mg/kg of body weight, about 100 µg to about 50 mg/kg of body weight, about 100 µg to about 10 mg/kg of body weight, about 100 µg to about 1 mg/kg of body weight, about 1 mg to about 100 mg/kg of body weight, about 1 mg to about 50 mg/kg of body weight, about 1 mg to about 10 mg/kg of body weight, about 10 mg to about 100 mg/kg of body weight, about 10 mg to about 50 mg/kg of body weight, about 50 mg to about 100 mg/kg of body weight.

Doses may be given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of the present invention could be intravenous, intraarterial, intraperitoneal, intramuscular, subcutaneous, intrapleural, intrathecal, intracavitary, by perfusion through a catheter or by direct intralesional injection. This may be administered once or more times daily, once or more times weekly, once or more times monthly, and once or more times annually.

IV. Therapeutic Applications

It is contemplated that the multi-specific binding proteins can be used either alone or in combination with other therapeutic agents.

A. Indications

The present disclosure provides methods for the treatment or amelioration of a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease in a subject in need thereof, the method comprising administration of the multi-specific binding proteins described herein.

In certain embodiments, the cancer to be treated is non-Hodgkin's lymphoma, such as a B-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, chronic lymphocytic leukemia, or primary central nervous system lymphoma. In certain other embodiments, the cancer to be treated is multiple myeloma. In certain other embodiments, the cancer to be treated is acute lymphoblastic leukemia (ALL). In certain embodiments, the ALL is relapsed/refractory adult and pediatric ALL.

B. Combination Therapies

The methods and compositions described herein can be used alone or in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In one aspect, the present disclosure provides a method of treating a subject by the administration of a second therapeutic agent in combination with one or more of the multi-specific binding proteins described herein.

Exemplary therapeutic agents that may be used as part of a combination therapy in treating cancer, include, for example, radiation, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, luteinizing hormone releasing factor and variations of the aforementioned agents that may exhibit differential binding to its cognate receptor, and increased or decreased serum half-life.

An additional class of agents that may be used as part of a combination therapy in treating cancer is immune checkpoint inhibitors. The checkpoint inhibitor may, for example, be selected from a PD-1 antagonist, PD-L1 antagonist, CTLA-4 antagonist, adenosine A2A receptor antagonist, B7-H3 antagonist, B7-H4 antagonist, BTLA antagonist, KIR antagonist, LAG3 antagonist, TIM-3 antagonist, VISTA antagonist or TIGIT antagonist.

In certain embodiments, the checkpoint inhibitor is a PD-1 or PD-L1 inhibitor. PD-1 is a receptor present on the surface of T-cells that serves as an immune system checkpoint that inhibits or otherwise modulates T-cell activity at the appropriate time to prevent an overactive immune response. Cancer cells, however, can take advantage of this checkpoint by expressing ligands, for example, PD-L1, that interact with PD-1 on the surface of T-cells to shut down or modulate T-cell activity. Exemplary PD-1/PD-L1 based immune checkpoint inhibitors include antibody based therapeutics. Exemplary treatment methods that employ PD-1/PD-L1 based immune checkpoint inhibition are described in U.S. Pat. Nos. 8,728,474 and 9,073,994, and EP U.S. Pat. No. 1,537,878B1, and, for example, include the use of anti-PD-1 antibodies. Exemplary anti-PD-1 antibodies are described, for example, in U.S. Pat. Nos. 8,952,136, 8,779, 105, 8,008,449, 8,741,295, 9,205,148, 9,181,342, 9,102,728, 9,102,727, 8,952,136, 8,927,697, 8,900,587, 8,735,553, and 7,488,802. Exemplary anti-PD-1 antibodies include, for example, nivolumab (available under the tradename Opdivo® from Bristol-Myers Squibb Co.), pembrolizumab (available under the tradename Keytruda® from Merck Sharp & Dohme Corp.), PDR001 (Novartis Pharmaceuticals), and pidilizumab (CT-011, Cure Tech). Exemplary anti-PD-L1 antibodies are described, for example, in U.S. Pat. Nos. 9,273,135, 7,943,743, 9,175,082, 8,741,295, 8,552,154, and 8,217,149. Exemplary anti-PD-L1 antibodies include, for example, atezolizumab (available under the tradename Tecentriq® from Genentech®), duvalumab (AstraZeneca®), MEDI4736, avelumab, and BMS 936559 (Bristol Myers Squibb Co.).

In certain embodiments, a method or composition described herein is administered in combination with a CTLA-4 inhibitor. In the CTLA-4 pathway, the interaction of CTLA-4 on a T-cell with its ligands (e.g., CD80, also known as B7-1, and CD86) on the surface of an antigen presenting cells (rather than cancer cells) leads to T-cell inhibition. Exemplary CTLA-4 based immune checkpoint inhibition methods are described in U.S. Pat. Nos. 5,811, 097, 5,855,887, 6,051,227. Exemplary anti-CTLA-4 antibodies are described in U.S. Pat. Nos. 6,984,720, 6,682,736, 7,311,910; 7,307,064, 7,109,003, 7,132,281, 6,207,156, 7,807,797, 7,824,679, 8,143,379, 8,263,073, 8,318,916, 8,017,114, 8,784,815, and 8,883,984, International (PCT) Publication Nos. WO98/42752, WO00/37504, and WO01/14424, and European Patent No. EP 1212422 B1. Exemplary CTLA-4 antibodies include ipilimumab or tremelimumab.

In certain embodiments, a method or composition described herein is administered in combination with (i) a PD-1 or PD-L1 inhibitor, e.g., a PD-1 or PD-L1 inhibitor disclosed herein, and (ii) CTLA-4 inhibitor, e.g., a CTLA-4 inhibitor disclosed herein.

In certain embodiments, a method or composition described herein is administered in combination with an IDO inhibitor. Exemplary IDO inhibitors include 1-methyl-D-tryptophan (known as indoximod), epacadostat (INCB24360), navoximod (GDC-0919), and BMS-986205.

Yet other agents that may be used as part of a combination therapy in treating cancer are monoclonal antibody agents that target non-checkpoint targets (e.g., herceptin) and non-cytotoxic agents (e.g., tyrosine-kinase inhibitors).

Yet other categories of anti-cancer agents include, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxy-adenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEE1 Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF.

It is understood that the multi-specific antibody disclosed herein, which is designed to activate T lymphocytes, may cause side effects such as neurotoxicity. Accordingly, in certain embodiments, the second therapeutic agent that can be used in combination with the multi-specific binding protein comprises an agent that mitigates a side effect of the multi-specific binding protein, e.g., reduces neurotoxicity. In certain embodiments, the second therapeutic agent inhibits T cell trafficking, for example, reduces or inhibits immune cells from crossing the blood-brain barrier. Non-limiting examples of such therapeutic agents include antagonists (e.g., antagonistic antibodies) of adhesion molecules on immune cells (e.g., α4 integrin), such as natalizumab. In certain embodiments, the second therapeutic agent increases the internalization of a sphingosine-1-phosphate (SIP) receptor (e.g., S1PR1 or S1PR5), such as fingolimod or ozanimod. In certain embodiments, the second therapeutic agent is a nitric oxide synthase (NOS) inhibitor, such as ronopterin, cindunistat, A-84643, ONO-1714, L-NOARG, NCX-456, VAS-2381, GW-273629, NXN-462, CKD-712, KD-7040, or guanidinoethyldisulfide. In certain embodiments, the second therapeutic agent is an antagonist of CSF1 or CSFIR, such as pexidartinib, emactuzumab, cabiralizumab, LY-3022855, JNJ-40346527, or MCS110. Additional non-limiting examples of the second therapeutic agents include pentosan polysulfate, minocycline, anti-ICAM-1 antibodies, anti-P-selectin antibodies, anti-CD11a antibodies, anti-CD162 antibodies, and anti-IL-6R antibodies (e.g., tocilizumab).

The amount of the multi-specific binding protein and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a multi-specific binding protein may be administered during a time when the additional therapeutic agent(s) exerts its prophylactic or therapeutic effect, or vice versa.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/ or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

The description above describes multiple aspects and embodiments of the invention. The patent application specifically contemplates all combinations and permutations of the aspects and embodiments.

EXAMPLES

The invention now being generally described, will be more readily understood by reference to the following examples, which are included merely for purposes of illustration of certain aspects and embodiments of the present invention, and is not intended to limit the invention.

Example 1. Production of Multi-Specific Binding Proteins

This example describes the production and purification of multi-specific binding proteins.

Nucleic acids encoding single-chain multi-specific binding proteins (see Table 5) were constructed and codon optimized for expression in human cells and cloned into a mammalian expression vector following standard procedures. Following sequence verification, the expression vectors, in the form of plasmids, were prepared in sufficient quantity for transfection using Plasmid Plus purification kits (Qiagen®). Human embryonic kidney 293 (HEK 293) cells were passaged to appropriate density for transient transfection. Cells were transiently transfected with the expression vectors and cultured for six days.

The amino acid sequences of the various multi-specific binding proteins are summarized in Table 5. Constructs tAb0027 to tAb0032 each contained an anti-CD19 scFv having the amino acid sequence set forth in SEQ ID NO: 9, an anti-CD3 scFv having the amino acid sequence set forth in SEQ ID NO: 105, and an anti-HSA sdAb having the amino acid sequence set forth in SEQ ID NO: 121. Constructs tAb0033 to tAb0038 each contained an anti-CD19 scFv having the amino acid sequence set forth in SEQ ID NO: 18, an anti-CD3 scFv having the amino acid sequence set forth in SEQ ID NO: 105, and an anti-HSA sdAb having the amino acid sequence set forth in SEQ ID NO: 121.

TABLE 5

Exemplary Multi-specific Binding Proteins

| Construct | Format | Amino Acid Sequence |
|---|---|---|
| tAb0027 | CD19:CD3:<br>HSA | QVQLVQSGAEVKKPGASVKVSCKASGYTFTDYIMHWVRQAPGQ<br>GLEWMGYINPYNDGSKYTEKFQGRVTMTSDTSISTAYMELSRLRS<br>DDTAVYYCARGTYYYGPQLFDYWGQGTTVTVSSGGGGSGGGGS<br>GGGGSDIVMTQTPLSLSVTPGQPASISCKSSQSLETSTGTTYLNWY<br>LQKPGQSPQLLIYRVSKRFSGVPDRFSGSGSGTDFTLKISRVEAEDV<br>GVYYCLQLLEDPYTFGQGTKLEIKGGGGSGGGGSDIVMTQSPDSLA<br>VSLGERATINCKSSQSLLNARTGKNYLAWYQQKPGQPPKLLIYWA<br>STRESGVPDRFSGSGSGTDFTLTISSLQAEDVAVYYCKQSYSRRTF<br>GGGTKVEIKGGGGSGGGGSGGGGSGGGGSQVQLVQSGAEVKKP<br>GASVKVSCKASGFNIKDYYMHWVRQAPGQRLEWMGWIDLENAN<br>TIYDAKFQGRVTITRDTSASTAYMELSSLRSEDTAVYYCARDAYG<br>RYFYDVWGQGTLVTVSSGGGGSGGGGSEVQLVESGGGLVQPGNSL<br>RLSCAASGFTFSSFGMSWVRQAPGKGLEWVSSISGSGSDTLYADS<br>VKGRFTISRDNAKTTLYLQMNSLRPEDTAVYYCTIGGSLSRSSQGT<br>LVTVSSHHHHHHHHHH (SEQ ID NO: 303) |
| tAb0029 | CD3:CD19:<br>HSA | DIVMTQSPDSLAVSLGERATINCKSSQSLLNARTGKNYLAWYQQK<br>PGQPPKLLIYWASTRESGVPDRFSGSGSGTDFTLTISSLQAEDVAV<br>YYCKQSYSRRTFGGGTKVEIKGGGGSGGGGSGGGGSGGGGSQVQ<br>LVQSGAEVKKPGASVKVSCKASGFNIKDYYMHWVRQAPGQRLE<br>WMGWIDLENANTIYDAKFQGRVTITRDTSASTAYMELSSLRSEDT<br>AVYYCARDAYGRYFYDVWGQGTLVTVSSGGGGSGGGSQVQLVQ<br>SGAEVKKPGASVKVSCKASGYTFTDYIMHWVRQAPGQGLEWMG<br>YINPYNDGSKYTEKFQGRVTMTSDTSISTAYMELSRLRSDDTAVY<br>YCARGTYYYGPQLFDYWGQGTTVTVSSGGGGSGGGGSGGGGSDI<br>VMTQTPLSLSVTPGQPASISCKSSQSLETSTGTTYLNWYLQKPGQS<br>PQLLIYRVSKRFSGVPDRFSGSGSGTDFTLKISRVEAEDVGVYYCL<br>QLLEDPYTFGQGTKLEIKGGGGSGGGSEVQLVESGGGLVQPGNSL<br>RLSCAASGFTFSSFGMSWVRQAPGKGLEWVSSISGSGSDTLYADS<br>VKGRFTISRDNAKTTLYLQMNSLRPEDTAVYYCTIGGSLSRSSQGT<br>LVTVSSHHHHHHHHHH (SEQ ID NO: 304) |
| tAb0030 | CD3:HSA:<br>CD19 | DIVMTQSPDSLAVSLGERATINCKSSQSLLNARTGKNYLAWYQQK<br>PGQPPKLLIYWASTRESGVPDRFSGSGSGTDFTLTISSLQAEDVAV<br>YYCKQSYSRRTFGGGTKVEIKGGGGSGGGGSGGGGSGGGGSQVQ<br>LVQSGAEVKKPGASVKVSCKASGFNIKDYYMHWVRQAPGQRLE<br>WMGWIDLENANTIYDAKFQGRVTITRDTSASTAYMELSSLRSEDT<br>AVYYCARDAYGRYFYDVWGQGTLVTVSSGGGGSGGGSEVQLVE<br>SGGGLVQPGNSLRLSCAASGFTFSSFGMSWVRQAPGKGLEWVSSI<br>SGSGSDTLYADSVKGRFTISRDNAKTTLYLQMNSLRPEDTAVYYC<br>TIGGSLSRSSQGTLVTVSSGGGGSGGGGSQVQLVQSGAEVKKPGAS<br>VKVSCKASGYTFTDYIMHWVRQAPGQGLEWMGYINPYNDGSKY<br>TEKFQGRVTMTSDTSISTAYMELSRLRSDDTAVYYCARGTYYYGP<br>QLFDYWGQGTTVTVSSGGGGSGGGGSGGGGSDIVMTQTPLSLSV<br>TPGQPASISCKSSQSLETSTGTTYLNWYLQKPGQSPQLLIYRVSKRF<br>SGVPDRFSGSGSGTDFTLKISRVEAEDVGVYYCLQLLEDPYTFGQG<br>TKLEIKHHHHHHHHHH (SEQ ID NO: 305) |
| tAb0031 | HSA:CD3:<br>CD19 | EVQLVESGGGLVQPGNSLRLSCAASGFTFSSFGMSWVRQAPGKGL<br>EWVSSISGSGSDTLYADSVKGRFTISRDNAKTTLYLQMNSLRPEDT<br>AVYYCTIGGSLSRSSQGTLVTVSSGGGGSGGGGSDIVMTQSPDSLAV<br>SLGERATINCKSSQSLLNARTGKNYLAWYQQKPGQPPKLLIYWAS<br>TRESGVPDRFSGSGSGTDFTLTISSLQAEDVAVYYCKQSYSRRTFG<br>GGTKVEIKGGGGSGGGGSGGGGSGGGGSQVQLVQSGAEVKKPG<br>ASVKVSCKASGFNIKDYYMHWVRQAPGQRLEWMGWIDLENANT<br>IYDAKFQGRVTITRDTSASTAYMELSSLRSEDTAVYYCARDAYGR<br>YFYDVWGQGTLVTVSSGGGGSGGGSQVQLVQSGAEVKKPGASV<br>KVSCKASGYTFTDYIMHWVRQAPGQGLEWMGYINPYNDGSKYT<br>EKFQGRVTMTSDTSISTAYMELSRLRSDDTAVYYCARGTYYYGPQ<br>LFDYWGQGTTVTVSSGGGGSGGGGSGGGGSDIVMTQTPLSLSVTP<br>GQPASISCKSSQSLETSTGTTYLNWYLQKPGQSPQLLIYRVSKRFS<br>GVPDRFSGSGSGTDFTLKISRVEAEDVGVYYCLQLLEDPYTFGQG<br>TKLEIKHHHHHHHHHH (SEQ ID NO: 306) |
| tAb0032 | HSA:CD19:<br>CD3 | EVQLVESGGGLVQPGNSLRLSCAASGFTFSSFGMSWVRQAPGKGL<br>EWVSSISGSGSDTLYADSVKGRFTISRDNAKTTLYLQMNSLRPEDT<br>AVYYCTIGGSLSRSSQGTLVTVSSGGGGSGGGGSQVQLVQSGAEVK<br>KPGASVKVSCKASGYTFTDYIMHWVRQAPGQGLEWMGYINPYN<br>DGSKYTEKFQGRVTMTSDTSISTAYMELSRLRSDDTAVYYCARGT<br>YYYGPQLFDYWGQGTTVTVSSGGGGSGGGGSGGGGSDIVMTQTP<br>LSLSVTPGQPASISCKSSQSLETSTGTTYLNWYLQKPGQSPQLLIYR<br>VSKRFSGVPDRFSGSGSGTDFTLKISRVEAEDVGVYYCLQLLEDPY<br>TFGQGTKLEIKGGGGSGGGSDIVMTQSPDSLAVSLGERATINCKSS |

TABLE 5-continued

Exemplary Multi-specific Binding Proteins

| Construct | Format | Amino Acid Sequence |
|---|---|---|
| | | QSLLNARTGKNYLAWYQQKPGQPPKLLIYWASTRESGVPDRESGS<br>GSGTDFTLTISSLQAEDVAVYYCKQSYSRRTFGGGTKVEIKGGGG<br>SGGGGSGGGGSGGGGSQVQLVQSGAEVKKPGASVKVSCKASGEN<br>IKDYYMHWVRQAPGQRLEWMGWIDLENANTIYDAKFQGRVTITR<br>DTSASTAYMELSSLRSEDTAVYYCARDAYGRYFYDVWGQGTLVT<br>VSSHHHHHHHHHH (SEQ ID NO: 307) |
| tAb0033 | CD19:CD3:<br>HSA | QVQLQESGPGLVKPSQTLSLTCTVSGGSISTSGMGVGWIRQHPGK<br>GLEWIGHIWWDDDKRYNPALKSRVTISVDTSKNQFSLKLSSVTAA<br>DTAVYYCARMELWSYYFDYWGQGTLVTVSSGGGGSGGGGSGGG<br>GSEIVLTQSPATLSLSPGERATLSCSASSSVSYMHWYQQKPGQAPR<br>LLIYDTSKLASGIPARFSGSGSGTDFTLTISSLEPEDFAVYYCFQGSV<br>YPFTFGQGTKLEIKRGGGGSGGGGSDIVMTQSPDSLAVSLGERATIN<br>CKSSQSLLNARTGKNYLAWYQQKPGQPPKLLIYWASTRESGVPD<br>RFSGSGSGTDFTLTISSLQAEDVAVYYCKQSYSRRTFGGGTKVEIK<br>GGGGSGGGGSGGGGSGGGGSQVQLVQSGAEVKKPGASVKVSCK<br>ASGFNIKDYYMHWVRQAPGQRLEWMGWIDLENANTIYDAKFQG<br>RVTITRDTSASTAYMELSSLRSEDTAVYYCARDAYGRYFYDVWG<br>QGTLVTVSSGGGGSGGGSEVQLVESGGGLVQPGNSLRLSCAASGF<br>TFSSFGMSWVRQAPGKGLEWVSSISGSGSDTLYADSVKGRFTISRD<br>NAKTTLYLQMNSLRPEDTAVYYCTIGGSLSRSSQGTLVTVSSHHH<br>HHHHHHH (SEQ ID NO: 308) |
| tAb0034 | CD19:HSA:<br>CD3 | QVQLQESGPGLVKPSQTLSLTCTVSGGSISTSGMGVGWIRQHPGK<br>GLEWIGHIWWDDDKRYNPALKSRVTISVDTSKNQFSLKLSSVTAA<br>DTAVYYCARMELWSYYFDYWGQGTLVTVSSGGGGSGGGGSGGG<br>GSEIVLTQSPATLSLSPGERATLSCSASSSVSYMHWYQQKPGQAPR<br>LLIYDTSKLASGIPARFSGSGSGTDFTLTISSLEPEDFAVYYCFQGSV<br>YPFTFGQGTKLEIKRGGGGSGGGSEVQLVESGGGLVQPGNSLRLS<br>CAASGFTFSSFGMSWVRQAPGKGLEWVSSISGSGSDTLYADSVKG<br>RFTISRDNAKTTLYLQMNSLRPEDTAVYYCTIGGSLSRSSQGTLVT<br>VSSGGGGSGGGGSDIVMTQSPDSLAVSLGERATINCKSSQSLLNART<br>GKNYLAWYQQKPGQPPKLLIYWASTRESGVPDRFSGSGSGTDFTL<br>TISSLQAEDVAVYYCKQSYSRRTFGGGTKVEIKGGGGSGGGGSGG<br>GGSGGGGSQVQLVQSGAEVKKPGASVKVSCKASGFNIKDYYMH<br>WVRQAPGQRLEWMGWIDLENANTIYDAKFQGRVTITRDTSASTA<br>YMELSSLRSEDTAVYYCARDAYGRYFYDVWGQGTLVTVSSHHH<br>HHHHHH (SEQ ID NO: 309) |
| tAb0035 | CD3:CD19:<br>HSA | DIVMTQSPDSLAVSLGERATINCKSSQSLLNARTGKNYLAWYQQK<br>PGQPPKLLIYWASTRESGVPDRESGSGSGTDFTLTISSLQAEDVAV<br>YYCKQSYSRRTFGGGTKVEIKGGGGSGGGGSGGGGSGGGGSQVQ<br>LVQSGAEVKKPGASVKVSCKASGFNIKDYYMHWVRQAPGQRLE<br>WMGWIDLENANTIYDAKFQGRVTITRDTSASTAYMELSSLRSEDT<br>AVYYCARDAYGRYFYDVWGQGTLVTVSSGGGGSGGGSQVQLQE<br>SGPGLVKPSQTLSLTCTVSGGSISTSGMGVGWIRQHPGKGLEWIGH<br>IWWDDDKRYNPALKSRVTISVDTSKNQFSLKLSSVTAADTAVYYC<br>ARMELWSYYFDYWGQGTLVTVSSGGGGSGGGGSGGGGSEIVLTQ<br>SPATLSLSPGERATLSCSASSSVSYMHWYQQKPGQAPRLLIYDTSK<br>LASGIPARFSGSGSGTDFTLTISSLEPEDFAVYYCFQGSVYPFTFGQ<br>GTKLEIKRGGGGSGGGSEVQLVESGGGLVQPGNSLRLSCAASGFT<br>FSSFGMSWVRQAPGKGLEWVSSISGSGSDTLYADSVKGRFTISRD<br>NAKTTLYLQMNSLRPEDTA VYYCTIGGSLSRSSQGTLVTVSSHHH<br>HHHHHH (SEQ ID NO: 310) |
| tAb0036 | CD3:HSA:<br>CD19 | DIVMTQSPDSLAVSLGERATINCKSSQSLLNARTGKNYLAWYQQK<br>PGQPPKLLIYWASTRESGVPDRFSGSGSGTDFTLTISSLQAEDVAV<br>YYCKQSYSRRTFGGGTKVEIKGGGGSGGGGSGGGGSGGGGSQVQ<br>LVQSGAEVKKPGASVKVSCKASGFNIKDYYMHWVRQAPGQRLE<br>WMGWIDLENANTIYDAKFQGRVTITRDTSASTAYMELSSLRSEDT<br>AVYYCARDAYGRYFYDVWGQGTLVTVSSGGGGSGGGSEVQLVE<br>SGGGLVQPGNSLRLSCAASGFTFSSFGMSWVRQAPGKGLEWVSSI<br>SGSGSDTLYADSVKGRFTISRDNAKTTLYLQMNSLRPEDTAVYYC<br>TIGGSLSRSSQGTLVTVSSGGGGSGGGGSQVQLQESGPGLVKPSQTL<br>SLTCTVSGGSISTSGMGVGWIRQHPGKGLEWIGHIWWDDDKRYN<br>PALKSRVTISVDTSKNQFSLKLSSVTAADTAVYYCARMELWSYYF<br>DYWGQGTLVTVSSGGGGSGGGGSGGGGSEIVLTQSPATLSLSPGE<br>RATLSCSASSSVSYMHWYQQKPGQAPRLLIYDTSKLASGIPARFSG<br>SGSGTDFTLTISSLEPEDFAVYYCFQGSVYPFTFGQGTKLEIKRHHH<br>HHHHHH (SEQ ID NO: 311) |
| tAb0037 | HSA:CD3:<br>CD19 | EVQLVESGGGLVQPGNSLRLSCAASGFTFSSFGMSWVRQAPGKGL<br>EWVSSISGSGSDTLYADSVKGRFTISRDNAKTTLYLQMNSLRPEDT<br>AVYYCTIGGSLSRSSQGTLVTVSSGGGGSGGGSDIVMTQSPDSLAV<br>SLGERATINCKSSQSLLNARTGKNYLAWYQQKPGQPPKLLIYWAS<br>TRESGVPDRESGSGSGTDFTLTISSLQAEDVAVYYCKQSYSRRTFG |

TABLE 5-continued

Exemplary Multi-specific Binding Proteins

| Construct | Format | Amino Acid Sequence |
|---|---|---|
| | | GGTKVEIKGGGGSGGGGSGGGGSGGGGSQVQLVQSGAEVKKPG<br>ASVKVSCKASGFNIKDYYMHWVRQAPGQRLEWMGWIDLENANT<br>IYDAKFQGRVTITRDTSASTAYMELSSLRSEDTAVYYCARDAYGR<br>YFYDVWGQGTLVTVSSGGGGSGGGGSQVQLQESGPGLVKPSQTLS<br>LTCTVSGGSISTSGMGVGWIRQHPGKGLEWIGHIWWDDDKRYNP<br>ALKSRVTISVDTSKNQFSLKLSSVTAADTAVYYCARMELWSYYFD<br>YWGQGTLVTVSSGGGGSGGGGSGGGGSEIVLTQSPATLSLSPGER<br>ATLSCSASSSVSYMHWYQQKPGQAPRLLIYDTSKLASGIPARFSGS<br>GSGTDFTLTISSLEPEDFAVYYCFQGSVYPFTFGQGTKLEIKRHHH<br>HHHHHHH (SEQ ID NO: 312) |
| tAb0038 | HSA:CD19v<br>CD3 | EVQLVESGGGLVQPGNSLRLSCAASGFTFSSFGMSWVRQAPGKGL<br>EWVSSISGSGSDTLYADSVKGRFTISRDNAKTTLYLQMNSLRPEDT<br>AVYYCTIGGSLSRSSQGTLVTVSSGGGGSGGGSQVQLQESGPGLV<br>KPSQTLSLTCTVSGGSISTSGMGVGWIRQHPGKGLEWIGHIWWDD<br>DKRYNPALKSRVTISVDTSKNQFSLKLSSVTAADTAVYYCARMEL<br>WSYYFDYWGQGTLVTVSSGGGGSGGGGSGGGGSEIVLTQSPATL<br>SLSPGERATLSCSASSSVSYMHWYQQKPGQAPRLLIYDTSKLASGI<br>PARFSGSGSGTDFTLTISSLEPEDFAVYYCFQGSVYPFTFGQGTKLE<br>IKRGGGGSGGGSDIVMTQSPDSLAVSLGERATINCKSSQSLLNART<br>GKNYLAWYQQKPGQPPKLLIYWASTRESGVPDRFSGSGSGTDFTL<br>TISSLQAEDVAVYYCKQSYSRRTFGGGTKVEIKGGGGSGGGGSGG<br>GGSGGGGSQVQLVQSGAEVKKPGASVKVSCKASGFNIKDYYMH<br>WVRQAPGQRLEWMGWIDLENANTIYDAKFQGRVTITRDTSASTA<br>YMELSSLRSEDTAVYYCARDAYGRYFYDVWGQGTLVTVSSHHH<br>HHHHHHH (SEQ ID NO: 313) |
| tAb0042 | CD3:HSA:<br>CD19 | EVQLVESGGGLVQPGGSLKLSCAASGFTFNKYAINWVRQAPGKG<br>LEWVARIRSKYNNYATYYADQVKDRFTISRDDSKNTAYLQMNNL<br>KTEDTAVYYCVRHANFGNSYISYWAYWGQGTLVTVSSGGGGSG<br>GGGSGGGGSQTVVTQEPSLTVSPGGTVTLTCASSTGAVTSGNYPN<br>WVQQKPGQAPRGLIGGTKFLVPGTPARFSGSLLGGKAALTLSGVQ<br>PEDEAEYYCTLWYSNRWVFGGGTKLTVLGGGGSGGGSEVQLVES<br>GGGLVQPGNSLRLSCAASGFTFSSFGMSWVRQAPGKGLEWVSSIS<br>GSGSDTLYADSVKGRFTISRDNAKTTLYLQMNSLRPEDTAVYYCT<br>IGGSLSRSSQGTLVTVSSGGGGSGGGSQVQLQESGPGLVKPSQTLS<br>LTCTVSGGSISTSGMGVGWIRQHPGKGLEWIGHIWWDDDKRYNP<br>ALKSRVTISVDTSKNQFSLKLSSVTAADTAVYYCARMELWSYYFD<br>YWGQGTLVTVSSGGGGSGGGGSGGGGSEIVLTQSPATLSLSPGER<br>ATLSCSASSSVSYMHWYQQKPGQAPRLLIYDTSKLASGIPARFSGS<br>GSGTDFTLTISSLEPEDFAVYYCFQGSVYPFTFGQGTKLEIKRHHH<br>HHHHHHH (SEQ ID NO: 406) |

The cultures were harvested by centrifugation at 4000 rpm, and the supernatant filtered through a 0.22 mm filter. The multi-specific binding proteins, which carried a 10×His tag at the C-terminus, were purified in two steps. The first step was Nickel affinity chromatography with elution using PBS containing 400 mM imidazole. The second step was size exclusion chromatography with elution in PBS (phosphate buffered saline) pH7.2. Multi-specific binding protein concentrations were determined by UV spectroscopy, and the protein samples were concentrated when necessary. The purity of the proteins was determined by sodium dodecyl sulphate polyacrylamide gel electrophoresis (SDS-PAGE) and high performance liquid chromatography (HPLC). Specifically, HPLC was performed on an Agilent® 1100 series instrument using MabPac size exclusion column run in PBS at 0.2 mL/min. The fractions with an elution time of about 225-240 minutes were collected for further characterization.

As noted above, the constructs produced contained an anti-CD19 scFv having the amino acid sequence set forth in SEQ ID NO: 9 or 18. The binding affinity of the two CD19 binding domains to CD19 were measured by SPR using a monomeric CD19 extracellular domain and a dimeric CD19 extracellular domain fused with human IgG1 Fc. Binding kinetic parameters were measured using an instrument (available under the tradename ForteBio™ from Pall Corporation®) generally as previously described (see, Estep et al. (2013) MAbs, 5 (2): 270-78). When measured with the monomeric CD19 protein, the $K_D$ value of the CD19 binding domain having the sequence of SEQ ID NO: 9 was 7 nM, and the $K_D$ value of the CD19 binding domain having the sequence of SEQ ID NO: 18 was 11 nM. When measured with the dimeric CD19 protein, the $K_D$ value of the CD19 binding domain having the sequence of SEQ ID NO: 9 was 5 nM, and the $K_D$ value of the CD19 binding domain having the sequence of SEQ ID NO: 18 was 15 nM.

Example 2. Multi-Specific Binding Proteins Induce T Cell Cytotoxicity Against CD19+ Target Cells This example describes the cytotoxic activity of multi-specific binding proteins.

The T cell redirection activity of multi-specific binding proteins and BiTE® proteins were evaluated using a cell model available under the trade name KILR® Raji from Eurofins DiscoverX®. Briefly, pan T cells were isolated from primary human PBMCs from a single healthy donor by negative selection using a commercial kit (e.g. available under the name Easy Sep Human T Cell Enrichment Kit, StemCell Technologies®). T cells were maintained in RPMI 1640 medium supplemented with 10% serum and 300 IU/mL IL-2 to expand T cells. The harvested T cells were washed twice to remove any serum.

KILR® Raji cells, which expressed CD19 on the surface, were used as target cells. To opsonize the target cells, each multi-specific binding protein or BiTE® (see Table 5) was incubated with the target cells for 30 minutes at 37° C. in RPMI 1640 medium supplemented with 5% heat inactivated low IgG fetal bovine serum and penicillin-streptomycin-glutamine. The proteins were added in serial dilution at 10 different doses, with each dose run in duplicate. Human serum albumin was added to the medium of certain samples at a final concentration of 15 mg/mL. Selective proteins were also evaluated with KILR® SKOV3 cells, which were CD19-negative, as negative controls.

After opsonization, the target cells were incubated with the pan T cells at an effector-to-target (E:T) ratio of 10:1 for 6 hours at 37° C. Killing of the KILR® Raji cells resulted in release of a labeled housekeeping protein from these cells into the medium, which was quantified by addition of a KILR® detection reagent (Eurofins DiscoverX®). The luminescence signals from all wells were read on an Envision plate reader. Spontaneous release and total lysis controls were included on each plate to allow calculation of percent killing.

Percent killing was calculated from the luminescence signal values using the following formula: % killing=(value from test protein sample-mean value from spontaneous release control)/(mean value from total lysis control-mean value from spontaneous release control)×100. The EC50 values were calculated from the percent killing by fitting with a dose-response curve using software available under the trade name GraphPad® from GraphPad Software, LLC.

Table 6 lists the EC50 values of T cell-redirected killing in the absence and presence of human serum albumin for exemplary multi-specific binding proteins and comparator anti-CD19 BiTE® protein. No substantial killing was observed with the CD19-negative KILR® SKOV3 cells.

TABLE 6

Cytotoxic Activity of Multi-specific Binding Proteins

| Construct | Format | EC50 (pg/mL) -HSA | EC50 (pg/mL) +HSA | Fold change |
|---|---|---|---|---|
| tAb0027 | CD19:CD3:HSA | 2.33 | 67.9 | 29.1 |
| tAb0029 | CD3:CD19:HSA | 5.48 | 188.1 | 34.3 |
| tAb0030 | CD3:HSA:CD19 | 3.17 | 141.7 | 44.7 |
| tAb0031 | HSA:CD3:CD19 | 6.55 | 189.3 | 28.9 |
| tAb0032 | HSA:CD19:CD3 | 5.71 | 88.4 | 15.5 |
| tAb0033 | CD19:CD3:HSA | 20.4 | 1294 | 63.4 |
| tAb0034 | CD19:HSA:CD3 | 59.3 | 2376 | 40.1 |
| tAb0035 | CD3:CD19:HSA | 51.4 | 2184 | 42.5 |
| tAb0036 | CD3:HSA:CD19 | 103.8 | 4195 | 40.4 |
| tAb0037 | HSA:CD3:CD19 | 175.1 | 2151 | 12.3 |
| tAb0038 | HSA:CD19:CD3 | 52.6 | 288 | 5.5 |
| tAb0042 | CD3:HSA:CD19 | 69.9 | 13290 | 190.1 |
| blinatumomab | CD19:CD3 | 2854 | 10750 | 3.8 |

As shown in Table 6, the multi-specific binding proteins containing the anti-CD19 scFv having the amino acid sequence of SEQ ID NO: 9 showed stronger cytotoxic activity than those containing the anti-CD19 scFv having the amino acid sequence of SEQ ID NO: 18, regardless of the construct format, CD3 binding domain, HSA binding domain, and the presence or absence of HSA in the assay medium. From this data, it is contemplated that constructs containing this anti-CD19 scFv with the higher binding affinity to CD19 will demonstrate stronger therapeutic activity than constructs containing the other anti-CD19 scFv with the lower binding affinity.

Furthermore, all the multi-specific binding proteins tested showed lower $EC_{50}$ value (namely, stronger ability to induce cytotoxicity) in the absence of HSA than in the presence of HSA. Without wishing to be bound by theory, it appears that the presence of HSA causes a change in the protein complex, which was specific to the multi-specific binding proteins containing an HSA binding domain, rather than a nonspecific effect as observed with blinatumomab. The ratio of the $EC_{50}$ value in the presence of HSA to the $EC_{50}$ value in the absence of HSA, also called "fold change" herein, was used to assess the effect of HSA on the potential therapeutic activity of the multi-specific binding protein. As shown in Table 6, the construct formats with the HSA binding domain N-terminal to both the CD19 binding domain and the CD3 binding domain (namely, tAb0031, tAb0032, tAb0037, and tAb0038) showed lower fold changes than the other construct formats, regardless of which CD19 binding domain was used in the construct.

Furthermore, among the constructs having the same CD19 binding domain, CD3 binding domain, and HSA binding domain, the constructs in the CD19:CD3:HSA format (i.e., the CD19 binding domain positioned N-terminal to the CD3 binding domain, and the CD3 binding domain positioned N-terminal to the HSA binding domain), namely, tAb0027 and tAb0033, showed the lowest or second lowest $EC_{50}$ values both in the absence and in the presence of HSA.

Example 3. Cytotoxicity of Multi-Specific Binding Proteins Against CD19$^+$ Target Cells This example provides alternative methods for determining the cytotoxic activity of a multi-specific binding protein.

The multi-specific binding proteins disclosed herein can be evaluated in in vitro assays on their mediation of T cell dependent cytotoxicity to B cell antigen positive target cells. For example, the CD19-binding multi-specific binding protein disclosed herein is evaluated in in vitro assays on its mediation of T cell dependent cytotoxicity to CD19$^+$ target cells.

Fluorescence labeled CD19$^+$ MEC-1 cells (a CD19$^+$ human chronic B cell leukemia cell line) are incubated with isolated PBMC of random donors or CB15 T-cells (standardized T-cell line) as effector cells in the presence of the CD19-binding multi-specific binding protein. After incubation for 4 hours at 37° C. in a humidified incubator, the release of the fluorescent dye from the target cells into the supernatant is determined in a spectrofluorimeter. Target cells incubated without the CD19-binding multi-specific binding protein and target cells totally lysed by the addition of saponin at the end of the incubation serve as negative and positive controls, respectively. Based on the measured remaining living target cells, the percentage of specific cell lysis can be calculated according to the following formula: $[1-(\text{number of living targets}_{(sample)}/\text{number of living targets}_{(spontaneous)})] \times 100\%$. Sigmoidal dose response curves and $EC_{50}$ values are calculated by non-linear regression/4-parameter logistic fit using software available under the trade name GraphPad® from GraphPad Software, LLC. The lysis values obtained for a given multi-specific binding protein concentration are used to calculate sigmoidal dose-response curves by 4 parameter logistic fit analysis using the Prism software. It is expected that the target cell lysis rate induced by CD19-binding multi-specific binding protein is higher than the target cell lysis rate induced by similar constructs lacking either a CD19-binding domain or a CD3-binding domain.

Alternatively, a human T-cell dependent cellular cytotoxicity (TDCC) assay is used to measure the ability of the multi-specific binding protein to direct T cells to kill tumor cells (Nazarian et al. 2015, *J. Biomol. Screen,* 20:519-27). In this assay, T cells and target cancer cell line cells are mixed together at a 10:1 ratio in a 384 wells plate, and varying amounts of the multi-specific binding proteins are added. After 48 hours, the T cells are washed away leaving attached to the plate target cells that were not killed by the T cells. To quantitate the remaining viable cells, a luminescent cell viability assay (available under the tradename CellTiter-GLO® from Promega®) is used. It is contemplated that the killing rate of B-cell antigen expressing cancer cell induced by CD19-binding multi-specific binding protein will be higher than that induced by similar constructs lacking either a CD19-binding domain or a CD3-binding domain and/or other negative control molecules.

Example 4. Pharmacokinetics of Multi-Specific Binding Proteins with HSA Binding Domain This example is designed to determine the pharmacokinetics of multi-specific binding proteins.

Multi-specific binding proteins containing a domain that binds CD19, a domain that binds CD3, and a domain that binds serum albumin are tested in the cynomolgus monkey in the context of pharmacokinetic (PK) studies to evaluate the serum elimination time of the multi-specific binding protein.

The multi-specific binding proteins are administered as intravenous bolus or intravenous infusion. The multi-specific binding proteins are administered in a dose-linear, pharmacokinetic relevant range of 0.5 µg/kg to 3 µg/kg, 6 µg/kg, 12 µg/kg, and 15 µg/kg, respectively. For purposes of comparability, the serum concentrations of the multi-specific binding proteins are does-normalized and molecular weight-normalized (described in nmol).

For each multi-specific binding protein, a group of at least two to three animals are used. Blood samples are collected and serum is prepared for determination of serum concentrations of the multi-specific binding proteins. Serum multi-specific binding protein levels are measured using an immunoassay. The assay is performed by capturing the multi-specific binding protein via its CD19-binding domain, while an antibody directed against the CD3-binding domain of the multi-specific binding protein is used for detection. The serum concentration-time profiles are used to determine PK parameters using known analytical methods such as those described in Ritschel W A and Kearns G L, 1999, IN: *Handbook Of Basic Pharmacokinetics Including Clinical Applications,* 5th edition, American Pharmaceutical Assoc., Washington, D.C. and software available under the trade name WinNonlin® professional V. 3.1 from Certara, L.P.).

Alternatively, the serum half-life of the various multi-specific binding proteins containing the serum albumin binding domain is compared to that of control constructs capable of binding CD19 and CD3 but lacking a serum albumin binding domain by including in the experiment another cynomolgus monkey group that receives the control constructs. Additional domains can be included such that the control constructs are similar in size to the multi-specific binding proteins.

It is expected that CD19-binding multi-specific binding protein will have significantly longer serum half-life compared to similar constructs capable of binding CD19 and CD3 but lacking a serum albumin binding domain and/or other negative control molecules.

Example 5. Determination of Antigen Affinity by Flow Cytometry

This example is designed to determine the affinity of a multi-specific binding protein to an antigen.

Various multi-specific binding proteins disclosed herein are tested for their binding affinities to human $CD3^+$ cells and the corresponding B cell surface antigen positive cells, such as human $CD19^+$ cells. The multi-specific binding proteins are also tested for their binding affinities to cynomolgus $CD3^+$ cells and the corresponding B cell surface antigen positive cells, such as cynomolgus $CD19^+$ cells.

$CD3^+$ and $CD19^+$ cells are incubated with 100 µL of serial dilutions of the multi-specific binding protein. After washing three times with FACS buffer the cells are incubated with 0.1 mL of 10 µg/mL mouse monoclonal anti-idiotype antibody in the same buffer for 45 mins on ice. After a second washing cycle, the cells are incubated with 0.1 mL of 15 µg/mL FITC-conjugated goat anti-mouse IgG antibodies under the same conditions as before. As a control, cells are incubated with the anti-His IgG followed by the FITC-conjugated goat anti-mouse IgG antibodies without the multi-specific binding protein. The cells are then washed again and resuspended in 0.2 mL of FACS buffer containing 2 µg/mL propidium iodide (PI) in order to exclude dead cells. The fluorescence of $1 \times 10^4$ living cells is measured using a commercially available flow cytometer and software. Mean fluorescence intensities of the cell samples are calculated using software available under the trade names CXP software (Beckman-Coulter®, Krefeld, Germany) or Incyte™ software (Merck Millipore, Schwalbach, Germany). $K_D$ values for one-site binding can be calculated using normalized fluorescence intensity values with known computational equations such as those supplied under the trade name GraphPad Prism® software from GraphPad® Software, La Jolla Calif. USA. CD3 binding affinity and cross-reactivity are evaluated in titration and flow cytometric experiments on $CD3^+$ Jurkat cells and the cynomolgus $CD3^+$ HSC-F cell line. CD19 binding and cross-reactivity are assessed on the human $CD19^+$ tumor cell lines. The $K_D$ ratio of cross-reactivity can be calculated using the $K_D$ values determined on the CHO cell lines expressing either recombinant human or recombinant cynomolgus antigens.

Example 6. Cytokine Production Induced by Multi-Specific Binding Proteins

This example is designed to determine the ability of a multi-specific binding protein to induce cytokine production from immune cells.

Assays available under the trade name AlphaLISA® (Perkin Elmer®) for TNFα and Interferon γ are used to obtain evidence that T cells are activated by the multi-specific binding proteins of current invention, such as CD19-binding multi-specific binding protein, in the presence of target cells, such as $CD19^+$ B cells. For this assay, primary human T cells and human tumor cells expressing B cell surface antigen are incubated in the presence of the CD19-binding multi-specific binding protein as described under cytotoxicity assays. After 48 hours of incubation, 2 microliter aliquots of the assay supernatants are analyzed according to the manufacturer's instructions. It is contemplated that the TNFα or Interferon γ level induced by CD19-binding multi-specific binding protein is higher than that induced by similar constructs lacking either a CD19-binding domain or a CD3-binding domain and/or other negative control molecules.

Example 7. Identification of scFv Variants that Bind Human CD3ε

This example is designed to identify variants of the antigen-binding sites disclosed herein that bind human CD3ε.

The binding properties of the parental CD3ε binding construct to biotin-CD3ε and to biotin-HSA are characterized. To construct the anti-CD3ε scFv phage libraries, a single substitution library is provided for the heavy chain CDR1, heavy chain CDR2, heavy chain CDR3, light chain CDR1, light chain CDR2, and light chain CDR3 domains. Residues are varied one at a time via mutagenesis. For selection of clones and determination of binding affinity, single substitution libraries are bound to biotinylated human CD3ε, washed, eluted, and counted. Biotinylated cynomolgus CD3ε is used as the round 1 selection target, and washed for 4 hours after combinatorial phage binding from the two independent libraries (~2× selection). Biotinylated human CD3ε is used as the round 2 selection target, and washed for 3 hours after binding of both libraries (<2× selection). PCRed inserts from the second round of selection are sub-cloned into the pcDNA3.4 His6 expression vector. 180 clones are picked and DNA is purified, sequenced, and transfected into an expression system available under the trade name Expi293® from Thermo Fisher®. A panel of sixteen clones with a range of affinities for human CD3& are selected for more precise determination of the parameters such as the dissociation constant ($K_D$), the dissociation rate ($k_d$ or $k_{off}$), and the association rate ($k_a$ or $k_{on}$).

INCORPORATION BY REFERENCE

All publications and patents cited throughout the text of this specification (including all patents, patent applications, scientific publications, manufacturer's specifications, instructions, etc.), whether supra or infra, are hereby incorporated by reference in their entirety for all purposes. To the extent the material incorporated by reference contradicts or is inconsistent with this specification, the specification will supersede any such material.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A multi-specific binding protein comprising:
   (a) a first antigen-binding site that binds to human CD19 comprising heavy chain complementarity determining regions (HCDR) and light chain complementarity determining regions (LCDR), wherein:
      HCDR1 comprises the amino acid sequence of SEQ ID NO: 3, HCDR2 comprises the amino acid sequence of SEQ ID NO: 4, HCDR3 comprises the amino acid sequence of SEQ ID NO: 5, LCDR1 comprises the amino acid sequence of SEQ ID NO: 6, LCDR2 comprises the amino acid sequence of SEQ ID NO: 7, and LCDR3 comprises the amino acid sequence of SEQ ID NO: 8;
   (b) a second antigen-binding site that binds to human CD3 comprising heavy chain complementarity determining regions (HCDR) and light chain complementarity determining regions (LCDR), wherein HCDR1 comprises the amino acid sequence of SEQ ID NO: 99, HCDR2 comprises the amino acid sequence of SEQ ID NO: 100, HCDR3 comprises the amino acid sequence of SEQ ID NO: 101, LCDR1 comprises the amino acid sequence of SEQ ID NO: 102, LCDR2 comprises the amino acid sequence of SEQ ID NO: 103, and LCDR3 comprises the amino acid sequence of SEQ ID NO: 104;
   (c) a third antigen-binding site that binds to human serum albumin (HSA) comprising a heavy chain complementarity determining regions (HCDR) wherein HCDR1 comprises the amino acid sequence of SEQ ID NO: 122 or 123, HCDR2 comprises the amino acid sequence of SEQ ID NO: 124 or 125, HCDR3 comprises the amino acid sequence of SEQ ID NO: 126,
   and wherein the first antigen-binding site and second antigen-binding site comprise a single-chain variable fragment (scFv) and the third antigen-binding site comprises a single-domain antibody (sdAb).

2. The multi-specific binding protein of claim 1, wherein the third antigen-binding site is not positioned between the first antigen-binding site and the second antigen-binding site in the polypeptide chain.

3. The multi-specific binding protein of claim 2, wherein the third antigen-binding site is positioned N-terminal to both the first antigen-binding site and the second antigen-binding site in the polypeptide chain.

4. The multi-specific binding protein of claim 3, wherein the third antigen-binding site is positioned N-terminal to the first antigen-binding site, and the first antigen-binding site is positioned N-terminal to the second antigen-binding site in the polypeptide chain.

5. The multi-specific binding protein of claim 3, wherein the third antigen-binding site is positioned N-terminal to the second antigen-binding site, and the second antigen-binding site is positioned N-terminal to the first antigen-binding site in the polypeptide chain.

6. The multi-specific binding protein of claim 2, wherein the third antigen-binding site is positioned C-terminal to both the first antigen-binding site and the second antigen-binding site in the polypeptide chain.

7. The multi-specific binding protein of claim 6, wherein:
   (i) the first antigen-binding site is positioned N-terminal to the second antigen-binding site, and the second antigen-binding site is positioned N-terminal to the third antigen-binding site in the polypeptide chain; or
   (ii) the second antigen-binding site is positioned N-terminal to the first antigen-binding site, and the first antigen-binding site is positioned N-terminal of the third antigen-binding site in the polypeptide chain.

8. The multi-specific binding protein of claim 1, wherein:
   (i) the first antigen-binding site is positioned N-terminal to the third antigen-binding site, and the third antigen-binding site is positioned N-terminal to the second antigen-binding site in the polypeptide chain; or
   (ii) the second antigen-binding site is positioned N-terminal to the third antigen-binding site, and the third antigen-binding site is positioned N-terminal binding protein the first antigen-binding site in the polypeptide chain.

9. The multi-specific binding protein of claim 8, wherein at least two adjacent antigen-binding sites are connected by a peptide linker comprising the amino acid sequence of SEQ ID NO: 298, 299, or 302.

10. The multi-specific binding protein of claim 1, wherein the first antigen-binding site binds to human CD19 with a dissociation constant ($K_D$) equal to or lower than 20 nM.

11. The multi-specific binding protein of claim 1, wherein the first antigen-binding site has a melting temperature of at least 60° C.

12. The multi-specific binding protein of claim 1, wherein the second antigen-binding site binds to human CD3 with a $K_D$ equal to or lower than 10 nM.

13. The multi-specific binding protein of claim 1, wherein the second antigen-binding site has a melting temperature of at least 60° C.

14. The multi-specific binding protein of claim 1, wherein the third antigen-binding site binds to HSA with a $K_D$ equal to or lower than 20 nM.

15. The multi-specific binding protein of claim 1, wherein the third antigen-binding site has a melting temperature of at least 60° C.

16. The multi-specific binding protein of claim 1, wherein the multi-specific binding protein does not comprise an antibody Fc region.

17. The multi-specific binding protein of claim 1, wherein the molecular weight of the multi-specific binding protein is at least 65 kD.

18. The multi-specific binding protein of claim 1, wherein the serum half-life of the multi-specific binding protein is at least 24 hours.

19. A pharmaceutical composition comprising the multi-specific binding protein of claim 1 and a pharmaceutically acceptable carrier.

20. A complex comprising a T cell expressing CD3, a B cell expressing CD19, and the multi-specific binding protein of claim 1, wherein the multi-specific binding protein is capable of simultaneously binding to both the T cell and the B cell.

21. An isolated polynucleotide encoding the multi-specific binding protein of claim 1.

22. A vector comprising the polynucleotide of claim 21.

23. An isolated recombinant host cell comprising the polynucleotide of claim 21.

24. A method of producing a multi-specific binding protein, the method comprising culturing the host cell of claim 23 under suitable conditions that allow expression of the multi-specific binding protein.

25. A method of stimulating an immune response against a cell expressing CD19, the method comprising exposing the cell and a T lymphocyte to the multi-specific binding protein of claim 1.

26. A multi-specific binding protein comprising:
   (a) a first antigen-binding site that binds to CD19 comprising
      a heavy chain variable domain (VH) and a light chain variable domain (VL), wherein
      (i) the VH comprises the amino acid sequence of SEQ ID NO: 1, and the VL comprises the amino acid sequence of SEQ ID NO: 2; or
      (ii) the VH comprises the amino acid sequence of SEQ ID NO: 10 and the VL comprises the amino acid sequence of SEQ ID NO: 11;
   (b) a second antigen-binding site that binds to human CD3 comprising a VH, wherein the VH comprises the amino acid sequence of SEQ ID NO: 97 and a VL wherein the VL comprises the amino acid sequence of SEQ ID NO: 98; and
      a third antigen-binding site that binds to human serum albumin (HSA) comprising a VH, wherein the VH comprises the amino acid sequence of SEQ ID NO: 121.

\* \* \* \* \*

SEQUENCE LISTING

```
<160> NUMBER OF SEQ ID NOS: 407

<210> SEQ ID NO 1
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ile Met His Trp Val Arg Gln Ala Pro Gly Gln Gly Leu Glu Trp Met
            35                  40                  45

Gly Tyr Ile Asn Pro Tyr Asn Asp Gly Ser Lys Tyr Thr Glu Lys Phe
        50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Pro Gln Leu Phe Asp Tyr Trp Gly
                100                 105                 110

Gln Gly Thr Thr Val Thr Val Ser Ser
            115                 120

<210> SEQ ID NO 2
<211> LENGTH: 112
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 2

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Glu Thr Ser
            20                  25                  30

Thr Gly Thr Thr Tyr Leu Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Leu
                85                  90                  95

Leu Glu Asp Pro Tyr Thr Phe Gly Gln Gly Thr Lys Leu Glu Ile Lys
            100                 105                 110

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Tyr Ile Met His
1               5

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Ile Asn Pro Tyr Asn Asp Gly Ser Lys Tyr Thr Glu Lys Phe Gln
1               5                   10                  15

Gly

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Thr Tyr Tyr Tyr Gly Pro Gln Leu Phe Asp Tyr
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 6

Lys Ser Ser Gln Ser Leu Glu Thr Ser Thr Gly Thr Thr Tyr Leu Asn
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Val Ser Lys Arg Phe Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Gln Leu Leu Glu Asp Pro Tyr Thr
1               5

<210> SEQ ID NO 9
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ile Met His Trp Val Arg Gln Ala Pro Gly Gln Gly Leu Glu Trp Met
            35                  40                  45

Gly Tyr Ile Asn Pro Tyr Asn Asp Gly Ser Lys Tyr Thr Glu Lys Phe
        50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Pro Gln Leu Phe Asp Tyr Trp Gly
                100                 105                 110

Gln Gly Thr Thr Val Thr Val Ser Ser Gly Gly Gly Ser Gly Gly
            115                 120                 125

Gly Gly Ser Gly Gly Gly Ser Asp Ile Val Met Thr Gln Thr Pro
        130                 135                 140

Leu Ser Leu Ser Val Thr Pro Gly Gln Pro Ala Ser Ile Ser Cys Lys
145                 150                 155                 160

Ser Ser Gln Ser Leu Glu Thr Ser Thr Gly Thr Thr Tyr Leu Asn Trp
                165                 170                 175

Tyr Leu Gln Lys Pro Gly Gln Ser Pro Gln Leu Leu Ile Tyr Arg Val

```
                    180               185                   190
Ser Lys Arg Phe Ser Gly Val Pro Asp Arg Phe Ser Gly Ser Gly Ser
            195                 200                 205

Gly Thr Asp Phe Thr Leu Lys Ile Ser Arg Val Glu Ala Glu Asp Val
    210                 215                 220

Gly Val Tyr Tyr Cys Leu Gln Leu Leu Glu Asp Pro Tyr Thr Phe Gly
225                 230                 235                 240

Gln Gly Thr Lys Leu Glu Ile Lys
                245

<210> SEQ ID NO 10
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Lys Arg Tyr Asn Pro Ala
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
        115                 120

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95

Phe Gly Gln Gly Thr Lys Leu Glu Ile Lys Arg
```

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Ser Gly Met Gly Val Gly
1               5

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

His Ile Trp Trp Asp Asp Asp Lys Arg Tyr Asn Pro Ala Leu Lys Ser
1               5                   10                  15

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Glu Leu Trp Ser Tyr Tyr Phe Asp Tyr
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Ala Ser Ser Ser Val Ser Tyr Met His
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Thr Ser Lys Leu Ala Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Phe Gln Gly Ser Val Tyr Pro Phe Thr
1               5

<210> SEQ ID NO 18
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Lys Arg Tyr Asn Pro Ala
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Ala
    130                 135                 140

Thr Leu Ser Leu Ser Pro Gly Glu Arg Ala Thr Leu Ser Cys Ser Ala
145                 150                 155                 160

Ser Ser Ser Val Ser Tyr Met His Trp Tyr Gln Gln Lys Pro Gly Gln
                165                 170                 175

Ala Pro Arg Leu Leu Ile Tyr Asp Thr Ser Lys Leu Ala Ser Gly Ile
            180                 185                 190

Pro Ala Arg Phe Ser Gly Ser Gly Ser Gly Thr Asp Phe Thr Leu Thr
        195                 200                 205

Ile Ser Ser Leu Glu Pro Glu Asp Phe Ala Val Tyr Tyr Cys Phe Gln
    210                 215                 220

Gly Ser Val Tyr Pro Phe Thr Phe Gly Gln Gly Thr Lys Leu Glu Ile
225                 230                 235                 240

Lys Arg

<210> SEQ ID NO 19
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Glu Ser Gly Gly Gly Leu Val Lys Pro Gly Gly
1               5                   10                  15

```
Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
            35                  40                  45

Gly Tyr Ile Asn Pro Tyr Asn Asp Gly Thr Lys Tyr Asn Glu Lys Phe
 50                  55                  60

Gln Gly Arg Val Thr Ile Ser Ser Asp Lys Ser Ile Ser Thr Ala Tyr
 65                  70                  75                  80

Met Glu Leu Ser Ser Leu Arg Ser Glu Asp Thr Ala Met Tyr Tyr Cys
                 85                  90                  95

Ala Arg Gly Thr Tyr Tyr Tyr Gly Thr Arg Val Phe Asp Tyr Trp Gly
                100                 105                 110

Gln Gly Thr Leu Val Thr Val Ser Ser
            115                 120

<210> SEQ ID NO 20
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Val Met Thr Gln Ser Pro Ala Thr Leu Ser Leu Ser Pro Gly
 1               5                  10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
            35                  40                  45

Pro Gln Leu Leu Ile Tyr Arg Met Ser Asn Leu Asn Ser Gly Val Pro
 50                  55                  60

Asp Arg Phe Ser Gly Ser Gly Ser Gly Thr Glu Phe Thr Leu Thr Ile
 65                  70                  75                  80

Ser Ser Leu Glu Pro Glu Asp Phe Ala Val Tyr Tyr Cys Met Gln His
                 85                  90                  95

Leu Glu Tyr Pro Ile Thr Phe Gly Ala Gly Thr Lys Leu Glu Ile Lys
                100                 105                 110

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Tyr Val Met His
 1               5

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Trp Ile Gly Tyr Ile Asn Pro Tyr Asn Asp Gly Thr Lys Tyr
```

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Thr Tyr Tyr Tyr Gly Thr Arg Val Phe Asp Tyr
1               5                   10

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ser Ser Lys Ser Leu Gln Asn Val Asn Gly Asn Thr Tyr Leu Tyr
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Met Ser Asn Leu Asn Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Met Gln His Leu Glu Tyr Pro Ile Thr
1               5

<210> SEQ ID NO 27
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe

```
                    50                  55                  60
Lys Gly Lys Ala Thr Leu Thr Ala Asp Glu Ser Ser Ser Thr Ala Tyr
 65                  70                  75                  80

Met Gln Leu Ser Ser Leu Ala Ser Glu Asp Ser Ala Val Tyr Phe Cys
                 85                  90                  95

Ala Arg Arg Glu Thr Thr Thr Val Gly Arg Tyr Tyr Tyr Ala Met Asp
            100                 105                 110

Tyr Trp Gly Gln Gly Thr Ser Val Thr Val Ser Ser
        115                 120
```

<210> SEQ ID NO 28
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Asp Ile Leu Leu Thr Gln Thr Pro Ala Ser Leu Ala Val Ser Leu Gly
 1               5                  10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
         35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys
            100                 105                 110
```

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Ser Tyr Trp Met Asn
 1               5
```

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Gln Ile Trp Pro Gly Asp Gly Asp Thr Asn Tyr Asn Gly Lys Phe Lys
 1               5                  10                  15

Gly
```

<210> SEQ ID NO 31
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Glu Thr Thr Thr Val Gly Arg Tyr Tyr Tyr Ala Met Asp Tyr
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Ala Ser Gln Ser Val Asp Tyr Asp Gly Asp Ser Tyr Leu Asn
1               5                   10                  15

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Ala Ser Asn Leu Val Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Gln Ser Thr Glu Asp Pro Trp Thr
1               5

<210> SEQ ID NO 35
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Ala Phe Ser Ser Tyr
                20                  25                  30

Trp Met Asn Trp Val Arg Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
        50                  55                  60

Lys Gly Arg Ala Thr Ile Thr Ala Asp Glu Ser Thr Asn Thr Ala Tyr
65                  70                  75                  80
```

```
Met Glu Leu Ser Ser Leu Arg Ser Glu Asp Thr Ala Phe Tyr Ser Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120

<210> SEQ ID NO 36
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Leu Asn Trp Tyr Gln Gln Ile Pro Gly Lys Ala Pro
        35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Tyr Thr Phe Thr Ile Ser
65                  70                  75                  80

Ser Leu Gln Pro Glu Asp Ile Ala Thr Tyr His Cys Gln Gln Ser Thr
                85                  90                  95

Glu Asp Pro Trp Thr Phe Gly Gly Gly Thr Lys Leu Gln Ile Lys Arg
            100                 105                 110

<210> SEQ ID NO 37
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Glu Gln Pro Gly Ala Glu Val Val Lys Pro Gly Ala
1               5                   10                  15

Ser Val Lys Val Ser Cys Lys Thr Ser Gly Tyr Thr Phe Thr Ser Asn
            20                  25                  30

Trp Met His Trp Val Lys Gln Thr Pro Gly Lys Gly Leu Glu Trp Ile
        35                  40                  45

Gly Glu Ile Asp Pro Ser Asp Ser Tyr Thr Asn Tyr Asn Gln Lys Phe
50                  55                  60

Asp Gly Lys Ala Lys Leu Thr Val Asp Lys Ser Ser Ser Thr Ala Tyr
65                  70                  75                  80

Met Glu Val Ser Asp Leu Thr Ala Glu Asp Ser Ala Thr Tyr Tyr Cys
                85                  90                  95

Ala Arg Gly Ser Asn Pro Tyr Tyr Tyr Ala Met Asp Tyr Trp Gly Gln
            100                 105                 110

Gly Thr Ser Val Thr Val Ser Ser
        115                 120

<210> SEQ ID NO 38
<211> LENGTH: 104
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Ile Val Leu Thr Gln Ser Pro Ala Thr Leu Ser Ala Ser Pro Gly
1               5                   10                  15

Glu Lys Ala Thr Met Thr Cys Ser Ala Ser Ser Gly Val Asn Tyr Met
            20                  25                  30

His Trp Tyr Gln Gln Lys Pro Gly Thr Ser Pro Lys Arg Trp Ile Tyr
        35                  40                  45

Asp Thr Asp Lys Thr Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys
            100

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ser Asn Trp Met His
1               5

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Ile Asp Pro Ser Asp Ser Tyr Thr Asn
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Ser Asn Pro Tyr Tyr Tyr Ala Met Asp Tyr
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 42

Ser Ala Ser Ser Gly Val Asn Tyr Met His
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Thr Asp Lys Thr Ala Ser
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

His Gln Arg Gly Ser Tyr Thr
1               5

<210> SEQ ID NO 45
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Ser Ser
                20                  25                  30

Trp Ile Gly Trp Val Arg Gln Met Pro Gly Lys Gly Leu Glu Trp Met
            35                  40                  45

Gly Ile Ile Tyr Pro Asp Asp Ser Asp Thr Arg Tyr Ser Pro Ser Phe
        50                  55                  60

Gln Gly Gln Val Thr Ile Ser Ala Asp Lys Ser Ile Arg Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Thr Met Ile Trp Gly Val Ile Ile Asp Phe Trp Gly
            100                 105                 110

Gln Gly Thr Leu Val Thr Val Ser Ser
        115                 120

<210> SEQ ID NO 46
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

-continued

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys
            100                 105

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Ser Trp Ile Gly
1               5

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ile Ile Tyr Pro Asp Ser Asp Thr Arg Tyr Ser Pro Ser Phe Gln
1               5                   10                  15

Gly

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

His Val Thr Met Ile Trp Gly Val Ile Ile Asp Phe
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Ala Ser Gln Gly Ile Ser Ser Ala Leu Ala
1               5                   10
```

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Ala Ser Ser Leu Glu Ser
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Gln Phe Asn Ser Tyr Pro Phe Thr
1               5

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys
            100                 105

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Gln Phe Asn Ser Tyr Pro Tyr Thr
1               5

<210> SEQ ID NO 55
<211> LENGTH: 119
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Asp Ser Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Thr Asn Tyr Ala Gln Gln Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Val Ala Ala Asp Trp Leu Asp Pro Trp Gly Gln Gly
            100                 105                 110

Thr Leu Val Thr Val Ser Ser
        115

<210> SEQ ID NO 56
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Arg
                85                  90                  95

Phe Thr Phe Gly Pro Gly Thr Lys Val Asp Ile Lys
            100                 105

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser Tyr Ala Ile Ser
1               5

<210> SEQ ID NO 58

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Ile Ile Pro Ile Phe Gly Thr Thr Asn Tyr Ala Gln Gln Phe Gln
1               5                   10                  15

Gly

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Glu Ala Val Ala Ala Asp Trp Leu Asp Pro
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Ala Ser Gln Ser Val Ser Ser Ser Tyr Leu Ala
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Ala Ser Ser Arg Ala Thr
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Gln Tyr Gly Ser Ser Arg Phe Thr
1               5

<210> SEQ ID NO 63
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 63

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Ala Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gly Tyr Ser Ser Gly Trp Asp Ser Tyr Tyr Gly Met Gly
            100                 105                 110

Val Trp Gly Gln Gly Thr Thr Val Thr Val Ser Ser
        115                 120

<210> SEQ ID NO 64
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys
            100                 105

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Tyr Trp Ile Ala
1               5

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 66

Ile Ile Tyr Pro Gly Asp Ser Asp Thr Arg Tyr Ser Pro Ser Phe Gln
1               5                   10                  15

Gly

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Gly Tyr Ser Ser Gly Trp Asp Ser Tyr Tyr Gly Met Gly Val
1               5                   10                  15

<210> SEQ ID NO 68
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Thr Ile Asn Trp Val Arg Gln Ala Pro Gly Gln Gly Leu Glu Trp Met
            35                  40                  45

Gly Gly Ile Ile Pro Ile Phe Gly Ile Pro Asn Tyr Ala Gln Lys Phe
        50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ala Glu Asp Thr Ala Val Tyr Tyr Cys
                85                  90                  95

Ala Arg Ala Ser Gly Gly Ser Ala Asp Tyr Ser Tyr Gly Met Asp Val
                100                 105                 110

Trp Gly Gln Gly Thr Ala Val Thr Val Ser Ser
            115                 120

<210> SEQ ID NO 69
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
```

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Lys Arg Tyr Pro Tyr
                 85                  90                  95

Thr Phe Gly Gln Gly Thr Lys Leu Glu Ile Lys
            100                 105

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Tyr Thr Ile Asn
1               5

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ile Ile Pro Ile Phe Gly Ile Pro Asn Tyr Ala Gln Lys Phe Gln
1               5                   10                  15

Gly

<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Ser Gly Gly Ser Ala Asp Tyr Ser Tyr Gly Met Asp Val
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Ala Ser Gln Gly Ile Ser Ser Trp Leu Ala
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74
```

Ala Ala Ser Ser Leu Gln Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Gln Tyr Lys Arg Tyr Pro Tyr Thr
1               5

<210> SEQ ID NO 76
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Gln Ser Gly Ala Glu Val Lys Lys Pro Gly Glu
1               5                   10                  15
Ser Leu Asn Ile Ser Cys Lys Gly Ser Gly Tyr Ser Phe Thr Ser Tyr
            20                  25                  30
Trp Ile Gly Trp Val Arg Gln Met Pro Gly Lys Gly Leu Glu Trp Met
        35                  40                  45
Gly Ile Ile Tyr Pro Gly Asp Ser Asp Thr Arg Tyr Ser Pro Ser Phe
    50                  55                  60
Gln Gly Gln Val Thr Ile Ser Ala Asp Lys Ser Ile Asn Thr Ala Tyr
65                  70                  75                  80
Leu Gln Trp Ser Ser Leu Lys Ala Ser Asp Thr Ala Met Tyr Tyr Cys
                85                  90                  95
Ala Arg Gly Val Ser Met Ile Trp Gly Val Ile Met Asp Val Trp Gly
            100                 105                 110
Gln Gly Thr Thr Val Thr Val Ser Ser
        115                 120

<210> SEQ ID NO 77
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Ala Ile Gln Leu Thr Gln Ser Pro Ser Ser Leu Ser Ala Ser Val Gly
1               5                   10                  15
Asp Arg Val Thr Ile Thr Cys Arg Ala Ser Gln Gly Ile Ser Ser Ala
            20                  25                  30
Leu Ala Trp Tyr Gln Gln Lys Pro Gly Lys Ala Pro Lys Leu Leu Ile
        35                  40                  45
Tyr Asp Ala Ser Ser Leu Glu Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Phe Asn Ser Tyr Pro Trp
                85                  90                  95

Thr Phe Gly Gln Gly Thr Lys Val Glu Ile Lys
            100                 105

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ser Tyr Trp Ile Gly
1               5

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Val Ser Met Ile Trp Gly Val Ile Met Asp Val
1               5                   10

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Gln Phe Asn Ser Tyr Pro Trp Thr
1               5

<210> SEQ ID NO 81
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Val Gln Leu Val Gln Ser Gly Ala Glu Val Lys Lys Pro Gly Glu
1               5                   10                  15

Ser Leu Gln Ile Ser Cys Lys Gly Ser Gly Tyr Thr Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Gly Leu Lys Ala Ser Asp Thr Ala Met Tyr Tyr Cys
                85                  90                  95

Ala Arg Gln Gly Tyr Ser Ser Gly Trp Arg Ser Tyr Tyr Gly Met Gly
            100                 105                 110
```

Val Trp Gly Gln Gly Thr Thr Val Thr Val Ser Ser
            115                 120

<210> SEQ ID NO 82
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro His
                85                  90                  95

Thr Phe Gly Gln Gly Thr Lys Leu Glu Ile Lys
            100                 105

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asn Tyr Trp Ile Ala
1               5

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Gly Tyr Ser Ser Gly Trp Arg Ser Tyr Tyr Gly Met Gly Val
1               5                   10                  15

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Gln Phe Asn Ser Tyr Pro His Thr
1               5

```
<210> SEQ ID NO 86
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Val Ser Gly Ile Tyr Asn Leu His Gly Phe Asp Ile Trp
            100                 105                 110

Gly Gln Gly Thr Leu Val Thr Val Ser Ser
        115                 120

<210> SEQ ID NO 87
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Phe Gly Ser Pro
                85                  90                  95

Phe Thr Phe Gly Gln Gly Thr Lys Val Glu Ile Lys
            100                 105

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Tyr Ser Phe Thr Ser Tyr Trp
1               5
```

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ile Tyr Pro Gly Asp Ser Asp Thr
1               5

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Arg Gly Val Ser Gly Ile Tyr Asn Leu His Gly Phe Asp Ile
1               5                   10                  15

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Ser Ile Ser Ser Tyr
1               5

<210> SEQ ID NO 92
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ala Ala Ser
1

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Gln Gly Arg Phe Gly Ser Pro Phe Thr
1               5                   10

<210> SEQ ID NO 94
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Tyr Ser Arg Leu Asp Tyr Trp Gly Gln Gly Thr Leu
            100                 105                 110

Val Thr Val Ser Ser
        115

<210> SEQ ID NO 95
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Thr Val Val Thr Gln Glu Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Thr Gly Thr Lys Leu Thr Val Leu Gly Ser
            100                 105                 110

Arg

<210> SEQ ID NO 96
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Thr Val Val Thr Gln Glu Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu

-continued

```
                35                  40                  45
Ile Tyr Asp Asn Asn Lys Arg Pro Ser Gly Ile Pro Asp Arg Phe Ser
 50                  55                  60
Gly Ser Lys Ser Gly Thr Ser Ala Thr Leu Gly Ile Thr Gly Leu Gln
 65                  70                  75                  80
Thr Gly Asp Glu Ala Asp Tyr Tyr Cys Gly Thr Trp Asp Ser Ser Leu
                 85                  90                  95
Ser Ala Gly Val Phe Gly Thr Gly Thr Lys Leu Thr Val Leu Gly Ser
                100                 105                 110
Arg Gly Gly Gly Ser Gly Gly Gly Ser Gly Gly Gly Gly Ser
                115                 120                 125
Leu Glu Met Ala Gln Val Gln Leu Val Glu Thr Gly Gly Gly Leu Val
130                 135                 140
Gln Pro Gly Gly Ser Leu Arg Leu Ser Cys Ala Ala Ser Gly Phe Thr
145                 150                 155                 160
Phe Ser Ser Tyr Ala Met Ser Trp Val Arg Gln Ala Pro Gly Lys Gly
                165                 170                 175
Leu Glu Trp Val Ser Ala Ile Ser Gly Ser Gly Gly Ser Thr Tyr Tyr
                180                 185                 190
Ala Asp Ser Val Lys Gly Arg Phe Thr Ile Ser Arg Asp Asn Ser Lys
                195                 200                 205
Asn Thr Leu Tyr Leu Gln Met Asn Ser Leu Arg Ala Glu Asp Thr Ala
210                 215                 220
Val Tyr Tyr Cys Ala Arg Tyr Tyr Ser Arg Leu Asp Tyr Trp Gly
225                 230                 235                 240
Gln Gly Thr Leu Val Thr Val Ser Ser
                245

<210> SEQ ID NO 97
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Val Gln Leu Val Gln Ser Gly Ala Glu Val Lys Lys Pro Gly Ala
 1               5                  10                  15
Ser Val Lys Val Ser Cys Lys Ala Ser Gly Phe Asn Ile Lys Asp Tyr
                20                  25                  30
Tyr Met His Trp Val Arg Gln Ala Pro Gly Gln Arg Leu Glu Trp Met
             35                  40                  45
Gly Trp Ile Asp Leu Glu Asn Ala Asn Thr Ile Tyr Asp Ala Lys Phe
 50                  55                  60
Gln Gly Arg Val Thr Ile Thr Arg Asp Thr Ser Ala Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Asp Ala Tyr Gly Arg Tyr Phe Tyr Asp Val Trp Gly Gln Gly
                100                 105                 110
Thr Leu Val Thr Val Ser Ser
                115

<210> SEQ ID NO 98
<211> LENGTH: 112
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Phe Asn Ile Lys Asp Tyr Tyr Met His
1               5

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Trp Ile Asp Leu Glu Asn Ala Asn Thr Ile Tyr Asp Ala Lys Phe Gln
1               5                   10                  15

Gly

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Arg Asp Ala Tyr Gly Arg Tyr Phe Tyr Asp Val
1               5                   10

<210> SEQ ID NO 102
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 102

Lys Ser Ser Gln Ser Leu Leu Asn Ala Arg Thr Gly Lys Asn Tyr Leu
1               5                   10                  15

Ala

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Trp Ala Ser Thr Arg Glu Ser
1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Lys Gln Ser Tyr Ser Arg Arg Thr
1               5

<210> SEQ ID NO 105
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Gln Val Gln Leu Val Gln Ser Gly Ala Glu Val Lys
    130                 135                 140

Lys Pro Gly Ala Ser Val Lys Val Ser Cys Lys Ala Ser Gly Phe Asn
145                 150                 155                 160
```

-continued

```
Ile Lys Asp Tyr Tyr Met His Trp Val Arg Gln Ala Pro Gly Gln Arg
            165                 170                 175

Leu Glu Trp Met Gly Trp Ile Asp Leu Glu Asn Ala Asn Thr Ile Tyr
        180                 185                 190

Asp Ala Lys Phe Gln Gly Arg Val Thr Ile Thr Arg Asp Thr Ser Ala
        195                 200                 205

Ser Thr Ala Tyr Met Glu Leu Ser Ser Leu Arg Ser Glu Asp Thr Ala
    210                 215                 220

Val Tyr Tyr Cys Ala Arg Asp Ala Tyr Gly Arg Tyr Phe Tyr Asp Val
225                 230                 235                 240

Trp Gly Gln Gly Thr Leu Val Thr Val Ser Ser
                245                 250

<210> SEQ ID NO 106
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Ile Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Gln Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Ala Asn Phe Gly Asn Ser Tyr Ile Ser Tyr Trp
            100                 105                 110

Ala Tyr Trp Gly Gln Gly Thr Leu Val Thr Val Ser Ser
        115                 120                 125

<210> SEQ ID NO 107
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Thr Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Val Pro Gly Thr Pro Ala Arg Phe
    50                  55                  60

Ser Gly Ser Leu Leu Gly Gly Lys Ala Ala Leu Thr Leu Ser Gly Val
65                  70                  75                  80
```

```
Gln Pro Glu Asp Glu Ala Glu Tyr Tyr Cys Thr Leu Trp Tyr Ser Asn
                85                  90                  95

Arg Trp Val Phe Gly Gly Gly Thr Lys Leu Thr Val Leu
            100                 105

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Phe Thr Phe Asn Lys Tyr Ala Ile Asn
1               5                   10

<210> SEQ ID NO 109
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Ile Arg Ser Lys Tyr Asn Asn Tyr Ala Thr Tyr Tyr Ala Asp Gln
1               5                   10                  15

Val Lys

<210> SEQ ID NO 110
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

His Ala Asn Phe Gly Asn Ser Tyr Ile Ser Tyr Trp Ala Tyr
1               5                   10

<210> SEQ ID NO 111
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ala Ser Ser Thr Gly Ala Val Thr Ser Gly Asn Tyr Pro Asn
1               5                   10

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Thr Lys Phe Leu Val Pro
1               5
```

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Thr Leu Trp Tyr Ser Asn Arg Trp Val
1               5

<210> SEQ ID NO 114
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 114

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Ile Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Gln Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Ala Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Ala Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Val Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Thr Leu Trp Tyr Ser Asn Arg Trp Val Phe
225                 230                 235                 240

Gly Gly Gly Thr Lys Leu Thr Val Leu
                245

<210> SEQ ID NO 115
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Ala Asn Thr Ile Tyr Asp Ala Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Tyr Gly Arg Tyr Phe Tyr Asp Val Trp Gly Gln Gly
            100                 105                 110

Thr Leu Val Thr Val Ser Ser
        115

<210> SEQ ID NO 116
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

<210> SEQ ID NO 117
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Ala Asn Thr Ile Tyr Asp Ala Lys Phe
            50                  55                  60
Gln Gly Arg Val Thr Ile Thr Arg Asp Thr Ser Ala Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Asp Val Tyr Gly Arg Tyr Phe Tyr Asp Leu Trp Gly Gln Gly
                100                 105                 110
Thr Leu Val Thr Val Ser Ser
            115

<210> SEQ ID NO 118
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Asp Ile Val Met Thr Gln Ser Pro Asp Ser Leu Ala Val Ser Leu Gly
 1               5                  10                  15
Glu Arg Ala Thr Ile Asn Cys Lys Ser Ser Gln Ser Leu Leu Glu Ser
                20                  25                  30
Arg Thr Gly Lys Asn Tyr Leu Ala Trp Tyr Gln Gln Lys Pro Gly Gln
            35                  40                  45
Pro Pro Lys Leu Leu Ile Tyr Trp Ala Ser Thr Arg Glu Ser Gly Val
 50                  55                  60
Pro Asp Arg Phe Ser Gly Ser Gly Ser Gly Thr Asp Phe Thr Leu Thr
 65                  70                  75                  80
Ile Ser Ser Leu Gln Ala Glu Asp Val Ala Val Tyr Tyr Cys Lys Gln
                 85                  90                  95
Ser Tyr Ser Arg Arg Thr Phe Gly Gly Gly Thr Lys Val Glu Ile Lys
                100                 105                 110

<210> SEQ ID NO 119
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Asp Ile Lys Leu Gln Gln Ser Gly Ala Glu Leu Ala Arg Pro Gly Ala
 1               5                  10                  15
Ser Val Lys Met Ser Cys Lys Thr Ser Gly Tyr Thr Phe Thr Arg Tyr
                20                  25                  30
Thr Met His Trp Val Lys Gln Arg Pro Gly Gln Gly Leu Glu Trp Ile
            35                  40                  45
Gly Tyr Ile Asn Pro Ser Arg Gly Tyr Thr Asn Tyr Asn Gln Lys Phe
 50                  55                  60
Lys Asp Lys Ala Thr Leu Thr Thr Asp Lys Ser Ser Ser Thr Ala Tyr
 65                  70                  75                  80
Met Gln Leu Ser Ser Leu Thr Ser Glu Asp Ser Ala Val Tyr Tyr Cys
                 85                  90                  95
Ala Arg Tyr Tyr Asp Asp His Tyr Cys Leu Asp Tyr Trp Gly Gln Gly
                100                 105                 110

Thr Thr Leu Thr Val Ser Ser Val Glu
        115                 120

<210> SEQ ID NO 120
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Val Asp Asp Ile Gln Leu Thr Gln Ser Pro Ala Ile Met Ser Ala Ser
1               5                   10                  15

Pro Gly Glu Lys Val Thr Met Thr Cys Arg Ala Ser Ser Ser Val Ser
            20                  25                  30

Tyr Met Asn Trp Tyr Gln Gln Lys Ser Gly Thr Ser Pro Lys Arg Trp
        35                  40                  45

Ile Tyr Asp Thr Ser Lys Val Ala Ser Gly Val Pro Tyr Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Asn Pro
                85                  90                  95

Leu Thr Phe Gly Ala Gly Thr Lys Leu Glu Leu Lys
            100                 105

<210> SEQ ID NO 121
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 122

Ser Phe Gly Met Ser
1               5

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Phe Thr Phe Ser Ser Phe Gly Met Ser
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ser Ile Ser Gly Ser Gly Ser Asp Thr Leu
1               5                   10

<210> SEQ ID NO 125
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ser Ile Ser Gly Ser Gly Ser Asp Thr Leu Tyr Ala Asp Ser Val Lys
1               5                   10                  15

Gly

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Gly Ser Leu Ser Arg
1               5

<210> SEQ ID NO 127
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
```

```
                20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Phe Thr Phe Arg Ser Phe Gly Met Ser
1               5                   10

<210> SEQ ID NO 129
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 130
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 131
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 132
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45
```

```
Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 133
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Ser Ser Phe
             20                  25                  30

Gly Met Ser Trp Val Arg Gln Ala Pro Gly Lys Gly Leu Glu Trp Val
         35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 134
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Ser Ser Phe
             20                  25                  30

Gly Met Ser Trp Val Arg Gln Ala Pro Gly Lys Gly Leu Glu Trp Val
         35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95
```

```
Thr Ile Gly Gly Ser Leu Ser Arg Ser Gly Gln Gly Thr Leu Val Thr
            100                 105                 110

Val Ser Ser
        115

<210> SEQ ID NO 135
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 136
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Ala Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 137
```

<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Ala Val Gln Leu Val Asp Ser Gly Gly Gly Leu Val Gln Pro Gly Gly
1               5                   10                  15

Ser Leu Arg Leu Ser Cys Ala Ala Ser Gly Phe Ser Phe Gly Ser Phe
            20                  25                  30

Gly Met Ser Trp Val Arg Gln Tyr Pro Gly Lys Glu Pro Glu Trp Val
        35                  40                  45

Ser Ser Ile Asn Gly Arg Gly Asp Asp Thr Arg Tyr Ala Asp Ser Val
50                  55                  60

Lys Gly Arg Phe Ser Ile Ser Arg Asp Asn Ala Lys Asn Thr Leu Tyr
65                  70                  75                  80

Leu Gln Met Asn Ser Leu Lys Pro Glu Asp Thr Ala Glu Tyr Tyr Cys
                85                  90                  95

Thr Ile Gly Arg Ser Val Ser Arg Ser Arg Thr Gln Gly Thr Gln Val
            100                 105                 110

Thr Val Ser Ser
            115

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Phe Ser Phe Gly Ser Phe Gly Met Ser
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ser Ile Asn Gly Arg Gly Asp Asp Thr Arg
1               5                   10

<210> SEQ ID NO 140
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ser Ile Asn Gly Arg Gly Asp Asp Thr Arg Tyr Ala Asp Ser Val Lys
1               5                   10                  15

Gly

<210> SEQ ID NO 141

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Arg Ser Val Ser Arg Ser
1               5

<210> SEQ ID NO 142
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Ala Val Gln Leu Val Glu Ser Gly Gly Leu Val Gln Pro Gly Gly
1               5                   10                  15

Ser Leu Arg Leu Thr Cys Thr Ala Ser Gly Phe Thr Phe Arg Ser Phe
                20                  25                  30

Gly Met Ser Trp Val Arg Gln Ala Pro Gly Lys Asp Gln Glu Trp Val
            35                  40                  45

Ser Ala Ile Ser Ala Asp Ser Ser Thr Lys Asn Tyr Ala Asp Ser Val
        50                  55                  60

Lys Gly Arg Phe Thr Ile Ser Arg Asp Asn Ala Lys Lys Met Leu Tyr
65                  70                  75                  80

Leu Glu Met Asn Ser Leu Lys Pro Glu Asp Thr Ala Val Tyr Tyr Cys
                85                  90                  95

Val Ile Gly Arg Gly Ser Pro Ser Pro Gly Thr Gln Val Thr Val
            100                 105                 110

Ser Ser

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ala Ile Ser Ala Asp Ser Ser Thr Lys Asn
1               5                   10

<210> SEQ ID NO 144
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Ile Ser Ala Asp Ser Ser Thr Lys Asn Tyr Ala Asp Ser Val Lys
1               5                   10                  15

Gly

<210> SEQ ID NO 145
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Arg Gly Ser Pro
1               5

<210> SEQ ID NO 146
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Val Gln Leu Ala Glu Ser Gly Gly Gly Leu Val Gln Pro Gly Gly
1               5                   10                  15

Ser Leu Arg Leu Thr Cys Thr Ala Ser Gly Phe Thr Phe Gly Ser Phe
            20                  25                  30

Gly Met Ser Trp Val Arg Gln Ala Pro Gly Glu Gly Leu Glu Trp Val
        35                  40                  45

Ser Ala Ile Ser Ala Asp Ser Ser Asp Lys Arg Tyr Ala Asp Ser Val
    50                  55                  60

Lys Gly Arg Phe Thr Ile Ser Arg Asp Asn Ala Lys Lys Met Leu Tyr
65                  70                  75                  80

Leu Glu Met Asn Ser Leu Lys Ser Glu Asp Thr Ala Val Tyr Tyr Cys
                85                  90                  95

Val Ile Gly Arg Gly Ser Pro Ala Ser Gln Gly Thr Gln Val Thr Val
            100                 105                 110

Ser Ser

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Phe Thr Phe Gly Ser Phe Gly Met Ser
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ala Ile Ser Ala Asp Ser Ser Asp Lys Arg
1               5                   10

<210> SEQ ID NO 149
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 149

Ala Ile Ser Ala Asp Ser Ser Asp Lys Arg Tyr Ala Asp Ser Val Lys
1               5                   10                  15

Gly

<210> SEQ ID NO 150
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Val Ala Pro Gly Lys Gly Leu Glu Arg Ile
        35                  40                  45

Ser Arg Asp Ile Ser Thr Gly Gly Tyr Tyr Tyr Ala Asp Ser
    50                  55                  60

Val Lys Gly Arg Phe Thr Ile Ser Arg Asp Asn Ala Lys Asn Thr Leu
65                  70                  75                  80

Tyr Leu Gln Met Asn Ser Leu Lys Pro Glu Asp Thr Ala Leu Tyr Tyr
                85                  90                  95

Cys Ala Lys Asp Arg Glu Ala Gln Val Asp Thr Leu Asp Phe Asp Tyr
            100                 105                 110

Arg Gly Gln Gly Thr Gln Val Thr Val Ser Ser
        115                 120

<210> SEQ ID NO 151
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Asn Tyr Trp Met Tyr
1               5

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Phe Thr Phe Ser Asn Tyr Trp Met Tyr
1               5                   10

<210> SEQ ID NO 153
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 153

Arg Asp Ile Ser Thr Gly Gly Gly Tyr Ser Tyr
1               5                   10

<210> SEQ ID NO 154
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Arg Asp Ile Ser Thr Gly Gly Gly Tyr Ser Tyr Tyr Ala Asp Ser Val
1               5                   10                  15

Lys Gly

<210> SEQ ID NO 155
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asp Arg Glu Ala Gln Val Asp Thr Leu Asp Phe Asp Tyr
1               5                   10

<210> SEQ ID NO 156
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Ala Val Gln Leu Val Glu Ser Gly Gly Gly Leu Val Gln Gly Gly Gly
1               5                   10                  15

Ser Leu Arg Leu Ala Cys Ala Ala Ser Glu Arg Ile Phe Asp Leu Asn
                20                  25                  30

Leu Met Gly Trp Tyr Arg Gln Gly Pro Gly Asn Glu Arg Glu Leu Val
            35                  40                  45

Ala Thr Cys Ile Thr Val Gly Asp Ser Thr Asn Tyr Ala Asp Ser Val
        50                  55                  60

Lys Gly Arg Phe Thr Ile Ser Met Asp Tyr Thr Lys Gln Thr Val Tyr
65                  70                  75                  80

Leu His Met Asn Ser Leu Arg Pro Glu Asp Thr Gly Leu Tyr Tyr Cys
                85                  90                  95

Lys Ile Arg Arg Thr Trp His Ser Glu Leu Trp Gly Gln Gly Thr Gln
            100                 105                 110

Val Thr Val Ser Ser
        115

<210> SEQ ID NO 157
<211> LENGTH: 5
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 157

Leu Asn Leu Met Gly
1               5

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Glu Arg Ile Phe Asp Leu Asn Leu Met Gly
1               5                   10

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Thr Cys Ile Thr Val Gly Asp Ser Thr Asn
1               5                   10

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Thr Cys Ile Thr Val Gly Asp Ser Thr Asn Tyr Ala Asp Ser Val Lys
1               5                   10                  15

Gly

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Arg Arg Thr Trp His Ser Glu Leu
1               5

<210> SEQ ID NO 162
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Glu Val Gln Leu Val Glu Ser Gly Gly Gly Leu Val Gln Glu Gly Gly
1               5                   10                  15
```

```
Ser Leu Arg Leu Ala Cys Ala Ala Ser Glu Arg Ile Trp Asp Ile Asn
             20                  25                  30

Leu Leu Gly Trp Tyr Arg Gln Gly Pro Gly Asn Glu Arg Glu Leu Val
         35                  40                  45

Ala Thr Ile Thr Val Gly Asp Ser Thr Ser Tyr Ala Asp Ser Val Lys
 50                  55                  60

Gly Arg Phe Thr Ile Ser Arg Asp Tyr Asp Lys Asn Thr Leu Tyr Leu
 65                  70                  75                  80

Gln Met Asn Ser Leu Arg Pro Glu Asp Thr Gly Leu Tyr Tyr Cys Lys
             85                  90                  95

Ile Arg Arg Thr Trp His Ser Glu Leu Trp Gly Gln Gly Thr Gln Val
            100                 105                 110

Thr Val Ser Ser
        115

<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ile Asn Leu Leu Gly
1               5

<210> SEQ ID NO 164
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ser Glu Arg Ile Trp Asp Ile Asn Leu Leu Gly
1               5                   10

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Thr Ile Thr Val Gly Asp Ser Thr Ser
1               5

<210> SEQ ID NO 166
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Thr Ile Thr Val Gly Asp Ser Thr Ser Tyr Ala Asp Ser Val Lys Gly
1               5                   10                  15
```

<210> SEQ ID NO 167
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 167

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 168
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 168

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 169
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 169

-continued

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 170
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 171
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45
```

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 172
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Glu Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala
        115

<210> SEQ ID NO 173
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Glu Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                85                  90                  95

```
Thr Ile Gly Gly Ser Leu Ser Arg Ser Ser Gln Gly Thr Leu Val Thr
            100                 105                 110

Val Ser Ser Ala Ala Ala
        115

<210> SEQ ID NO 174
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly
        115

<210> SEQ ID NO 175
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly
        115

<210> SEQ ID NO 176
```

<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly
        115

<210> SEQ ID NO 177
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Glu Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser
        115

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

```
Gly Phe Thr Phe Ser Lys Phe Gly Met Ser
1               5                   10
```

<210> SEQ ID NO 179
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

```
Ser Ile Ser Gly Ser Gly Arg Asp Thr Leu Tyr Ala Glu Ser Val Lys
1               5                   10                  15
```

<210> SEQ ID NO 180
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

```
Gly Gly Ser Leu Ser Val
1               5
```

<210> SEQ ID NO 181
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Arg Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Glu Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115
```

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

```
Gly Phe Thr Phe Ser Arg Phe Gly Met Ser
1               5                   10
```

<210> SEQ ID NO 183
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ser Ile Ser Gly Ser Gly Ser Asp Thr Leu Tyr Ala Glu Ser Val Lys
1               5                   10                  15

<210> SEQ ID NO 184
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Thr Asp Thr Leu Tyr Ala Glu Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 185
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ser Ile Ser Gly Ser Gly Thr Asp Thr Leu Tyr Ala Glu Ser Val Lys
1               5                   10                  15

<210> SEQ ID NO 186
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr

```
                    20                  25                  30

Tyr Met His Trp Val Arg Gln Ala Pro Gly Gln Arg Leu Glu Trp Met
            35                  40                  45

Gly Trp Ile Asp Leu Glu Asn Ala Asn Thr Ile Tyr Asp Ala Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Tyr Gly Gly Tyr Phe Tyr Asp Val Trp Gly Gln Gly
            100                 105                 110

Thr Leu Val Thr Val Ser Ser
        115

<210> SEQ ID NO 187
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Cys Gly Thr Lys Val Glu Ile Lys
            100                 105                 110

<210> SEQ ID NO 188
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Gly Asn Thr Ile Tyr Asp Ala Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
```

```
                    85                  90                  95

Ala Arg Asp Gly Tyr Gly Arg Tyr Phe Tyr Asp Val Trp Gly Gln Gly
                100                 105                 110

Thr Leu Val Thr Val Ser Ser
        115

<210> SEQ ID NO 189
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
                100                 105                 110

<210> SEQ ID NO 190
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
                20                  25                  30

Tyr Met His Trp Val Arg Gln Ala Pro Gly Gln Arg Leu Glu Trp Met
            35                  40                  45

Gly Trp Ile Asp Leu Glu Asn Ala Asn Thr Ile Tyr Asp Ala Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Tyr Gly Arg Tyr Leu Tyr Asp Val Trp Gly Gln Gly
                100                 105                 110

Thr Leu Val Thr Val Ser Ser
        115

<210> SEQ ID NO 191
<211> LENGTH: 112
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 191

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Asn
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

<210> SEQ ID NO 192
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Gly Asn Thr Ile Tyr Asp Pro Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Tyr Gly Arg Tyr Phe Tyr Asp Val Trp Gly Gln Gly
            100                 105                 110

Thr Leu Val Thr Val Ser Ser
        115

<210> SEQ ID NO 193
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Leu Asn Ser
            20                  25                  30
```

```
Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95

Ser Tyr Ser Arg Arg Thr Phe Gly Gly Gly Thr Lys Val Glu Ile Lys
                100                 105                 110

<210> SEQ ID NO 194
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Glu Gly Asn Thr Ile Tyr Asp Ala Lys Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Ala Tyr Gly Arg Tyr Phe Tyr Asp Val Trp Gly Gln Gly
                100                 105                 110

Thr Leu Val Thr Val Ser Ser
        115

<210> SEQ ID NO 195
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Gly
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Thr Gly Asp Phe Thr Leu Thr
 65                  70                  75                  80

Ile Ser Ser Leu Gln Ala Glu Asp Val Ala Val Tyr Tyr Cys Lys Gln
                 85                  90                  95
```

```
Ser Tyr Ser Arg Arg Thr Phe Gly Gly Gly Thr Lys Val Glu Ile Lys
                100                 105                 110
```

<210> SEQ ID NO 196
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Ala Asn Thr Ile Tyr Asp Ala Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asn Tyr Gly Gly Tyr Phe Tyr Asp Val Trp Gly Gln Gly
                100                 105                 110

Thr Leu Val Thr Val Ser Ser
        115
```

<210> SEQ ID NO 197
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

```
Asp Ile Val Met Thr Gln Ser Pro Asp Ser Leu Ala Val Pro Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
                100                 105                 110
```

<210> SEQ ID NO 198
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Gly Asn Thr Ile Tyr Asp Pro Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Arg Tyr Phe Tyr Asp Val Trp Gly Gln Gly
            100                 105                 110

Thr Leu Val Thr Val Ser Ser
        115

<210> SEQ ID NO 199
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Leu Arg Thr Phe Gly Gly Gly Thr Lys Val Glu Ile Lys
            100                 105                 110

<210> SEQ ID NO 200
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Gly Asn Thr Ile Tyr Asp Pro Lys Phe
            50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Tyr Gly Arg Tyr Phe Phe Asp Val Trp Gly Gln Gly
             100                 105                 110

Thr Leu Val Thr Val Ser Ser
            115

<210> SEQ ID NO 201
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
             20                  25                  30

Arg Thr Arg Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95

Ser Tyr Asn Leu Arg Thr Phe Gly Gly Gly Thr Lys Val Glu Ile Lys
             100                 105                 110

<210> SEQ ID NO 202
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asn Ile Lys Asp Tyr
             20                  25                  30

Tyr Met His Trp Val Arg Gln Ala Pro Gly Gln Arg Leu Glu Trp Met
         35                  40                  45

Gly Trp Ile Asp Leu Glu Asn Gly Asn Thr Ile Tyr Asp Pro Lys Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Tyr Gly Arg Tyr Phe Tyr Asp Val Trp Gly Gln Gly
             100                 105                 110

Thr Leu Val Thr Val Ser Ser
            115

<210> SEQ ID NO 203
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Phe Arg Arg Ala Phe Gly Gly Gly Thr Lys Val Glu Ile Lys
            100                 105                 110

<210> SEQ ID NO 204
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Gly Asn Thr Ile Tyr Asp Pro Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Arg Tyr Tyr Tyr Asp Val Trp Gly Gln Gly
            100                 105                 110

Thr Leu Val Thr Val Ser Ser
            115

<210> SEQ ID NO 205
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 205

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110

<210> SEQ ID NO 206
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Arg Leu Glu Trp Met
        35                  40                  45

Gly Trp Ile Asp Leu Glu Asn Gly Asn Thr Ile Tyr Gln Pro Lys Phe
50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Arg Tyr Phe Tyr Asp Val Trp Gly Gln Gly
            100                 105                 110

Thr Leu Val Thr Val Ser Ser
        115

<210> SEQ ID NO 207
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val

```
                    50                  55                  60
Pro Asp Arg Phe Thr Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                     85                  90                  95

Ser Tyr Ser Leu Arg Thr Phe Gly Gly Gly Thr Lys Val Glu Ile Lys
                100                 105                 110
```

<210> SEQ ID NO 208
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

```
Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asn Ile Lys Asp Tyr
                20                  25                  30

Tyr Met His Trp Val Arg Gln Ala Pro Gly Gln Arg Leu Glu Trp Met
             35                  40                  45

Gly Trp Ile Asp Leu Glu Asn Gly Asn Thr Ile Tyr Asp Pro Lys Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Tyr Gly Arg Tyr Phe Tyr Asp Tyr Trp Gly Gln Gly
                100                 105                 110

Thr Leu Val Thr Val Ser Ser
        115
```

<210> SEQ ID NO 209
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Glu Ser
                20                  25                  30

Arg Thr Gly Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95

Ser Tyr Ser Leu Arg Thr Phe Gly Gly Gly Thr Lys Val Glu Ile Lys
                100                 105                 110
```

<210> SEQ ID NO 210
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ala Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Leu Ser Gln Ile Asp Ser Trp Gly Gln Gly Thr Leu
            100                 105                 110

Val Thr Val Ser Ser
        115

<210> SEQ ID NO 211
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Arg Gln Leu Pro Gly Thr Ala Pro Lys Leu Leu
        35                  40                  45

Ile Tyr Glu Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Arg Ala Gly Val Phe Gly Thr Gly Thr Lys Val Thr Val Leu
            100                 105                 110

<210> SEQ ID NO 212
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
             20                  25                  30

Tyr Val Ser Trp Tyr Arg Gln Leu Pro Gly Thr Ala Pro Lys Leu Leu
         35                  40                  45

Ile Tyr Glu Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Arg Ala Gly Val Phe Gly Thr Gly Thr Lys Val Thr Val Leu Gly Ser
            100                 105                 110

Arg Gly Gly Gly Gly Ser Gly Gly Gly Ser Gly Gly Gly Gly Ser
            115                 120                 125

Leu Glu Met Ala Gln Val Gln Leu Val Glu Ser Gly Gly Gly Leu Val
130                 135                 140

Gln Pro Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
                165                 170                 175

Leu Glu Trp Val Ser Gly Ile Ser Ala Ser Gly Gly Ser Thr Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
210                 215                 220

Val Tyr Tyr Cys Ala Arg Tyr Tyr Leu Ser Gln Ile Asp Ser Trp Gly
225                 230                 235                 240

Gln Gly Thr Leu Val Thr Val Ser Ser
                245

<210> SEQ ID NO 213
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
         35                  40                  45

Gly Leu Val Asp Pro Glu Asp Gly Glu Thr Ile Tyr Ala Glu Lys Phe
 50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Gly Ile Tyr Ser Arg Pro Leu Gly Tyr Trp Gly Gln Gly Thr
            100                 105                 110

Leu Val Thr Val Ser Ser

<210> SEQ ID NO 214
<211> LENGTH: 111
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 214

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly His Val Val Phe Gly Gly Gly Thr Lys Leu Thr Val Leu
            100                 105                 110

<210> SEQ ID NO 215
<211> LENGTH: 251
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 215

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly His Val Val Phe Gly Gly Gly Thr Lys Leu Thr Val Leu Gly
            100                 105                 110

Ser Arg Gly Gly Gly Gly Ser Gly Gly Gly Ser Gly Gly Gly Gly
        115                 120                 125

Ser Leu Glu Met Ala Glu Val Gln Leu Val Gln Ser Gly Ala Glu Val
    130                 135                 140

Lys Lys Pro Gly Ala Thr Val Lys Ile Ser Cys Lys Val Ser Gly Tyr
145                 150                 155                 160

Thr Phe Thr Asp Tyr Tyr Met His Trp Val Gln Gln Ala Pro Gly Lys
                165                 170                 175

Gly Leu Glu Trp Met Gly Leu Val Asp Pro Glu Asp Gly Glu Thr Ile

```
                    180                 185                 190
Tyr Ala Glu Lys Phe Gln Gly Arg Val Thr Ile Thr Ala Asp Thr Ser
            195                 200                 205

Thr Asp Thr Ala Tyr Met Glu Leu Ser Ser Leu Arg Ser Glu Asp Thr
        210                 215                 220

Ala Val Tyr Tyr Cys Ala Thr Gly Ile Tyr Ser Arg Pro Leu Gly Tyr
225                 230                 235                 240

Trp Gly Gln Gly Thr Leu Val Thr Val Ser Ser
                245                 250

<210> SEQ ID NO 216
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Asp Gly Lys His Phe Trp Gln Gln Tyr Asp Ala Trp Gly
            100                 105                 110

Gln Gly Thr Leu Val Thr Val Ser Ser
        115                 120

<210> SEQ ID NO 217
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser His
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu
```

100             105             110

<210> SEQ ID NO 218
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser His
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
            100                 105                 110

Arg Gly Gly Gly Gly Ser Gly Gly Gly Ser Gly Gly Gly Gly Ser
            115                 120                 125

Leu Glu Met Ala Glu Val Gln Leu Val Glu Thr Gly Gly Gly Leu Val
130                 135                 140

Gln Pro Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
                165                 170                 175

Leu Glu Trp Val Ser Ala Ile Ser Gly Ser Gly Gly Ser Thr Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Ser Asp Gly Lys His Phe Trp Gln Gln Tyr
225                 230                 235                 240

Asp Ala Trp Gly Gln Gly Thr Leu Val Thr Val Ser Ser
                245                 250

<210> SEQ ID NO 219
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val

```
                35                  40                  45
Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Met Asn Ile Asp Tyr Trp Gly Gln Gly Thr Leu Val Thr Val
                100                 105                 110

Ser Ser

<210> SEQ ID NO 220
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Asp Ile Gln Leu Thr Gln Ser Pro Ser Ser Leu Ser Ala Tyr Val Gly
 1               5                  10                  15

Asp Arg Val Thr Ile Thr Cys Arg Ala Ser Gln Gly Ile Thr Asn Ser
                 20                  25                  30

Leu Ala Trp Tyr Gln Gln Lys Pro Gly Lys Ala Pro Lys Leu Leu Leu
             35                  40                  45

His Ala Ala Ser Arg Leu Glu Ser Gly Val Pro Ser Arg Phe Ser Gly
 50                  55                  60

Ser Gly Phe Gly Thr Asp Phe Thr Leu Thr Ile Ser Ser Leu Gln Pro
 65                  70                  75                  80

Glu Asp Phe Ala Val Tyr Tyr Cys Gln His Tyr Leu Gly Thr Pro Tyr
                 85                  90                  95

Ser Phe Gly Gln Gly Thr Lys Val Glu Ile Lys
                100                 105

<210> SEQ ID NO 221
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Asp Ile Gln Leu Thr Gln Ser Pro Ser Ser Leu Ser Ala Tyr Val Gly
 1               5                  10                  15

Asp Arg Val Thr Ile Thr Cys Arg Ala Ser Gln Gly Ile Thr Asn Ser
                 20                  25                  30

Leu Ala Trp Tyr Gln Gln Lys Pro Gly Lys Ala Pro Lys Leu Leu Leu
             35                  40                  45

His Ala Ala Ser Arg Leu Glu Ser Gly Val Pro Ser Arg Phe Ser Gly
 50                  55                  60

Ser Gly Phe Gly Thr Asp Phe Thr Leu Thr Ile Ser Ser Leu Gln Pro
 65                  70                  75                  80

Glu Asp Phe Ala Val Tyr Tyr Cys Gln His Tyr Leu Gly Thr Pro Tyr
                 85                  90                  95

Ser Phe Gly Gln Gly Thr Lys Val Glu Ile Lys Arg Ser Arg Gly Gly
                100                 105                 110
```

Gly Gly Ser Gly Gly Gly Ser Gly Gly Gly Ser Leu Glu Met
        115                 120                 125

Ala Glu Val Gln Leu Val Glu Ser Gly Gly Leu Val Gln Pro Gly
        130                 135                 140

Gly Ser Leu Arg Leu Ser Cys Ala Ala Ser Gly Phe Thr Val Ser
145                 150                 155                 160

Asn Tyr Met Ser Trp Val Arg Gln Ala Pro Gly Lys Gly Leu Glu Trp
                165                 170                 175

Val Ser Ala Ile Ser Gly Ser Gly Gly Ser Thr Tyr Tyr Ala Asp Ser
                180                 185                 190

Val Lys Gly Arg Phe Thr Ile Ser Arg Asp Asn Ser Lys Asn Thr Leu
            195                 200                 205

Tyr Leu Gln Met Asn Ser Leu Arg Ala Glu Asp Thr Ala Val Tyr Tyr
        210                 215                 220

Cys Ala Arg Met Asn Ile Asp Tyr Trp Gly Gln Gly Thr Leu Val Thr
225                 230                 235                 240

Val Ser Ser

<210> SEQ ID NO 222
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Glu Val Gln Leu Val Gln Ser Gly Ala Glu Val Lys Arg Pro Gly Glu
1               5                   10                  15

Ser Leu Thr Ile Ser Cys Lys Gly Ser Glu Tyr Ser Phe Ala Ser Tyr
            20                  25                  30

Trp Ile Thr Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Arg Pro Phe Gln Tyr Asp Tyr Gly Gly Tyr Ser Asp Ala Phe Asp
            100                 105                 110

Ile Trp Gly Gln Gly Thr Met Val Thr Val Ser Ser
        115                 120

<210> SEQ ID NO 223
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Glu Ile Val Leu Thr Gln Ser Pro Ser Ser Leu Ser Ala Ser Val Gly
1               5                   10                  15

Asp Arg Val Thr Ile Ser Cys Arg Ala Ser Gln Ser Val Ser Arg Phe
            20                  25                  30

Leu Asn Trp Tyr Gln Gln Lys Pro Gly Lys Ala Pro Lys Leu Leu Ile
            35                  40                  45

Tyr Gly Val Ser Thr Leu Glu Arg Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Glu Ser Tyr Ile Ile Pro Leu
                 85                  90                  95

Thr Phe Gly Gly Gly Thr Lys Leu Glu Ile Lys
            100                 105

<210> SEQ ID NO 224
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Glu Ile Val Leu Thr Gln Ser Pro Ser Ser Leu Ser Ala Ser Val Gly
 1               5                  10                  15

Asp Arg Val Thr Ile Ser Cys Arg Ala Ser Gln Ser Val Ser Arg Phe
                 20                  25                  30

Leu Asn Trp Tyr Gln Gln Lys Pro Gly Lys Ala Pro Lys Leu Leu Ile
            35                  40                  45

Tyr Gly Val Ser Thr Leu Glu Arg Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Glu Ser Tyr Ile Ile Pro Leu
                 85                  90                  95

Thr Phe Gly Gly Gly Thr Lys Leu Glu Ile Lys Arg Ser Arg Gly Gly
            100                 105                 110

Gly Gly Ser Gly Gly Gly Gly Ser Gly Gly Gly Gly Ser Leu Glu Met
            115                 120                 125

Ala Glu Val Gln Leu Val Gln Ser Gly Ala Glu Val Lys Arg Pro Gly
130                 135                 140

Glu Ser Leu Thr Ile Ser Cys Lys Gly Ser Glu Tyr Ser Phe Ala Ser
145                 150                 155                 160

Tyr Trp Ile Thr Trp Val Arg Gln Met Pro Gly Lys Gly Leu Glu Trp
                165                 170                 175

Met Gly Arg Ile Asp Pro Ser Asp Ser Tyr Thr Asn Tyr Ser Pro Ser
            180                 185                 190

Phe Gln Gly His Val Thr Ile Ser Ala Asp Lys Ser Ile Ser Thr Ala
            195                 200                 205

Tyr Leu Gln Trp Ser Ser Leu Lys Ala Ser Asp Thr Ala Ile Tyr Tyr
        210                 215                 220

Cys Ala Arg Pro Phe Gln Tyr Asp Tyr Gly Gly Tyr Ser Asp Ala Phe
225                 230                 235                 240

Asp Ile Trp Gly Gln Gly Thr Met Val Thr Val Ser Ser
                245                 250

<210> SEQ ID NO 225
<211> LENGTH: 118
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 225

Gln Met Gln Leu Val Gln Ser Gly Ala Glu Val Lys Lys Ala Gly Ser
1               5                   10                  15

Ser Val Lys Val Ser Cys Glu Thr Ser Gly Gly Thr Phe Ser Ser Ser
                20                  25                  30

Ser Val Asn Trp Val Arg Gln Ala Pro Gly Gln Gly Leu Glu Trp Met
            35                  40                  45

Gly Gly Ile Ile Pro Ile Val Gly Thr Pro Asn Tyr Ala Gln Lys Phe
        50                  55                  60

Gln Asp Arg Val Thr Ile Thr Ala Val Glu Ser Thr Phe Thr Ala Tyr
65                  70                  75                  80

Met Glu Leu Ser Gly Leu Arg Ser Glu Asp Thr Ala Val Tyr Tyr Cys
                85                  90                  95

Ala Arg Gly Gly Tyr Arg Asp Tyr Met Asp Val Trp Gly Arg Gly Thr
                100                 105                 110

Thr Val Thr Val Ser Ser
            115

<210> SEQ ID NO 226
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Glu Ile Val Met Thr Gln Ser Pro Leu Ser Leu Ser Val Thr Pro Gly
1               5                   10                  15

Glu Pro Ala Ser Ile Ser Cys Arg Ser Ser Gln Ser Leu Leu Asp Ser
                20                  25                  30

Asn Gly Phe Asn Ser Leu Asp Trp Tyr Leu Gln Lys Pro Gly Gln Ser
            35                  40                  45

Pro Gln Leu Leu Ile His Leu Gly Ser Asp Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ser
                85                  90                  95

Leu Gln Ile Pro Thr Phe Gly Gln Gly Thr Lys Val Glu Ile Lys
            100                 105                 110

<210> SEQ ID NO 227
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Glu Ile Val Met Thr Gln Ser Pro Leu Ser Leu Ser Val Thr Pro Gly
1               5                   10                  15

Glu Pro Ala Ser Ile Ser Cys Arg Ser Ser Gln Ser Leu Leu Asp Ser
                20                  25                  30
```

```
Asn Gly Phe Asn Ser Leu Asp Trp Tyr Leu Gln Lys Pro Gly Gln Ser
            35                  40                  45

Pro Gln Leu Leu Ile His Leu Gly Ser Asp Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Ile Tyr Tyr Cys Met Gln Ser
                 85                  90                  95

Leu Gln Ile Pro Thr Phe Gly Gln Gly Thr Lys Val Glu Ile Lys Arg
            100                 105                 110

Ser Arg Gly Gly Gly Gly Ser Gly Gly Gly Ser Gly Gly Gly Gly
            115                 120                 125

Ser Leu Glu Met Ala Gln Met Gln Leu Val Gln Ser Gly Ala Glu Val
130                 135                 140

Lys Lys Ala Gly Ser Ser Val Lys Val Ser Cys Glu Thr Ser Gly Gly
145                 150                 155                 160

Thr Phe Ser Ser Ser Val Asn Trp Val Arg Gln Ala Pro Gly Gln
                165                 170                 175

Gly Leu Glu Trp Met Gly Gly Ile Ile Pro Ile Val Gly Thr Pro Asn
            180                 185                 190

Tyr Ala Gln Lys Phe Gln Asp Arg Val Thr Ile Thr Ala Val Glu Ser
            195                 200                 205

Thr Phe Thr Ala Tyr Met Glu Leu Ser Gly Leu Arg Ser Glu Asp Thr
210                 215                 220

Ala Val Tyr Tyr Cys Ala Arg Gly Gly Tyr Arg Asp Tyr Met Asp Val
225                 230                 235                 240

Trp Gly Arg Gly Thr Thr Val Thr Val Ser Ser
                245                 250

<210> SEQ ID NO 228
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Gly Phe Gly Ala Glu Phe Asp Tyr Trp Gly Gln Gly Thr Leu
            100                 105                 110

Val Thr Val Ser Ser
        115

<210> SEQ ID NO 229
```

```
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu
            100                 105                 110

<210> SEQ ID NO 230
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu Gly Ser
            100                 105                 110

Arg Gly Gly Gly Gly Ser Gly Gly Gly Ser Gly Gly Gly Gly Ser
            115                 120                 125

Leu Glu Met Ala Glu Val Gln Leu Val Glu Ser Gly Gly Gly Leu Ile
            130                 135                 140

Gln Pro Gly Gly Ser Leu Arg Leu Ser Cys Ala Ala Ser Gly Phe Thr
145                 150                 155                 160

Val Ser Ser Asn Tyr Met Ser Trp Val Arg Gln Ala Pro Gly Lys Gly
                165                 170                 175

Leu Glu Trp Val Ser Val Ile Tyr Ser Gly Gly Ser Thr Tyr Tyr Ala
            180                 185                 190

Asp Ser Val Lys Gly Arg Phe Thr Ile Ser Arg Asp Asn Ser Lys Asn
        195                 200                 205
```

```
Thr Leu Tyr Leu Gln Met Asn Ser Leu Arg Ala Glu Asp Thr Ala Val
    210                 215                 220

Tyr Tyr Cys Ala Arg Gly Gly Phe Gly Ala Glu Phe Asp Tyr Trp Gly
225                 230                 235                 240

Gln Gly Thr Leu Val Thr Val Ser Ser
                245

<210> SEQ ID NO 231
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Ile Ser Asp Asp Tyr Tyr Gly Ser Gly Ser Tyr Asp Asn
            100                 105                 110

Trp Gly Gln Gly Thr Leu Val Thr Val Ser Ser
        115                 120

<210> SEQ ID NO 232
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Ser Tyr Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Glu Asp
                85                  90                  95

Val Phe Gly Pro Gly Thr Lys Val Thr Val Leu
            100                 105

<210> SEQ ID NO 233
```

```
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Ser Tyr Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Glu Asp
                85                  90                  95

Val Phe Gly Pro Gly Thr Lys Val Thr Val Leu Gly Ser Arg Gly Gly
            100                 105                 110

Gly Gly Ser Gly Gly Gly Gly Ser Gly Gly Gly Gly Ser Leu Glu Met
        115                 120                 125

Ala Glu Val Gln Leu Val Glu Ser Gly Gly Gly Leu Ile Gln Pro Gly
    130                 135                 140

Gly Ser Leu Arg Leu Ser Cys Ala Ala Ser Gly Phe Thr Val Ser Ser
145                 150                 155                 160

Asn Tyr Met Ser Trp Val Arg Gln Ala Pro Gly Lys Gly Leu Glu Trp
                165                 170                 175

Val Ser Val Ile Tyr Ser Gly Gly Ser Thr Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Arg Gly Gly Ile Ser Asp Asp Tyr Tyr Gly Ser Gly Ser Tyr Asp
225                 230                 235                 240

Asn Trp Gly Gln Gly Thr Leu Val Thr Val Ser Ser
                245                 250

<210> SEQ ID NO 234
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60
```

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Arg Gly Met Gly Tyr Ala Phe Asp Ile Trp Gly Gln Gly Thr
            100                 105                 110

Met Val Thr Val Ser Ser
        115

<210> SEQ ID NO 235
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Gly Gly Thr Lys Val Glu Ile Lys
            100                 105

<210> SEQ ID NO 236
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Gly Gly Thr Lys Val Glu Ile Lys Arg Ser Arg Gly Gly
            100                 105                 110

Gly Gly Ser Gly Gly Gly Gly Ser Gly Gly Gly Gly Ser Leu Glu Met
        115                 120                 125

```
Ala Glu Val Gln Leu Val Glu Ser Gly Gly Gly Leu Val Gln Pro Gly
            130                 135                 140

Gly Ser Leu Arg Leu Ser Cys Ala Ala Ser Gly Phe Thr Val Ser Ser
145                 150                 155                 160

Asn Tyr Met Ser Trp Val Arg Gln Ala Pro Gly Lys Gly Leu Glu Trp
                165                 170                 175

Val Ser Val Ile Tyr Ser Gly Gly Ser Thr Tyr Tyr Ala Asp Ser Val
                180                 185                 190

Lys Gly Arg Phe Thr Ile Ser Arg Asp Asn Ser Lys Asn Thr Leu Tyr
                195                 200                 205

Leu Gln Met Asn Ser Leu Arg Ala Glu Asp Thr Ala Val Tyr Tyr Cys
            210                 215                 220

Ala Arg Glu Arg Gly Met Gly Tyr Ala Phe Asp Ile Trp Gly Gln Gly
225                 230                 235                 240

Thr Met Val Thr Val Ser Ser
                245
```

<210> SEQ ID NO 237
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

```
Gln Leu Gln Leu Gln Glu Ser Gly Pro Gly Leu Val Lys Pro Ser Glu
1               5                   10                  15

Thr Leu Ser Leu Thr Cys Ser Val Ser Gly Val Ser Met Ser Glu Asn
                20                  25                  30

Tyr Trp Ser Trp Ile Arg Gln Pro Pro Gly Lys Arg Leu Glu Trp Ile
                35                  40                  45

Gly Cys Ala His Tyr Thr Gly Asp Thr His Tyr Asn Pro Ser Leu Lys
            50                  55                  60

Gly Arg Val Thr Ile Ser Leu Asp Thr Ser Met Asn Gln Phe Ser Leu
65                  70                  75                  80

Arg Leu Asn Ser Val Thr Ala Ala Asp Thr Ala Val Tyr Tyr Cys Ala
                85                  90                  95

Ser Tyr His Pro Phe Asn Tyr Trp Gly Gln Gly Thr Leu Val Thr Val
                100                 105                 110

Ser Ser
```

<210> SEQ ID NO 238
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Tyr
                20                  25                  30

Leu Ala Trp Tyr Gln Gln Lys Pro Gly Lys Ala Pro Lys Leu Leu Ile
                35                  40                  45
```

```
Tyr Pro Ala Ser Thr Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Leu Phe Gly
                 85                  90                  95

Gln Gly Thr Arg Leu Glu Ile Lys
                100
```

<210> SEQ ID NO 239
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Gly Ser Tyr
                 20                  25                  30

Leu Ala Trp Tyr Gln Gln Lys Pro Gly Lys Ala Pro Lys Leu Leu Ile
             35                  40                  45

Tyr Pro Ala Ser Thr Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Leu Phe Gly
                 85                  90                  95

Gln Gly Thr Arg Leu Glu Ile Lys Arg Ser Arg Gly Gly Gly Gly Ser
                100                 105                 110

Gly Gly Gly Gly Ser Gly Gly Gly Ser Leu Glu Met Ala Gln Leu
            115                 120                 125

Gln Leu Gln Glu Ser Gly Pro Gly Leu Val Lys Pro Ser Glu Thr Leu
        130                 135                 140

Ser Leu Thr Cys Ser Val Ser Gly Val Ser Met Ser Glu Asn Tyr Trp
145                 150                 155                 160

Ser Trp Ile Arg Gln Pro Pro Gly Lys Arg Leu Glu Trp Ile Gly Cys
                165                 170                 175

Ala His Tyr Thr Gly Asp Thr His Tyr Asn Pro Ser Leu Lys Gly Arg
            180                 185                 190

Val Thr Ile Ser Leu Asp Thr Ser Met Asn Gln Phe Ser Leu Arg Leu
        195                 200                 205

Asn Ser Val Thr Ala Ala Asp Thr Ala Val Tyr Tyr Cys Ala Ser Tyr
    210                 215                 220

His Pro Phe Asn Tyr Trp Gly Gln Gly Thr Leu Val Thr Val Ser Ser
225                 230                 235                 240
```

<210> SEQ ID NO 240
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

```
Glu Val Gln Leu Val Gln Ser Gly Ala Glu Val Arg Arg Pro Gly Ala
1               5                   10                  15

Thr Val Lys Ile Ser Cys Lys Val Ser Gly Tyr Thr Phe Asn Asp Phe
            20                  25                  30

Tyr Leu His Trp Val Arg Gln Ala Pro Gly Lys Gly Leu Glu Trp Met
        35                  40                  45

Gly Arg Ile Asp Pro Glu Asp Gly Lys Thr Arg Tyr Ala Glu Lys Phe
    50                  55                  60

Gln Gly Arg Leu Thr Ile Thr Ala Asp Thr Ser Thr Asp Thr Leu Tyr
65                  70                  75                  80

Met Gln Leu Gly Gly Leu Thr Ser Asp Asp Thr Ala Val Tyr Tyr Cys
                85                  90                  95

Thr Thr Asp Trp Gly Tyr Ser Ser Leu Arg Glu Glu Asp Ile Trp
                100                 105                 110

Tyr Asp Cys Trp Gly Gln Gly Thr Leu Val Thr Val Ser Ser
            115                 120                 125
```

<210> SEQ ID NO 241
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Thr Lys
            20                  25                  30

Thr Val Asn Trp Tyr Gln Val Leu Pro Gly Thr Ala Pro Lys Leu Leu
        35                  40                  45

Ile Tyr Ser Asn Tyr Arg Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Asp Asp Glu Ala Asp Tyr Tyr Cys Ala Leu Trp Asp Asp Ser Leu
                85                  90                  95

Asp Gly Tyr Val Phe Gly Thr Gly Thr Lys Val Thr Val Leu
                100                 105                 110
```

<210> SEQ ID NO 242
<211> LENGTH: 258
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Thr Lys
            20                  25                  30

Thr Val Asn Trp Tyr Gln Val Leu Pro Gly Thr Ala Pro Lys Leu Leu
        35                  40                  45

Ile Tyr Ser Asn Tyr Arg Arg Pro Ser Gly Val Pro Asp Arg Phe Ser
    50                  55                  60
```

```
Gly Ser Lys Ser Gly Thr Ser Ala Ser Leu Ala Ile Ser Gly Leu Gln
 65                  70                  75                  80

Ser Asp Asp Glu Ala Asp Tyr Tyr Cys Ala Leu Trp Asp Asp Ser Leu
                 85                  90                  95

Asp Gly Tyr Val Phe Gly Thr Gly Thr Lys Val Thr Val Leu Gly Ser
            100                 105                 110

Arg Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Arg
        130                 135                 140

Arg Pro Gly Ala Thr Val Lys Ile Ser Cys Lys Val Ser Gly Tyr Thr
145                 150                 155                 160

Phe Asn Asp Phe Tyr Leu His Trp Val Arg Gln Ala Pro Gly Lys Gly
                165                 170                 175

Leu Glu Trp Met Gly Arg Ile Asp Pro Glu Asp Gly Lys Thr Arg Tyr
            180                 185                 190

Ala Glu Lys Phe Gln Gly Arg Leu Thr Ile Thr Ala Asp Thr Ser Thr
        195                 200                 205

Asp Thr Leu Tyr Met Gln Leu Gly Gly Leu Thr Ser Asp Asp Thr Ala
    210                 215                 220

Val Tyr Tyr Cys Thr Thr Asp Trp Gly Tyr Ser Ser Leu Arg Glu
225                 230                 235                 240

Glu Asp Ile Trp Tyr Asp Cys Trp Gly Gln Gly Thr Leu Val Thr Val
                245                 250                 255

Ser Ser

<210> SEQ ID NO 243
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Tyr Gly Tyr Gly Asp Tyr Gly Asp Ala Phe Asp Ile Trp
            100                 105                 110

Gly Gln Gly Thr Met Val Thr Val Ser Ser
        115                 120

<210> SEQ ID NO 244
<211> LENGTH: 108
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 244

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu
            100                 105

<210> SEQ ID NO 245
<211> LENGTH: 252
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 245

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Gln Ser Gly Ala Glu Val Lys Lys Pro
    130                 135                 140

Gly Ser Ser Val Lys Val Ser Cys Lys Ala Ser Gly Gly Thr Phe Ser
145                 150                 155                 160

Ser Tyr Ala Ile Ser Trp Val Arg Gln Ala Pro Gly Gln Gly Leu Glu
                165                 170                 175

Trp Met Gly Gly Ile Ile Pro Ile Phe Gly Thr Ala Asn Tyr Ala Gln
            180                 185                 190

Lys Phe Gln Gly Arg Val Thr Ile Thr Ala Asp Glu Ser Thr Ser Thr
        195                 200                 205

Ala Tyr Met Glu Leu Ser Ser Leu Arg Ser Glu Asp Thr Ala Val Tyr
    210                 215                 220

```
Tyr Cys Ala Arg Asp Tyr Gly Tyr Gly Asp Tyr Gly Asp Ala Phe Asp
225                 230                 235                 240

Ile Trp Gly Gln Gly Thr Met Val Thr Val Ser Ser
                245                 250
```

<210> SEQ ID NO 246
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Val Gly Thr Ile Tyr Ser Met Gln Tyr Asp Val Trp Gly
            100                 105                 110

Gln Gly Thr Leu Val Thr Val Ser Ser
        115                 120
```

<210> SEQ ID NO 247
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

```
Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Arg Pro Gly Gln Ala Pro Val Leu Val Val Tyr
            35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Ser Cys Gln Val Trp Asp Ser Ser Ser Asp His
                85                  90                  95

Tyr Val Phe Gly Pro Gly Thr Lys Val Thr Val Leu
            100                 105
```

<210> SEQ ID NO 248
<211> LENGTH: 251
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 248

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Arg Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Ser Cys Gln Val Trp Asp Ser Ser Ser Asp His
                85                  90                  95

Tyr Val Phe Gly Pro Gly Thr Lys Val Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Gln Ser Gly Ala Glu Val Lys Lys Pro
    130                 135                 140

Gly Glu Ser Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
            180                 185                 190

Ser Phe Gln Gly Gln Val Thr Ile Ser Ala Asp Lys Ser Ile Ser Thr
        195                 200                 205

Ala Tyr Leu Gln Trp Ser Ser Leu Lys Ala Ser Asp Thr Ala Met Tyr
    210                 215                 220

Tyr Cys Ala Arg Val Val Gly Thr Ile Tyr Ser Met Gln Tyr Asp Val
225                 230                 235                 240

Trp Gly Gln Gly Thr Leu Val Thr Val Ser Ser
                245                 250

<210> SEQ ID NO 249
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

```
Leu Gln Trp Ser Ser Leu Lys Ala Ser Asp Thr Ala Met Tyr Tyr Cys
                85                  90                  95

Ala Arg Gln Val Trp Gly Trp Gln Gly Gly Met Tyr Pro Arg Ser Asn
            100                 105                 110

Trp Trp Tyr Asn Met Asp Ser Trp Gly Gln Gly Thr Leu Val Thr Val
        115                 120                 125

Ser Ser
    130

<210> SEQ ID NO 250
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu
            100                 105

<210> SEQ ID NO 251
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu Gly Ser Arg Gly
            100                 105                 110

Gly Gly Gly Ser Gly Gly Gly Ser Gly Gly Gly Ser Leu Glu
        115                 120                 125
```

```
Met Ala Glu Val Gln Leu Val Gln Ser Gly Ala Glu Val Lys Lys Pro
    130                 135                 140

Gly Glu Ser Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
                180                 185                 190

Ser Phe Gln Gly Gln Val Thr Ile Ser Ala Asp Lys Ser Ile Ser Thr
            195                 200                 205

Ala Tyr Leu Gln Trp Ser Ser Leu Lys Ala Ser Asp Thr Ala Met Tyr
    210                 215                 220

Tyr Cys Ala Arg Gln Val Trp Gly Trp Gln Gly Met Tyr Pro Arg
225                 230                 235                 240

Ser Asn Trp Trp Tyr Asn Met Asp Ser Trp Gly Gln Gly Thr Leu Val
                245                 250                 255

Thr Val Ser Ser
            260

<210> SEQ ID NO 252
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Ser Ser Thr Trp Asp Ser Met Tyr Met Asp Tyr Trp Gly
            100                 105                 110

Gln Gly Thr Leu Val Thr Val Ser Ser
        115                 120

<210> SEQ ID NO 253
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Gln Ala Val Leu Thr Gln Pro Pro Ser Val Ser Glu Ala Pro Arg Gln
1               5                   10                  15

Arg Val Thr Ile Ser Cys Ser Gly Ser Ser Ser Asn Val Gly Asn Asn
            20                  25                  30
```

Ala Val Asn Trp Tyr Gln Gln Val Pro Gly Lys Ala Pro Lys Leu Leu
            35                  40                  45

Ile Tyr Tyr Asp Asp Leu Leu Ser Ser Gly Val Ser Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Pro Val Phe Gly Gly Gly Thr Lys Leu Thr Val Leu
                100                 105                 110

<210> SEQ ID NO 254
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Gln Ala Val Leu Thr Gln Pro Pro Ser Val Ser Glu Ala Pro Arg Gln
 1               5                  10                  15

Arg Val Thr Ile Ser Cys Ser Gly Ser Ser Asn Val Gly Asn Asn
             20                  25                  30

Ala Val Asn Trp Tyr Gln Gln Val Pro Gly Lys Ala Pro Lys Leu Leu
             35                  40                  45

Ile Tyr Tyr Asp Asp Leu Leu Ser Ser Gly Val Ser Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Pro Val Phe Gly Gly Gly Thr Lys Leu Thr Val Leu Gly Ser
                100                 105                 110

Arg Gly Gly Gly Ser Gly Gly Gly Ser Gly Gly Gly Ser
            115                 120                 125

Leu Glu Met Ala Glu Val Gln Leu Val Gln Ser Gly Ala Glu Val Lys
            130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly Gln Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Trp Ser Ser Thr Trp Asp Ser Met Tyr Met
225                 230                 235                 240

Asp Tyr Trp Gly Gln Gly Thr Leu Val Thr Val Ser Ser
                245                 250

<210> SEQ ID NO 255
<211> LENGTH: 121
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 255

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Thr Tyr Ser Met Asp Ser Tyr Tyr Phe Asp Ser Trp Gly
            100                 105                 110

Gln Gly Thr Leu Val Thr Val Ser Ser
        115                 120

<210> SEQ ID NO 256
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Gln Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Glu Ser Val
            20                  25                  30

His Trp Tyr Gln Gln Lys Pro Gly Gln Ala Pro Met Val Val Ile Tyr
        35                  40                  45

Tyr Asp Ser Asn Arg Pro Ser Gly Ile Pro Glu Arg Phe Ser Gly Ser
    50                  55                  60

Asn Ser Gly Asn Thr Ala Thr Leu Thr Val Ser Arg Val Glu Ala Glu
65                  70                  75                  80

Asp Glu Ala Asp Tyr Tyr Cys Gln Val Trp Asn Ser Ser Ser Asp His
                85                  90                  95

Arg Gly Val Phe Gly Gly Gly Thr Lys Leu Thr Val
            100                 105

<210> SEQ ID NO 257
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Gln Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Glu Ser Val
            20                  25                  30
```

His Trp Tyr Gln Gln Lys Pro Gly Gln Ala Pro Met Val Ile Tyr
            35                  40                  45

Tyr Asp Ser Asn Arg Pro Ser Gly Ile Pro Glu Arg Phe Ser Gly Ser
 50                  55                  60

Asn Ser Gly Asn Thr Ala Thr Leu Thr Val Ser Arg Val Glu Ala Glu
 65                  70                  75                  80

Asp Glu Ala Asp Tyr Tyr Cys Gln Val Trp Asn Ser Ser Ser Asp His
                 85                  90                  95

Arg Gly Val Phe Gly Gly Gly Thr Lys Leu Thr Val Leu Gly Ser Arg
            100                 105                 110

Gly Gly Gly Gly Ser Gly Gly Gly Ser Gly Gly Gly Gly Ser Leu
            115                 120                 125

Glu Met Ala Glu Val Gln Leu Val Gln Ser Gly Ala Glu Val Lys Lys
130                 135                 140

Pro Gly Glu Ser Leu Arg Ile Ser Cys Lys Gly Ser Gly Tyr Ser Phe
145                 150                 155                 160

Thr Ser Tyr Trp Ile Gly Trp Val Arg Gln Met Pro Gly Lys Gly Leu
                165                 170                 175

Glu Trp Met Gly Ile Ile Tyr Pro Gly Asp Ser Asp Thr Arg Tyr Ser
            180                 185                 190

Pro Ser Phe Gln Gly Gln Val Thr Ile Ser Ala Asp Lys Ser Ile Ser
            195                 200                 205

Thr Ala Tyr Leu Gln Trp Ser Ser Leu Lys Ala Ser Asp Thr Ala Met
210                 215                 220

Tyr Tyr Cys Ala Arg Val Thr Tyr Ser Met Asp Ser Tyr Tyr Phe Asp
225                 230                 235                 240

Ser Trp Gly Gln Gly Thr Leu Val Thr Val Ser Ser
                245                 250

<210> SEQ ID NO 258
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Asp Ile Lys Leu Gln Gln Ser Gly Ala Glu Leu Ala Arg Pro Gly Ala
 1               5                  10                  15

Ser Val Lys Met Ser Cys Lys Thr Ser Gly Tyr Thr Phe Thr Arg Tyr
             20                  25                  30

Thr Met His Trp Val Lys Gln Arg Pro Gly Gln Gly Leu Glu Trp Ile
             35                  40                  45

Gly Tyr Ile Asn Pro Ser Arg Gly Tyr Thr Asn Tyr Asn Gln Lys Phe
         50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
            115                 120                 125

Gly Ser Gly Gly Ser Gly Gly Val Asp Asp Ile Gln Leu Thr Gln Ser
        130                 135                 140

```
Pro Ala Ile Met Ser Ala Ser Pro Gly Glu Lys Val Thr Met Thr Cys
145                 150                 155                 160

Arg Ala Ser Ser Val Ser Tyr Met Asn Trp Tyr Gln Gln Lys Ser
            165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
        210                 215                 220

Gln Gln Trp Ser Ser Asn Pro Leu Thr Phe Gly Ala Gly Thr Lys Leu
225                 230                 235                 240

Glu Leu Lys

<210> SEQ ID NO 259
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Lys Phe Ser Gly Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Met Gly Tyr Trp His Phe Asp Leu Trp Gly Arg Gly Thr
            100                 105                 110

Leu Val Thr Val Ser Ser
        115

<210> SEQ ID NO 260
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60
```

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Leu Thr Phe Gly Gly Gly Thr Lys Val Glu Ile Lys
            100                 105

<210> SEQ ID NO 261
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gly Tyr Gly Met His
1               5

<210> SEQ ID NO 262
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Val Ile Trp Tyr Asp Gly Ser Lys Lys Tyr Tyr Val Asp Ser Val Lys
1               5                   10                  15

Gly

<210> SEQ ID NO 263
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Gln Met Gly Tyr Trp His Phe Asp Leu
1               5

<210> SEQ ID NO 264
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Arg Ala Ser Gln Ser Val Ser Ser Tyr Leu Ala
1               5                   10

<210> SEQ ID NO 265
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Asp Ala Ser Asn Arg Ala Thr

<210> SEQ ID NO 266
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 266

Gln Gln Arg Ser Asn Trp Pro Pro Leu Thr
1               5                   10

<210> SEQ ID NO 267
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 267

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Pro Met Ala Trp Val Arg Gln Ala Pro Gly Lys Gly Leu Glu Trp Val
        35                  40                  45

Ser Thr Ile Ser Thr Ser Gly Gly Arg Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Arg Gln Tyr Ser Gly Gly Phe Asp Tyr Trp Gly Gln Gly
            100                 105                 110

Thr Leu Val Thr Val Ser Ser
        115

<210> SEQ ID NO 268
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 268

Asp Phe Met Leu Thr Gln Pro His Ser Val Ser Glu Ser Pro Gly Lys
1               5                   10                  15

Thr Val Ile Ile Ser Cys Trp Tyr Gln Gln Arg Pro Gly Arg Ala Pro
            20                  25                  30

Thr Thr Val Ile Phe Gly Val Pro Asp Arg Phe Ser Gly Ser Ile Asp
        35                  40                  45

Arg Ser Ser Asn Ser Ala Ser Leu Thr Ile Ser Gly Leu Gln Thr Glu
    50                  55                  60

Asp Glu Ala Asp Tyr Tyr Cys Phe Gly Gly Gly Thr Lys Leu Thr Val
65                  70                  75                  80

Leu Gly Gln Pro Lys Ala Ala Pro Ser Val Thr Leu Phe Pro Pro Ser
                85                  90                  95

Ser Glu Glu Leu Gln
        100

<210> SEQ ID NO 269
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Pro Met Ala Trp Val Arg Gln Ala Pro Gly Lys Gly Leu Glu Trp Val
        35                  40                  45

Ser Thr Ile Ser Thr Ser Gly Gly Arg Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Arg Gln Tyr Ser Gly Gly Phe Asp Tyr Trp Gly Gln Gly
            100                 105                 110

Thr Leu Val Thr Val Ser Ser
        115

<210> SEQ ID NO 270
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Asp Ile Gln Leu Thr Gln Pro Asn Ser Val Ser Thr Ser Leu Gly Ser
1               5                   10                  15

Thr Val Lys Leu Ser Cys Thr Leu Ser Ser Gly Asn Ile Glu Asn Asn
            20                  25                  30

Tyr Val His Trp Tyr Gln Leu Tyr Glu Gly Arg Ser Pro Thr Thr Met
        35                  40                  45

Ile Tyr Asp Asp Asp Lys Arg Pro Asp Gly Val Pro Asp Arg Phe Ser
    50                  55                  60

Gly Ser Ile Asp Arg Ser Ser Asn Ser Ala Phe Leu Thr Ile His Asn
65                  70                  75                  80

Val Ala Ile Glu Asp Glu Ala Ile Tyr Phe Cys His Ser Tyr Val Ser
                85                  90                  95

Ser Phe Asn Val Phe Gly Gly Gly Thr Lys Leu Thr Val Leu Arg
            100                 105                 110

<210> SEQ ID NO 271
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 271

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser
        115

<210> SEQ ID NO 272
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Val Ala Ser Gly Val Pro Ala Arg Phe Ser Gly Ser
    50                  55                  60

Gly Ser Gly Thr Asp Tyr Ser Leu Thr Ile Asn Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 273
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

```
Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
 65                 70                  75                  80

Met Glu Leu Ser Ser Leu Arg Ser Glu Asp Thr Ala Thr Tyr Tyr Cys
                 85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
                115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
                195                 200                 205

Leu Thr Ile Asn Ser Leu Glu Ala Glu Asp Ala Ala Thr Tyr Tyr Cys
            210                 215                 220

Gln Gln Trp Ser Ser Asn Pro Leu Thr Phe Gly Gly Gly Thr Lys Val
225                 230                 235                 240

Glu Ile Lys
```

<210> SEQ ID NO 274
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

```
Gln Val Gln Leu Val Gln Ser Gly Gly Gly Val Val Gln Pro Gly Arg
 1               5                  10                  15

Ser Leu Arg Leu Ser Cys Lys Ala Ser Gly Tyr Thr Phe Thr Arg Tyr
                20                  25                  30

Thr Met His Trp Val Arg Gln Ala Pro Gly Lys Gly Leu Glu Trp Ile
             35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
 65                 70                  75                  80

Leu Gln Met Asp Ser Leu Arg Pro Glu Asp Thr Gly Val Tyr Phe Cys
                 85                  90                  95

Ala Arg Tyr Tyr Asp Asp His Tyr Cys Leu Asp Tyr Trp Gly Gln Gly
            100                 105                 110

Thr Pro Val Thr Val Ser Ser
                115
```

<210> SEQ ID NO 275
<211> LENGTH: 107
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 275

Asp Asp Ile Gln Met Thr Gln Ser Pro Ser Ser Leu Ser Ala Ser Val
1               5                   10                  15

Gly Asp Arg Val Thr Ile Thr Cys Ser Ala Ser Ser Val Ser Tyr
            20                  25                  30

Met Asn Trp Tyr Gln Gln Thr Pro Gly Lys Ala Pro Lys Arg Trp Ile
        35                  40                  45

Tyr Asp Thr Ser Lys Leu Ala Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Trp Ser Ser Asn Pro Phe
                85                  90                  95

Thr Phe Gly Gln Gly Thr Lys Leu Gln Ile Thr
            100                 105

<210> SEQ ID NO 276
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Thr Asp Lys Ser Lys Ser Thr Ala Phe
65                  70                  75                  80

Leu Gln Met Asp Ser Leu Arg Pro Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser
        115

<210> SEQ ID NO 277
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Asn Trp Tyr Gln Gln Thr Pro Gly Lys Ala Pro Lys Arg Trp Ile Tyr

```
                 35                  40                  45

Asp Thr Ser Lys Leu Ala Ser Gly Val Pro Ser Arg Phe Ser Gly Ser
         50                  55                  60

Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gln Gly Thr Lys Leu Gln Ile Thr Arg
                100                 105

<210> SEQ ID NO 278
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
             35                  40                  45

Ser Arg Ile Arg Ser Lys Tyr Asn Asn Tyr Ala Thr Tyr Tyr Ala Asp
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125

<210> SEQ ID NO 279
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
             35                  40                  45

Leu Ile Gly Gly Thr Asn Lys Arg Ala Pro Gly Thr Pro Ala Arg Phe
 50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu
```

<210> SEQ ID NO 280
<211> LENGTH: 123
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 280

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Thr Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Asn Ser Gly Tyr Gly His Tyr Tyr Tyr Gly Met Asp Val
            100                 105                 110

Trp Gly Gln Gly Thr Thr Val Thr Val Ala Ser
        115                 120

<210> SEQ ID NO 281
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 281

Ala Glu Ile Val Met Thr Gln Ser Pro Ala Thr Leu Ser Val Ser Pro
1               5                   10                  15

Gly Glu Arg Ala Thr Leu Ser Cys Arg Ala Ser Gln Ser Val Ser Ser
                20                  25                  30

Asn Leu Ala Trp Tyr Gln Gln Lys Pro Gly Gln Ala Pro Arg Leu Leu
            35                  40                  45

Ile Tyr Gly Ala Ser Thr Arg Ala Thr Gly Ile Pro Ala Arg Phe Ser
        50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln His Tyr Ile Asn Trp Pro
                85                  90                  95

Leu Thr Phe Gly Gly Gly Thr Lys Val Glu Ile Lys
            100                 105

<210> SEQ ID NO 282
<211> LENGTH: 45
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 282

```
Leu Lys Glu Ala Lys Glu Lys Ala Ile Glu Leu Lys Lys Ala Gly
1               5                   10                  15

Ile Thr Ser Asp Tyr Tyr Phe Asp Leu Ile Asn Lys Ala Lys Thr Val
            20                  25                  30

Glu Gly Val Asn Ala Leu Lys Asp Glu Ile Leu Lys Ala
            35                  40                  45
```

<210> SEQ ID NO 283
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Trp Met Ser Trp Val Arg Gln Ala Pro Gly Lys Gly Leu Glu Trp Val
            35                  40                  45

Ser Ser Ile Asp Phe Met Gly Pro His Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Thr Ser Met Leu Pro Met Lys Gly Lys Phe Asp Tyr
                100                 105                 110

Trp Gly Gln Gly Thr Leu Val Thr Val Ser Ser
            115                 120
```

<210> SEQ ID NO 284
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

```
Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Asp Glu Tyr
            20                  25                  30

Asn Met Ser Trp Val Arg Gln Ala Pro Gly Lys Gly Leu Glu Trp Val
            35                  40                  45

Ser Thr Ile Leu Pro His Gly Asp Arg Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Asp Pro Leu Tyr Arg Phe Asp Tyr Trp Gly Gln Gly Thr
                100                 105                 110

Leu Val Thr Val Ser Ser
            115
```

<210> SEQ ID NO 285
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Ala Thr Tyr
            20                  25                  30

Leu Asn Trp Tyr Gln Gln Lys Pro Gly Lys Ala Pro Lys Leu Leu Ile
        35                  40                  45

Tyr Arg Ser Ser Ser Leu Gln Ser Ala Val Pro Ser Arg Phe Ser Gly
    50                  55                  60

Ser Gly Ser Gly Thr Val Phe Thr Leu Thr Ile Ser Ser Leu Gln Pro
65                  70                  75                  80

Glu Asp Phe Ala Thr Tyr Tyr Cys Gln Gln Thr Tyr Ala Val Pro Pro
                85                  90                  95

Thr Phe Gly Gln Gly Thr Lys Val Glu Ile Lys Arg
            100                 105

<210> SEQ ID NO 286
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Asn Ser Pro Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Arg Val Pro Pro
                85                  90                  95

Thr Phe Gly Gln Gly Thr Lys Val Glu Ile Lys Arg
            100                 105

<210> SEQ ID NO 287
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Gln Val Gln Leu Gln Glu Ser Gly Gly Gly Leu Val Gln Pro Gly Gly
1               5                   10                  15

```
Ser Leu Arg Leu Ser Cys Glu Ala Ser Gly Phe Thr Phe Ser Arg Phe
            20                  25                  30

Gly Met Thr Trp Val Arg Gln Ala Pro Gly Lys Gly Val Glu Trp Val
        35                  40                  45

Ser Gly Ile Ser Ser Leu Gly Asp Ser Thr Leu Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                85                  90                  95

Thr Ile Gly Gly Ser Leu Asn Pro Gly Gly Gln Gly Thr Gln Val Thr
            100                 105                 110

Val Ser Ser
    115

<210> SEQ ID NO 288
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Glu Val Gln Leu Leu Glu Ser Gly Gly Gly Leu Val Gln Pro Gly Gly
 1               5                  10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 289
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Asp Ile Gln Met Thr Gln Ser Pro Ser Ser Val Ser Ala Ser Val Gly
 1               5                  10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
            35                  40                  45

Ile Tyr Glu Ala Ser Lys Leu Thr Ser Gly Val Pro Ser Arg Phe Ser
 50                  55                  60
```

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Cys Gly Thr Lys Val Glu Ile Lys Arg Thr
            100                 105                 110

<210> SEQ ID NO 290
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 291
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Gly Gly Thr Lys Val Glu Ile Lys Arg Thr
            100                 105                 110

<210> SEQ ID NO 292
<211> LENGTH: 20

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Gly Ser Gly Ser Gly Ser Gly Ser Gly Ser Gly Ser Gly Ser Gly Ser
1               5                   10                  15

Gly Ser Gly Ser
            20

<210> SEQ ID NO 293
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 294
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 295
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
        35                  40

<210> SEQ ID NO 296
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 296

Gly Gly Ser Gly Gly Gly Ser Gly Gly Gly Ser Gly Gly
1               5                   10                  15

Gly Ser Gly Gly Gly Ser Gly Gly Gly Ser Gly Gly Gly
            20                  25                  30

Ser Gly Gly Gly Gly Ser Gly Gly Gly Ser Gly Gly Gly Ser
        35                  40                  45

Gly Gly
    50

<210> SEQ ID NO 297
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser Gly Gly Gly Ser Gly Gly Gly
        35                  40                  45

Gly Ser
    50

<210> SEQ ID NO 298
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Gly Gly Gly Gly Ser Gly Gly Gly Gly Ser Gly Gly Gly Gly Ser Gly
1               5                   10                  15

Gly Gly Gly Ser
            20

<210> SEQ ID NO 299
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Gly Gly Gly Gly Ser Gly Gly Gly Gly Ser Gly Gly Gly Gly Ser
1               5                   10                  15

<210> SEQ ID NO 300
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Ser Gly Gly Gly Ser Gly Gly Gly
            35                  40                  45

Gly Ser Gly Gly Gly Ser Gly Gly Gly Ser Gly Gly Gly Gly
        50                  55                  60

Ser Gly Gly Gly Ser Gly Gly Gly Ser Gly Gly Gly Gly Ser
65                  70                  75                  80

Gly Gly Gly Gly Ser Gly Gly Gly Ser Gly Gly Gly Ser Gly
                85                  90                  95

Gly Gly Gly Ser
            100

<210> SEQ ID NO 301
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Gly Gly Ser Gly Gly Gly Ser Gly Gly Gly Ser Gly Gly Gly
1               5                   10                  15

Gly Ser Gly Gly Gly Ser Gly Gly Gly Ser Gly Gly Gly Gly
                20                  25                  30

Ser Gly Gly Gly Ser Gly Gly Gly Ser Gly Gly Gly Gly Ser
            35                  40                  45

Gly Gly Gly Ser Gly Gly Gly Ser Gly Gly Gly Ser Gly Gly
        50                  55                  60

Gly Gly Ser Gly Gly Gly Ser Gly Gly Gly Ser Gly Gly Gly
65                  70                  75                  80

Gly Gly Ser Gly Gly Gly Ser Gly Gly Gly Ser Gly Gly Gly
                85                  90                  95

Gly Ser Gly Gly
            100

<210> SEQ ID NO 302
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Gly Gly Gly Gly Ser Gly Gly Gly Ser
1               5

<210> SEQ ID NO 303
<211> LENGTH: 642
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Gly Ser Lys Tyr Thr Glu Lys Phe
    50                  55                  60

Gln Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Gly Pro Gln Leu Phe Asp Tyr Trp Gly
            100                 105                 110        Gly

Gln Gly Thr Thr Val Thr Val Ser Ser Gly Gly Gly Ser Gly Gly
            115                 120                 125

Gly Gly Ser Gly Gly Gly Ser Asp Ile Val Met Thr Gln Thr Pro
130                 135                 140

Leu Ser Leu Ser Val Thr Pro Gly Gln Pro Ala Ser Ile Ser Cys Lys
145                 150                 155                 160

Ser Ser Gln Ser Leu Glu Thr Ser Thr Gly Thr Thr Tyr Leu Asn Trp
            165                 170                 175

Tyr Leu Gln Lys Pro Gly Gln Ser Pro Gln Leu Leu Ile Tyr Arg Val
            180                 185                 190

Ser Lys Arg Phe Ser Gly Val Pro Asp Arg Phe Ser Gly Ser Gly Ser
            195                 200                 205

Gly Thr Asp Phe Thr Leu Lys Ile Ser Arg Val Glu Ala Glu Asp Val
    210                 215                 220

Gly Val Tyr Tyr Cys Leu Gln Leu Leu Glu Asp Pro Tyr Thr Phe Gly
225                 230                 235                 240

Gln Gly Thr Lys Leu Glu Ile Lys Gly Gly Gly Gly Ser Gly Gly Gly
            245                 250                 255

Ser Asp Ile Val Met Thr Gln Ser Pro Asp Ser Leu Ala Val Ser Leu
            260                 265                 270

Gly Glu Arg Ala Thr Ile Asn Cys Lys Ser Ser Gln Ser Leu Leu Asn
            275                 280                 285

Ala Arg Thr Gly Lys Asn Tyr Leu Ala Trp Tyr Gln Gln Lys Pro Gly
            290                 295                 300

Gln Pro Pro Lys Leu Leu Ile Tyr Trp Ala Ser Thr Arg Glu Ser Gly
305                 310                 315                 320

Val Pro Asp Arg Phe Ser Gly Ser Gly Ser Gly Thr Asp Phe Thr Leu
            325                 330                 335

Thr Ile Ser Ser Leu Gln Ala Glu Asp Val Ala Val Tyr Tyr Cys Lys
            340                 345                 350

Gln Ser Tyr Ser Arg Arg Thr Phe Gly Gly Gly Thr Lys Val Glu Ile
            355                 360                 365

Lys Gly Gly Gly Gly Ser Gly Gly Gly Gly Ser Gly Gly Gly Gly Ser
    370                 375                 380

Gly Gly Gly Gly Ser Gln Val Gln Leu Val Gln Ser Gly Ala Glu Val
385                 390                 395                 400

Lys Lys Pro Gly Ala Ser Val Lys Val Ser Cys Lys Ala Ser Gly Phe
            405                 410                 415

Asn Ile Lys Asp Tyr Tyr Met His Trp Val Arg Gln Ala Pro Gly Gln
```

```
                    420                 425                 430
Arg Leu Glu Trp Met Gly Trp Ile Asp Leu Glu Asn Ala Asn Thr Ile
                435                 440                 445

Tyr Asp Ala Lys Phe Gln Gly Arg Val Thr Ile Thr Arg Asp Thr Ser
            450                 455                 460

Ala Ser Thr Ala Tyr Met Glu Leu Ser Ser Leu Arg Ser Glu Asp Thr
465                 470                 475                 480

Ala Val Tyr Tyr Cys Ala Arg Asp Ala Tyr Gly Arg Tyr Phe Tyr Asp
                485                 490                 495

Val Trp Gly Gln Gly Thr Leu Val Thr Val Ser Ser Gly Gly Gly Gly
                500                 505                 510

Ser Gly Gly Gly Ser Glu Val Gln Leu Val Glu Ser Gly Gly Gly Leu
            515                 520                 525

Val Gln Pro Gly Asn Ser Leu Arg Leu Ser Cys Ala Ala Ser Gly Phe
            530                 535                 540

Thr Phe Ser Ser Phe Gly Met Ser Trp Val Arg Gln Ala Pro Gly Lys
545                 550                 555                 560

Gly Leu Glu Trp Val Ser Ser Ile Ser Gly Ser Gly Ser Asp Thr Leu
                565                 570                 575

Tyr Ala Asp Ser Val Lys Gly Arg Phe Thr Ile Ser Arg Asp Asn Ala
            580                 585                 590

Lys Thr Thr Leu Tyr Leu Gln Met Asn Ser Leu Arg Pro Glu Asp Thr
                595                 600                 605

Ala Val Tyr Tyr Cys Thr Ile Gly Gly Ser Leu Ser Arg Ser Ser Gln
            610                 615                 620

Gly Thr Leu Val Thr Val Ser Ser His His His His His His His His
625                 630                 635                 640

His His

<210> SEQ ID NO 304
<211> LENGTH: 642
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

Gly Gly Gly Gly Ser Gly Gly Gly Ser Gly Gly Gly Gly Ser
        115                 120                 125

Gly Gly Gly Ser Gln Val Gln Leu Val Gln Ser Gly Ala Glu Val Lys
```

```
          130                 135                 140
Lys Pro Gly Ala Ser Val Lys Val Ser Cys Lys Ala Ser Gly Phe Asn
145                 150                 155                 160

Ile Lys Asp Tyr Tyr Met His Trp Val Arg Gln Ala Pro Gly Gln Arg
                165                 170                 175

Leu Glu Trp Met Gly Trp Ile Asp Leu Glu Asn Ala Asn Thr Ile Tyr
            180                 185                 190

Asp Ala Lys Phe Gln Gly Arg Val Thr Ile Thr Arg Asp Thr Ser Ala
        195                 200                 205

Ser Thr Ala Tyr Met Glu Leu Ser Ser Leu Arg Ser Glu Asp Thr Ala
    210                 215                 220

Val Tyr Tyr Cys Ala Arg Asp Ala Tyr Gly Arg Tyr Phe Tyr Asp Val
225                 230                 235                 240

Trp Gly Gln Gly Thr Leu Val Thr Val Ser Ser Gly Gly Gly Gly Ser
                245                 250                 255

Gly Gly Gly Ser Gln Val Gln Leu Val Gln Ser Gly Ala Glu Val Lys
            260                 265                 270

Lys Pro Gly Ala Ser Val Lys Val Ser Cys Lys Ala Ser Gly Tyr Thr
        275                 280                 285

Phe Thr Asp Tyr Ile Met His Trp Val Arg Gln Ala Pro Gly Gln Gly
    290                 295                 300

Leu Glu Trp Met Gly Tyr Ile Asn Pro Tyr Asn Asp Gly Ser Lys Tyr
305                 310                 315                 320

Thr Glu Lys Phe Gln Gly Arg Val Thr Met Thr Ser Asp Thr Ser Ile
                325                 330                 335

Ser Thr Ala Tyr Met Glu Leu Ser Arg Leu Arg Ser Asp Asp Thr Ala
            340                 345                 350

Val Tyr Tyr Cys Ala Arg Gly Thr Tyr Tyr Gly Pro Gln Leu Phe
        355                 360                 365

Asp Tyr Trp Gly Gln Gly Thr Thr Val Thr Val Ser Ser Gly Gly Gly
    370                 375                 380

Gly Ser Gly Gly Gly Gly Ser Gly Gly Gly Gly Ser Asp Ile Val Met
385                 390                 395                 400

Thr Gln Thr Pro Leu Ser Leu Ser Val Thr Pro Gly Gln Pro Ala Ser
                405                 410                 415

Ile Ser Cys Lys Ser Ser Gln Ser Leu Glu Thr Ser Thr Gly Thr Thr
            420                 425                 430

Tyr Leu Asn Trp Tyr Leu Gln Lys Pro Gly Gln Ser Pro Gln Leu Leu
        435                 440                 445

Ile Tyr Arg Val Ser Lys Arg Phe Ser Gly Val Pro Asp Arg Phe Ser
    450                 455                 460

Gly Ser Gly Ser Gly Thr Asp Phe Thr Leu Lys Ile Ser Arg Val Glu
465                 470                 475                 480

Ala Glu Asp Val Gly Val Tyr Tyr Cys Leu Gln Leu Leu Glu Asp Pro
                485                 490                 495

Tyr Thr Phe Gly Gln Gly Thr Lys Leu Glu Ile Lys Gly Gly Gly Gly
            500                 505                 510

Ser Gly Gly Gly Ser Glu Val Gln Leu Val Glu Ser Gly Gly Gly Leu
        515                 520                 525

Val Gln Pro Gly Asn Ser Leu Arg Leu Ser Cys Ala Ala Ser Gly Phe
    530                 535                 540

Thr Phe Ser Ser Phe Gly Met Ser Trp Val Arg Gln Ala Pro Gly Lys
545                 550                 555                 560
```

-continued

```
Gly Leu Glu Trp Val Ser Ser Ile Ser Gly Ser Gly Ser Asp Thr Leu
                565                 570                 575

Tyr Ala Asp Ser Val Lys Gly Arg Phe Thr Ile Ser Arg Asp Asn Ala
            580                 585                 590

Lys Thr Thr Leu Tyr Leu Gln Met Asn Ser Leu Arg Pro Glu Asp Thr
        595                 600                 605

Ala Val Tyr Tyr Cys Thr Ile Gly Gly Ser Leu Ser Arg Ser Ser Gln
    610                 615                 620

Gly Thr Leu Val Thr Val Ser Ser His His His His His His His His
625                 630                 635                 640

His His
```

<210> SEQ ID NO 305
<211> LENGTH: 642
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Ser Gln Val Gln Leu Val Gln Ser Gly Ala Glu Val Lys
    130                 135                 140

Lys Pro Gly Ala Ser Val Lys Val Ser Cys Lys Ala Ser Gly Phe Asn
145                 150                 155                 160

Ile Lys Asp Tyr Tyr Met His Trp Val Arg Gln Ala Pro Gly Gln Arg
                165                 170                 175

Leu Glu Trp Met Gly Trp Ile Asp Leu Glu Asn Ala Asn Thr Ile Tyr
            180                 185                 190

Asp Ala Lys Phe Gln Gly Arg Val Thr Ile Thr Arg Asp Thr Ser Ala
        195                 200                 205

Ser Thr Ala Tyr Met Glu Leu Ser Ser Leu Arg Ser Glu Asp Thr Ala
    210                 215                 220

Val Tyr Tyr Cys Ala Arg Asp Ala Tyr Gly Arg Tyr Phe Tyr Asp Val
225                 230                 235                 240

Trp Gly Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270
```

Gln Pro Gly Asn Ser Leu Arg Leu Ser Cys Ala Ala Ser Gly Phe Thr
                275                 280                 285

Phe Ser Ser Phe Gly Met Ser Trp Val Arg Gln Ala Pro Gly Lys Gly
290                 295                 300

Leu Glu Trp Val Ser Ser Ile Ser Gly Ser Gly Ser Asp Thr Leu Tyr
305                 310                 315                 320

Ala Asp Ser Val Lys Gly Arg Phe Thr Ile Ser Arg Asp Asn Ala Lys
                325                 330                 335

Thr Thr Leu Tyr Leu Gln Met Asn Ser Leu Arg Pro Glu Asp Thr Ala
                340                 345                 350

Val Tyr Tyr Cys Thr Ile Gly Gly Ser Leu Ser Arg Ser Ser Gln Gly
                355                 360                 365

Thr Leu Val Thr Val Ser Ser Gly Gly Gly Gly Ser Gly Gly Gly Ser
                370                 375                 380

Gln Val Gln Leu Val Gln Ser Gly Ala Glu Val Lys Lys Pro Gly Ala
385                 390                 395                 400

Ser Val Lys Val Ser Cys Lys Ala Ser Gly Tyr Thr Phe Thr Asp Tyr
                405                 410                 415

Ile Met His Trp Val Arg Gln Ala Pro Gly Gln Gly Leu Glu Trp Met
                420                 425                 430

Gly Tyr Ile Asn Pro Tyr Asn Asp Gly Ser Lys Tyr Thr Glu Lys Phe
                435                 440                 445

Gln Gly Arg Val Thr Met Thr Ser Asp Thr Ser Ile Ser Thr Ala Tyr
                450                 455                 460

Met Glu Leu Ser Arg Leu Arg Ser Asp Asp Thr Ala Val Tyr Tyr Cys
465                 470                 475                 480

Ala Arg Gly Thr Tyr Tyr Gly Pro Gln Leu Phe Asp Tyr Trp Gly
                485                 490                 495

Gln Gly Thr Thr Val Thr Val Ser Ser Gly Gly Gly Ser Gly Gly
                500                 505                 510

Gly Gly Ser Gly Gly Gly Gly Ser Asp Ile Val Met Thr Gln Thr Pro
                515                 520                 525

Leu Ser Leu Ser Val Thr Pro Gly Gln Pro Ala Ser Ile Ser Cys Lys
530                 535                 540

Ser Ser Gln Ser Leu Glu Thr Ser Thr Gly Thr Thr Tyr Leu Asn Trp
545                 550                 555                 560

Tyr Leu Gln Lys Pro Gly Gln Ser Pro Gln Leu Leu Ile Tyr Arg Val
                565                 570                 575

Ser Lys Arg Phe Ser Gly Val Pro Asp Arg Phe Ser Gly Ser Gly Ser
                580                 585                 590

Gly Thr Asp Phe Thr Leu Lys Ile Ser Arg Val Glu Ala Glu Asp Val
                595                 600                 605

Gly Val Tyr Tyr Cys Leu Gln Leu Leu Glu Asp Pro Tyr Thr Phe Gly
                610                 615                 620

Gln Gly Thr Lys Leu Glu Ile Lys His His His His His His His
625                 630                 635                 640

His His

<210> SEQ ID NO 306
<211> LENGTH: 642
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 306

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Asp Ile Val Met
        115                 120                 125

Thr Gln Ser Pro Asp Ser Leu Ala Val Ser Leu Gly Glu Arg Ala Thr
130                 135                 140

Ile Asn Cys Lys Ser Ser Gln Ser Leu Leu Asn Ala Arg Thr Gly Lys
145                 150                 155                 160

Asn Tyr Leu Ala Trp Tyr Gln Gln Lys Pro Gly Gln Pro Pro Lys Leu
                165                 170                 175

Leu Ile Tyr Trp Ala Ser Thr Arg Glu Ser Gly Val Pro Asp Arg Phe
            180                 185                 190

Ser Gly Ser Gly Ser Gly Thr Asp Phe Thr Leu Thr Ile Ser Ser Leu
        195                 200                 205

Gln Ala Glu Asp Val Ala Val Tyr Tyr Cys Lys Gln Ser Tyr Ser Arg
    210                 215                 220

Arg Thr Phe Gly Gly Gly Thr Lys Val Glu Ile Lys Gly Gly Gly Gly
225                 230                 235                 240

Ser Gly Gly Gly Gly Ser Gly Gly Gly Ser Gly Gly Gly Gly Ser
                245                 250                 255

Gln Val Gln Leu Val Gln Ser Gly Ala Glu Val Lys Lys Pro Gly Ala
            260                 265                 270

Ser Val Lys Val Ser Cys Lys Ala Ser Gly Phe Asn Ile Lys Asp Tyr
        275                 280                 285

Tyr Met His Trp Val Arg Gln Ala Pro Gly Gln Arg Leu Glu Trp Met
    290                 295                 300

Gly Trp Ile Asp Leu Glu Asn Ala Asn Thr Ile Tyr Asp Ala Lys Phe
305                 310                 315                 320

Gln Gly Arg Val Thr Ile Thr Arg Asp Thr Ser Ala Ser Thr Ala Tyr
                325                 330                 335

Met Glu Leu Ser Ser Leu Arg Ser Glu Asp Thr Ala Val Tyr Tyr Cys
            340                 345                 350

Ala Arg Asp Ala Tyr Gly Arg Tyr Phe Tyr Asp Val Trp Gly Gln Gly
        355                 360                 365

Thr Leu Val Thr Val Ser Ser Gly Gly Gly Ser Gly Gly Gly Ser
    370                 375                 380

Gln Val Gln Leu Val Gln Ser Gly Ala Glu Val Lys Lys Pro Gly Ala
385                 390                 395                 400

-continued

Ser Val Lys Val Ser Cys Lys Ala Ser Gly Tyr Thr Phe Thr Asp Tyr
             405                 410                 415

Ile Met His Trp Val Arg Gln Ala Pro Gly Gln Gly Leu Glu Trp Met
        420                 425                 430

Gly Tyr Ile Asn Pro Tyr Asn Asp Gly Ser Lys Tyr Thr Glu Lys Phe
            435                 440                 445

Gln Gly Arg Val Thr Met Thr Ser Asp Thr Ser Ile Ser Thr Ala Tyr
        450                 455                 460

Met Glu Leu Ser Arg Leu Arg Ser Asp Asp Thr Ala Val Tyr Tyr Cys
465                 470                 475                 480

Ala Arg Gly Thr Tyr Tyr Gly Pro Gln Leu Phe Asp Tyr Trp Gly
            485                 490                 495

Gln Gly Thr Thr Val Thr Val Ser Ser Gly Gly Gly Ser Gly Gly
        500                 505                 510

Gly Gly Ser Gly Gly Gly Ser Asp Ile Val Met Thr Gln Thr Pro
            515                 520                 525

Leu Ser Leu Ser Val Thr Pro Gly Gln Pro Ala Ser Ile Ser Cys Lys
        530                 535                 540

Ser Ser Gln Ser Leu Glu Thr Ser Thr Gly Thr Thr Tyr Leu Asn Trp
545                 550                 555                 560

Tyr Leu Gln Lys Pro Gly Gln Ser Pro Gln Leu Leu Ile Tyr Arg Val
            565                 570                 575

Ser Lys Arg Phe Ser Gly Val Pro Asp Arg Phe Ser Gly Ser Gly Ser
            580                 585                 590

Gly Thr Asp Phe Thr Leu Lys Ile Ser Arg Val Glu Ala Glu Asp Val
            595                 600                 605

Gly Val Tyr Tyr Cys Leu Gln Leu Leu Glu Asp Pro Tyr Thr Phe Gly
            610                 615                 620

Gln Gly Thr Lys Leu Glu Ile Lys His His His His His His His His
625                 630                 635                 640

His His

<210> SEQ ID NO 307
<211> LENGTH: 642
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Ser Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

```
Val Ser Ser Gly Gly Gly Gly Ser Gly Gly Gly Ser Gln Val Gln Leu
        115                 120                 125

Val Gln Ser Gly Ala Glu Val Lys Lys Pro Gly Ala Ser Val Lys Val
    130                 135                 140

Ser Cys Lys Ala Ser Gly Tyr Thr Phe Thr Asp Tyr Ile Met His Trp
145                 150                 155                 160

Val Arg Gln Ala Pro Gly Gln Gly Leu Glu Trp Met Gly Tyr Ile Asn
                165                 170                 175

Pro Tyr Asn Asp Gly Ser Lys Tyr Thr Glu Lys Phe Gln Gly Arg Val
            180                 185                 190

Thr Met Thr Ser Asp Thr Ser Ile Ser Thr Ala Tyr Met Glu Leu Ser
        195                 200                 205

Arg Leu Arg Ser Asp Asp Thr Ala Val Tyr Tyr Cys Ala Arg Gly Thr
    210                 215                 220

Tyr Tyr Tyr Gly Pro Gln Leu Phe Asp Tyr Trp Gly Gln Gly Thr Thr
225                 230                 235                 240

Val Thr Val Ser Ser Gly Gly Gly Gly Ser Gly Gly Gly Gly Ser Gly
                245                 250                 255

Gly Gly Gly Ser Asp Ile Val Met Thr Gln Thr Pro Leu Ser Leu Ser
            260                 265                 270

Val Thr Pro Gly Gln Pro Ala Ser Ile Ser Cys Lys Ser Ser Gln Ser
    275                 280                 285

Leu Glu Thr Ser Thr Gly Thr Thr Tyr Leu Asn Trp Tyr Leu Gln Lys
    290                 295                 300

Pro Gly Gln Ser Pro Gln Leu Leu Ile Tyr Arg Val Ser Lys Arg Phe
305                 310                 315                 320

Ser Gly Val Pro Asp Arg Phe Ser Gly Ser Gly Ser Gly Thr Asp Phe
                325                 330                 335

Thr Leu Lys Ile Ser Arg Val Glu Ala Glu Asp Val Gly Val Tyr Tyr
            340                 345                 350

Cys Leu Gln Leu Leu Glu Asp Pro Tyr Thr Phe Gly Gln Gly Thr Lys
        355                 360                 365

Leu Glu Ile Lys Gly Gly Gly Gly Ser Gly Gly Gly Ser Asp Ile Val
    370                 375                 380

Met Thr Gln Ser Pro Asp Ser Leu Ala Val Ser Leu Gly Glu Arg Ala
385                 390                 395                 400

Thr Ile Asn Cys Lys Ser Ser Gln Ser Leu Leu Asn Ala Arg Thr Gly
                405                 410                 415

Lys Asn Tyr Leu Ala Trp Tyr Gln Gln Lys Pro Gly Gln Pro Pro Lys
            420                 425                 430

Leu Leu Ile Tyr Trp Ala Ser Thr Arg Glu Ser Gly Val Pro Asp Arg
        435                 440                 445

Phe Ser Gly Ser Gly Ser Gly Thr Asp Phe Thr Leu Thr Ile Ser Ser
450                 455                 460

Leu Gln Ala Glu Asp Val Ala Val Tyr Tyr Cys Lys Gln Ser Tyr Ser
465                 470                 475                 480

Arg Arg Thr Phe Gly Gly Gly Thr Lys Val Glu Ile Lys Gly Gly Gly
                485                 490                 495

Gly Ser Gly Gly Gly Gly Ser Gly Gly Gly Ser Gly Gly Gly Gly
            500                 505                 510

Ser Gln Val Gln Leu Val Gln Ser Gly Ala Glu Val Lys Lys Pro Gly
        515                 520                 525

Ala Ser Val Lys Val Ser Cys Lys Ala Ser Gly Phe Asn Ile Lys Asp
```

```
                530             535             540
Tyr Tyr Met His Trp Val Arg Gln Ala Pro Gly Gln Arg Leu Glu Trp
545             550             555             560

Met Gly Trp Ile Asp Leu Glu Asn Ala Asn Thr Ile Tyr Asp Ala Lys
            565             570             575

Phe Gln Gly Arg Val Thr Ile Thr Arg Asp Thr Ser Ala Ser Thr Ala
            580             585             590

Tyr Met Glu Leu Ser Ser Leu Arg Ser Glu Asp Thr Ala Val Tyr Tyr
            595             600             605

Cys Ala Arg Asp Ala Tyr Gly Arg Tyr Phe Tyr Asp Val Trp Gly Gln
            610             615             620

Gly Thr Leu Val Thr Val Ser Ser His His His His His His
625             630             635             640

His His

<210> SEQ ID NO 308
<211> LENGTH: 636
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Lys Arg Tyr Asn Pro Ala
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Ala
    130                 135                 140

Thr Leu Ser Leu Ser Pro Gly Glu Arg Ala Thr Leu Ser Cys Ser Ala
145                 150                 155                 160

Ser Ser Ser Val Ser Tyr Met His Trp Tyr Gln Gln Lys Pro Gly Gln
                165                 170                 175

Ala Pro Arg Leu Leu Ile Tyr Asp Thr Ser Lys Leu Ala Ser Gly Ile
            180                 185                 190

Pro Ala Arg Phe Ser Gly Ser Gly Ser Gly Thr Asp Phe Thr Leu Thr
        195                 200                 205

Ile Ser Ser Leu Glu Pro Glu Asp Phe Ala Val Tyr Tyr Cys Phe Gln
    210                 215                 220

Gly Ser Val Tyr Pro Phe Thr Phe Gly Gln Gly Thr Lys Leu Glu Ile
225                 230                 235                 240

Lys Arg Gly Gly Gly Gly Ser Gly Gly Gly Gly Ser Asp Ile Val Met Thr
```

```
            245                 250                 255
Gln Ser Pro Asp Ser Leu Ala Val Ser Leu Gly Glu Arg Ala Thr Ile
            260                 265                 270

Asn Cys Lys Ser Ser Gln Ser Leu Leu Asn Ala Arg Thr Gly Lys Asn
        275                 280                 285

Tyr Leu Ala Trp Tyr Gln Gln Lys Pro Gly Gln Pro Pro Lys Leu Leu
    290                 295                 300

Ile Tyr Trp Ala Ser Thr Arg Glu Ser Gly Val Pro Asp Arg Phe Ser
305                 310                 315                 320

Gly Ser Gly Ser Gly Thr Asp Phe Thr Leu Thr Ile Ser Ser Leu Gln
            325                 330                 335

Ala Glu Asp Val Ala Val Tyr Tyr Cys Lys Gln Ser Tyr Ser Arg Arg
            340                 345                 350

Thr Phe Gly Gly Gly Thr Lys Val Glu Ile Lys Gly Gly Gly Gly Ser
            355                 360                 365

Gly Gly Gly Gly Ser Gly Gly Gly Ser Gly Gly Gly Ser Gln
            370                 375                 380

Val Gln Leu Val Gln Ser Gly Ala Glu Val Lys Lys Pro Gly Ala Ser
385                 390                 395                 400

Val Lys Val Ser Cys Lys Ala Ser Gly Phe Asn Ile Lys Asp Tyr Tyr
                405                 410                 415

Met His Trp Val Arg Gln Ala Pro Gly Gln Arg Leu Glu Trp Met Gly
                420                 425                 430

Trp Ile Asp Leu Glu Asn Ala Asn Thr Ile Tyr Asp Ala Lys Phe Gln
            435                 440                 445

Gly Arg Val Thr Ile Thr Arg Asp Thr Ser Ala Ser Thr Ala Tyr Met
        450                 455                 460

Glu Leu Ser Ser Leu Arg Ser Glu Asp Thr Ala Val Tyr Tyr Cys Ala
465                 470                 475                 480

Arg Asp Ala Tyr Gly Arg Tyr Phe Tyr Asp Val Trp Gly Gln Gly Thr
                485                 490                 495

Leu Val Thr Val Ser Ser Gly Gly Gly Gly Ser Gly Gly Gly Ser Glu
            500                 505                 510

Val Gln Leu Val Glu Ser Gly Gly Gly Leu Val Gln Pro Gly Asn Ser
        515                 520                 525

Leu Arg Leu Ser Cys Ala Ala Ser Gly Phe Thr Phe Ser Ser Phe Gly
    530                 535                 540

Met Ser Trp Val Arg Gln Ala Pro Gly Lys Gly Leu Glu Trp Val Ser
545                 550                 555                 560

Ser Ile Ser Gly Ser Gly Ser Asp Thr Leu Tyr Ala Asp Ser Val Lys
                565                 570                 575

Gly Arg Phe Thr Ile Ser Arg Asp Asn Ala Lys Thr Thr Leu Tyr Leu
            580                 585                 590

Gln Met Asn Ser Leu Arg Pro Glu Asp Thr Ala Val Tyr Tyr Cys Thr
            595                 600                 605

Ile Gly Gly Ser Leu Ser Arg Ser Ser Gln Gly Thr Leu Val Thr Val
        610                 615                 620

Ser Ser His His His His His His His His
625                 630                 635

<210> SEQ ID NO 309
<211> LENGTH: 636
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 309

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Lys Arg Tyr Asn Pro Ala
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Ala
    130                 135                 140

Thr Leu Ser Leu Ser Pro Gly Glu Arg Ala Thr Leu Ser Cys Ser Ala
145                 150                 155                 160

Ser Ser Ser Val Ser Tyr Met His Trp Tyr Gln Gln Lys Pro Gly Gln
                165                 170                 175

Ala Pro Arg Leu Leu Ile Tyr Asp Thr Ser Lys Leu Ala Ser Gly Ile
            180                 185                 190

Pro Ala Arg Phe Ser Gly Ser Gly Ser Gly Thr Asp Phe Thr Leu Thr
        195                 200                 205

Ile Ser Ser Leu Glu Pro Glu Asp Phe Ala Val Tyr Tyr Cys Phe Gln
    210                 215                 220

Gly Ser Val Tyr Pro Phe Thr Phe Gly Gln Gly Thr Lys Leu Glu Ile
225                 230                 235                 240

Lys Arg Gly Gly Gly Gly Ser Gly Gly Gly Ser Glu Val Gln Leu Val
                245                 250                 255

Glu Ser Gly Gly Gly Leu Val Gln Pro Gly Asn Ser Leu Arg Leu Ser
            260                 265                 270

Cys Ala Ala Ser Gly Phe Thr Phe Ser Ser Phe Gly Met Ser Trp Val
        275                 280                 285

Arg Gln Ala Pro Gly Lys Gly Leu Glu Trp Val Ser Ser Ile Ser Gly
    290                 295                 300

Ser Gly Ser Asp Thr Leu Tyr Ala Asp Ser Val Lys Gly Arg Phe Thr
305                 310                 315                 320

Ile Ser Arg Asp Asn Ala Lys Thr Thr Leu Tyr Leu Gln Met Asn Ser
                325                 330                 335

Leu Arg Pro Glu Asp Thr Ala Val Tyr Tyr Cys Thr Ile Gly Gly Ser
            340                 345                 350

Leu Ser Arg Ser Ser Gln Gly Thr Leu Val Thr Val Ser Ser Gly Gly
        355                 360                 365

Gly Gly Ser Gly Gly Gly Ser Asp Ile Val Met Thr Gln Ser Pro Asp
    370                 375                 380

Ser Leu Ala Val Ser Leu Gly Glu Arg Ala Thr Ile Asn Cys Lys Ser
```

```
                385                 390                 395                 400
Ser Gln Ser Leu Leu Asn Ala Arg Thr Gly Lys Asn Tyr Leu Ala Trp
                405                 410                 415

Tyr Gln Gln Lys Pro Gly Gln Pro Lys Leu Leu Ile Tyr Trp Ala
            420                 425                 430

Ser Thr Arg Glu Ser Gly Val Pro Asp Arg Phe Ser Gly Ser Gly Ser
            435                 440                 445

Gly Thr Asp Phe Thr Leu Thr Ile Ser Ser Leu Gln Ala Glu Asp Val
        450                 455                 460

Ala Val Tyr Tyr Cys Lys Gln Ser Tyr Ser Arg Arg Thr Phe Gly Gly
465                 470                 475                 480

Gly Thr Lys Val Glu Ile Lys Gly Gly Gly Ser Gly Gly Gly
            485                 490                 495

Ser Gly Gly Gly Gly Ser Gly Gly Gly Ser Gln Val Gln Leu Val
            500                 505                 510

Gln Ser Gly Ala Glu Val Lys Lys Pro Gly Ala Ser Val Lys Val Ser
        515                 520                 525

Cys Lys Ala Ser Gly Phe Asn Ile Lys Asp Tyr Tyr Met His Trp Val
530                 535                 540

Arg Gln Ala Pro Gly Gln Arg Leu Glu Trp Met Gly Trp Ile Asp Leu
545                 550                 555                 560

Glu Asn Ala Asn Thr Ile Tyr Asp Ala Lys Phe Gln Gly Arg Val Thr
                565                 570                 575

Ile Thr Arg Asp Thr Ser Ala Ser Thr Ala Tyr Met Glu Leu Ser Ser
            580                 585                 590

Leu Arg Ser Glu Asp Thr Ala Val Tyr Tyr Cys Ala Arg Asp Ala Tyr
            595                 600                 605

Gly Arg Tyr Phe Tyr Asp Val Trp Gly Gln Gly Thr Leu Val Thr Val
        610                 615                 620

Ser Ser His His His His His His His His
625                 630                 635

<210> SEQ ID NO 310
<211> LENGTH: 636
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Arg Thr Gly Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110
```

-continued

Gly Gly Gly Gly Ser Gly Gly Gly Ser Gly Gly Gly Ser Gly
            115                 120                 125

Gly Gly Gly Ser Gln Val Gln Leu Val Gln Ser Gly Ala Glu Val Lys
            130                 135                 140

Lys Pro Gly Ala Ser Val Lys Val Ser Cys Lys Ala Ser Gly Phe Asn
145                 150                 155                 160

Ile Lys Asp Tyr Tyr Met His Trp Val Arg Gln Ala Pro Gly Gln Arg
                165                 170                 175

Leu Glu Trp Met Gly Trp Ile Asp Leu Glu Asn Ala Asn Thr Ile Tyr
            180                 185                 190

Asp Ala Lys Phe Gln Gly Arg Val Thr Ile Thr Arg Asp Thr Ser Ala
            195                 200                 205

Ser Thr Ala Tyr Met Glu Leu Ser Ser Leu Arg Ser Glu Asp Thr Ala
210                 215                 220

Val Tyr Tyr Cys Ala Arg Asp Ala Tyr Gly Arg Tyr Phe Tyr Asp Val
225                 230                 235                 240

Trp Gly Gln Gly Thr Leu Val Thr Val Ser Ser Gly Gly Gly Gly Ser
            245                 250                 255

Gly Gly Gly Ser Gln Val Gln Leu Gln Glu Ser Gly Pro Gly Leu Val
            260                 265                 270

Lys Pro Ser Gln Thr Leu Ser Leu Thr Cys Thr Val Ser Gly Gly Ser
            275                 280                 285

Ile Ser Thr Ser Gly Met Gly Val Gly Trp Ile Arg Gln His Pro Gly
            290                 295                 300

Lys Gly Leu Glu Trp Ile Gly His Ile Trp Trp Asp Asp Lys Arg
305                 310                 315                 320

Tyr Asn Pro Ala Leu Lys Ser Arg Val Thr Ile Ser Val Asp Thr Ser
                325                 330                 335

Lys Asn Gln Phe Ser Leu Lys Leu Ser Ser Val Thr Ala Ala Asp Thr
            340                 345                 350

Ala Val Tyr Tyr Cys Ala Arg Met Glu Leu Trp Ser Tyr Tyr Phe Asp
            355                 360                 365

Tyr Trp Gly Gln Gly Thr Leu Val Thr Val Ser Ser Gly Gly Gly Gly
370                 375                 380

Ser Gly Gly Gly Gly Ser Gly Gly Gly Gly Ser Glu Ile Val Leu Thr
385                 390                 395                 400

Gln Ser Pro Ala Thr Leu Ser Leu Ser Pro Gly Glu Arg Ala Thr Leu
            405                 410                 415

Ser Cys Ser Ala Ser Ser Ser Val Ser Tyr Met His Trp Tyr Gln Gln
            420                 425                 430

Lys Pro Gly Gln Ala Pro Arg Leu Leu Ile Tyr Asp Thr Ser Lys Leu
            435                 440                 445

Ala Ser Gly Ile Pro Ala Arg Phe Ser Gly Ser Gly Ser Gly Thr Asp
450                 455                 460

Phe Thr Leu Thr Ile Ser Ser Leu Glu Pro Glu Asp Phe Ala Val Tyr
465                 470                 475                 480

Tyr Cys Phe Gln Gly Ser Val Tyr Pro Phe Thr Phe Gly Gln Gly Thr
            485                 490                 495

Lys Leu Glu Ile Lys Arg Gly Gly Gly Ser Gly Gly Gly Ser Glu
            500                 505                 510

Val Gln Leu Val Glu Ser Gly Gly Leu Val Gln Pro Gly Asn Ser
            515                 520                 525

Leu Arg Leu Ser Cys Ala Ala Ser Gly Phe Thr Phe Ser Ser Phe Gly

```
                    530                 535                 540
Met Ser Trp Val Arg Gln Ala Pro Gly Lys Gly Leu Glu Trp Val Ser
545                 550                 555                 560

Ser Ile Ser Gly Ser Gly Ser Asp Thr Leu Tyr Ala Asp Ser Val Lys
                    565                 570                 575

Gly Arg Phe Thr Ile Ser Arg Asp Asn Ala Lys Thr Thr Leu Tyr Leu
                580                 585                 590

Gln Met Asn Ser Leu Arg Pro Glu Asp Thr Ala Val Tyr Tyr Cys Thr
                595                 600                 605

Ile Gly Gly Ser Leu Ser Arg Ser Ser Gln Gly Thr Leu Val Thr Val
                610                 615                 620

Ser Ser His His His His His His His His
625                 630                 635
```

<210> SEQ ID NO 311
<211> LENGTH: 636
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 311

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
                20                  25                  30

Arg Thr Gly Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Ser Arg Arg Thr Phe Gly Gly Gly Thr Lys Val Glu Ile Lys
            100                 105                 110

Gly Gly Gly Gly Ser Gly Gly Gly Ser Gly Gly Gly Gly Ser Gly
    115                 120                 125

Gly Gly Gly Ser Gln Val Gln Leu Val Gln Ser Gly Ala Glu Val Lys
130                 135                 140

Lys Pro Gly Ala Ser Val Lys Val Ser Cys Lys Ala Ser Gly Phe Asn
145                 150                 155                 160

Ile Lys Asp Tyr Tyr Met His Trp Val Arg Gln Ala Pro Gly Gln Arg
                165                 170                 175

Leu Glu Trp Met Gly Trp Ile Asp Leu Glu Asn Ala Asn Thr Ile Tyr
            180                 185                 190

Asp Ala Lys Phe Gln Gly Arg Val Thr Ile Thr Arg Asp Thr Ser Ala
        195                 200                 205

Ser Thr Ala Tyr Met Glu Leu Ser Ser Leu Arg Ser Glu Asp Thr Ala
    210                 215                 220

Val Tyr Tyr Cys Ala Arg Asp Ala Tyr Gly Arg Tyr Phe Tyr Asp Val
225                 230                 235                 240

Trp Gly Gln Gly Thr Leu Val Thr Val Ser Ser Gly Gly Gly Gly Ser
                245                 250                 255
```

Gly Gly Gly Ser Glu Val Gln Leu Val Glu Ser Gly Gly Leu Val
            260                 265                 270

Gln Pro Gly Asn Ser Leu Arg Leu Ser Cys Ala Ala Ser Gly Phe Thr
275                 280                 285

Phe Ser Ser Phe Gly Met Ser Trp Val Arg Gln Ala Pro Gly Lys Gly
    290                 295                 300

Leu Glu Trp Val Ser Ile Ser Gly Ser Gly Ser Asp Thr Leu Tyr
305                 310                 315                 320

Ala Asp Ser Val Lys Gly Arg Phe Thr Ile Ser Arg Asp Asn Ala Lys
                325                 330                 335

Thr Thr Leu Tyr Leu Gln Met Asn Ser Leu Arg Pro Glu Asp Thr Ala
            340                 345                 350

Val Tyr Tyr Cys Thr Ile Gly Gly Ser Leu Ser Arg Ser Ser Gln Gly
        355                 360                 365

Thr Leu Val Thr Val Ser Ser Gly Gly Gly Ser Gly Gly Gly Ser
    370                 375                 380

Gln Val Gln Leu Gln Glu Ser Gly Pro Gly Leu Val Lys Pro Ser Gln
385                 390                 395                 400

Thr Leu Ser Leu Thr Cys Thr Val Ser Gly Ser Ile Ser Thr Ser
            405                 410                 415

Gly Met Gly Val Gly Trp Ile Arg Gln His Pro Gly Lys Gly Leu Glu
        420                 425                 430

Trp Ile Gly His Ile Trp Trp Asp Asp Lys Arg Tyr Asn Pro Ala
            435                 440                 445

Leu Lys Ser Arg Val Thr Ile Ser Val Asp Thr Ser Lys Asn Gln Phe
450                 455                 460

Ser Leu Lys Leu Ser Ser Val Thr Ala Ala Asp Thr Ala Val Tyr Tyr
465                 470                 475                 480

Cys Ala Arg Met Glu Leu Trp Ser Tyr Tyr Phe Asp Tyr Trp Gly Gln
                485                 490                 495

Gly Thr Leu Val Thr Val Ser Ser Gly Gly Gly Ser Gly Gly Gly
            500                 505                 510

Gly Ser Gly Gly Gly Gly Ser Glu Ile Val Leu Thr Gln Ser Pro Ala
        515                 520                 525

Thr Leu Ser Leu Ser Pro Gly Glu Arg Ala Thr Leu Ser Cys Ser Ala
530                 535                 540

Ser Ser Ser Val Ser Tyr Met His Trp Tyr Gln Gln Lys Pro Gly Gln
545                 550                 555                 560

Ala Pro Arg Leu Leu Ile Tyr Asp Thr Ser Lys Leu Ala Ser Gly Ile
                565                 570                 575

Pro Ala Arg Phe Ser Gly Ser Gly Ser Gly Thr Asp Phe Thr Leu Thr
            580                 585                 590

Ile Ser Ser Leu Glu Pro Glu Asp Phe Ala Val Tyr Tyr Cys Phe Gln
        595                 600                 605

Gly Ser Val Tyr Pro Phe Thr Phe Gly Gln Gly Thr Lys Leu Glu Ile
    610                 615                 620

Lys Arg His His His His His His His His
625                 630                 635

<210> SEQ ID NO 312
<211> LENGTH: 636
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 312

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Asp Ile Val Met
        115                 120                 125

Thr Gln Ser Pro Asp Ser Leu Ala Val Ser Leu Gly Glu Arg Ala Thr
130                 135                 140

Ile Asn Cys Lys Ser Ser Gln Ser Leu Leu Asn Ala Arg Thr Gly Lys
145                 150                 155                 160

Asn Tyr Leu Ala Trp Tyr Gln Gln Lys Pro Gly Gln Pro Pro Lys Leu
                165                 170                 175

Leu Ile Tyr Trp Ala Ser Thr Arg Glu Ser Gly Val Pro Asp Arg Phe
            180                 185                 190

Ser Gly Ser Gly Ser Gly Thr Asp Phe Thr Leu Thr Ile Ser Ser Leu
        195                 200                 205

Gln Ala Glu Asp Val Ala Val Tyr Tyr Cys Lys Gln Ser Tyr Ser Arg
    210                 215                 220

Arg Thr Phe Gly Gly Gly Thr Lys Val Glu Ile Lys Gly Gly Gly Gly
225                 230                 235                 240

Ser Gly Gly Gly Gly Ser Gly Gly Gly Ser Gly Gly Gly Gly Ser
                245                 250                 255

Gln Val Gln Leu Val Gln Ser Gly Ala Glu Val Lys Lys Pro Gly Ala
            260                 265                 270

Ser Val Lys Val Ser Cys Lys Ala Ser Gly Phe Asn Ile Lys Asp Tyr
        275                 280                 285

Tyr Met His Trp Val Arg Gln Ala Pro Gly Gln Arg Leu Glu Trp Met
    290                 295                 300

Gly Trp Ile Asp Leu Glu Asn Ala Asn Thr Ile Tyr Asp Ala Lys Phe
305                 310                 315                 320

Gln Gly Arg Val Thr Ile Thr Arg Asp Thr Ser Ala Ser Thr Ala Tyr
                325                 330                 335

Met Glu Leu Ser Ser Leu Arg Ser Glu Asp Thr Ala Val Tyr Tyr Cys
            340                 345                 350

Ala Arg Asp Ala Tyr Gly Arg Tyr Phe Tyr Asp Val Trp Gly Gln Gly
        355                 360                 365

Thr Leu Val Thr Val Ser Ser Gly Gly Gly Gly Ser Gly Gly Gly Ser
    370                 375                 380

Gln Val Gln Leu Gln Glu Ser Gly Pro Gly Leu Val Lys Pro Ser Gln
385                 390                 395                 400

-continued

Thr Leu Ser Leu Thr Cys Thr Val Ser Gly Gly Ser Ile Ser Thr Ser
                405                 410                 415

Gly Met Gly Val Gly Trp Ile Arg Gln His Pro Gly Lys Gly Leu Glu
            420                 425                 430

Trp Ile Gly His Ile Trp Trp Asp Asp Lys Arg Tyr Asn Pro Ala
            435                 440                 445

Leu Lys Ser Arg Val Thr Ile Ser Val Asp Thr Ser Lys Asn Gln Phe
    450                 455                 460

Ser Leu Lys Leu Ser Ser Val Thr Ala Ala Asp Thr Ala Val Tyr Tyr
465                 470                 475                 480

Cys Ala Arg Met Glu Leu Trp Ser Tyr Tyr Phe Asp Tyr Trp Gly Gln
            485                 490                 495

Gly Thr Leu Val Thr Val Ser Ser Gly Gly Gly Gly Ser Gly Gly Gly
            500                 505                 510

Gly Ser Gly Gly Gly Gly Ser Glu Ile Val Leu Thr Gln Ser Pro Ala
            515                 520                 525

Thr Leu Ser Leu Ser Pro Gly Glu Arg Ala Thr Leu Ser Cys Ser Ala
            530                 535                 540

Ser Ser Ser Val Ser Tyr Met His Trp Tyr Gln Gln Lys Pro Gly Gln
545                 550                 555                 560

Ala Pro Arg Leu Leu Ile Tyr Asp Thr Ser Lys Leu Ala Ser Gly Ile
            565                 570                 575

Pro Ala Arg Phe Ser Gly Ser Gly Ser Gly Thr Asp Phe Thr Leu Thr
            580                 585                 590

Ile Ser Ser Leu Glu Pro Glu Asp Phe Ala Val Tyr Tyr Cys Phe Gln
            595                 600                 605

Gly Ser Val Tyr Pro Phe Thr Phe Gly Gln Gly Thr Lys Leu Glu Ile
            610                 615                 620

Lys Arg His His His His His His His His
625                 630                 635

<210> SEQ ID NO 313
<211> LENGTH: 636
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
            85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Gln Val Gln Leu
        115                 120                 125

```
Gln Glu Ser Gly Pro Gly Leu Val Lys Pro Ser Gln Thr Leu Ser Leu
    130                 135                 140

Thr Cys Thr Val Ser Gly Gly Ser Ile Ser Thr Ser Gly Met Gly Val
145                 150                 155                 160

Gly Trp Ile Arg Gln His Pro Gly Lys Gly Leu Glu Trp Ile Gly His
                165                 170                 175

Ile Trp Trp Asp Asp Asp Lys Arg Tyr Asn Pro Ala Leu Lys Ser Arg
            180                 185                 190

Val Thr Ile Ser Val Asp Thr Ser Lys Asn Gln Phe Ser Leu Lys Leu
        195                 200                 205

Ser Ser Val Thr Ala Ala Asp Thr Ala Val Tyr Tyr Cys Ala Arg Met
    210                 215                 220

Glu Leu Trp Ser Tyr Tyr Phe Asp Tyr Trp Gly Gln Gly Thr Leu Val
225                 230                 235                 240

Thr Val Ser Ser Gly Gly Gly Ser Gly Gly Gly Ser Gly Gly
                245                 250                 255

Gly Gly Ser Glu Ile Val Leu Thr Gln Ser Pro Ala Thr Leu Ser Leu
            260                 265                 270

Ser Pro Gly Glu Arg Ala Thr Leu Ser Cys Ser Ala Ser Ser Ser Val
    275                 280                 285

Ser Tyr Met His Trp Tyr Gln Gln Lys Pro Gly Gln Ala Pro Arg Leu
    290                 295                 300

Leu Ile Tyr Asp Thr Ser Lys Leu Ala Ser Gly Ile Pro Ala Arg Phe
305                 310                 315                 320

Ser Gly Ser Gly Ser Gly Thr Asp Phe Thr Leu Thr Ile Ser Ser Leu
                325                 330                 335

Glu Pro Glu Asp Phe Ala Val Tyr Tyr Cys Phe Gln Gly Ser Val Tyr
            340                 345                 350

Pro Phe Thr Phe Gly Gln Gly Thr Lys Leu Glu Ile Lys Arg Gly Gly
        355                 360                 365

Gly Gly Ser Gly Gly Gly Ser Asp Ile Val Met Thr Gln Ser Pro Asp
    370                 375                 380

Ser Leu Ala Val Ser Leu Gly Glu Arg Ala Thr Ile Asn Cys Lys Ser
385                 390                 395                 400

Ser Gln Ser Leu Leu Asn Ala Arg Thr Gly Lys Asn Tyr Leu Ala Trp
                405                 410                 415

Tyr Gln Gln Lys Pro Gly Gln Pro Pro Lys Leu Leu Ile Tyr Trp Ala
            420                 425                 430

Ser Thr Arg Glu Ser Gly Val Pro Asp Arg Phe Ser Gly Ser Gly Ser
        435                 440                 445

Gly Thr Asp Phe Thr Leu Thr Ile Ser Ser Leu Gln Ala Glu Asp Val
    450                 455                 460

Ala Val Tyr Tyr Cys Lys Gln Ser Tyr Ser Arg Arg Thr Phe Gly Gly
465                 470                 475                 480

Gly Thr Lys Val Glu Ile Lys Gly Gly Gly Ser Gly Gly Gly
                485                 490                 495

Ser Gly Gly Gly Gly Ser Gly Gly Gly Ser Gln Val Gln Leu Val
            500                 505                 510

Gln Ser Gly Ala Glu Val Lys Lys Pro Gly Ala Ser Val Lys Val Ser
        515                 520                 525

Cys Lys Ala Ser Gly Phe Asn Ile Lys Asp Tyr Tyr Met His Trp Val
    530                 535                 540
```

```
Arg Gln Ala Pro Gly Gln Arg Leu Glu Trp Met Gly Trp Ile Asp Leu
545                 550                 555                 560

Glu Asn Ala Asn Thr Ile Tyr Asp Ala Lys Phe Gln Gly Arg Val Thr
                565                 570                 575

Ile Thr Arg Asp Thr Ser Ala Ser Thr Ala Tyr Met Glu Leu Ser Ser
            580                 585                 590

Leu Arg Ser Glu Asp Thr Ala Val Tyr Tyr Cys Ala Arg Asp Ala Tyr
595                 600                 605

Gly Arg Tyr Phe Tyr Asp Val Trp Gly Gln Gly Thr Leu Val Thr Val
        610                 615                 620

Ser Ser His His His His His His His His
625                 630                 635
```

<210> SEQ ID NO 314
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

```
Glu Val Gln Leu Val Gln Ser Gly Ala Glu Val Lys Lys Pro Gly Glu
1               5                   10                  15

Ser Leu Gln Ile Ser Cys Lys Gly Ser Gly Tyr Thr Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Gly Leu Lys Ala Ser Asp Thr Ala Met Tyr Tyr Cys
                85                  90                  95

Ala Arg Gln Gly Tyr Ser Ser Gly Trp Arg Ser Tyr Tyr Gly Met Gly
            100                 105                 110

Val Trp Gly Gln Gly Thr Thr Val Thr Val Ser Ser
        115                 120
```

<210> SEQ ID NO 315
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Phe Asn Ser Tyr Pro His
            85                  90                  95

Thr Phe Gly Gln Gly Thr Lys Leu Glu Ile Lys
        100                 105

<210> SEQ ID NO 316
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Val Lys Gln Lys Pro Gly Gln Gly Leu Glu Trp Ile
        35                  40                  45

Gly Tyr Phe Asn Pro Tyr Asn Asp Gly Thr Glu Tyr Asn Glu Lys Phe
    50                  55                  60

Lys Ala Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
            85                  90                  95

Ala Lys Gly Pro Tyr Tyr Tyr Gly Ser Ser Pro Phe Asp Tyr Trp Gly
            100                 105                 110

Gln Gly Thr Thr Leu Thr Val Ser Ser
        115                 120

<210> SEQ ID NO 317
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
            85                  90                  95

Thr His Val Pro Tyr Thr Phe Gly Gly Gly Thr Lys Leu Glu Ile Lys
            100                 105                 110

<210> SEQ ID NO 318
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 318

Gly Tyr Thr Phe Thr Asn Tyr Val Ile His
1               5                   10

<210> SEQ ID NO 319
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Tyr Phe Asn Pro Tyr Asn Asp Gly Thr Glu Tyr Asn Glu Lys Phe Lys
1               5                   10                  15

Ala

<210> SEQ ID NO 320
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Gly Pro Tyr Tyr Tyr Gly Ser Ser Pro Phe Asp Tyr
1               5                   10

<210> SEQ ID NO 321
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Arg Ser Ser Gln Ser Leu Glu Asn Ser Asn Gly Asn Thr Tyr Leu Asn
1               5                   10                  15

<210> SEQ ID NO 322
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Arg Val Ser Asn Arg Phe Ser
1               5

<210> SEQ ID NO 323
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Arg Val Ser Asn Arg Phe Ser
1               5
```

<210> SEQ ID NO 324
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Thr Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Asp Thr Lys Tyr Asn Gly Lys Phe
    50                  55                  60

Lys Gly Lys Ala Ser Leu Thr Ala Asp Lys Ser Ser Thr Ala Tyr
65                  70                  75                  80

Met Gln Leu Ile Ser Leu Thr Ser Glu Asp Ser Ala Val Tyr Phe Cys
                85                  90                  95

Ala Arg Arg Tyr Phe Arg Tyr Asp Tyr Trp Tyr Ser Asp Val Trp Gly
            100                 105                 110

Ala Gly Thr Thr Val Thr Val Thr Ser
        115                 120

<210> SEQ ID NO 325
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ala Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys His Gln Gly Asn Thr Leu Pro Leu
                85                  90                  95

Thr Phe Gly Ala Gly Thr Lys Leu Glu Leu Lys
            100                 105

<210> SEQ ID NO 326
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Gly Tyr Ala Phe Ser Thr Tyr Trp Met Asn
1               5                   10

<210> SEQ ID NO 327
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Gln Ile Tyr Pro Gly Asp Asp Thr Lys Tyr Asn Gly Lys Phe Lys
1               5                   10                  15

Gly

<210> SEQ ID NO 328
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Arg Tyr Phe Arg Tyr Asp Tyr Trp Tyr Ser Asp Val
1               5                   10

<210> SEQ ID NO 329
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Arg Ala Ser Gln Asp Ile Ser Asn Tyr Leu Asn
1               5                   10

<210> SEQ ID NO 330
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Tyr Thr Ser Arg Leu His Ser
1               5

<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

His Gln Gly Asn Thr Leu Pro Leu Thr
1               5

<210> SEQ ID NO 332
<211> LENGTH: 116
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 332

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
            20                  25                  30

Asn Met Tyr Trp Val Lys Gln Ser His Gly Lys Ser Leu Glu Trp Ile
        35                  40                  45

Gly Tyr Ile Asp Pro Tyr Asn Gly Asp Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met His Leu Asn Ser Leu Thr Ser Glu Asp Ser Ala Val Tyr Tyr Cys
                85                  90                  95

Leu Thr Thr Ala Tyr Ala Met Asp Tyr Trp Gly Gln Gly Thr Ser Val
            100                 105                 110

Thr Val Ser Ser
            115

<210> SEQ ID NO 333
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Gln Ile Val Leu Thr Gln Ser Pro Ala Ile Met Ser Ala Ser Leu Gly
1               5                   10                  15

Glu Glu Ile Thr Leu Thr Cys Ser Ala Ser Ser Thr Val Asn Tyr Met
            20                  25                  30

His Trp Tyr Gln Gln Lys Ser Gly Thr Ser Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Phe Tyr Ser Leu Thr Ile Arg Ser Val Glu Ala Glu
65                  70                  75                  80

Asp Ala Ala Asp Tyr Tyr Cys His Gln Trp Ser Ser Tyr Pro Tyr Thr
                85                  90                  95

Phe Gly Gly Gly Thr Lys Leu Glu Ile Lys
            100                 105

<210> SEQ ID NO 334
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Gly Tyr Ala Phe Thr Ser Tyr Asn Met Tyr
1               5                   10

<210> SEQ ID NO 335

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Tyr Ile Asp Pro Tyr Asn Gly Asp Thr Thr Tyr Asn Gln Lys Phe Lys
1               5                   10                  15

Gly

<210> SEQ ID NO 336
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Thr Ala Tyr Ala Met Asp Tyr
1               5

<210> SEQ ID NO 337
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Ser Ala Ser Ser Thr Val Asn Tyr Met His
1               5                   10

<210> SEQ ID NO 338
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Ser Thr Ser Asn Leu Ala Ser
1               5

<210> SEQ ID NO 339
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

His Gln Trp Ser Ser Tyr Pro Tyr Thr
1               5

<210> SEQ ID NO 340
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 340

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Val Ile His Trp Val Arg Gln Ala Pro Gly Gln Gly Leu Glu Trp Met
        35                  40                  45

Gly Tyr Phe Asn Pro Tyr Asn Asp Gly Thr Glu Tyr Asn Glu Lys Phe
    50                  55                  60

Lys Ala Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Tyr Tyr Tyr Gly Ser Ser Pro Phe Asp Tyr Trp Gly
            100                 105                 110

Gln Gly Thr Thr Val Thr Val Ser Ser
        115                 120

<210> SEQ ID NO 341
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Gly Tyr Thr Phe Thr Asn Tyr Val Ile His
1               5                   10

<210> SEQ ID NO 342
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Tyr Phe Asn Pro Tyr Asn Asp Gly Thr Glu Tyr Asn Glu Lys Phe Lys
1               5                   10                  15

Ala

<210> SEQ ID NO 343
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Gly Pro Tyr Tyr Tyr Gly Ser Ser Pro Phe Asp Tyr
1               5                   10

<210> SEQ ID NO 344
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 344

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Glu Asn Ser
            20                  25                  30

Asn His Asn Thr Tyr Ile Asn Trp Tyr Leu Gln Lys Pro Gly Gln Ser
        35                  40                  45

Pro Gln Leu Leu Ile Tyr Arg Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys His Gln Val
                85                  90                  95

Thr His Val Pro Tyr Thr Phe Gly Gln Gly Thr Lys Leu Glu Ile Lys
            100                 105                 110

<210> SEQ ID NO 345
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Arg Ser Ser Gln Ser Leu Glu Asn Ser Asn His Asn Thr Tyr Ile Asn
1               5                   10                  15

<210> SEQ ID NO 346
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Arg Val Ser Lys Arg Phe Ser
1               5

<210> SEQ ID NO 347
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

His Gln Val Thr His Val Pro Tyr Thr
1               5

<210> SEQ ID NO 348
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Ala Phe Ser Thr Tyr
                20                  25                  30

Trp Met Asn Trp Val Arg Gln Ala Pro Gly Gln Gly Leu Glu Trp Met
            35                  40                  45

Gly Gln Ile Tyr Pro Gly Asp Asp Thr Lys Tyr Ser Gly Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Arg Tyr Phe Arg Tyr Asp Tyr Trp Tyr Ser Asp Val Trp Gly
            100                 105                 110

Gln Gly Thr Thr Val Thr Val Ser Ser
        115                 120

<210> SEQ ID NO 349
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Val Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys His Gln Gly Asn Thr Leu Pro Leu
                85                  90                  95

Thr Phe Gly Gln Gly Thr Lys Leu Glu Ile Lys
            100                 105

<210> SEQ ID NO 350
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Gly Tyr Ala Phe Ser Thr Tyr Trp Met Asn
 1               5                  10

<210> SEQ ID NO 351
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Gln Ile Tyr Pro Gly Asp Asp Thr Lys Tyr Ser Gly Lys Phe Lys
```

```
                    1               5                  10                 15

Gly

<210> SEQ ID NO 352
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Arg Tyr Phe Arg Tyr Asp Tyr Trp Tyr Ser Asp Val
1               5                   10

<210> SEQ ID NO 353
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Arg Ala Ser Gln Asp Ile Ser Asn Tyr Leu Asn
1               5                   10

<210> SEQ ID NO 354
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Tyr Thr Ser Arg Leu His Ser
1               5

<210> SEQ ID NO 355
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

His Gln Gly Asn Thr Leu Pro Leu Thr
1               5

<210> SEQ ID NO 356
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Ala Phe Thr Ser Tyr
                20                  25                  30

Asn Met Tyr Trp Val Arg Gln Ala Arg Gly Gln Arg Leu Glu Trp Ile
            35                  40                  45
```

Gly Tyr Ile Asp Pro Tyr Asn Ala Asp Thr Thr Tyr Asn Gln Lys Phe
            50                  55                  60

Lys Gly Arg Val Thr Ile Thr Arg Asp Met Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Leu Thr Thr Ala Tyr Ala Met Asp Tyr Trp Gly Gln Gly Thr Leu Val
            100                 105                 110

Thr Val Ser Ser
        115

<210> SEQ ID NO 357
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Asp Ile Gln Leu Thr Gln Ser Pro Ser Phe Leu Ser Ala Ser Val Gly
 1               5                  10                  15

Asp Arg Val Thr Ile Thr Cys Ser Ala Ser Ser Thr Val Asn Tyr Met
             20                  25                  30

His Trp Tyr Gln Gln Lys Pro Gly Lys Ala Pro Lys Leu Leu Ile Tyr
         35                  40                  45

Ser Thr Ser Asn Leu Ala Ser Gly Val Pro Ser Arg Phe Ser Gly Ser
 50                  55                  60

Gly Ser Gly Thr Glu Phe Thr Leu Thr Ile Ser Ser Leu Gln Pro Glu
 65                  70                  75                  80

Asp Phe Ala Thr Tyr Tyr Cys His Gln Trp Ser Ser Tyr Pro Tyr Thr
                 85                  90                  95

Phe Gly Gln Gly Thr Lys Leu Glu Ile Lys
            100                 105

<210> SEQ ID NO 358
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Gly Tyr Ala Phe Thr Ser Tyr Asn Met Tyr
 1               5                  10

<210> SEQ ID NO 359
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Tyr Ile Asp Pro Tyr Asn Ala Asp Thr Thr Tyr Asn Gln Lys Phe Lys
 1               5                  10                  15

Gly

```
<210> SEQ ID NO 360
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Thr Ala Tyr Ala Met Asp Tyr
1               5

<210> SEQ ID NO 361
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Ser Ala Ser Ser Thr Val Asn Tyr Met His
1               5                   10

<210> SEQ ID NO 362
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ser Thr Ser Asn Leu Ala Ser
1               5

<210> SEQ ID NO 363
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

His Gln Trp Ser Ser Tyr Pro Tyr Thr
1               5

<210> SEQ ID NO 364
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Gln Val Lys Leu Glu Glu Ser Gly Gly Glu Leu Val Gln Pro Gly Gly
1               5                   10                  15

Pro Leu Arg Leu Ser Cys Ala Ala Ser Gly Asn Ile Phe Ser Ile Asn
            20                  25                  30

Arg Met Gly Trp Tyr Arg Gln Ala Pro Gly Lys Gln Arg Ala Phe Val
        35                  40                  45

Ala Ser Ile Thr Val Arg Gly Ile Thr Asn Tyr Ala Asp Ser Val Lys
    50                  55                  60

Gly Arg Phe Thr Ile Ser Val Asp Lys Ser Lys Asn Thr Ile Tyr Leu
```

```
                65                  70                  75                  80
Gln Met Asn Ala Leu Lys Pro Glu Asp Thr Ala Val Tyr Tyr Cys Asn
                    85                  90                  95
Ala Val Ser Ser Asn Arg Asp Pro Asp Tyr Trp Gly Gln Gly Thr Gln
                    100                 105                 110

Val Thr Val Ser Ser
            115

<210> SEQ ID NO 365
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ile Asn Arg Met Gly
1               5

<210> SEQ ID NO 366
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Ser Ile Thr Val Arg Gly Ile Thr Asn Tyr Ala Asp Ser Val Lys Gly
1               5                   10                  15

<210> SEQ ID NO 367
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Val Ser Ser Asn Arg Asp Pro Asp Tyr
1               5

<210> SEQ ID NO 368
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Ala Arg Asp Ser Tyr Gly Arg Tyr Phe Tyr Asp Val
1               5                   10

<210> SEQ ID NO 369
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Ala Arg Asp Val Tyr Gly Arg Tyr Phe Tyr Asp Leu
```

-continued

```
1               5                   10
```

<210> SEQ ID NO 370
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

```
Ala Arg Asp Ala Tyr Gly Gly Tyr Phe Tyr Asp Val
1               5                   10
```

<210> SEQ ID NO 371
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 371

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Glu Ser Leu Arg Ala Glu Asp Thr Ala Val Tyr
                85                  90                  95

Tyr Cys Val Arg His Gly Asn Phe Gly Asn Tyr Ala Val Ser Trp Phe
            100                 105                 110

Ala His Trp Gly Gln Gly Thr Leu Val Thr Val Ser Ser
        115                 120                 125
```

<210> SEQ ID NO 372
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 372

```
Gln Thr Val Val Thr Gln Glu Pro Ser Leu Ser Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Thr Pro Gly Gln Ala Pro Arg Gly
        35                  40                  45

Leu Ile Gly Gly Thr Asp Lys Arg Ala Pro Gly Val Pro Asp Arg Phe
    50                  55                  60

Ser Gly Ser Leu Leu Gly Asp Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95
```

```
His Trp Val Phe Gly Gly Gly Thr Lys Leu Thr Val Leu
            100                 105

<210> SEQ ID NO 373
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Phe Thr Phe Asp Thr Tyr Ala Met Asn
1               5

<210> SEQ ID NO 374
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Arg Ile Arg Ser Lys Tyr Asn Asn Tyr Ala Thr Tyr Tyr Ala Asp Ser
1               5                   10                  15

Val Lys Asp

<210> SEQ ID NO 375
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Val Arg His Gly Asn Phe Gly Asn Tyr Ala Val Ser Trp Phe Ala His
1               5                   10                  15

<210> SEQ ID NO 376
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Gly Ser Ser Thr Gly Ala Val Thr Thr Ser Asn Tyr Ala Asn
1               5                   10

<210> SEQ ID NO 377
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Gly Thr Asp Lys Arg Ala Pro
1               5

<210> SEQ ID NO 378
<211> LENGTH: 9
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Ala Leu Trp Tyr Ser Asn His Trp Val
1               5

<210> SEQ ID NO 379
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Thr
65                  70                  75                  80

Leu Tyr Leu Gln Met Glu Ser Leu Arg Ala Glu Asp Thr Ala Val Tyr
                85                  90                  95

Tyr Cys Val Arg His Gly Ser Phe Gly Asn His Ile Val Ser Trp Phe
            100                 105                 110

Ala His Trp Gly Gln Gly Thr Leu Val Thr Val Ser Ser
        115                 120                 125

<210> SEQ ID NO 380
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Thr Tyr
            20                  25                  30

Tyr Ile His Trp Val Arg Gln Ala Pro Gly Gln Gly Leu Glu Trp Met
        35                  40                  45

Gly Trp Ile Phe Pro Gly Asn Asp Asn Ile Lys Tyr Ser Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Asp Ser Val Ser Ile Tyr Tyr Phe Asp Tyr Trp Gly Gln Gly
            100                 105                 110

Thr Leu Val Thr Val Ser Ser

115

<210> SEQ ID NO 381
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 381

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gly Gly Thr Lys Val Glu Ile Lys
            100                 105                 110

<210> SEQ ID NO 382
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Gly Tyr Ser Phe Thr Thr Tyr Tyr Ile His
1               5                   10

<210> SEQ ID NO 383
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Trp Ile Phe Pro Gly Asn Asp Asn Ile Lys Tyr Ser Glu Lys Phe Lys
1               5                   10                  15

Gly

<210> SEQ ID NO 384
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Asp Ser Val Ser Ile Tyr Tyr Phe Asp Tyr
1               5                   10

```
<210> SEQ ID NO 385
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Lys Ser Ser Gln Ser Leu Leu Asn Ser Arg Thr Arg Lys Asn Tyr Leu
1               5                   10                  15

Ala

<210> SEQ ID NO 386
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Trp Ala Ser Thr Arg Lys Ser
1               5

<210> SEQ ID NO 387
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Thr Gln Ser Phe Ile Leu Arg Thr
1               5

<210> SEQ ID NO 388
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 388

Gln Val Gln Leu Val Gln Ser Gly Ala Glu Val Lys Lys Pro Gly Ser
1               5                   10                  15

Ser Val Lys Val Ser Cys Lys Ala Ser Gly Phe Ala Phe Thr Asp Tyr
                20                  25                  30

Tyr Ile His Trp Val Arg Gln Ala Pro Gly Gln Gly Leu Glu Trp Met
            35                  40                  45

Gly Trp Ile Ser Pro Gly Asn Val Asn Thr Lys Tyr Asn Glu Asn Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Ser Leu Tyr Tyr Phe Asp Tyr Trp Gly Gln Gly
                100                 105                 110

Thr Leu Val Thr Val Ser Ser
            115
```

```
<210> SEQ ID NO 389
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 389

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Lys Pro Gly Gln
        35                  40                  45

Pro Pro Lys Leu Leu Ile Tyr Trp Ala Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser His Thr Leu Arg Thr Phe Gly Gly Gly Thr Lys Val Glu Ile Lys
            100                 105                 110

<210> SEQ ID NO 390
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Gly Phe Ala Phe Thr Asp Tyr Tyr Ile His
1               5                   10

<210> SEQ ID NO 391
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Trp Ile Ser Pro Gly Asn Val Asn Thr Lys Tyr Asn Glu Asn Phe Lys
1               5                   10                  15

Gly

<210> SEQ ID NO 392
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Asp Gly Tyr Ser Leu Tyr Tyr Phe Asp Tyr
1               5                   10

<210> SEQ ID NO 393
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 393

Trp Ala Ser Thr Arg Gln Ser
1               5

<210> SEQ ID NO 394
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Thr Gln Ser His Thr Leu Arg Thr
1               5

<210> SEQ ID NO 395
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 395

Met Ala Glu Ser Gly Gly Gly Ser Val Gln Thr Gly Gly Ser Leu Arg
1               5                   10                  15

Leu Ser Cys Ala Tyr Thr Ala Ser Ser Val Cys Met Ala Trp Phe Arg
                20                  25                  30

Gln Ala Pro Gly Lys Glu Arg Glu Gly Val Ala Val Thr Arg Glu Gly
            35                  40                  45

Leu Thr Lys Thr Gly Tyr Ala Asp Ser Val Lys Gly Arg Phe Ala Ile
        50                  55                  60

Ser Gln Asp Tyr Ala Lys Lys Thr Leu Tyr Leu Gln Met Ser Ser Leu
65                  70                  75                  80

Lys Pro Glu Asp Thr Ala Arg Tyr Tyr Cys Ala Ala Arg Pro Thr Ser
                85                  90                  95

Pro Cys Thr Val Asp Gly Glu Leu Leu Ala Ser Thr Tyr Asn Tyr Trp
                100                 105                 110

Gly Gln Gly Thr Gln Val Thr Val
            115                 120

<210> SEQ ID NO 396
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

Met Ala Glu Ser Gly Gly Gly Ser Val Gln Thr Gly Gly Ser Leu Arg
1               5                   10                  15

Leu Ser Cys Ala Tyr Thr Ala Ser Ser Val Cys Met Ala Trp Phe Arg
                20                  25                  30

Gln Ala Pro Gly Lys Glu Arg Glu Gly Val Ala Val Thr Arg Glu Gly
            35                  40                  45
```

```
Leu Thr Lys Thr Gly Tyr Ala Asp Ser Val Lys Gly Arg Phe Ala Ile
    50                  55                  60

Ser Gln Asp Tyr Ala Lys Lys Thr Leu Tyr Leu Gln Met Ser Ser Leu
65                  70                  75                  80

Lys Pro Glu Asp Thr Ala Arg Tyr Tyr Cys Ala Ala Arg Pro Thr Ser
                    85                  90                  95

Pro Cys Thr Val Asp Gly Glu Leu Leu Ala Ser Thr Tyr Asp Tyr Trp
                100                 105                 110

Gly Gln Gly Thr Gln Val Thr Val
            115                 120

<210> SEQ ID NO 397
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

Met Ala Glu Ser Gly Gly Gly Ser Val Gln Thr Gly Gly Ser Leu Arg
1               5                   10                  15

Leu Ser Cys Ala Tyr Thr Ala Ser Ser Val Cys Met Ala Trp Phe Arg
                20                  25                  30

Gln Ala Pro Gly Lys Glu Arg Glu Gly Val Ala Val Thr Arg Glu Gly
            35                  40                  45

Leu Thr Gln Thr Gly Tyr Ala Asp Ser Val Lys Gly Arg Phe Ala Ile
    50                  55                  60

Ser Gln Asp Tyr Ala Lys Lys Thr Leu Tyr Leu Gln Met Ser Ser Leu
65                  70                  75                  80

Lys Pro Glu Asp Thr Ala Arg Tyr Tyr Cys Ala Ala Arg Pro Thr Ser
                    85                  90                  95

Pro Cys Thr Val Asp Gly Glu Leu Leu Ala Ser Thr Tyr Asn Tyr Trp
                100                 105                 110

Gly Gln Gly Thr Gln Val Thr Val
            115                 120

<210> SEQ ID NO 398
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 398

Met Ala Glu Ser Gly Gly Gly Ser Val Gln Thr Gly Gly Ser Leu Arg
1               5                   10                  15

Leu Ser Cys Ala Tyr Thr Ala Ser Ser Val Cys Met Ala Trp Phe Arg
                20                  25                  30

Gln Ala Pro Gly Lys Glu Arg Glu Gly Val Ala Val Thr Arg Glu Gly
            35                  40                  45

Leu Thr Gln Thr Gly Tyr Ala Asp Ser Val Lys Gly Arg Phe Ala Ile
    50                  55                  60

Ser Gln Asp Tyr Ala Lys Lys Thr Leu Tyr Leu Gln Met Ser Ser Leu
65                  70                  75                  80

Lys Pro Glu Asp Thr Ala Arg Tyr Tyr Cys Ala Ala Arg Pro Thr Ser
                    85                  90                  95
```

Pro Cys Thr Val Asp Gly Glu Leu Leu Ala Ser Thr Tyr Asp Tyr Trp
            100                 105                 110

Gly Gln Gly Thr Gln Val Thr Val
        115                 120

<210> SEQ ID NO 399
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Val Arg His Gly Ser Phe Gly Asn His Ile Val Ser Trp Phe Ala His
1               5                   10                  15

<210> SEQ ID NO 400
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-20 "Gly Ser"
      repeating units

<400> SEQUENCE: 400

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser Gly Ser
            20                  25                  30

Gly Ser Gly Ser Gly Ser Gly Ser
        35                  40

<210> SEQ ID NO 401
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(60)
<223> OTHER INFORMATION: This sequence may encompass 1-20 "Gly Gly Ser"
      repeating units

<400> SEQUENCE: 401

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser
    50                  55                  60

<210> SEQ ID NO 402
<211> LENGTH: 80
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<221> NAME/KEY: MISC_FEATURE
<222> LOCATION: (1)..(80)
<223> OTHER INFORMATION: This sequence may encompass 1-20 "Gly Gly Gly
      Ser" repeating units

<400> SEQUENCE: 402

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

Gly Gly Gly Ser Gly Gly Gly Ser Gly Gly Gly Ser Gly Gly Gly Ser
    50                  55                  60

Gly Gly Gly Ser Gly Gly Gly Ser Gly Gly Gly Ser Gly Gly Gly Ser
65                  70                  75                  80

<210> SEQ ID NO 403
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(80)
<223> OTHER INFORMATION: This sequence may encompass 1-20 "Gly Gly Ser
      Gly" repeating units

<400> SEQUENCE: 403

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly Gly Gly Ser Gly Gly Gly Ser Gly
        35                  40                  45

Gly Gly Ser Gly Gly Gly Ser Gly Gly Gly Ser Gly Gly Gly Ser Gly
    50                  55                  60

Gly Gly Ser Gly Gly Gly Ser Gly Gly Gly Ser Gly Gly Gly Ser Gly
65                  70                  75                  80

<210> SEQ ID NO 404
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(100)
<223> OTHER INFORMATION: This sequence may encompass 1-20 "Gly Gly Ser
      Gly Gly" repeating units

<400> SEQUENCE: 404

Gly Gly Ser Gly Gly Gly Gly Ser Gly Gly Gly Gly Ser Gly Gly Gly
1               5                   10                  15

Gly Ser Gly Gly Gly Gly Ser Gly Gly Gly Gly Ser Gly Gly Gly Gly
            20                  25                  30

Ser Gly Gly Gly Gly Ser Gly Gly Gly Gly Ser Gly Gly Gly Gly Ser
```

```
                35              40              45
Gly Gly Gly Gly Ser Gly Gly Gly Ser Gly Gly Gly Ser Gly
    50              55              60

Gly Gly Gly Ser Gly Gly Gly Ser Gly Gly Gly Ser Gly Gly
65              70              75              80

Gly Gly Ser Gly Gly Gly Ser Gly Gly Gly Ser Gly Gly Gly
            85              90              95

Gly Ser Gly Gly
        100

<210> SEQ ID NO 405
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(100)
<223> OTHER INFORMATION: This sequence may encompass 1-20 "Gly Gly Gly
      Gly Ser" repeating units

<400> SEQUENCE: 405

Gly Gly Gly Gly Ser Gly Gly Gly Ser Gly Gly Gly Ser Gly
1               5               10              15

Gly Gly Gly Ser Gly Gly Gly Ser Gly Gly Gly Ser Gly Gly
            20              25              30

Gly Gly Ser Gly Gly Gly Ser Gly Gly Gly Ser Gly Gly Gly
        35              40              45

Gly Ser Gly Gly Gly Ser Gly Gly Gly Ser Gly Gly Gly Gly
    50              55              60

Ser Gly Gly Gly Ser Gly Gly Gly Ser Gly Gly Gly Gly Ser
65              70              75              80

Gly Gly Gly Gly Ser Gly Gly Gly Ser Gly Gly Gly Ser Gly
            85              90              95

Gly Gly Gly Ser
        100

<210> SEQ ID NO 406
<211> LENGTH: 634
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 406

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Ile Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Gln Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95
```

```
Tyr Cys Val Arg His Ala Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Ser Gln Thr Val Val
130                 135                 140

Thr Gln Glu Pro Ser Leu Thr Val Ser Pro Gly Gly Thr Val Thr Leu
145                 150                 155                 160

Thr Cys Ala Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Val Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
210                 215                 220

Glu Ala Glu Tyr Tyr Cys Thr Leu Trp Tyr Ser Asn Arg Trp Val Phe
225                 230                 235                 240

Gly Gly Gly Thr Lys Leu Thr Val Leu Gly Gly Gly Ser Gly Gly
                245                 250                 255

Gly Ser Glu Val Gln Leu Val Glu Ser Gly Gly Gly Leu Val Gln Pro
            260                 265                 270

Gly Asn Ser Leu Arg Leu Ser Cys Ala Ala Ser Gly Phe Thr Phe Ser
            275                 280                 285

Ser Phe Gly Met Ser Trp Val Arg Gln Ala Pro Gly Lys Gly Leu Glu
            290                 295                 300

Trp Val Ser Ser Ile Ser Gly Ser Gly Ser Asp Thr Leu Tyr Ala Asp
305                 310                 315                 320

Ser Val Lys Gly Arg Phe Thr Ile Ser Arg Asp Asn Ala Lys Thr Thr
                325                 330                 335

Leu Tyr Leu Gln Met Asn Ser Leu Arg Pro Glu Asp Thr Ala Val Tyr
            340                 345                 350

Tyr Cys Thr Ile Gly Gly Ser Leu Ser Arg Ser Ser Gln Gly Thr Leu
            355                 360                 365

Val Thr Val Ser Ser Gly Gly Gly Gly Ser Gly Gly Gly Ser Gln Val
            370                 375                 380

Gln Leu Gln Glu Ser Gly Pro Gly Leu Val Lys Pro Ser Gln Thr Leu
385                 390                 395                 400

Ser Leu Thr Cys Thr Val Ser Gly Ser Ile Ser Thr Ser Gly Met
                405                 410                 415

Gly Val Gly Trp Ile Arg Gln His Pro Gly Lys Gly Leu Glu Trp Ile
            420                 425                 430

Gly His Ile Trp Trp Asp Asp Lys Arg Tyr Asn Pro Ala Leu Lys
            435                 440                 445

Ser Arg Val Thr Ile Ser Val Asp Thr Ser Lys Asn Gln Phe Ser Leu
            450                 455                 460

Lys Leu Ser Ser Val Thr Ala Ala Asp Thr Ala Val Tyr Tyr Cys Ala
465                 470                 475                 480

Arg Met Glu Leu Trp Ser Tyr Tyr Phe Asp Tyr Trp Gly Gln Gly Thr
            485                 490                 495

Leu Val Thr Val Ser Ser Gly Gly Gly Gly Ser Gly Gly Gly Gly Ser
            500                 505                 510
```

```
Gly Gly Gly Gly Ser Glu Ile Val Leu Thr Gln Ser Pro Ala Thr Leu
            515                 520                 525

Ser Leu Ser Pro Gly Glu Arg Ala Thr Leu Ser Cys Ser Ala Ser Ser
    530                 535                 540

Ser Val Ser Tyr Met His Trp Tyr Gln Gln Lys Pro Gly Gln Ala Pro
545                 550                 555                 560

Arg Leu Leu Ile Tyr Asp Thr Ser Lys Leu Ala Ser Gly Ile Pro Ala
                565                 570                 575

Arg Phe Ser Gly Ser Gly Ser Gly Thr Asp Phe Thr Leu Thr Ile Ser
            580                 585                 590

Ser Leu Glu Pro Glu Asp Phe Ala Val Tyr Tyr Cys Phe Gln Gly Ser
            595                 600                 605

Val Tyr Pro Phe Thr Phe Gly Gln Gly Thr Lys Leu Glu Ile Lys Arg
    610                 615                 620

His His His His His His His His His His
625                 630

<210> SEQ ID NO 407
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 407

His His His His His His His His His His
1               5                   10
```